US009572874B2

(12) United States Patent
Fotin-Mleczek et al.

(10) Patent No.: US 9,572,874 B2

(45) Date of Patent: Feb. 21, 2017

(54) COMPOSITION COMPRISING A COMPLEXED (M)RNA AND A NAKED MRNA FOR PROVIDING OR ENHANCING AN IMMUNOSTIMULATORY RESPONSE IN A MAMMAL AND USES THEREOF

(75) Inventors: Mariola Fotin-Mleczek, Sindelfingen (DE); Söhnke Voss, Dossenheim (DE)

(73) Assignee: CureVac AG, Tübingen (DE)

( * ) Notice: Subject to any disclaimer, the term of this patent is extended or adjusted under 35 U.S.C. 154(b) by 883 days.

(21) Appl. No.: 12/994,407

(22) PCT Filed: Sep. 30, 2009

(86) PCT No.: PCT/EP2009/007032

§ 371 (c)(1), (2), (4) Date: Nov. 23, 2010

(87) PCT Pub. No.: WO2010/037539

PCT Pub. Date: Apr. 8, 2010

(65) Prior Publication Data

US 2011/0250225 A1 Oct. 13, 2011

(30) Foreign Application Priority Data

Sep. 30, 2008 (WO) ................. PCT/EP2008/008304

(51) Int. Cl.

*A61K 48/00* (2006.01)
*A61K 47/06* (2006.01)
*A61K 39/00* (2006.01)

(52) U.S. Cl.

CPC ........ *A61K 39/0011* (2013.01); *A61K 2039/53* (2013.01); *A61K 2039/55511* (2013.01)

(58) Field of Classification Search

CPC .................... A61K 2039/53; A61K 2039/555; A61K 2039/70; A61K 2039/55511; A61K 39/011

USPC .................................... 514/44 R; 424/278.1

See application file for complete search history.

(56) References Cited

U.S. PATENT DOCUMENTS

| | | | |
|---|---|---|---|
| 3,906,092 | A | 9/1975 | Hilleman et al. |
| 4,373,071 | A | 2/1983 | Itakura |
| 4,401,796 | A | 8/1983 | Itakura |
| 4,415,732 | A | 11/1983 | Caruthers et al. |
| 4,578,399 | A | 3/1986 | Schorlemmer et al. |
| 5,516,652 | A | 5/1996 | Abramovitz et al. |
| 5,663,153 | A | 9/1997 | Hutcherson et al. |
| 5,663,163 | A | 9/1997 | Takaya et al. |
| 5,844,075 | A | 12/1998 | Kawakami et al. |
| 5,965,720 | A | 10/1999 | Gryaznov et al. |
| 6,096,307 | A | 8/2000 | Braswell et al. |
| 6,218,371 | B1 | 4/2001 | Krieg et al. |
| 6,239,116 | B1 | 5/2001 | Krieg et al. |
| 6,322,967 | B1 | 11/2001 | Parkin |
| 6,406,705 | B1 | 6/2002 | Davis et al. |
| 6,498,148 | B1 | 12/2002 | Raz |
| 6,514,948 | B1 | 2/2003 | Raz et al. |
| 6,552,006 | B2 | 4/2003 | Raz et al. |
| 6,589,940 | B1 | 7/2003 | Raz et al. |
| 6,610,661 | B1 | 8/2003 | Carson et al. |
| 6,689,757 | B1 | 2/2004 | Craig |
| 6,716,434 | B1 | 4/2004 | Ansley et al. |
| 7,001,890 | B1 | 2/2006 | Wagner et al. |
| 7,208,478 | B2 | 4/2007 | Carson et al. |
| 7,407,944 | B2 | 8/2008 | Agrawal et al. |
| 7,470,674 | B2 | 12/2008 | Agrawal et al. |
| 7,517,862 | B2 | 4/2009 | Agrawal et al. |
| 2003/0225016 | A1 | 12/2003 | Fearon et al. |
| 2004/0006010 | A1 | 1/2004 | Carson et al. |
| 2004/0006034 | A1 | 1/2004 | Raz et al. |
| 2004/0047869 | A1 | 3/2004 | Garcon et al. |
| 2004/0052763 | A1 | 3/2004 | Mond et al. |
| 2005/0032730 | A1* | 2/2005 | Von Der Mulbe et al. .... 514/44 |
| 2005/0037494 | A1 | 2/2005 | Hecker et al. |

(Continued)

FOREIGN PATENT DOCUMENTS

| | | |
|---|---|---|
| CA | 2376634 | 12/2000 |
| DE | 1014 8886 | 4/2003 |
| DE | 10 2004 035 227 | 2/2006 |
| DE | 102006007433 | 8/2007 |
| DE | 698 19 150 | 12/2007 |

(Continued)

OTHER PUBLICATIONS

Sheel et al. (2006) Eur. J. Immunol., vol. 36, 2807-2816.*

Lochmann, et al., "Drug delivery of oligonucleotides by peptides", European Journal of Pharmaceutics and Biopharmaceutics, vol. 58, No. 2, Sep. 1, 2004, pp. 237-251.

Scheel, et al., "Therapeutic anti-tumor immunity triggered by injections of immunostimulating single-stranded RNA", European Journal of Immunology, vol. 36, No. 10, Oct. 1, 2006, pp. 2807-2816.

(Continued)

*Primary Examiner* — Anne Marie S Wehbe

(74) *Attorney, Agent, or Firm* — Parker Highlander PLLC

(57) ABSTRACT

The present invention relates to an immunostimulatory composition comprising a) an adjuvant component, comprising or consisting of at least one (m)RNA, complexed with a cationic or polycationic compound, and b) at least one free mRNA, encoding at least one therapeutically active protein, antigen, allergen and/or antibody, wherein the immunostimulatory composition is capable to elicit or enhance an innate and optionally an adaptive immune response in a mammal. The inventive immunostimulatory composition may be a pharmaceutical composition or a vaccine. The invention furthermore relates to a method of preparation of the inventive immunostimulatory composition. The invention also relates to the use of the inventive immunostimulatory composition or its components (for the preparation of a pharmaceutical composition or a vaccine) for the treatment of various diseases. Finally, the invention relates to kits containing the inventive immunostimulatory composition, its components and/or the pharmaceutical composition or vaccine.

22 Claims, 14 Drawing Sheets

(56) References Cited

U.S. PATENT DOCUMENTS

Figure 1:
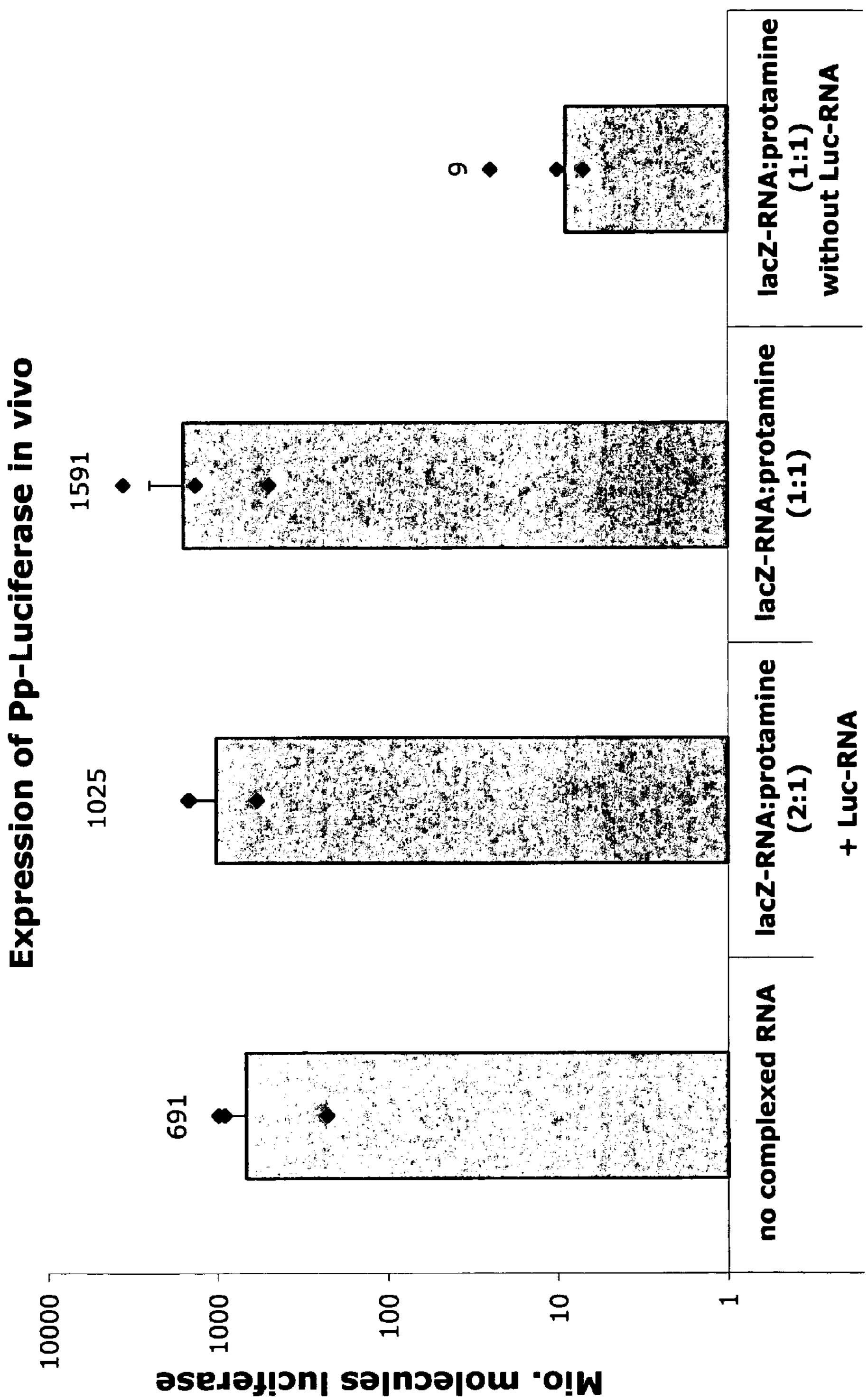

| | | | |
|---|---|---|---|
| 2005/0059624 A1 | 3/2005 | Hoerr et al. | |
| 2005/0063975 A1 | 3/2005 | Afar et al. | |
| 2005/0130918 A1 | 6/2005 | Agrawal et al. | |
| 2005/0250723 A1 | 11/2005 | Hoerr et al. | |
| 2006/0172966 A1 | 8/2006 | Lipford et al. | |
| 2006/0188490 A1 | 8/2006 | Hoerr et al. | |
| 2007/0056859 A1 | 3/2007 | Sherman et al. | |
| 2007/0065859 A1 | 3/2007 | Wang et al. | |
| 2008/0025944 A1 | 1/2008 | Hoerr et al. | |
| 2008/0071711 A1 | 3/2008 | Zhang et al. | |
| 2008/0267873 A1 | 10/2008 | Hoerr et al. | |
| 2009/0203767 A1 | 8/2009 | Hecker et al. | |
| 2009/0324584 A1* | 12/2009 | Hoerr et al. | 424/130.1 |
| 2010/0048883 A1 | 2/2010 | Ketterer et al. | |
| 2010/0189729 A1 | 7/2010 | Hoerr et al. | |
| 2010/0203076 A1 | 8/2010 | Fotin-Mleczek et al. | |
| 2010/0291156 A1 | 11/2010 | Barner et al. | |
| 2010/0303851 A1 | 12/2010 | Hoerr et al. | |
| 2010/0305196 A1 | 12/2010 | Probst et al. | |
| 2011/0182927 A1 | 7/2011 | Raz et al. | |
| 2011/0300164 A1 | 12/2011 | Lipford et al. | |
| 2012/0009221 A1 | 1/2012 | Hoerr et al. | |
| 2012/0021043 A1 | 1/2012 | Kramps et al. | |

FOREIGN PATENT DOCUMENTS

| | | |
|---|---|---|
| EP | 0347 501 | 12/1989 |
| EP | 0 772 619 | 2/1996 |
| EP | 0 839 912 | 5/1998 |
| EP | 1083232 | 3/2001 |
| EP | 1 167 379 | 1/2002 |
| EP | 1 374 894 | 1/2004 |
| EP | 1 393 745 | 3/2004 |
| EP | 1 564 291 | 8/2005 |
| EP | 1905844 | 4/2008 |
| JP | 2003-504080 A | 2/2003 |
| JP | 2003-517306 A | 5/2003 |
| JP | 2006-512047 A | 4/2006 |
| WO | WO 91/05560 | 5/1991 |
| WO | WO 94/17093 | 8/1994 |
| WO | WO 94/17792 | 8/1994 |
| WO | WO 98/19710 | 5/1998 |
| WO | WO 98/47913 | 10/1998 |
| WO | WO 99/53961 | 10/1999 |
| WO | WO 00/49158 | 6/2000 |
| WO | WO 00/75304 | 12/2000 |
| WO | WO 01/04135 | 1/2001 |
| WO | WO01/04143 | 1/2001 |
| WO | WO01/40276 | 6/2001 |
| WO | WO 01/75164 | 10/2001 |
| WO | WO 01/93902 | 12/2001 |
| WO | WO 01/97843 | 12/2001 |
| WO | WO 02/00594 | 1/2002 |
| WO | WO 02/00694 | 1/2002 |
| WO | WO 02/078614 | 10/2002 |
| WO | WO 02/098443 | 12/2002 |
| WO | WO 03/028656 | 4/2003 |
| WO | WO 03/057822 | 7/2003 |
| WO | WO 03/059381 | 7/2003 |
| WO | WO 03/065649 | 8/2003 |
| WO | WO 03/068942 | 8/2003 |
| WO | WO 03/074551 | 9/2003 |
| WO | WO 03/056280 | 10/2003 |
| WO | WO03/104272 | 12/2003 |
| WO | WO 2004/004743 | 1/2004 |
| WO | WO 2004/016643 | 2/2004 |
| WO | WO 2004/058159 | 7/2004 |
| WO | WO 2004/064782 | 8/2004 |
| WO | WO 2004/067570 | 8/2004 |
| WO | WO 2004/092329 | 10/2004 |
| WO | WO 2005/000887 | 1/2005 |
| WO | WO 2005/001022 | 1/2005 |
| WO | WO 2005/016376 | 2/2005 |
| WO | WO 2005/030259 | 4/2005 |
| WO | WO 2005/030800 | 4/2005 |
| WO | WO 2006/097993 | 10/2005 |
| WO | WO2005/113601 | 12/2005 |
| WO | WO 2006/008154 | 1/2006 |
| WO | WO2006/024518 | 3/2006 |
| WO | WO 2006/029223 | 3/2006 |
| WO | WO 2006/046978 | 5/2006 |
| WO | WO 2006/118458 | 11/2006 |
| WO | WO 2007/031319 | 3/2007 |
| WO | WO 2007/031322 | 3/2007 |
| WO | WO 2007/042554 | 4/2007 |
| WO | WO 2007/051303 | 5/2007 |
| WO | WO 2007/069068 | 6/2007 |
| WO | WO 2007/124755 | 11/2007 |
| WO | WO 2008/014979 * | 2/2008 |
| WO | WO2008/014979 | 2/2008 |
| WO | WO 2008/022046 | 2/2008 |
| WO | WO 2009/030254 | 3/2009 |
| WO | WO 2009/030481 | 3/2009 |
| WO | WO 2009/053700 | 4/2009 |
| WO | WO 2009/086640 | 7/2009 |
| WO | WO 2010/037408 | 4/2010 |
| WO | WO 2010/037539 | 4/2010 |
| WO | WO 2011/026641 | 3/2011 |

OTHER PUBLICATIONS

Heil, et al., "Species-Specific Recognition of Single-Stranded RNA via Toll-like Receptor 7 and 8", Science, vol. 303, Mar. 5, 2004, pp. 1526-1529.

Scheel, et al., "Toll-like receptor-dependent activation of several human blood cell types by protamine-condensed mRNA", European Journal of Immunology, vol. 35, No. 5, May 1, 2005, pp. 1557-1566.

Adams AD et al., Preparation and hybridization properties of oligonucleotides containing 1-alpha-D-arabinofuranosylthymine, Nucleic Acids Res. Jul. 11, 1991: 19(13):3647-51.

Agrawal, 1996; Antisense olignucleotides: towards clinical trials; Trends in Biotechnology; vol. 14; No. 10; pp. 376-387.

Ara et al., 2001; Zymosan enhances the immune response to DNA vaccine for human Immunodeficiency virus type-1 through the activation of complement system; Immunology; vol. 103, pp. 98-105.

Bayard et al.; Antiviral activity in L1210 cells of lipo-encapsulated (2'-5')oligo(adenylate)analogues; Eur. J. Biochem., vol. 151, No. 2, pp. 319-326, 1985.

Bettinger T., et al., Peptide-mediated RNA delivery: a novel approach for enhanced transfection of primary and Post-mitotic cells, Nucleic Acids Research, 2001, vol. 29, No. 18, 3882-3891.

Blaxter et al., 2002, The Brugia malayi genome project: expressed sequence tags and gene discovery; 2002; Transactions of the Royal Society of Tropical Medicine and Hygiene, vol. 96, No. 1, pp. 1-17.

Bocchia et al., 2000; Antitumor vaccination: where we stand; Heamatologica, vol. 85, No. 11, pp. 1172-1206.

Bolhassani Azam et al., Improvement of different vaccine delivery systems for cancer therapy, Molecular Cancer, Biomed Central, London, GB, vol. 10, No. 1, Jan. 7, 2011, p. 3.

Bot A. et al.: Enhanced protection against influenza virus of mice immunized as newborns with a mixture of plasmids expressing hemagglutinin and nucleoprotein, Vaccine, Elsevier Ltd., GB, vol. 16, No. 17, Oct. 1, 1998, pp. 1675-1682.

Bot A. et al.: Genetic immunization of neonates, Microbes and Infection, Institut Pasteaur, Apr. 2002 LNKD-PUBMED: 11932202, vol. 4, No. 4, Apr. 2002, pp. 511-520.

Bot A. et al.: Induction of humoral and cellular immunity against influenza virus by immunization of newborn mice with plasmid bearing a hemagglutinin gene, International Immunology, vol. 9, No. 11, Dec. 31, 1997, pp. 1641-1650.

Burke RS et al., Extracellular barriers to in Vivo PEI and PEGylated PEI polyplex-mediated gene delivery to the liver, Bioconjug Chem. Mar. 2008: 19(3):693-704, 2008.

Buteau et al., 2002; Challenges in the Development of Effective Peptide Vaccines for Cancer; Mayo Clin Proc, vol. 77, pp. 339-349.

CAPLUS accession No. 190686-49-8; Brugia maleyi strain TRS Labs conle RRAMCA1537 EST; Chemical Abstracts Services; Database CAPLUS.

(56) References Cited

OTHER PUBLICATIONS

Carralot J-P. et al: Polarization of immunity included by direct injection of naked sequence-stabilized mRNA vaccines, CMLS Cellular and Molecular Life Sciences, Birkhauser Verlag, Heidelberg, DE vol. 61, No. 18, Sep. 1, 2004, pp. 2416-2424.
Deshayes S et al., Cell-penetrating peptides: tools for intracellular delivery of therpeutics, Cell Mol Life Sci. Aug. 2005 62(15):1839-49. Review.
Diebold et al., 2004: Innate Antiviral Responses by Means of TLR7-Mediated Recognition of Single-Stranded RNA: Science; vol. 303: pp. 1529-1531.
EBI Database accession No. BP836659; *Arabidopsis thaliana* clone RAFL22-17-C17 EST; Dadabase EMBL 2005.
EBI Database accession No. CZ193289; PST12107-MICB1 Mus musculus genomic clone PST12107-NR; Database EMBL 2005.
EBI Database accession No. DN868844; NEIBank analysis of Dog lens; Wistow, G., Database EMBL 2005.
EMBL accession No. AA430815; Brugia malayi strain TRS Labs clone RRAMCA1537 EST; Database EMBL 1997.
Fajac I et al., Histidylated polysine as a synthetic vector for gene transfer into immortalized cystic fibrosis airway surface and airway gland serous cells, J Gene Med. Sep.-Oct. 2000; 2(5):368-78.
Feroze-Merzoug et al., 2001: Molecular profiling in prostate cancer, Cancer and Metaastasis reviews, vol. 20, pp. 165-171.
Fire et al., 1998; Potent and specific genetic interference by double-stranded RNA in Caenorhabditis elegans; Nature; vol. 391; pp. 806-811.
Foerg C et al., On the biomedical promise of cell penetrating peptides: limits versus prospects, J Pharm Sci. Jan. 2008; 97(1):144-62. Review.
Fotin-Mleczek, Mariola et al: Messenger RNA-based vaccines with dual activity induce balanced TLR-7 dependant adaptive immune responses and provide antitumor activity, Journal of Immunotherapy, Raven Press, NY, US, vol. 34, No. 1, Jan. 1, 2011, pp. 1-15.
Fujita T et al., Calcium enhanced delivery of tetraarginine-PEG-lipid-coated DNA/protamine complexes, International Journal of Pharmaceutics, Elsivier BV, NL, vol. 368, No. 1-2, Feb. 23, 2009, pp. 186-192.
Galbraith et al., 1994; Complement Activation and Hemodynamic Changes Following Intravenous Administration of Phosphorothicate Oligonucleotides in the Monkey; Antisense Research and Development; vol. 4, pp. 201-206.
Gao et al., 2007; Nonviral gene delivery: what we know and what is next; The AAPS Journal, vol. 9, No. 1, pp. E92-104, XP02609380.
Garinot et al., PEGylated PLGA-based nanoparticles targeting M cells for oral vaccination, Journal of controlled release, Elssevier, Amsterdam, NL, vol. 120, No. 3, Jul. 17, 2007, pp. 195-204.
GenBank Accession No. JK489756.1, GI: , 346421249, publically available Sep. 2011.
Georgieva et al., Comparative study on the changes in the photo-synthesis activity of the homoiochlorophyllous desiccation-tolerant Haveriea rhodopensis and desiccation-sensitive spinach leaves during desiccation and rehydration, Photosynthesis Research, vol. 85, pp. 191-203, Aug. 2005.
Giel-Peitraszuk Malgorzata et al.; Database Biosis, DB Acc. No. Prev199800116011 1997.
Gravekamp et al.: Cancer vaccines in old age, Experimental Gerontology, Elsevier Science, Oxford, GB, vol. 42, No. 5, Apr. 14, 2007, pp. 441-450.
Grunebach F et al., New developments in Dendritic cell-based vaccinations: RNA translated into clinics, Cancer Immunol Immunother. Jun. 2005; 54(6):517-25. Epub Jan. 27, 2005 Review.
Gryaznov, 1999; Oligonucleotide N3'→P5'phosphoramidates as potential therapeutic agents; Biochimica et Biophysica Acta; vol. 1489, pp. 131-140.
Hamidi M et al., Pharmacokinetic consequences of pegylation, Drug Deliv. Nov.-Dec. 2006; 13(6):399-409.
Hardy et al., 2009; Synergistic effects on gene delivery—co-formulation of small dusulfide-linked dendritic polycations with Lipofectamine 2000; Organic & Biomolecular Chemistry, vol. 7, No. 4, pp. 789-793, XP002609381.
Hausch et al.; 1998: A novel carboxy-functionalized photocleavable dinucleotide analog for the selection for RNA catalysts; Tetrahedron Letters, vol. 39, No. 34, pp. 6157-6158.
Heidenreich et al., 1993; Chemically modified RNA: approaches and applications; FASEB Journal; vol. 7, No. 1, pp. 90-96.
Heil et al., 2004; Species-specific recognition of single-stranded RNA via Toll-like receptor 7 and 8; Science, vol. 303, pp. 1526-1529.
Heiser A et al., Autologous dendritic cells transfected with prostate-specific antigen RNA stimulate CTL responses against metastic prostate tumors, J Clin Invest. Feb. 2002; 109(3):409-17.
Herbert et al., The Dictionary of Immunology, Academic Press, $4^{th}$ edition, 1995.
Herbert et al.; 2005; Lipid modification of GRN163, an N3'→P5'thio-phosphoramidate oligonucleotide, enhances the potency of telomerase inhibition; Oncogene; vol. 24; pp. 5262-5268.
Heymann, 1990; The immune complex: possible ways of regulating the antibody response; Immunology Today; vol. 11, No. 9, pp. 310-313.
Hoerr et al., 2000; In vivo apllication of RNA leads to induction of specific cytotoxic T lymphocytes and antibodies; Eur. J. Immunol., vol. 30, No. 1, pp. 1-7.
Hubert RS et al., STEAP: a prostate-specific cell-surface antigen highly expressed in human prostate tumors, Proc Natl Acad Sci USA Dec. 7, 1999; 96(25): 14523-5.
Janssen et al., 2003; Role of Toll-Like Receptors in Pathogen Recognition; Clinical Microbiology Reviews, vol. 16, No. 4; pp. 637-646.
Kim et al., 2009; VeGF siRNA delivery system using arginine-grafted bioreducible poly(disulfide-amine); Molecular Pharmaceutics, vol. 6, No. 3, pp. 718-726, XP002609382.
Kovarik J. et al: Optimization of vaccine responses in early life: the role of delivery systems and immunomodulators, Immunology and Cell Biology, Jun. 1998 LNKD-PUBMED: 96822966, vol. 76, No. 3, Jun. 1998, pp. 222-236.
Kwiatkowski et al., 1984; The 9-(4-Octadecyloxyphenylxanthen)-9-yl-Group. A new Acid-labile Hydroxyl Protective Group and $1^{st}$ Application in the Preparative Reserve-phase Chromatographic Seperation of Oligoribonucleotides; Acta Chemica Scandinavic; B36(8); pp. 657-671.
Kwok KY et al., Formulation of highly soluble poly(ethylene glycol)-peptide DNA condensates, J Pharm Sci. Oct. 1999; 88(10):996-1003.
Kyte JA et al., Immuno-gene therapy of cancer with tumour-mRNA transfected dendritic cells, Cancer Immunol Immunother, Nov. 2006; 55(11);1432-42, Epub Apr. 13, 2006. Review.
Lo et al., 2008; An endosomolytic Tat peptide produced by incorporation of histidine and cysteine residues as a nonviral vector for DNA transfection; Biomaterials, vol. 29, No. 15, pp. 2408-2414, XP022525913.
Marrari A et al., Vaccination therapy in prostate cancer, Cancer Immunol Immunother. 207 Apr.;56(4):429-45. Epub Oct. 10, 2006.
Martin ME et al., Peptide-guided gene delivery, AAPS J Feb. 9, 2007;9(1):E18-29. Review.
Mateo et al., 1999; An HLA-A2 Polyepitope Vaccine for melanoma Immunotherapy; J Immunol, vo. 163, pp. 4056-4063.
Matray et al., 1999; Synthesis and properties of RNA analogs—oligoribonucleotides N3'→P5'phosphoramidates; Nucleic Acids Research; vol. 27, No. 20. pp. 3976-3985.
McKenzie et al., 2000; A potent new class of reductively activated peptide gene delivery agents; Journal of Biological Chemistry, vol. 275, No. 14, pp. 9970-9977, XP002238140.
McKenzie et al., 2000; Low molecular weight disulfide cross-linking peptides as nonviral gene delivery carriers; Bioconjugate Chemistry, vol. 11, No. 6, pp. 901-909, XP002609379.
Milich et al., 1997; The Hepatitis B Virus Core and e Antigens Elicit Different Th Cell Subsets: Antigen Structure Can Affect TH Cell Phenotype; Journal of Virology, vol. 71, No. 3, pp. 2192-2201.

(56) References Cited

OTHER PUBLICATIONS

Minks et al., 1979; Structural requirements of Double-stranded RNA for the Activation of 2', 5'-Oligo(A) Polymerase and Protein Kinase of Interferon-treated HeLa Cells; The Journal of Biological Chemistry; vol. 254, No. 20; pp. 10180-10183.
Miyata et al., 2004; BlockCatiomer Polyplexes with Regulated Densities of Charge and Disulfide Cross-Linking Directed to Enhance Gene Expression; Journal of American Chemical Society, vol. 126, No. 8, pp. 2355-2361, XP002993261.
Nakamura Y et al., Octaarginine-modified multifunctional envelope-type nano device for siRNA, J Contrl Release. Jun. 22, 2007; 119(3):360-7. Epub Mar. 23, 2007.
Neu M et al., Recent advances in rational gene transfer vector design based on poly(ethylene eimine) and its derivatives, J Gene Med. Aug. 2005;7(8):992-1009.
Nicholson et al., 1988; Accurate in vitro cleavage by Rnase III of phosphothioate-substituted RNA processing signals in bacteriophage T7 early nRNA; Nucleic Acids Res., vol. 16, No. 4, pp. 1577-1591.
Oupicky D et al., Importance of lateral and steric stabilization of polyelectrolyte gene delivery vectors for extended systemic circulation, Mol Ther. Apr. 2002;5(4):463-72.
Oupicky D et al., Laterally stabilized complexes of DNA with linear reducible polycations: strategy triggered intracellular activation of DNA delivery vectors, J Am Chem Soc. Jan. 9, 2002;124(1):8-9.
Parker AL et al., Enhanced gene transfer activity of peptide-targeted gene-delivery vectors, J Drug Target. Jan. 2005;13(1):39-51.
Parkinson et al., 2004, A transcriptomic analysis of the phyium Nematoda; Nature Genetics, vol. 36, No. 12, pp. 1259-1267.
Pichon C et al., Poly[Lys-(AEDTP)]: a cationic polymer that allows dissociation of pDNA/cationic polymer complexes in a reductive medium and enhances polyfection, Bioconjug Chem. Jan.-Feb. 2002;13(1):76-82.
Pomroy NC et al., Solubilization of hydrophobic peptides by reversible cysteine PEGylation, Biochem Biophys Res Commun. Apr. 17, 1998;245(2):618-21.
Radu D.L. et al: Plasmid expressing the influenza HA gene protects old mice from lethal challenge with influenza viraus, Viral Immunology 1999, LNKD-PUBMED: 10532650, vol. 12, No. 3, 1999, pp. 217-226.
Ramazeilles et al., 1994; Antisense phosphorothioate oligonucleotides: Selective killing of the intracellular parasite Leishmania amazonansis; Proc. Natl. Acad. Sci., vol. 91, pp. 7859-7863.
Read et al., 2003; Vectors based on reducible polycations facilitate intracellular release of nucleic acids; Journal of Gene Medicine, vol. 5, No. 3, pp. 232-245, XP002461542.
Read et al., 2005; A versatile reducible polycationic-based system for efficient delivery of a broad range of nucleic acids; Nucleic acids research, vol. 33, No. 9, pp. 1-16; XP002447464.
Read ML et al., RNA-based therapeutic strategies for cancer, Expert Opinion on Therapeutic Patents, 2003, vol. 13, No. 5, pp. 627-638.
Riedl et al., 2002; Priming Th1 Immunity to Voral Core Particles is Facilitated by Trace Amounts of RNA Bound to 1$^{st}$ Arginine-Rich Domain; the Journal of Immunology, vol. 168, pp. 4951-4959.
Romagne F., Current and future drugs targeting one class of innate immunity receptors: the Toll-like receptors, Drug Discov Today. Jan. 2007; 12(1-2):80-7. Epub Nov. 23, 2006.
Saenz-Badillos, 2001; RNA as a tumor vaccine: a review of the literature; Exp. Dermatol.; vol. 10, No. 3, pp. 143-154.
Sakae M et al., Highly efficient in vivo gene transfection by plasmid/PEI complexes coated by anionic PEG derivatives beraring carboxyl groups and RGD peptide, Biomedicine and Pharmacotherapy, Elsevier, FR, vol. 62, No. 7, Sep. 1, 2008, pp. 448-453.
Scheel et al., 2004; Immunostimulating capacities of stabilized RNA molecules; Eur. J. Immunol., vol. 24, pp. 537-547.
Scheel et al., 2005; Toll-like receptor-dependentt activation of several human blood cell types by protamine-condensed mRNA, Eur J Immunol, vol. 35, pp. 1557-1566.
Scheel et al., Therapeutic anti-tumor immunity triggered by injections of immunostimulating single-stranded RNA; Eur J Immunol, vol. 36, No. 10, pp. 2807-2616, 2004.
Schirrmacher et al., 2000; Intra-pinna anti-tumor vaccination with self-replicating infectious RNA or with DANN encoding a model tumor antigen and a cytokine; Gene Therapy, vol. 7, No. 13, pp. 1137-1147.
Shea et al., 1990, Synthsis hybridization properties and antiviral activity of lipid-oligodeoxynucleotide conjugates; Nucleic Acids Research: vol. 18, No. 13, pp. 3777-3783.
Sobel RE et al., Cell lines used in prostate cancer research: a compendium of old new lines—part2, J Urol. Feb. 2005;173(2):360-72. Review.
Stephens et al., Sequence analysis of the major outer membrane protein gene from Chlamydia trachomatics serovar L2, Journal of Bacteriology, vol. 168, No. 3, pp. 1277-1282, Dec. 1986.
Su Z et al., Enhanced induction of telomerase-specific CD4(+) T cells using transfected with RNA encoding a chimeric gene product, Cancer Res. Sep. 1, 2002;(17):5041-8.
Takae et al., 2008: PEG-detachable polyplex micelles based on disulfide-linked block catiomers as bioresponsive nonviral gene vectors; Journal of the American Chemical Society, vol. 130, No. 18, pp. 6011-6009, XP 002609383.
Teplova et al., 1999; Crystal structure and improved antisense properties of 2'-O-(2-methoxythyl)-RNA; Nature Structural Biology; vol. 6, No. 6, pp. 535-539.
Tokunaga et al., 2004; Effect of oligopeptides on gene expression: comparison of DNA/peptide and DNA/peptide/liposome complexes; International Journal of Pharmaceutics, vol. 269, No. 1, pp. 71-80, XP002609384.
Tonges L et al., Stearylated octaarginine and artificial virus-like particle for transfection of siRNA into primary rat neurons, RNA Jul. 2006;12(7):1431-8. Epub May 12, 2006.
Trinchieri et al., 2007; Cooperation of Toll-like receptor signals in innate immune defense, Nature Reviews Immunolgy, vol. 7, Mar. 2007; pp. 179-190.
Tse K et al., Update on toll-like receptor directed therapies for human disease. Ann Rheum Dis. Nov. 2007; 66 Suppl 3:iii77-80. Review.
Unnamalai N et al., Cationic oligopeptide-mediated delivery of dsRNA for the post-transcriptional gene silencing in plant cells, FEBS Lett. May 21, 2004;566(1-3):307-10.
Vives E et al., A truncated HIV-1 Tat protein basic domain rapidly translocates through the plasma membrane and accumulates in the cell nucleus, J Biol Chem. Jun. 20, 1997;272(25): 16010-7.
Wang YH et al., An intracellular delivery system for siRNA by an arginine-rich peptide, J Biochem Biophys Methods. Jun. 10, 2007;70(4):579-86. Epub Jan. 30, 2007.
Yang D et al., Murine six-membrane epithelial antigen of the prostate stem cell antigen, and prostate-specific cell-surface anitgens highly expressed in prostate cancer of transgenic adenocarcinoma mouse prostate mice, Cancer Res. Aug. 1, 2001; 61(15):5857-60.
Zhou et al., 1999; RNA Melanoma Vaccine: Induction of Antitumor Immunity by Human Glycoprotein 100 mRNA Immunization; Human Gene Therapy; vol. 10; pp. 2719-2714.
Zimmerman S et al., Immunostimulatory DNA as adjuvant: efficacy of phosphodiester CpG oligonucleotides is enhanced by 3'sequence modifications, Vaccine. Feb. 14, 2003; 21(9-10):990-5. (only abstract).
English Abstract of DE 10346721, which corresponds to EP 15545291.
Berzofsky J.A., et al., "Progress on new vaccine strategies against chronic viral infections", J Clin Invest. Aug. 2004;114(4):450-462.
Huang Z., et al., "Recent development of therapeutics for chronic HCV infection", Antiviral Res. Sep. 2006;71(2-3):351-362. Epub Jun. 23, 2006.
Huget R., et al., "Adjuvant and suppressor activity of the polycation protamine hydrochloride in the primary immune response of mice", Z Immunitatsforsch Immunobiol., Nov. 1976;152(3):190-199. (Abstract only).

(56) References Cited

OTHER PUBLICATIONS

Koziel M. J., et al., "Hepatitis C virus (HCV)-specific cytotoxic T lymphocytes recognize epitopes in the core and envelope proteins of HCV", J Virol., Dec. 1993;67(12):7522-7532.
Racanelli V., et al., "Presentation of HCV antigens to naïve CD8+T cells; why the where, when, what and how are important for virus control and infection outcome", Clin Immunol., Jul. 2007;124(1):5-12. Epub May 31, 2007.
Rollier C., et al., "Control of heterologous hepatitis C virus infection in chimpanzees is associated with the quality of vaccine-induced peripheral T-helper immune response", J. Virol. Jan. 2004;78(1):187-196.
Shiffman M. L., et al., "Protein dissociation from DNA in model systems and chromatin", Nucleic Acids Res., Sep. 1978;5(9):3409-3426.
Shirai M., et al., "An epitope in hepatitis C virus core region recognized by cytotoxic T cells in mice and humans", J Virol. May 1994;68(5):3334-3342.
Tan S. L., et al., "Strategies for hepatitis C therapeutic intervention: now and next", Curr Opin Pharmacol. Oct. 2004;4(5):465-470.
Zohra F.T., et al., "Effective delivery with enhanced translational activity synergistically accelerates mRNA-based transfection", Biochem Biophys Res Commun. Jun. 22, 2007;358(1):373-378. Epub May 1, 2007.
"Cell-penetrating peptide," Wikipedia, located at http://en.wikipedia.org/wiki/cell-penetrating_peptide, downloaded on Dec. 11, 2012.
"DOC/Alum Complex," Violin: Vaccine investigation and online information network, located at http://www.violinet.org/vaxjo/vaxjo_detail.php?c_vaxjo_id=49, downloaded on Aug. 28, 2012.
"QS21," Wikipedia, located at http://en.wikipedia.org/wiki/QS21, downloaded on Dec. 11, 2012.
"Ribi vaccine adjuvant," Violin: Vaccine investigation and online information network, located at http://www.violinet.org/vaxjo/vaxjo_detail.php?c_vaxjo_id=21, downloaded on Dec. 17, 2012.
"SPT (Antigen Formulation)," Violin: Vaccine investigation and online information network, located at http://www.violinet.org/vaxjo/vaxjo_detail.php?c_vaxjo_id=72, downloaded on Aug. 21, 2012.
"Virus-like particle," Wikipedia, located at http://en.wikipedia.org/wiki/virus-like_particle, downloaded on Sep. 3, 2012.
Ahern, "Biochemical, reagents kits offer scientists good return on investment," *The Scientist*, 9(15):20, 1995.
Brito et al., "Non-viral eNOS gene delivery and transfection with stents for the treatment of restenosis," *Biomed Eng Online*, 9:56, 2010.
Casciato et al., Manual of Clinical Oncology, $6^{th}$ Edition, 2009.
Challita-Eid et al., "Monoclonal antibodies to six-transmembrane epithelial antigen of the prostate-1 inhibit intracellular communication in vitro and growth of human tumor xenografts in vivo," *Cancer Research*, 67(12):5798-5805, 2007.
Cooper et al., "CPG 7909 adjuvant improves hepatitis B virus vaccine seroprotection in antiretroviral-treated HIV-infected adults," *AIDS*, 19:1473-1479, 2005.
Danhier et al., "PLGA-based nanoparticles: an overview of biomedical applications," *J. Control Release*, 161(2):505-522,2012.
Dmitriev, "Bactenecin 7 peptide fragment as a tool for intracellular delivery of a phosphorescent oxygen sensor," *FEBS Journal*, 277:4651-4661, 2010.
Fox, "Squalene emulsions for parenteral vaccine and drug delivery," *Molecules*, 14:3286-3312, 2009.
Kilk, "Cell-penetrating peptides and bioactive cargoes. Strategies and mechanisms," *Department of Neurochemistry and Neurotoxicology Arrhenius Laboratories of Natural Sciences, Stockholm University*, 2004.
Mattner et al., "Vaccination with poly-L-arginine as immunostimulant for peptide vaccines: induction of potent and long-lasting T-cell responses against cancer antigens," *Cancer Research*, 62:1477-1480, 2002.
Mitchell et al., "mRNA turnover," *Current Opinion in Cell Biology*, 13(3):320-325, 2001.
Pesole et al., "UTRdb and UTRsite: specialized databases of sequences and functional elements of 5' and 3' untranslated regions of eukaryotic mRNAs," *Nucleic Acids Research*, 30(1):335-340, 2002.
Rittner et al., "New basic membrane-destabilizing peptides for plasmid-based gene delivery in vitro and in vivo," *Molecular Therapy*, 5(2):104-114, 2002.
Ross et al., "Control of messenger RNA stability in higher eukaryotes," *Trends Genet.*, 12(5):171-175, 1996.
Scheel et al., "mRNA as immunostimulatory molecule," Abstract 10, 2003.
Sun et al., "Advances in saponin-based adjuvants," *Vaccine*, 27:1787-1796, 2009.
Tourriere et al., "mRNA degradation machines in eukaryotic cells," *Biochimie*, 84(8):821-837, 2002.
Wilusz et al., "Bringing the role of mRNA decay in the control of gene expression into focus," *Trends Genetc.*, 20(10):491-497, 2004.
Wyman et al., "Design, synthesis, and characterization of a cationic peptide that binds to nucleic acids and permeabilizes bilayers," *Biochemistry*, 36:3008-3017, 1997.
Yoshitomi et al., "Design of core-shell-type nanoparticles carrying stable radicals in the core," *Biomacromolecules*, 10(3):596-601, 2009.
Zhang et al., "Delivery of telomerase reverse transcriptase small interfering RNA in complex with positively charged single-walled carbon nanotubes suppresses tumor growth," *Clinical Cancer Research*, 12(16):4933-4939, 2006.
Fisher and Wilson, "The transmembrane domain of diphtheria toxin improves molecular conjugate gene transfer", *Biochem J.*, 321:49-58, 1997.
Ohta et al., "Ethidium bromide and SYBR Green I enhance the genotoxicity of UV-irradiation and chemical mutagens in *E. coli*," *Mutat Res.*, 492(1-2):91-97, 2001. (Abstract only).
Kallen et al., "A novel, disruptive vaccination technology," *Human Vaccines & Immunotherapeutics*, 9:10, 2013.
Kübler et al.,"Self-adjuvanted mRNA vaccination in advanced prostate cancer patients: a first-in-man phase I/IIa study," *Journal for ImmunoTherapy of Cancer*, 3:26, 2015.
Petsch et al., "Protective efficacy of in vitro synthesized, specific mRNA vaccines against influenza A virus infection," *Nature Biotechnology*, 30(12):1210-1216, 2012.

* cited by examiner

1 GGGAGAAAGC UUACC*AUGGG CAGCAUCGGG GCCGCGUCGA UGGAGUUCUG*
51 *CUUCGACGUG UUCAAGGAGC UGAAGGUCCA CCACGCCAAC GAGAACAUCU*
101 *UCUACUGCCC GAUCGCCAUC AUGAGCGCGC UCGCCAUGGU GUACCUGGGC*
151 *GCCAAGGACA GCACCCGGAC GCAGAUCAAC AAGGUGGUCC GCUUCGACAA*
201 *GCUGCCCGGC UUCGGGGACU CGAUCGAGGC GCAGUGCGGC ACCAGCGUGA*
251 *ACGUGCACAG CUCGCUCCGG GACAUCCUGA ACCAGAUCAC CAAGCCGAAC*
301 *GACGUCUACA GCUUCAGCCU GGCCUCGCGG CUCUACGCCG AGGAGCGCUA*
351 *CCCGAUCCUG CCCGAGUACC UGCAGUGCGU GAAGGAGCUC UACCGGGGCG*
401 *GGCUGGAGCC GAUCAACUUC CAGACGGCGG CCGACCAGGC CCGGGAGCUG*
451 *AUCAACAGCU GGGUGGAGAG CCAGACCAAC GGCAUCAUCC GCAACGUCCU*
501 *CCAGCCGUCG AGCGUGGACA GCCAGACCGC GAUGGUGCUG GUCAACGCCA*
551 *UCGUGUUCAA GGGCCUGUGG GAGAAGACGU UCAAGGACGA GGACACCCAG*
601 *GCCAUGCCCU UCCGGGUGAC CGAGCAGGAG UCGAAGCCGG UCCAGAUGAU*
651 *GUACCAGAUC GGGCUCUUCC GGGUGGCGAG CAUGGCCAGC GAGAAGAUGA*
701 *AGAUCCUGGA GCUGCCGUUC GCCUCGGGCA CGAUGAGCAU GCUCGUGCUG*
751 *CUGCCCGACG AGGUCAGCGG CCUCGAGCAG CUGGAGUCGA UCAUCAACUU*
801 *CGAGAAGCUG ACCGAGUGGA CCAGCAGCAA CGUGAUGGAG GAGCGCAAGA*
851 *UCAAGGUGUA CCUCCCGCGG AUGAAGAUGG AGGAGAAGUA CAACCUGACG*
901 *UCGGUCCUGA UGGCGAUGGG GAUCACCGAC GUGUUCAGCA GCUCGGCCAA*
951 *CCUCAGCGGC AUCAGCUCGG CCGAGAGCCU GAAGAUCAGC CAGGCGGUGC*
1001 *ACGCCGCCCA CGCGGAGAUC AACGAGGCCG GCCGGGAGGU CGUGGGGUCG*
1051 *GCCGAGGCGG GCGUGGACGC CGCCAGCGUC AGCGAGGAGU UCCGCGCGGA*
1101 *CCACCCGUUC CUGUUCUGCA UCAAGCACAU CGCCACCAAC GCCGUGCUCU*
1151 *UCUUCGGCCG GUGCGUGUCG CCCUGA*CCAC UAGUUAUAAG ACUGACUAGC
1201 CCGAUGGGCC UCCCAACGGG CCCUCCUCCC CUCCUUGCAC CGAGAUUAAU
1251 AAAAAAAAAA AAAAAAAAAA AAAAAAAAAA AAAAAAAAAA AAAAAAAAAA
1301 AAAAAAAAAA AAAAUAUUCC CCCCCCCCCC CCCCCCCCCC CCCCCCCCUC
1351 UAGACAAUUG GAAUU

Figure 7

GGGAGACAAGCUUGGCAUUCCGGUACUGUUGGUAAAGCCACC*AUGGAAGACGCCAAAAACAU*
*AAAGAAAGGCCCGGCGCCAUUCUAUCCGCUGGAAGAUGGAACCGCUGGAGAGCAACUGCAUA*
*AGGCUAUGAAGAGAUACGCCCUGGUUCCUGGAACAAUUGCUUUUACAGAUGCACAUAUCGAG*
*GUGGACAUCACUUACGCUGAGUACUUCGAAAUGUCCGUUCGGUUGGCAGAAGCUAUGAAACG*
*AUAUGGGCUGAAUACAAAUCACAGAAUCGUCGUAUGCAGUGAAAACUCUCUUCAAUUCUUUA*
*UGCCGGUGUUGGGCGCGUUAUUUAUCGGAGUUGCAGUUGCGCCCGCGAACGACAUUUAUAAU*
*GAACGUGAAUUGCUCAACAGUAUGGGCAUUUCGCAGCCUACCGUGGUGUUCGUUUCCAAAAA*
*GGGGUUGCAAAAAAUUUUGAACGUGCAAAAAAAGCUCCCAAUCAUCCAAAAAAUUAUUAUCA*
*UGGAUUCUAAAACGGAUUACCAGGGAUUUCAGUCGAUGUACACGUUCGUCACAUCUCAUCUA*
*CCUCCCGGUUUUAAUGAAUACGAUUUUGUGCCAGAGUCCUUCGAUAGGGACAAGACAAUUGC*
*ACUGAUCAUGAACUCCUCUGGAUCUACUGGUCUGCCUAAAGGUGUCGCUCUGCCUCAUAGAA*
*CUGCCUGCGUGAGAUUCUCGCAUGCCAGAGAUCCUAUUUUUGGCAAUCAAAUCAUUCCGGAU*
*ACUGCGAUUUUAAGUGUUGUUCCAUUCCAUCACGGUUUUGGAAUGUUUACUACACUCGGAUA*
*UUUGAUAUGUGGAUUUCGAGUCGUCUUAAUGUAUAGAUUUGAAGAAGAGCUGUUUCUGAGGA*
*GCCUUCAGGAUUACAAGAUUCAAAGUGCGCUGCUGGUGCCAACCCUAUUCUCCUUCUUCGCC*
*AAAAGCACUCUGAUUGACAAAUACGAUUUAUCUAAUUUACACGAAAUUGCUUCUGGUGGCGC*
*UCCCCUCUCUAAGGAAGUCGGGGAAGCGGUUGCCAAGAGGUUCCAUCUGCCAGGUAUCAGGC*
*AAGGAUAUGGGCUCACUGAGACUACAUCAGCUAUUCUGAUUACACCCGAGGGGGAUGAUAAA*
*CCGGGCGCGGUCGGUAAAGUUGUUCCAUUUUUUGAAGCGAAGGUUGUGGAUCUGGAUACCGG*
*GAAAACGCUGGGCGUUAAUCAAAGAGGCGAACUGUGUGUGAGAGGUCCUAUGAUUAUGUCCG*
*GUUAUGUAAACAAUCCGGAAGCGACCAACGCCUUGAUUGACAAGGAUGGAUGGCUACAUUCU*
*GGAGACAUAGCUUACUGGGACGAAGACGAACACUUCUUCAUCGUUGACCGCCUGAAGUCUCU*
*GAUUAAGUACAAAGGCUAUCAGGUGGCUCCCGCUGAAUUGGAAUCCAUCUUGCUCCAACACC*
*CCAACAUCUUCGACGCAGGUGUCGCAGGUCUUCCCGACGAUGACGCCGGUGAACUUCCCGCC*
*GCCGUUGUUGUUUUGGAGCACGGAAAGACGAUGACGGAAAAAGAGAUCGUGGAUUACGUCGC*
*CAGUCAAGUAACAACCGCGAAAAAGUUGCGCGGAGGAGUUGUGUUUGUGGACGAAGUACCGA*
*AAGGUCUUACCGGAAAACUCGACGCAAGAAAAAUCAGAGAGAUCCUCAUAAAGGCCAAGAAG*
*GGCGGAAAGAUCGCCGUGUAA*UUCUAGU<u>AAAAAAAAAAAAAAAAAAAAAAAAAAAAAAAAAA</u>
<u>AAAAAAAAAAAAAAAAAAAAAAAAAAAAAAAAAAAA</u>CUGCAGGUCGACUCUAGAGGAUCCCC
GGGUACCGAGCUCGAAUU

Figure 8 anti-HA antibodies (IgG2a)

GGGAGAAAGCUUACCAUGAAGGCCAACCUGCUCGUGCUGCUGUGCGC
CCUCGCGGCCGCCGACGCCGACACCAUCUGCAUCGGCUACCACGCCA
ACAACAGCACCGACACGGUCGACACCGUGCUGGAGAAGAACGUGACC
GUCACCCACUCCGUGAACCUGCUCGAGGACAGCCACAACGGGAAGCU
GUGCCGGCUGAAGGGCAUCGCGCCCCUCCAGCUGGGGAAGUGCAACA
UCGCCGGCUGGCUGCUCGGGAACCCGGAGUGCGACCCCCUGCUGCCC
GUGCGCUCCUGGAGCUACAUCGUCGAGACGCCCAACUCCGAGAACGG
CAUCUGCUACCCGGGCGACUUCAUCGACUACGAGGAGCUCCGGGAGC
AGCUGAGCUCCGUGAGCUCCUUCGAGCGCUUCGAGAUCUUCCCCAAG
GAGAGCUCCUGGCCCAACCACAACACCAACGGGGUGACCGCCGCCUG
CAGCCACGAGGGCAAGUCCAGCUUCUACCGGAACCUGCUCUGGCUGA
CCGAGAAGGAGGGGUCCUACCCCAAGCUGAAGAACAGCUACGUCAAC
AAGAAGGGCAAGGAGGUGCUCGUGCUGUGGGGGAUCCACCACCCGCC
CAACUCCAAGGAGCAGCAGAACCUGUACCAGAACGAGAACGCGUACG
UCAGCGUGGUGACGUCCAACUACAACCGCCGGUUCACCCCCGAGAUC
GCCGAGCGCCCCAAGGUCCGGGACCAGGCCGGCCGCAUGAACUACUA
CUGGACCCUCCUGAAGCCGGGCGACACCAUCAUCUUCGAGGCCAACG
GGAACCUGAUCGCCCCGAUGUACGCGUUCGCCCUCAGCCGGGGCUUC
GGGAGCGGCAUCAUCACGUCCAACGCCAGCAUGCACGAGUGCAACAC
CAAGUGCCAGACCCCCCUGGGCGCCAUCAACUCCAGCCUGCCCUACC
AGAACAUCCACCCGGUGACCAUCGGGGAGUGCCCCAAGUACGUGCGC
UCCGCCAAGCUCCGGAUGGUCACGGGCCUGCGCAACAACCCCAGCAU
CCAGUCCCGGGGGCUGUUCGGCGCGAUCGCCGGGUUCAUCGAGGGCG
GCUGGACCGGGAUGAUCGACGGCUGGUACGGGUACCACCACCAGAAC
GAGCAGGGCAGCGGGUACGCCGCCGACCAGAAGUCCACCCAGAACGC
CAUCAACGGCAUCACCAACAAGGUGAACACGGUGAUCGAGAAGAUGA
ACAUCCAGUUCACCGCGGUCGGCAAGGAGUUCAACAAGCUCGAGAAG
CGCAUGGAGAACCUGAACAAGAAGGUGGACGACGGUUCCUGGACAU
CUGGACCUACAACGCCGAGCUCCUGGUGCUGCUCGAGAACGAGCGGA
CCCUGGACUUCCACGACAGCAACGUCAAGAACCUGUACGAGAAGGUG
AAGUCCCAGCUCAAGAACAACGCCAAGGAGAUCGGCAACGGGUGCUU
CGAGUUCUACCACAAGUGCGACAACGAGUGCAUGGAGAGCGUCCGCA
ACGGCACGUACGACUACCCCAAGUACUCCGAGGAGAGCAAGCUGAAC
CGGGAGAAGGUGGACGGGGUGAAGCUGGAGUCCAUGGGCAUCUACCA
GAUCCUCGCCAUCUACAGCACCGUCGCCUCCAGCCUGGUGCUGCUGG
UGUCCCUCGGCGCGAUCAGCUUCUGGAUGUGCAGCAACGGGUCCCUG
CAGUGCCGCAUCUGCAUCUGACCACUAGUUAUAAGACUGACUAGCCC
GAUGGGCCUCCCAACGGGCCCUCCUCCCCUCCUUGCACCGAGAUUAA
UAAAAAAAAAAAAAAAAAAAAAAAAAAAAAAAAAAAAAAAAAAAAAA
AAAAAAAAAAAAAAAAAAUAUUCCCCCCCCCCCCCCCCCCCCCCCCC
CCCCCUCUAGACAAUUGGAAUU

Figure 14

COMPOSITION COMPRISING A COMPLEXED (M)RNA AND A NAKED MRNA FOR PROVIDING OR ENHANCING AN IMMUNOSTIMULATORY RESPONSE IN A MAMMAL AND USES THEREOF

SEQUENCE LISTING

The instant application contains a Sequence Listing which has been submitted in ASCII format via EFS-Web and is hereby incorporated by reference in its entirety. Said ASCII copy, created on Jun. 7, 2011, is named 067802CU.txt and is 51,624 bytes in size.

The present invention relates to an immunostimulatory composition comprising a) an adjuvant component, comprising or consisting of at least one (m)RNA, complexed with a cationic or polycationic compound, and b) at least one free mRNA, encoding at least one therapeutically active protein, antigen, allergen and/or antibody, wherein the immunostimulatory composition is capable to elicit or enhance an innate and optionally an adaptive immune response in a mammal. The inventive immunostimulatory composition may be a pharmaceutical composition or a vaccine. The invention furthermore relates to a method of preparation of the inventive immunostimulatory composition. The invention also relates to the use of the inventive immunostimulatory composition or its components (for the preparation of a pharmaceutical composition or a vaccine) for the treatment of various diseases. Finally, the invention relates to kits containing the inventive immunostimulatory composition, its components and/or the pharmaceutical composition or vaccine.

Induction and/or enhancement of immune responses of the innate and/or the adaptive immune system plays an important role in the treatment and prevention of numerous diseases. For such a purpose, the immune system is typically modulated by, e.g., administration of an immunostimulatory agent or an adjuvant. However, the immune system of vertebrates such as humans is very complex and finely regulated. It consists of many types of proteins, cells, organs, and tissues, which interact in an elaborate and dynamic network. The immune system typically protects these organisms from infection with layered defenses of increasing specificity. One layer of defense comprises physical or chemical barriers and allows an a priori elimination of at least some pathogens and antigens. A further layer of defense includes the innate and the adaptive immune system.

The innate immune system as part of the immune system is the dominant system of host defense in most organisms and comprises barriers such as humoral and chemical barriers including, e.g., inflammation, the complement system and cellular barriers. The innate immune system is typically based on a small number of receptors, called pattern recognition receptors. They recognize conserved molecular patterns that distinguish foreign organisms, like viruses, bacteria, fungi and parasites from cells of their hosts. Such pathogen-associated molecular patterns include viral nucleic acids, components of bacterial and fungal walls, flagellar proteins, and more.

The first family of pattern recognition receptors studied in detail was the Toll-like receptor (TLR) family. TLRs are transmembrane proteins which recognize ligands of the extracellular milieu or of the lumen of endosomes. Following ligand-binding they transduce the signal via cytoplasmic adaptor proteins which leads to triggering of a host-defense response and entailing production of antimicrobial peptides, proinflammatory chemokines and cytokines, antiviral cytokines, etc. (see e.g. Meylan, E., J. Tschopp, et al. (2006). "Intracellular pattern recognition receptors in the host response." Nature 442(7098): 39-44). To date, at least 10 members of Toll-like receptors (TLRs 1-10) have been identified in human and 13 (TLRs 1-13) in mice. Those Toll-like receptors (TLRs) in human include TLR1-TLR2 (known ligand: Triacyl lipopeptide), TLR1-TLR6 (known ligand: Diacyl lipopeptide), TLR2 (known ligand: Peptidoglycan), TLR3 (known ligand: dsRNA), TLR4 (known ligand: LPS (lipopolysachharide) of Gram-negative bacteria)), TLR5 (known ligand: bacterial flagellin(s)), TLR7/8 (known ligands: imidazoquinolines, guanosine analogs and ssRNA), TLR9 (known ligands: CpG DNA of bacteria, viruses and protozoans and malaria pigment hemozoin (product of digestion of haemoglobin)) and TLR10. After recognition of microbial pathogens, these TLRs typically trigger intracellular signalling pathways that result in induction of inflammatory cytokines (e.g. TNF-alpha, IL-6, IL-1-beta and IL-12), type I interferon (IFN-beta and multiple IFN-alpha) and chemokines (Kawai, T. and S. Akira (2006). "TLR signaling." Cell Death Differ 13(5): 816-25).

As part of the more complex immune response of vertebrates, the immune system adapts over time to recognize particular pathogens or antigens more efficiently. This adaptation process creates immunological memories and allows even more effective protection during future encounters with these pathogens. This process of adaptive or acquired immunity forms the basis for vaccination strategies. In contrast to the innate immune system as described above, the adaptive immune system is antigen-specific and requires the recognition of specific "self" or "non-self" antigens during a process called antigen presentation. Furthermore, unlike cells of the innate immune system, which recognize and respond to pathogens in a generic way, the adaptive immune system confers long-lasting or protective immunity to the host and thus allows a more tailored response to specific pathogens, pathogen-infected cells or antigens. The ability to mount these tailored responses is maintained in the body by so called "memory cells". Should an antigen or a pathogen enter/infect the body more than once, these specific memory cells are used to quickly eliminate it. The adaptive immune system thus allows for a stronger immune response as well as an immunological memory, wherein different immune responses are possible in favor of specific diseases. E.g., in case of infections, each pathogen is "remembered" by a signature antigen, whereas in case of cancer diseases tumor antigens or self-antigens may be recognized and neutralized by the adaptive immune system.

The major components of the adaptive immune system in vertebrates predominantly include lymphocytes on the cellular level and antibodies on the molecular level. Lymphocytes as cellular components of the adaptive immune system include B cells and T cells which are derived from hematopoietic stem cells in the bone marrow. B cells are involved in the humoral response, whereas T cells are involved in the cell mediated immune response. Both B cells and T cells carry receptor molecules that recognize specific targets. T cells recognize a "non-self" target, such as a pathogenic target structure, only after antigens (e.g. small fragments of a pathogen) have been processed and presented in combination with a "self" receptor called a major histocompatibility complex (MHC) molecule. In contrast, the B cell antigen-specific receptor is an antibody molecule on the B cell surface, and recognizes pathogens as such when antibodies on its surface bind to a specific foreign antigen. This antigen/antibody complex is taken up by the B cell and processed by proteolysis into peptides. The B cell then displays these antigenic peptides on its surface MHC class II molecules. This combination of MHC and antigen attracts a matching helper T cell, which releases lymphokines and activates the B cell. As the activated B cell then begins to divide, its offspring secretes millions of copies of the antibody that recognizes this antigen. These antibodies circulate in blood plasma and lymph, bind to pathogens or tumor cells expressing the antigen and mark them for destruction by complement activation or for uptake and destruction by phagocytes. As a cellular component of the adaptive immune system cytotoxic T cells ($CD8^+$) may also form a CTL-response. Cytotoxic T cells ($CD8^+$) can recognize peptides from endogenous pathogens and self-antigens bound by MHC type 1 molecules. $CD8^+$-T cells carry out their killing function by releasing cytotoxic proteins in the cell.

Both basic mechanisms of the immune system, i.e. the innate immune system as well as the adaptive immune system, may thus form targets for curative treatments and prevention of numerous diseases. Appropriate methods, which are presently known in the art, either utilize adjuvants to elicit an innate immune response or utilize antigens, pathogens or immunogens in order to evoke an adaptive immune response, or, in some rare cases, both.

Particularly, an adaptive immune response may be elicited by administering the cells or the host organism a specific foreign antigen as described above either in the form of the peptide or protein antigens or the antigen may be encoded by a nucleic acid, e.g. a cDNA or a messenger RNA. In order to elicit an efficient adaptive immune response, an additional unspecific stimulation of the innate immune system is advantageous, e.g. when providing an unspecific stimulus parallel to the antigen specific signal. The parallel unspecific stimulus turns the immune system into an activated state, which improves an adaptive immune response. Compounds capable of providing such an unspecific immune response are typically termed “adjuvants”. A number of compounds and compositions have been proposed as adjuvants in the prior art, for example Freund’s adjuvant, metal oxides, e.g. alum (aluminium hydroxide), inorganic chelates or salts thereof, various paraffin-like oils, synthetic resins, alginates, mucoids, polysaccharide compounds, caseinates, as well as compounds isolated from blood and/or blood clots, such as, for example, fibrin derivatives, etc. These adjuvants typically may be used in combination with other compounds, such as e.g. proteins, peptides, DNA- or RNA-molecules or other therapeutically active compounds, dependent on the result to be achieved.

However, free messenger RNA (mRNA) molecules, cDNAs or nucleic acids in general, which may encode a specific antigen or any other therapeutically active protein, suitable for a specific therapy, typically do not show a significant or even no immunostimulatory properties. Nevertheless, such immunostimulatory properties may be conferred to the mRNA molecule, the cDNA or the nucleic acid, when complexed with a peptide or protein, such as protamin or a nucleic acid binding protein. In this context, the mRNA molecule or the nucleic acid may be formulated such, that a complex is formed between the mRNA molecule or the nucleic acid and the peptide or protein, wherein different complexes may be formed between the mRNA molecule or the nucleic acid and the peptide or protein. Particularly strong (adjuvant) complexes can occur, when the nucleic acid, which is usually negatively charged at neutral pH, is bound by a cationic or polycationic peptide or protein.

However, when using mRNA or nucleic acid molecules in vaccination methods, translation of the mRNA or nucleic acid molecule in vivo remains the most important and essential factor for inducing an adaptive immune response or for expressing the encoded protein in general, e.g. in case of a therapeutically active protein or peptide. Accordingly, the complexed mRNA or nucleic acid molecules will have to be released from the complex with the (cationic) peptide or protein subsequent to transfection of the complex into the cells to allow efficient translation of the mRNA. Unfortunately, this does not occur in most cases. More typically, complexing the mRNA molecule or the nucleic acid with a cationic or polycationic compound may even prevent the nucleic acid from translation or at least significantly reduces the translation rate in vivo due to the strong binding of the polycationic compound to the mRNA molecule, cDNA or nucleic acid molecule in general. Accordingly, it is difficult to obtain a good immunostimulatory property of the composition with regard to the innate immune system taking these compounds and to ensure in parallel an efficient translation of the mRNA molecule, cDNA or nucleic acid molecule in general when using such a formulation.

One possibility to circumvent the above problem may be the administration of an adjuvant and mRNA in separated formulations. This, however, renders the administration much more complicated. It is also preferred that the adjuvant and the antigen-encoding mRNA enter the same cell to achieve an optimal immune response. Furthermore, an adjuvant beneficially supports the induction of an adaptive immune response, if it induces an innate immune response in the same cell, in which the antigen is expressed by the encoding mRNA.

Another possibility to circumvent the above problem may be the exclusive administration of naked mRNA, cDNA or nucleic acid. Such an approach, though advantageous for the purpose of efficient translation of the mRNA, cDNA or nucleic acid in vivo, dispenses the advantageous activation of the innate immune system elicited by an adjuvant as described above.

Thus, none of these approaches is in fact convincing and leads to an innate immune response paralleled by a good translation of the administered mRNA, cDNA or nucleic acid. Accordingly, there is still the need in the art for providing an efficient immunostimulatory composition or method, which allows to elicit an innate and optionally an adaptive immune response, wherein the administration is not impaired by an inefficient translation of the mRNA due to formation of a complex with the complex partner, which confers immunostimulatory properties to the mRNA. In other words, it is the object of the present invention, to provide a method and an immunostimulatory composition which allows eliciting or enhancing an innate and optionally an adaptive immunostimulatory response in a mammal, thereby ensuring an efficient adjuvant (immunostimulatory) property and an efficient translation of the mRNA to be administered.

This object is solved by the subject matter of the present invention, preferably by the attached claims. Particularly, the present invention solves the above object by an immunostimulatory composition comprising a) an adjuvant component comprising or consisting of at least one (m)RNA, complexed with a cationic or polycationic compound, and b) at least one free mRNA, encoding at least one therapeutically active protein, antigen, allergen and/or antibody, wherein the immunostimulatory composition is capable to elicit or enhance an innate and optionally an adaptive immune response in a mammal.

In the context of the present invention, a mammal may be selected from any mammal, preferably from a mammal, selected from the group comprising, without being limited thereto, e.g. goat, cattle, swine, dog, cat, donkey, monkey, ape, a rodent such as a mouse, hamster, rabbit, and, in particular, human.

The main advantage of the inventive immunostimulatory composition is that an innate and optionally an adaptive immune response may be efficiently elicited in a mammal, wherein the translation of the at least one free mRNA, encoding at least one therapeutically active protein, is not impaired by the adjuvant component, particularly the complexation of the at least one (m)RNA with a cationic or polycationic compound. This is particularly due to the fact that the adjuvant component is formed by using a cationic or polycationic compound for complexation, which typically leads to a strong complex between the RNA and the cationic compound, that barely releases the RNA, with which it is complexed. Accordingly, the free mRNA is no-more disturbed by the cationic compound, even though the administration of the adjuvant component and the free mRNA together in one formulation also leads to a significantly improved transfection and expression in vivo of the free mRNA. The solution according to the present invention utilizes the surprising finding of the inventors of the present invention, that both properties of the immunostimulatory composition, i.e. an efficient immunostimulatory property and an efficient translation of the RNA, may be achieved in one and the same formulation, if the formulation per se is prepared in two separate steps. This solution is even more convincing as it allows mixing of the adjuvant component with any free mRNA without losing free mRNA by complexation with the cationic compound of the adjuvant component. The solution may be even stored for a considerable time without leading to an equilibration reaction between the complexed RNA and the free mRNA. In other words, there is no dissociation of the formed adjuvant component which may lead to a binding of free mRNA by the cationic compound of the adjuvant component and to a release of bound RNA from the complex.

As a first component, the inventive immunostimulatory composition comprises a so called "adjuvant component", comprising or consisting of at least one (m)RNA, complexed with a cationic or polycationic compound.

The so called "adjuvant component" is prepared according to a first step by complexing the at least one (m)RNA of the adjuvant component with a cationic or polycationic compound in a specific ratio to form a stable complex. In this context, it is important, that no free cationic or polycationic compound or only a neclectably small amount remains in the adjuvant component after complexing the (m)RNA. Accordingly, the ratio of the (m)RNA and the cationic or polycationic compound in the adjuvant component is typically selected in a range that the (m)RNA is entirely complexed and no free cationic or polycationic compound or only a neclectably small amount remains in the composition. Preferably the ratio of the adjuvant component, i.e. the ratio of the (m)RNA to the cationic or polycationic compound is selected from a range of about 6:1 (w/w) to about 0.25:1 (w/w), more preferably from about 5:1 (w/w) to about 0.5:1 (w/w), even more preferably of about 4:1 (w/w) to about 1:1 (w/w) or of about 3:1 (w/w) to about 1:1 (w/w), and most preferably a ratio of about 3:1 (w/w) to about 2:1 (w/w).

Furthermore, the ratio of the m(RNA) to the cationic or polycationic compound in the adjuvant component, may also be calculated on the basis of the nitrogen/phosphate ratio (N/P-ratio) of the entire RNA complex. For example, 1 μg RNA typically contains about 3 nmol phosphate residues, provided the RNA exhibits a statistical distribution of bases. Additionally, 1 μg peptide typically contains about x nmol nitrogen residues, dependent on the molecular weight and the number of basic amino acids. When exemplarily calculated for $(Arg)_9$ (molecular weight 1424 g/mol, 9 nitrogen atoms), 1 μg $(Arg)_9$ contains about 700 μmol $(Arg)_9$ and thus 700×9=6300 μmol basic amino acids=6.3 nmol nitrogen atoms. For a mass ratio of about 1:1 RNA/$(Arg)_9$ an N/P ratio of about 2 can be calculated. When exemplarily calculated for protamine (molecular weight about 4250 g/mol, 21 nitrogen atoms, when protamine from salmon is used) with a mass ratio of about 2:1 with 2 μg RNA, 6 nmol phosphate are to be calculated for the RNA; 1 μg protamine contains about 235 μmol protamine molecules and thus 235×21=4935 μmol basic nitrogen atoms=4.9 nmol nitrogen atoms. For a mass ratio of about 2:1 RNA/protamine an N/P ratio of about 0.81 can be calculated. For a mass ratio of about 8:1 RNA/protamine an N/P ratio of about 0.2 can be calculated. In the context of the present invention, an N/P-ratio is preferably in the range of about 0.1-10, preferably in a range of about 0.3-4 and most preferably in a range of about 0.5-2 or 0.7-2 regarding the ratio of RNA:peptide in the complex, and most preferably in the range of about 0.7-1.5.

In the context of the present invention, a cationic or polycationic compound is preferably selected from any cationic or polycationic compound, suitable for complexing and thereby stabilizing a nucleic acid, particularly the at least one (m)RNA, e.g. by associating the at least one (m)RNA with the cationic or polycationic compound. Such a cationic or polycationic compound per se does not need to exhibit any adjuvant properties, since an adjuvant property, particularly the capability of inducing an innate immune response, is preferably created upon complexing the at least one (m)RNA with the cationic or polycationic compound. When complexing the at least one (m)RNA with the cationic or polycationic compound, the adjuvant component is formed. Particularly preferred, cationic or polycationic peptides or proteins as component $P^2$ may be selected from protamine, nucleoline, spermine or spermidine, poly-L-lysine (PLL), basic polypeptides, poly-arginine, cell penetrating peptides (CPPs), chimeric CPPs, such as Transportan, or MPG peptides, HIV-binding peptides, Tat, HIV-1 Tat (HIV), Tat-derived peptides, oligoarginines, members of the penetratin family, e.g. Penetratin, *Antennapedia*-derived peptides (particularly from *Drosophila antennapedia*), pAntp, pIsl, etc., antimicrobial-derived CPPs e.g. Buforin-2, Bac715-24, SynB, SynB(1), pVEC, hCT-derived peptides, SAP, MAP, KALA, PpTG20, Proline-rich peptides, L-oligomers, Arginine-rich peptides, Calcitonin-peptides, FGF, Lactoferrin, poly-L-Lysine, poly-Arginine, histones, VP22 derived or analog peptides, HSV, VP22 (Herpes simplex), MAP, KALA or protein transduction domains (PTDs, PpT620, prolin-rich peptides, arginine-rich peptides, lysine-rich peptides, Pep-1, Calcitonin peptide(s), etc. Additionally, preferred cationic or polycationic proteins or peptides may be selected from following proteins or peptides having the following total formula: $(Arg)_l$; $(Lys)_m$; $(His)_n$; $(Orn)_o$; $(Xaa)_x$, wherein l+m+n+o+x=8-15, and l, m, n or o independently of each other may be any number selected from 0, 1, 2, 3, 4, 5, 6, 7, 8, 9, 10, 11, 12, 13, 14 or 15, provided that the overall content of Arg, Lys, His and Orn represents at least 50% of all amino acids of the oligopeptide; and Xaa may be any amino acid selected from native (=naturally occurring) or non-native amino acids except of Arg, Lys, His or Orn; and x may be any number selected from 0, 1, 2, 3, 4, 5, 6, 7, or 8 provided, that the overall content of Xaa does not exceed 50% of all amino acids of the oligopeptide. Particularly preferred oligoarginines in this context are e.g. $Arg_7$ (SEQ ID NO: 125), $Arg_8$ (SEQ ID NO: 126), $Arg_9$ (SEQ ID NO: 127), $Arg_7$ (SEQ ID NO: 125), $H_3R_9$ (SEQ ID NO: 128), $R_9H_3$ (SEQ ID NO: 129), $H_3R_9H_3$ (SEQ ID NO: 130), $YSSR_9SSY$ (SEQ ID NO: 131), $(RKH)_4$ (SEQ ID NO: 132), $Y(RKH)_2R$ (SEQ ID NO: 133), etc. Further preferred cationic or polycationic compounds, which can be used for complexing the at least one (m)RNA of the adjuvant component above may include cationic polysaccharides, for example chitosan, polybrene, cationic polymers, e.g. polyethyleneimine (PEI), cationic lipids, e.g. DOTMA: [1-(2,3-sioleyloxy)propyl]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicylspermin, DIMRI: Dimyristo-oxypropyl dimethyl hydroxyethyl ammonium bromide, DOTAP: dioleoyloxy-3-(trimethylammonio)propane, DC-6-14: O,O-ditetradecanoyl-N-(α-trimethylammonioaeetyl)diethanolamine chloride, CLIP1: rac-[2(2,3-dioctadecyloxypropyl)(2-hydroxyethyl)]-dimethylammonium chloride, CLIP6: rac-[2(2,3-dihexadecyloxypropyl-oxymethyloxy)ethyl] trimethylammonium, CLIP9: rac-[2(2,3-dihexadecyloxypropyl-oxysuccinyloxy)ethyl] trimethylammonium, oligofectamine, or cationic or polycationic polymers, e.g. modified polyaminoacids, such as β-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified Amidoamines such as pAMAM (poly(amidoamine)), etc., modified polybetaaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, Chitosan, etc., silan backbone based polymers, such as PMOXA-PDMS copolymers, etc., Block polymers consisting of a combination of one or more cationic blocks (e.g. selected og a cationic polymer as mentioned above) and of one or more hydrophilic- or hydrophobic blocks (e.g polyethyleneglycole); etc. Association or complexing the modified (m)RNA of the inventive immunostimulatory composition with cationic or polycationic compounds preferably provides adjuvant properties to the (m)RNA and confers a stabilizing effect to the (m)RNA of the adjuvant component by complexation. The procedure for stabilizing the modified (m)RNA is in general described in EP-A-1083232, the disclosure of which is incorporated by reference into the present invention in its entirety. Particularly preferred as cationic or polycationic compounds are compounds selected from the group consisting of protamine, nucleoline, spermin, spermidine, oligoarginines as defined above, such as $Arg_7$ (SEQ ID NO: 125), $Arg_8$ (SEQ ID NO: 126), $Arg_9$ (SEQ ID NO: 127), $Arg_7$ (SEQ ID NO: 125), $H_3R_9$ (SEQ ID NO: 128), $R_9H_3$ (SEQ ID NO: 129), $H_3R_9H_3$ (SEQ ID NO: 130), $YSSR_9SSY$ (SEQ ID NO: 131), $(RKH)_4$ (SEQ ID NO: 132), $Y(RKH)_2R$ (SEQ ID NO: 133), etc.

In the context of the present invention, the at least one (m)RNA of the "adjuvant component" of the inventive immunostimulatory composition may be any RNA, preferably, without being limited thereto, a short RNA oligonucleotide, a coding RNA, an immunostimulatory RNA, an siRNA, an antisense RNA, or riboswitches, ribozymes or aptamers. Furthermore, the at least one (m)RNA of the adjuvant component may be a single- or a double-stranded RNA (which may also be regarded as an RNA (molecule) due to non-covalent association of two single-stranded RNA (molecules)) or a partially double-stranded or partially single stranded RNA, which are at least partially self complementary (both of these partially double-stranded or partially single stranded RNA molecules are typically formed by a longer and a shorter single-stranded RNA molecule or by two single stranded RNA-molecules, which are about equal in length, wherein one single-stranded RNA molecule is in part complementary to the other single-stranded RNA molecule and both thus form a double-stranded RNA molecule in this region, i.e. a partially double-stranded or partially single stranded RNA). Preferably, the at least one (m)RNA of the adjuvant component may be a single-stranded RNA. Furthermore, the at least one (m)RNA of the adjuvant component may be a circular or linear RNA, preferably a linear RNA. More preferably, the at least one (m)RNA of the adjuvant component may be a (linear) single-stranded RNA. The at least one (m)RNA of the adjuvant component may be a ribosomal RNA (rRNA), a transfer RNA (tRNA), a messenger RNA (mRNA), or a viral RNA (vRNA), more preferably an mRNA. The present invention allows all of these RNAs to be part of the "adjuvant component" of the inventive composition, either alone or in combination. In the context of the present invention, an mRNA is typically an RNA, which is composed of several structural elements, e.g. an optional 5'-UTR region, an upstream positioned ribosomal binding site followed by a coding region, an optional 3'-UTR region, which may be followed by a poly-A tail (and/or a poly-C-tail). An mRNA may occur as a mono-, di-, or even multicistronic RNA, i.e. an RNA which carries the coding sequences of one, two or more proteins or peptides. Such coding sequences in di-, or even multicistronic mRNA may be separated by at least one IRES sequence, e.g. as defined herein.

Preferably, the at least one (m)RNA of the adjuvant component of the inventive immunostimulatory composition comprises a length of about 5 to about 20,000, or 100 to about 20,000 nucleotides, preferably of about 250 to about 20,000 nucleotides, more preferably of about 500 to about 10,000, even more preferably of about 500 to about 5,000, most preferably a length of about 100 to 10,000 nucleotides or a length of about 100 to 5,000 nucleotides.

According to a first embodiment, the at least one (m)RNA of the adjuvant component of the inventive immunostimulatory composition may be a short RNA oligonucleotide. Short RNA oligonucleotides in the context of the present invention may comprise any RNA as defined above. Preferably, the short RNA oligonucleotide may be a single- or a double-stranded RNA oligonucleotide, more preferably a single-stranded RNA oligonucleotide. Even more preferably, the short RNA oligonucleotide may be a linear single-stranded RNA oligonucleotide. Also preferably, the short RNA oligonucleotides as used herein may comprise a length as defined above in general for RNA molecules, more preferably a length of 5 to 100, of 5 to 50, or of 5 of 30, and even more preferably a length of 20 to 100, of 20 to 80, or of 20 of 60 nucleotides.

According to a second embodiment, the at least one (m)RNA of the adjuvant component of the inventive immunostimulatory composition may be an immunostimulatory RNA, i.e. an RNA derived from an immunostimulatory RNA, which triggers or increases an (innate) immune response. Preferably, the at least one (m)RNA of the adjuvant component of the inventive immunostimulatory composition may be a single-stranded, a double-stranded or a partially double-stranded or partially single-stranded RNA, more preferably a single-stranded RNA, and/or a circular or linear RNA, more preferably a linear RNA. More preferably, the at least one (m)RNA of the adjuvant component may be a (linear) single-stranded RNA. Even more preferably, the at least one (m)RNA of the adjuvant component may be a ((linear) single-stranded) messenger RNA (mRNA). The at least one (m)RNA of the adjuvant component of the inventive immunostimulatory composition may also occur as a short RNA oligonucleotide as defined above. The at least one (m)RNA of the adjuvant component of the inventive immunostimulatory composition may furthermore be selected from any class of RNA molecules, found in nature or being prepared synthetically, and which can induce an innate immune response. In this context, it is preferable, that the adjuvant component of the inventive immunostimulatory composition typically elicits an innate immune response, whereas the free mRNA of the inventive immunostimulatory composition may elicit an adaptive immune response, particularly if the free mRNA encodes an antigen or allergen as described herein or any further molecule, which is capable to elicit an adaptive immune response. Particularly, those classes of RNA molecules, which can induce an innate immune response, may be selected from ligands of Toll-like receptors (TLRs). The at least one immunostimulatory RNA of the adjuvant component of the inventive immunostimulatory composition may thus comprise any RNA sequence known to be immunostimulatory, including, without being limited thereto, RNA sequences representing and/or encoding ligands of TLRs, preferably selected from human family members TLR1-TLR10 or murine family members TLR1-TLR13, more preferably from TLR7 and TLR8, ligands for intracellular receptors for RNA (such as RIG-I or MDA-5, etc.) (see e.g. Meylan, E., Tschopp, J. (2006). Toll-like receptors and RNA helicases: two parallel ways to trigger antiviral responses. Mol. Cell. 22, 561-569), or any other immunostimulatory RNA sequence.

Typically, the immunostimulatory RNA used as an at least one (m)RNA of the adjuvant component of the inventive immunostimulatory composition may comprise a length as defined above in general for RNA molecules of the RNA of the adjuvant component of the inventive immunostimulatory composition. Preferably, the RNA may have a length of 1000 to 5000, of 500 to 5000, of 5 to 5000, or of 5 to 1000, 5 to 500, 5 to 250, of 5 to 100, of 5 to 50 or of 5 to 30 nucleotides.

Such immunostimulatory sequences may comprise e.g. a nucleic acid of formula (I):

$$G_lX_mG_n,$$

wherein:

G is guanosine, uracil or an analogue of guanosine or uracil;

X is guanosine, uracil, adenosine, thymidine, cytosine or an analogue of the above-mentioned nucleotides;

l is an integer from 1 to 40, wherein when l=1 G is guanosine or an analogue thereof, when l>1 at least 50% of the nucleotides are guanosine or an analogue thereof;

m is an integer and is at least 3;

wherein when m=3 X is uracil or an analogue thereof, when m>3 at least 3 successive uracils or analogues of uracil occur;

n is an integer from 1 to 40, wherein when n=1 G is guanosine or an analogue thereof, when n>1 at least 50% of the nucleotides are guanosine or an analogue thereof.

Such immunostimulatory sequences may also comprise e.g. a nucleic acid of formula (II):

$$C_lX_mC_n,$$

wherein:

C is cytosine, uracil or an analogue of cytosine or uracil;

X is guanosine, uracil, adenosine, thymidine, cytosine or an analogue of the above-mentioned nucleotides;

l is an integer from 1 to 40, wherein when l=1 C is cytosine or an analogue thereof, when l>1 at least 50% of the nucleotides are cytosine or an analogue thereof;

m is an integer and is at least 3;

wherein when m=3 X is uracil or an analogue thereof, when m>3 at least 3 successive uracils or analogues of uracil occur;

n is an integer from 1 to 40, wherein when n=1 C is cytosine or an analogue thereof, when n>1 at least 50% of the nucleotides are cytosine or an analogue thereof.

The nucleic acids of formula (I) or (II), which may be used for the at least one (m)RNA of the adjuvant component of the inventive immunostimulatory composition, are typically relatively short nucleic acid molecules and typically have a length of approximately from 5 to 100 (but may also be longer than 100 nucleotides for specific embodiments, e.g. up to 200 nucleotides), from 5 to 90 or from 5 to 80 nucleotides, preferably a length of approximately from 5 to 70, more preferably a length of approximately from 8 to 60 and, more preferably a length of approximately from 15 to 60 nucleotides, more preferably from 20 to 60, most preferably from 30 to 60 nucleotides. If the nucleic acid of the invention has a maximum length of e.g. 100 nucleotides, m will typically be <=98. The number of nucleotides G in the nucleic acid of formula (I) is determined by l or n. l and n, independently of one another, are each an integer from 1 to 40, wherein when l or n=1 G is guanosine or an analogue thereof, and when l or n>1 at least 50% of the nucleotides are guanosine or an analogue thereof. For example, without implying any limitation, when l or n=4 $G_l$ or $G_n$ can be, for example, a GUGU, GGUU, UGUG, UUGG, GUUG, GGGU, GGUG, GUGG, UGGG or GGGG, etc.; when l or n=5 $G_l$ or $G_n$ can be, for example, a GGGUU, GGUGU, GUGGU, UGGGU, UGGUG, UGUGG, UUGGG, GUGUG, GGGGU, GGGUG, GGUGG, GUGGG, UGGGG, or GGGGG, etc.; etc. A nucleotide adjacent to $X_m$ in the nucleic acid of formula (I) according to the invention is preferably not a uracil. Similarly, the number of nucleotides C in the nucleic acid of formula (II) according to the invention is determined by l or n. l and n, independently of one another, are each an integer from 1 to 40, wherein when l or n=1 C is cytosine or an analogue thereof, and when l or n>1 at least 50% of the nucleotides are cytosine or an analogue thereof. For example, without implying any limitation, when l or n=4, $C_l$ or $C_n$ can be, for example, a CUCU, CCUU, UCUC, UUCC, CUUC, CCCU, CCUC, CUCC, UCCC or CCCC, etc.; when l or n=5 $C_l$ or $C_n$ can be, for example, a CCCUU, CCUCU, CUCCU, UCCCU, UCCUC, UCUCC, UUCCC, CUCUC, CCCCU, CCCUC, CCUCC, CUCCC, UCCCC, or CCCCC, etc.; etc. A nucleotide adjacent to $X_m$ in the nucleic acid of formula (II) according to the invention is preferably not a uracil. Preferably, for formula (I), when l or n>1, at least 60%, 70%, 80%, 90% or even 100% of the nucleotides are guanosine or an analogue thereof, as defined above. The remaining nucleotides to 100% (when guanosine constitutes less than 100% of the nucleotides) in the flanking sequences $G_l$ and/or $G_n$ are uracil or an analogue thereof, as defined hereinbefore. Also preferably, l and n, independently of one another, are each an integer from 2 to 30, more preferably an integer from 2 to 20 and yet more preferably an integer from 2 to 15. The lower limit of l or n can be varied if necessary and is at least 1, preferably at least 2, more preferably at least 3, 4, 5, 6, 7, 8, 9 or 10. This definition applies correspondingly to formula (II).

According to a particularly preferred embodiment, a nucleic acid according to any of formulas (I) or (II) above, which may be used for the at least one (m)RNA of the adjuvant component of the inventive immunostimulatory composition, may be selected from a sequence consisting or comprising any of the following sequences:

(SEQ ID NO: 1)
GGUUUUUUUUUUUUUUUGGG;

(SEQ ID NO: 2)
GGGGGUUUUUUUUUUGGGGG;

(SEQ ID NO: 3)
GGGGGUUUUUUUUUUUUUUUUUUUUUUUUUUUUUUGGGGG;

(SEQ ID NO: 4)
GUGUGUGUGUUUUUUUUUUUUUUUUUUUGUGUGUGUGU;

(SEQ ID NO: 5)
GGUUGGUUGGUUUUUUUUUUUUUUUUUGGUUGGUUGGUU;

(SEQ ID NO: 6)
GGGGGGGGGUUUGGGGGGGG;

(SEQ ID NO: 7)
GGGGGGGGUUUUGGGGGGGG;

(SEQ ID NO: 8)
GGGGGGGUUUUUUGGGGGGG;

(SEQ ID NO: 9)
GGGGGGGUUUUUUUGGGGGG;

(SEQ ID NO: 10)
GGGGGGUUUUUUUUGGGGGG;

(SEQ ID NO: 11)
GGGGGGUUUUUUUUUGGGGG;

(SEQ ID NO: 12)
GGGGGGUUUUUUUUUUGGGG;

(SEQ ID NO: 13)
GGGGGUUUUUUUUUUUGGGG;

(SEQ ID NO: 14)
GGGGGUUUUUUUUUUUUGGG;

(SEQ ID NO: 15)
GGGGUUUUUUUUUUUUUGGG;

(SEQ ID NO: 16)
GGGGUUUUUUUUUUUUUUGG;

(SEQ ID NO: 17)
GGUUUUUUUUUUUUUUUUGG;

(SEQ ID NO: 18)
GUUUUUUUUUUUUUUUUUUG;

(SEQ ID NO: 19)
GGGGGGGGGGUUUGGGGGGGGG;

-continued (SEQ ID NO: 20)
GGGGGGGGGUUUUGGGGGGGGG;

(SEQ ID NO: 21)
GGGGGGGGUUUUUUGGGGGGGG;

(SEQ ID NO: 22)
GGGGGGGGUUUUUUUGGGGGGG;

(SEQ ID NO: 23)
GGGGGGGUUUUUUUUGGGGGGG;

(SEQ ID NO: 24)
GGGGGGGUUUUUUUUUGGGGGG;

(SEQ ID NO: 25)
GGGGGGGUUUUUUUUUUGGGGG;

(SEQ ID NO: 26)
GGGGGGUUUUUUUUUUUGGGGG;

(SEQ ID NO: 27)
GGGGGGUUUUUUUUUUUUGGGG;

(SEQ ID NO: 28)
GGGGGUUUUUUUUUUUUUGGGG;

(SEQ ID NO: 29)
GGGGGUUUUUUUUUUUUUUGGG;

(SEQ ID NO: 30)
GGGUUUUUUUUUUUUUUUUGGG;

(SEQ ID NO: 31)
GGUUUUUUUUUUUUUUUUUUGG;

(SEQ ID NO: 32)
GGGGGGGGGGGUUUGGGGGGGGGG;

(SEQ ID NO: 33)
GGGGGGGGGGUUUUGGGGGGGGGG;

(SEQ ID NO: 34)
GGGGGGGGGUUUUUUGGGGGGGGG;

(SEQ ID NO: 35)
GGGGGGGGGUUUUUUUGGGGGGGG;

(SEQ ID NO: 36)
GGGGGGGGUUUUUUUUGGGGGGGG;

(SEQ ID NO: 37)
GGGGGGGGUUUUUUUUUGGGGGGG;

(SEQ ID NO: 38)
GGGGGGGGUUUUUUUUUUGGGGGG;

(SEQ ID NO: 39)
GGGGGGGUUUUUUUUUUUGGGGGG;

(SEQ ID NO: 40)
GGGGGGGUUUUUUUUUUUUGGGGG;

(SEQ ID NO: 41)
GGGGGGUUUUUUUUUUUUUGGGGG;

(SEQ ID NO: 42)
GGGGGGUUUUUUUUUUUUUUGGGG;

(SEQ ID NO: 43)
GGGGUUUUUUUUUUUUUUUUGGGG;

(SEQ ID NO: 44)
GGGUUUUUUUUUUUUUUUUUUGGG;

(SEQ ID NO: 45)
GUUUUUUUUUUUUUUUUUUUUUUUUUUUUUUG;

(SEQ ID NO: 46)
GGUUUUUUUUUUUUUUUUUUUUUUUUUUUUUUGG;

-continued (SEQ ID NO: 47)
GGGUUUUUUUUUUUUUUUUUUUUUUUUUUUUUUGGG;

(SEQ ID NO: 48)
GGGGUUUUUUUUUUUUUUUUUUUUUUUUUUUUUUGGG;

(SEQ ID NO: 49)
GGGGGUUUUUUUUUUUUUUUUUUUUUUUUUUUUUUGGGG;

(SEQ ID NO: 50)
GGGGGGUUUUUUUUUUUUUUUUUUUUUUUUUUUUUUGGGGG;

(SEQ ID NO: 51)
GGGGGGGUUUUUUUUUUUUUUUUUUUUUUUUUUUUUUGGGGGG;

(SEQ ID NO: 52)
GGGGGGGGUUUUUUUUUUUUUUUUUUUUUUUUUUUUUUGGGGGGG;

(SEQ ID NO: 53)
GGGGGGGGGUUUUUUUUUUUUUUUUUUUUUUUUUUUUUUGGGGGGGG;

(SEQ ID NO: 54)
GGUUUGG;

(SEQ ID NO: 55)
GGUUUUGG;

(SEQ ID NO: 56)
GGUUUUUGG;

(SEQ ID NO: 57)
GGUUUUUUGG;

(SEQ ID NO: 58)
GGUUUUUUUGG;

(SEQ ID NO: 59)
GGUUUUUUUUGG;

(SEQ ID NO: 60)
GGUUUUUUUUUGG;

(SEQ ID NO: 61)
GGUUUUUUUUUUGG;

(SEQ ID NO: 62)
GGUUUUUUUUUUUGG;

(SEQ ID NO: 63)
GGUUUUUUUUUUUUGG;

(SEQ ID NO: 64)
GGUUUUUUUUUUUUUGG;

(SEQ ID NO: 65)
GGUUUUUUUUUUUUUUGG;

(SEQ ID NO: 66)
GGUUUUUUUUUUUUUUUGG;

(SEQ ID NO: 67)
GGGUUUGGG;

(SEQ ID NO: 68)
GGGUUUUGGG;

(SEQ ID NO: 69)
GGGUUUUUGGG;

(SEQ ID NO: 70)
GGGUUUUUUGGG;

(SEQ ID NO: 71)
GGGUUUUUUUGGG;

(SEQ ID NO: 72)
GGGUUUUUUUUGGG;

(SEQ ID NO: 73)
GGGUUUUUUUUUGGG;

-continued (SEQ ID NO: 74)
GGGUUUUUUUUUUGGG;

(SEQ ID NO: 75)
GGGUUUUUUUUUUUGGG;

(SEQ ID NO: 76)
GGGUUUUUUUUUUUUGGG;

(SEQ ID NO: 77)
GGGUUUUUUUUUUUUUGGG;

(SEQ ID NO: 78)
GGGUUUUUUUUUUUUUUUGGGUUUUUUUUUUUUUUUGGGUUUUUUUUUUU

UUUUGGG;

(SEQ ID NO: 79)
GGGUUUUUUUUUUUUUUUGGGGGUUUUUUUUUUUUUUUUGGG;

(SEQ ID NO: 80)
GGGUUUGGGUUUGGGUUUGGGUUUGGGUUUGGGUUUGGGUUUGGGUUUGG

G;
or (SEQ ID NO: 81)
CCCUUUUUUUUUUUUUUUCCCUUUUUUUUUUUUUUUCCCUUUUUUUUUUU

UUUUCCC (SEQ ID NO: 82)
CCCUUUCCCUUUCCCUUUCCCUUUCCCUUUCCCUUUCCCUUUCCCUUUCC

C (SEQ ID NO: 83)
CCCUUUUUUUUUUUUUUUCCCCCUUUUUUUUUUUUUUUUCCC or from a sequence having at least 60%, 70%, 80%, 90%, or even 95% sequence identity with any of these sequences In this context, the term "identity" in the present application means that the sequences are compared in relation to a reference sequence and the percentage identity is determined by comparing them. For example, in order to determine the percentage identity of two nucleic acid sequences, the sequences can first be arranged relative to one another (alignment) in order to permit subsequent comparison of the sequences. To this end, for example, gaps can be introduced into the sequence of the first nucleic acid sequence and the nucleotides can be compared with the corresponding position of the second nucleic acid sequence. When a position in the first nucleic acid sequence is occupied with the same nucleotide as in a position in the second sequence, then the two sequences are identical at that position. The percentage identity between two sequences is a function of the number of identical positions divided by the sequences. If, for example, a specific sequence identity is assumed for a particular nucleic acid in comparison with a reference nucleic acid having a defined length, then this percentage identity is indicated relatively in relation to the reference nucleic acid. Therefore, starting, for example, from a nucleic acid sequence that has 50% sequence identity with a reference nucleic acid sequence having a length of 100 nucleotides, that nucleic acid sequence can represent a nucleic acid sequence having a length of 50 nucleotides that is wholly identical with a section of the reference nucleic acid sequence having a length of 50 nucleotides. It can, however, also represent a nucleic acid sequence having a length of 100 nucleotides that has 50% identity, that is to say in this case 50% identical nucleic acids, with the reference nucleic acid sequence over its entire length. Alternatively, that nucleic acid sequence can be a nucleic acid sequence having a length of 200 nucleotides that, in a section of the nucleic acid sequence having a length of 100 nucleotides, is wholly identical with the reference nucleic acid sequence having a length of 100 nucleotides. Other nucleic acid sequences naturally fulfil these criteria equally.

The determination of the percentage identity of two sequences can be carried out by means of a mathematical algorithm. A preferred but non-limiting example of a mathematical algorithm which can be used for comparing two sequences is the algorithm of Karlin et al. (1993), PNAS USA, 90:5873-5877. Such an algorithm is integrated into the NBLAST program, with which sequences having a desired identity with the sequences of the present invention can be identified. In order to obtain a gapped alignment as described above, the "Gapped BLAST" program can be used, as described in Altschul et al. (1997), Nucleic Acids Res, 25:3389-3402. When using BLAST and Gapped BLAST programs, the default parameters of the particular program (e.g. NBLAST) can be used. The sequences can further be aligned using version 9 of GAP (global alignment program) from "Genetic Computing Group", using the default (BLOSUM62) matrix (values −4 to +11) with a gap open penalty of −12 (for the first zero of a gap) and a gap extension penalty of −4 (for each additional successive zero in the gap). After the alignment, the percentage identity is calculated by expressing the number of correspondences as a percentage of the nucleic acids in the claimed sequence. The described methods for determining the percentage identity of two nucleic acid sequences can also be applied correspondingly to amino acid sequences using the appropriate programs.

Additionally, such immunostimulatory sequences may also comprise e.g. a nucleic acid (molecule) of formula (III):

$$(N_uG_lX_mG_nN_v)_a,$$

wherein:

G is guanosine (guanine), uridine (uracil) or an analogue of guanosine (guanine) or uridine (uracil), preferably guanosine (guanine) or an analogue thereof;

X is guanosine (guanine), uridine (uracil), adenosine (adenine), thymidine (thymine), cytidine (cytosine), or an analogue of these nucleotides (nucleosides), preferably uridine (uracil) or an analogue thereof;

N is a nucleic acid sequence having a length of about 4 to 50, preferably of about 4 to 40, more preferably of about 4 to 30 or 4 to 20 nucleic acids, each N independently being selected from guanosine (guanine), uridine (uracil), adenosine (adenine), thymidine (thymine), cytidine (cytosine) or an analogue of these nucleotides (nucleosides);

a is an integer from 1 to 20, preferably from 1 to 15, most preferably from 1 to 10;

l is an integer from 1 to 40,
  wherein when l=1, G is guanosine (guanine) or an analogue thereof,
    when l>1, at least 50% of these nucleotides (nucleosides) are guanosine (guanine) or an analogue thereof;

m is an integer and is at least 3;
  wherein when m=3, X is uridine (uracil) or an analogue thereof, and
    when m>3, at least 3 successive uridines (uracils) or analogues of uridine (uracil) occur;

n is an integer from 1 to 40,
  wherein when n=1, G is guanosine (guanine) or an analogue thereof,
    when n>1, at least 50% of these nucleotides (nucleosides) are guanosine (guanine) or an analogue thereof;

u, v may be independently from each other an integer from 0 to 50,
  preferably wherein when u=0, v≥1, or
    when v=0, u≥1;

wherein the immunostimulatory sequence according to formula (III) has a length of at least 50 nucleotides, preferably of at least 100 nucleotides, more preferably of at least 150 nucleotides, even more preferably of at least 200 nucleotides and most preferably of at least 250 nucleotides.

The structure $(N_uG_lX_mG_nN_v)_a$ of formula (III) according to the present invention comprises the element $G_lX_mG_n$ as a core structure, which is preferably as defined above, and additionally the bordering elements $N_u$ and/or $N_v$, wherein the whole element $N_uG_lX_mG_nN_v$ may occur repeatedly, i.e. at least once, as determined by the integer a. As surprisingly found by the inventors a molecule according to formula (III), i.e. having the structure $(N_uG_lX_mG_nN_v)_a$ as defined above, leads to an increased innate immune response in a patient, which is particularly indicated by an increase of IFNalpha release, when compared to administration of the core structure $G_lX_mG_n$ as such. Furthermore, a molecule comprising the above core structure $G_lX_mG_n$ can be amplified in bacterial organisms with a significantly better yield, when it is bordered by a repetitive element $N_u$ and/or $N_v$ as defined in formula (III). This molecule design is particularly advantageous when preparing a molecule according structure $(N_uG_lX_mG_nN_v)_a$ of formula (III) as defined above by using in vitro transcription methods instead of solid phase synthesis methods as known in the art, which are typically limited to a specific size of nucleic acids.

The core structure $G_lX_mG_n$ of formula (III) is defined more closely in the following:

G in the nucleic acid molecule of formula (III) (and of formula (I) and (II)) is a nucleotide or deoxynucleotide or comprises a nucleoside, wherein the nucleotide (nucleoside) is guanosine (guanine) or uridine (uracil) or an analogue thereof, more preferably guanosine (guanine) or an analogue thereof. In this connection, guanosine (guanine) or uridine (uracil) nucleotide (nucleoside) analogues are defined as non-natively occurring variants of the naturally occurring nucleotides (nucleoside) guanosine (guanine) and uridine (uracil). Accordingly, guanosine (guanine) or uridine (uracil) analogues are typically chemically derivatized nucleotides (nucleoside) with non-natively occurring functional groups or components, which are preferably added to, modified or deleted from the naturally occurring guanosine (guanine) or uridine (uracil) nucleotide or which substitute the naturally occurring functional groups or components of a naturally occurring guanosine (guanine) or uridine (uracil) nucleotide. Accordingly, each functional group or component of the naturally occurring guanosine (guanine) or uridine (uracil) nucleotide may be modified or deleted therefrom, namely the base component, the sugar (ribose) component, any naturally occurring functional side group and/or the phosphate component forming the oligonucleotide's backbone. The phosphate moieties may be substituted by e.g. phosphoramidates, phosphorothioates, peptide nucleotides, methylphosphonates etc., however, naturally occurring phosphodiester backbones still being preferred in the context of the present invention. Additionally, the sugar (ribose) component is selected from a desoxyribose, particularly the nucleic acid is an RNA as defined above, wherein the sugar (ribose) component is selected from a desoxyribose.

Accordingly, analogues of guanosine (guanine) or uridine (uracil) include, without implying any limitation, any naturally occurring or non-naturally occurring guanosine (guanine) or uridine (uracil) that has been altered chemically, for example by acetylation, methylation, hydroxylation, etc., including, for example, 1-methyl-guanosine (guanine), 2-methyl-guanosine (guanine), 2,2-dimethyl-guanosine (guanine), 7-methyl-guanosine (guanine), dihydro-uridine (uracil), 4-thio-uridine (uracil), 5-carboxymethylaminomethyl-2-thio-uridine (uracil), 5-(carboxy-hydroxylmethyl)-uridine (uracil), 5-fluoro-uridine (uracil), 5-bromo-uridine (uracil), 5-carboxymethylaminomethyl-uridine (uracil), 5-methyl-2-thio-uridine (uracil), N-uridine (uracil)-5-oxyacetic acid methyl ester, 5-methylaminomethyl-uridine (uracil), 5-methoxyaminomethyl-2-thio-uridine (uracil), 5'-methoxycarbonylmethyl-uridine (uracil), 5-methoxy-uridine (uracil), uridine (uracil)-5-oxyacetic acid methyl ester, uridine (uracil)-5-oxyacetic acid (v). The preparation of such analogues is known to a person skilled in the art, for example from U.S. Pat. No. 4,373,071, U.S. Pat. No. 4,401,796, U.S. Pat. No. 4,415,732, U.S. Pat. No. 4,458,066, U.S. Pat. No. 4,500,707, U.S. Pat. No. 4,668,777, U.S. Pat. No. 4,973,679, U.S. Pat. No. 5,047,524, U.S. Pat. No. 5,132,418, U.S. Pat. No. 5,153,319, U.S. Pat. No. 5,262,530 and U.S. Pat. No. 5,700,642, the disclosures of which are incorporated by reference herein in their entirety. In the case of an analogue as described above, preference is given especially to those analogues that increase the immunogenity of the nucleic acid molecule of formula (III) (and of formula (I) and (II)) and/or do not interfere with a further modification that has been introduced. At least one guanosine (guanine) or uridine (uracil) or an analogue thereof can occur in the core structure elements $G_l$ and/or $G_n$, optionally at least 10%, 20%, 30%, 40%, 50%, 60%, 70%, 80% 90% or even 100% of the nucleotides of the core structure elements $G_l$ and/or $G_n$ are a naturally occurring guanosine (guanine), a naturally occurring uridine (uracil), and/or an analogue thereof and/or exhibit properties of an analogue thereof as defined herein. Preferably, the core structure element $G_l$ and/or $G_n$ contains at least one analogue of a naturally occurring guanosine (guanine) and/or a naturally occurring uridine (uracil) at all. Most preferably, all nucleotides (nucleosides) of these core structure elements $G_l$ and/or $G_n$ are analogues, which may—most preferably—be identical analogues for the same type of nucleotides (nucleosides) (e.g. all guanosine (guanine) nucleotides are provided as 1-methyl-guanosine (guanine)) or they may be distinct (e.g. at least two different guanosin analogues substitute the naturally occurring guanosin nucleotide).

The number of nucleotides (nucleosides) of core structure element G ($G_l$ and/or $G_n$) in the nucleic acid molecule of formula (III) (and of formula (I) and (II)) is determined by l and n. l and n, independently of one another, are each an integer from 1 to 100, 1 to 90, 1 to 80, 1 to 70, 1 to 60, preferably 1 to 50, yet more preferably 1 to 40, and even more preferably 1 to 30, wherein the lower limit of these ranges may be 1, but alternatively also 2, 3, 4, 5, 6, 7, 8, 9, 10, 11, 12, 13, 14, 15, 16, 17, 18, 19, 20, 21, 22, 23, 24, 25, 26, 27, 28, 29, 30, or even more. Preferably, for each integer, when l and/or n=1, G is guanosine (guanine) or an analogue thereof, and when l or n>1, at least 50%, more preferably at least 50%, 60%, 70%, 80%, 90% or even 100% of the nucleotides (nucleosides) of core structure element G ($G_l$ and/or $G_n$) are guanosine (guanine) or an analogue thereof. For example, without implying any limitation, when l or n=4, $G_l$ and/or $G_n$ can be, for example, a GUGU, GGUU, UGUG, UUGG, GUUG, GGGU, GGUG, GUGG, UGGG or GGGG, etc.; when l or n=5, $G_l$ and/or $G_n$ can be, for example, a GGGUU, GGUGU, GUGGU, UGGGU, UGGUG, UGUGG, UUGGG, GUGUG, GGGGU, GGGUG, GGUGG, GUGGG, UGGGG, or GGGGG, etc.; etc. A nucleotide (nucleoside) of core structure elements $G_l$ and/or $G_n$ directly adjacent to $X_m$ in the nucleic acid molecule of formula (III) (and of formula (I) and (II)) is preferably not an uridine (uracil) or an analogue thereof. More preferably nucleotides (nucleosides) of core structure elements $G_l$ and/or $G_n$ directly adjacent to $X_m$ in the nucleic acid molecule of formula (III) are at least one guanosine (guanine) or an analogue thereof, more preferably a stretch of at least 2, 3, 4, 5, 6, 7, 8, 9, 10, 11, 12, 13, 14, 15, 16, 17, 18, 19 or even 20 or more guanosines (guanines) or an analogue thereof. Additionally, a nucleotide of core structure elements $G_l$ and/or $G_n$ directly adjacent to N, e.g. $N_u$, and/or $N_v$ (or $N_{w1}$ or $N_{w2}$ as defined below) in the nucleic acid molecule of formula (III) (and of formula (I) and (II)) is preferably not an uridine (uracil) or an analogue thereof. More preferably, nucleotides (nucleosides) of core structure elements $G_l$ and/or $G_n$ directly adjacent to N, e.g. $N_u$, and/or $N_v$ (or $N_{w1}$ or $N_{w2}$ as defined below) in the nucleic acid molecule of formula (III) (and of formula (I) and (II)) are at least one guanosine (guanine) or an analogue thereof, more preferably a stretch of at least 2, 3, 4, 5, 6, 7, 8, 9, 10, 11, 12, 13, 14, 15, 16, 17, 18, 19 or even 20 or more guanosines (guanines) or an analogue thereof.

Likewise preferably, for formula (III) (and of formula (I) and (II)), when l or n>1, at least 60%, 70%, 80%, 90% or even 100% of the nucleotides (nucleosides) of the core structure elements $G_l$ and/or $G_n$ are guanosine (guanine) or an analogue thereof, as defined above. The remaining nucleotides (nucleosides) to 100% in the core structure elements $G_l$ and/or $G_n$ (when guanosine (guanine) constitutes less than 100% of these nucleotides (nucleosides)) may then be uridine (uracil) or an analogue thereof, as defined hereinbefore.

X, particularly $X_m$, in the nucleic acid molecule of formula (III) (and of formula (I) and (II)) is also a core structure element and is a nucleotide or deoxynucleotide or comprises a nucleoside, wherein the nucleotide (nucleoside) is typically selected from guanosine (guanine), uridine (uracil), adenosine (adenine), thymidine (thymine), cytidine (cytosine) or an analogue thereof, preferably uridine (uracil) or an analogue thereof. In this connection, nucleotide (nucleoside) analogues are defined as non-natively occurring variants of naturally occurring nucleotides (nucleosides). Accordingly, analogues are chemically derivatized nucleotides (nucleosides) with non-natively occurring functional groups, which are preferably added to or deleted from the naturally occurring nucleotide (nucleoside) or which substitute the naturally occurring functional groups of a nucleotide (nucleoside). Accordingly, each component of the naturally occurring nucleotide may be modified, namely the base component, the sugar (ribose or desoxyribose) component and/or the phosphate component forming the oligonucleotide's backbone. The phosphate moieties may be substituted by e.g. phosphoramidates, phosphorothioates, peptide nucleotides, methylphosphonates etc., wherein, however, the naturally occurring phosphodiester backbone is still preferred. Preferably, at least 10%, more preferably at least 20%, more preferably at least 30%, more preferably at least 50%, more preferably at least 70% and even more preferably at least 90% of all "X" nucleotides may exhibit properties of an analogue as defined herein, if the immunostimulatory sequence contains at least one analogue at all. The analogues substituting a specific nucleotide type within the core structure element "$X_m$" may be identical, e.g. all cytidine (cytosine) nucleotides (nucleosides) occurring in the core structure element "$X_m$" are formed by a specific cytidine (cytosine) analogue, e.g. 2-thio-cytidine (cytosine), or they may be distinct for a specific nucleotide (nucleosides), e.g. at least two distinct cytidine (cytosine) analogues are contained within the core structure element "$X_m$".

Analogues of guanosine (guanine), uridine (uracil), adenosine (adenine), thymidine (thymine), cytidine (cytosine) include, without implying any limitation, any naturally occurring or non-naturally occurring guanosine (guanine), uridine (uracil), adenosine (adenine), thymidine (thymine) or cytidine (cytosine) that has been altered chemically, for example by acetylation, methylation, hydroxylation, etc., including 1-methyl-adenosine (adenine), 2-methyl-adenosine (adenine), 2-methylthio-N6-isopentenyl-adenosine (adenine), N6-methyl-adenosine (adenine), N6-isopentenyl-adenosine (adenine), 2-thio-cytidine (cytosine), 3-methyl-cytidine (cytosine), 4-acetyl-cytidine (cytosine), 2,6-diaminopurine, 1-methyl-guanosine (guanine), 2-methyl-guanosine (guanine), 2,2-dimethyl-guanosine (guanine), 7-methyl-guanosine (guanine), inosine, 1-methyl-inosine, dihydro-uridine (uracil), 4-thio-uridine (uracil), 5-carboxymethylaminomethyl-2-thio-uridine (uracil), 5-(carboxyhydroxylmethyl)-uridine (uracil), 5-fluoro-uridine (uracil), 5-bromo-uridine (uracil), 5-carboxymethylaminomethyl-uridine (uracil), 5-methyl-2-thio-uridine (uracil), N-uridine (uracil)-5-oxyacetic acid methyl ester, 5-methylaminomethyl-uridine (uracil), 5-methoxyaminomethyl-2-thio-uridine (uracil), 5'-methoxycarbonylmethyl-uridine (uracil), 5-methoxy-uridine (uracil), uridine (uracil)-5-oxyacetic acid methyl ester, uridine (uracil)-5-oxyacetic acid (v), queosine, beta-D-mannosyl-queosine, wybutoxosine, and inosine. The preparation of such analogues is known to a person skilled in the art, for example from U.S. Pat. No. 4,373,071, U.S. Pat. No. 4,401,796, U.S. Pat. No. 4,415,732, U.S. Pat. No. 4,458,066, U.S. Pat. No. 4,500,707, U.S. Pat. No. 4,668,777, U.S. Pat. No. 4,973,679, U.S. Pat. No. 5,047,524, U.S. Pat. No. 5,132,418, U.S. Pat. No. 5,153,319, U.S. Pat. No. 5,262,530 and U.S. Pat. No. 5,700,642. In the case of an analogue as described above, particular preference is given to those analogues of nucleotides (nucleosides) that increase the immunogenity of the nucleic acid molecule of formula (III) (and of formula (I) and (II)) and/or do not interfere with a further modification that has been introduced.

The number of core structure element X in the nucleic acid molecule of formula (III) (and of formula (I) and (II)) is determined by m. m is an integer and is typically at least 3, 4, 5, 6, 7, 8, 9, 10, 11, 12, 13, 14, 15, 16, 17, 18, 19, 20, 20 to 30, 30 to 40, 40 to 50, 50 to 60, 60 to 70, 70 to 80, 80 to 90, 90 to 100, 100 to 150, 150 to 200, or even more, wherein when m=3, X is uridine (uracil) or an analogue thereof, and when m>3, at least 3 or more directly successive uridines (uracils) or an analogue thereof occur in the element X of formula (III) (and of formula (I) and (II)) above. Such a sequence of at least 3 or more directly successive uridines (uracils) is referred to in connection with this application as a "monotonic uridine (uracil) sequence". A monotonic uridine (uracil) sequence typically has a length of at least 3, 4, 5, 6, 7, 8, 9 or 10, 11, 12, 13, 14, 15, 16, 17, 18, 19, 20, 20 to 30, 30 to 40, 40 to 50, 50 to 60, 60 to 70, 70 to 80, 80 to 90, 90 to 100, 100 to 150, 150 to 200 uridines (uracils) or optionally analogues of uridine (uracil) as defined above. Such a monotonic uridine (uracil) sequence occurs at least once in the core structure element X of the nucleic acid molecule of formula (III) (and of formula (I) and (II)). It is therefore possible, for example, for 1, 2, 3, 4, 5 or more monotonic uridine (uracil) sequences having at least 3 or more uridines (uracils) or analogues thereof to occur, which monotonic uridine (uracil) sequences can be interrupted in the core structure element X by at least one guanosine (guanine), adenosine (adenine), thymidine (thymine), cytidine (cytosine) or an analogue thereof, preferably 2, 3, 4, 5 or more. For example, when m=3, $X_m$ is a UUU. When m=4, $X_m$ can be, for example, without implying any limitation, a UUUA, UUUG, UUUC, UUUU, AMU, GUUU or CUUU, etc. When n=10, $X_m$ can be, for example, without implying any limitation, a UUUAAUUUUC (SEQ ID NO: 1341, UUUUGUUUUA (SEQ ID NO: 135), UUUGUUUGUU (SEQ ID NO: 136), UUGUUUUGUU (SEQ ID NO: 137), UUUUUUUUUU (SEQ ID NO: 138), etc. The nucleotides of $X_m$ adjacent to $G_1$ or $G_n$ of the nucleic acid molecule of formula (III) preferably comprise uridine (uracil) or analogues thereof. When m>3, typically at least 50%, preferably at least 60%, 70%, 80%, 90% or even 100%, of the nucleotides of $X_m$ are uridine (uracil) or an analogue thereof, as defined above. The remaining nucleotides of $X_m$ to 100% (where there is less than 100% uridine (uracil) in the sequence $X_m$) are then guanosine (guanine), uridine (uracil), adenosine (adenine), thymidine (thymine), cytidine (cytosine) or an analogue thereof, as defined above.

The immunostimulatory sequence according formula (III) above also contains bordering element N. The bordering element N is typically a nucleic acid sequence having a length of about 4 to 50, preferably of about 4 to 40, more preferably of about 4 to 30 nucleotides (nucleosides), even more preferably of about 4 to 20 nucleotides (nucleosides), wherein the lower limit of these ranges alternatively also may be 5, 6, 7, 8, 9, 10, or more. Preferably, the nucleotides (nucleosides) of each N are independently selected from guanosine (guanine), uridine (uracil), adenosine (adenine), thymidine (thymine), cytidine (cytosine) and/or an analogue thereof. In other words, bordering element N in the nucleic acid molecule of formula (III) according to the present invention may be a sequence, which may be composed of any (random) sequence, available in the art, each N independently selected from guanosine (guanine), uridine (uracil), adenosine (adenine), thymidine (thymine), cytidine (cytosine) and/or an analogue of these nucleotides, or from a homopolymer of these nucleotides (nucleosides), in each case provided, that such a sequence has a length of about 4 to 50, preferably of about 4 to 40, more preferably of about 4 to 30 nucleotides (nucleosides) and even more preferably of about 4 to 30 or 4 to 20 nucleotides (nucleosides) according to the above definition.

According to a specific embodiment, N may be a nucleic acid sequence within the above definitions, wherein the sequence typically comprises not more than 2 identical nucleotides (nucleosides) as defined above in a directly neighboring position, i.e. the sequence typically comprises no stretches of more than two identical nucleotides (nucleosides) selected from adenosine (adenine), cytidine (cytosine), uridine (uracil) and/or guanosine (guanine), and/or an analogue thereof (i.e. a stretch of "aa", "cc", "uu", "gg" and/or an analogue thereof), more preferably no such stretch, i.e. no identical nucleotides (nucleosides) as defined above in a directly neighboring position. Additionally or alternatively, N may be a nucleic acid sequence within the above definitions, wherein the sequence typically comprises a content of adenosine (adenine) or an analogue thereof preferably of about 0 to 50%, 5 to 45%, or to 40%, more preferably of about 15 to 35%, even more preferably of about 20 to 30%, and most preferably of about 25%; a content of uridine (uracil) or an analogue thereof preferably of about 0 to 50%, 5 to 45%, or 10 to 40%, more preferably of about 15 to 35%, even more preferably of about 20 to 30%, and most preferably of about 25%; a content of cytidine (cytosine) or an analogue thereof preferably of about 0 to 50%, 5 to 45%, or 10 to 40%, more preferably of about 15 to 35%, even more preferably of about 20 to 30%, and most preferably of about 25%; a content of guanosine (guanine) or an analogue thereof preferably of about 0 to 50%, 5 to 45%, or 10 to 40%, more preferably of about 15 to 35%, even more preferably of about 20 to 30%, and most preferably of about 25%. Most preferably, N may be a nucleic acid sequence within the above definitions, wherein the sequence typically comprises a content of each adenosine (adenine), guanosine (guanine), cytidine (cytosine) and uridine (uracil) of about 25%. Examples of such sequences of N include e.g. agcu, aguc, augc, acgu, gcua, gcau, gacu, guca, cuag, caug, cagu, cgau, uagc, uacg, ucga, ucag, agcugcua, gcaucaug, caguucga, etc., The number of bordering element N in the nucleic acid molecule of formula (III), i.e. its repetition, is determined by integers u and/or v. Thus, N in the nucleic acid molecule of formula (III) may occur as a (repetitive) bordering element $N_u$ and/or $N_v$, wherein u and/or v may be, independently from each other, an integer from 0 or 1 to 100, more preferably from 0 or 1 to 50, even more preferably from 0 or 1 to 40, and most preferably from 0 or 1 to 30, e.g. 0 or 1 to 5, 10, 20, 25, or 30; or from 5 to 10, 10 to 15, 15 to 20, 20 to 25 or 25 to 30. More preferably, at least one (repetitive) bordering element $N_u$ and/or $N_v$, may be present in formula (III), i.e. either u or v are not 0, more preferably, both (repetitive) bordering elements $N_u$ and/or $N_v$ are present, even more preferably in the above definitions.

Additionally, the combination of core structure elements and bordering elements to the element $N_uG_lX_mG_nN_v$ may occur as repetitive elements according to the immunostimulatory sequence of formula (III), $(N_uG_lX_mG_nN_v)_a$, as defined above, wherein the number of repetitions of the combined element according to formula (III), $(N_uG_lX_mG_nN_v)_a$, is determined by integer a. Preferably, a is an integer from about 1 to 100, 1 to 50, 1 to 20, more preferably an integer from about 1 to 15, most preferably an integer from about 1 to 10. In this context, the repetitive elements $N_uG_lX_mG_nN$, may be equal or different from each other.

According to a particularly preferred embodiment, the immunostimulatory sequence of formula (III) $(N_uG_lX_mG_nN_v)_a$, as defined above, comprises a core structure $G_lX_mG_n$, preferably selected from at least one of the following sequences of SEQ ID NOs: 1-80 as defined above:

Furthermore, immunostimulatory sequences as defined herein may also comprise e.g. a nucleic acid (molecule) of formula (IIIa)

$$(N_uC_lX_mC_nN_v)_a$$

wherein:

C is cytidine (cytosine), uridine (uracil) or an analogue of cytidine (cytosine) or uridine (uracil), preferably cytidine (cytosine) or an analogue thereof;

X is guanosine (guanine), uridine (uracil), adenosine (adenine), thymidine (thymine), cytidine (cytosine) or an analogue of the above-mentioned nucleotides (nucleosides), preferably uridine (uracil) or an analogue thereof;

N is each a nucleic acid sequence having independent from each other a length of about 4 to 50, preferably of about 4 to 40, more preferably of about 4 to 30 or 4 to 20 nucleic acids, each N independently being selected from guanosine (guanine), uridine (uracil), adenosine (adenine), thymidine (thymine), cytidine (cytosine) or an analogue of these nucleotides (nucleosides);

a is an integer from 1 to 20, preferably from 1 to 15, most preferably from 1 to 10;

l is an integer from 1 to 40,
  wherein when l=1, C is cytidine (cytosine) or an analogue thereof,
    when l>1, at least 50% of these nucleotides (nucleosides) are cytidine (cytosine) or an analogue thereof;

m is an integer and is at least 3;
  wherein when m=3, X is uridine (uracil) or an analogue thereof,
    when m>3, at least 3 successive uridines (uracils) or analogues of uridine (uracil) occur;

n is an integer from 1 to 40,
  wherein when n=1, C is cytidine (cytosine) or an analogue thereof,
    when n>1, at least 50% of these nucleotides (nucleosides) are cytidine (cytosine) or an analogue thereof.

u, v may be independently from each other an integer from 0 to 50,
  preferably wherein when u=0, v≥1, or
    when v=0, u≥1;

wherein the nucleic acid molecule of formula (IIIa) has a length of at least 50 nucleotides, preferably of at least 100 nucleotides, more preferably of at least 150 nucleotides, even more preferably of at least 200 nucleotides and most preferably of at least 250 nucleotides.

For formula (IIIa), any of the definitions given above for elements N (i.e. $N_u$ and $N_v$) and X ($X_m$), particularly the core structure as defined above, as well as for integers a, l, m, n, u and v, similarly apply to elements of formula (IIIa) correspondingly, wherein in formula (IIIa) the core structure is defined by $C_lX_mC_n$. The definition of bordering elements $N_u$ and $N_v$ is identical to the definitions given above for $N_u$ and $N_v$.

More particularly, C in the nucleic acid molecule of formula (IIIa) is a nucleotide or deoxynucleotide or comprises a nucleoside, wherein the nucleotide (nucleoside) is typically cytidine (cytosine) or uridine (uracil) or an analogue thereof. In this connection, cytidine (cytosine) or uridine (uracil) nucleotide analogues are defined as non-natively occurring variants of naturally occurring cytidine (cytosine) or uridine (uracil) nucleotides. Accordingly, cytidine (cytosine) or uridine (uracil) analogues are chemically derivatized nucleotides (nucleosides) with non-natively occurring functional groups, which are preferably added to or deleted from the naturally occurring cytidine (cytosine) or uridine (uracil) nucleotide (nucleoside) or which substitute the naturally occurring functional groups of a cytidine (cytosine) or uridine (uracil) nucleotide (nucleoside). Accordingly, each component of the naturally occurring cytidine (cytosine) or uridine (uracil) nucleotide may be modified, namely the base component, the sugar (ribose) component and/or the phosphate component forming the oligonucleotide's backbone. The phosphate moieties may be substituted by e.g. phosphoramidates, phosphorothioates, peptide nucleotides, methylphosphonates etc., wherein the naturally occurring phosphodiester backbone is still preferred.

Accordingly, analogues of cytidine (cytosine) or uridine (uracil) include, without implying any limitation, any naturally occurring or non-naturally occurring cytidine (cytosine) or uridine (uracil) that has been altered chemically, for example by acetylation, methylation, hydroxylation, etc., including, for example, 2-thio-cytidine (cytosine), 3-methyl-cytidine (cytosine), 4-acetyl-cytidine (cytosine), dihydro-uridine (uracil), 4-thio-uridine (uracil), 5-carboxymethylaminomethyl-2-thio-uridine (uracil), 5-(carboxyhydroxylmethyl)-uridine (uracil), 5-fluoro-uridine (uracil), 5-bromo-uridine (uracil), 5-carboxymethylaminomethyl-uridine (uracil), 5-methyl-2-thio-uridine (uracil), N-uridine (uracil)-5-oxyacetic acid methyl ester, 5-methylaminomethyl-uridine (uracil), 5-methoxyaminomethyl-2-thio-uridine (uracil), 5'-methoxycarbonylmethyl-uridine (uracil), 5-methoxy-uridine (uracil), uridine (uracil)-5-oxyacetic acid methyl ester, uridine (uracil)-5-oxyacetic acid (v). The preparation of such analogues is known to a person skilled in the art, for example from U.S. Pat. No. 4,373,071, U.S. Pat. No. 4,401,796, U.S. Pat. No. 4,415,732, U.S. Pat. No. 4,458,066, U.S. Pat. No. 4,500,707, U.S. Pat. No. 4,668,777, U.S. Pat. No. 4,973,679, U.S. Pat. No. 5,047,524, U.S. Pat. No. 5,132,418, U.S. Pat. No. 5,153,319, U.S. Pat. No. 5,262,530 and U.S. Pat. No. 5,700,642, the disclosures of which are incorporated by reference herein in their entirety. In the case of an nucleotide (nucleoside) analogue as described above, preference is given especially to those analogues that increase the immunogenity of the nucleic acid molecule of formula (IIIa) and/or do not interfere with a further modification that has been introduced. At least one cytidine (cytosine) or uridine (uracil) or an analogue thereof can occur in the core structure elements $C_l$ and/or $C_n$, optionally at least 10%, 20%, 30%, 40%, 50%, 60%, 70%, 80% 90% or even 100% of the nucleotides (nucleosides) of the core structure elements $C_l$ and/or $C_n$ are a naturally occurring cytidine (cytosine), a naturally occurring uridine (uracil), and/or an analogue thereof and/or exhibit properties of an analogue thereof as defined herein. Preferably, the core structure element $C_l$ and/or $C_n$ contains at least one analogue of a naturally occurring cytidine (cytosine) and/or a naturally occurring uridine (uracil) at all. Most preferably, all nucleotides (nucleosides) of these core structure elements $C_l$ and/or $C_n$ are analogues, which may—most preferably—be identical analogues for the same type of nucleotides (nucleosides) (e.g. all cytidine (cytosine) nucleotides are provided as 2-thio-cytidine (cytosine)) or they may be distinct (e.g. at least two different cytidine (cytosine) analogues substitute the naturally occurring cytidine (cytosine) nucleotide).

The number of nucleotides (nucleosides) of core structure element C ($C_l$ and/or $C_n$) in the nucleic acid molecule of formula (IIIa) is determined by l and n. l and n, independently of one another, are each an integer from 1 to 90, 1 to 80, 1 to 70, 1 to 60, preferably 1 to 50, yet more preferably 1 to 40, and even more preferably 1 to 30, wherein the lower limit of these ranges may be 1, but alternatively also 2, 3, 4, 5, 6, 7, 8, 9, 10, 11, 12, 13, 14, 15, 16, 17, 18, 19, 20, 21, 22, 23, 24, 25, 26, 27, 28, 29, 30, or even more. Preferably, for each integer, when l and/or n=1, C is cytidine (cytosine) or an analogue thereof, and when l or n>1, at least 50%, more preferably at least 50%, 60%, 70%, 80%, 90% or even 100% of the nucleotides (nucleosides) of core structure element C ($C_l$ and/or $C_n$) are cytidine (cytosine) or an analogue thereof. For example, without implying any limitation, when l or n=4, $C_l$ and/or $C_n$ can be, for example, a CUCU, CCUU, UCUC, UUCC, CUUC, CCCU, CCUC, CUCC, UCCC or CCCC, etc.; when l or n=5, $C_l$ and/or $C_n$ can be, for example, a CCCUU, CCUCU, CUCCU, UCCCU, UCCUC, UCUCC, UUCCC, CUCUC, CCCCU, CCCUC, CCUCC, CUCCC, UCCCC, or CCCCC, etc.; etc. A nucleotide (nucleoside) of core structure elements $C_l$ and/or $C_n$ directly adjacent to $X_m$ in the nucleic acid molecule of formula (IIIa) is preferably not an uridine (uracil) or an analogue thereof. More preferably nucleotides (nucleosides) of core structure elements $C_l$ and/or $C_n$ directly adjacent to $X_m$ in the nucleic acid molecule of formula (IIIa) are at least one cytidine (cytosine) or an analogue thereof, more preferably a stretch of at least 2, 3, 4, 5, 6, 7, 8, 9, 10, 11, 12, 13, 14, 15, 16, 17, 18, 19 or even 20 or more cytidines (cytosines) or an analogue thereof. Additionally, a nucleotide (nucleoside) of core structure elements $C_l$ and/or $C_n$ directly adjacent to N, e.g. $N_u$, and/or $N_v$ (or $N_{w1}$ or $N_{w2}$ as defined below) in the nucleic acid molecule of formula (IIIa) is preferably not an uridine (uracil) or an analogue thereof. More preferably, nucleotides (nucleosides) of core structure elements $C_l$ and/or $C_n$ directly adjacent to N, e.g. $N_u$, and/or $N_v$ (or $N_{w1}$ or $N_{w2}$ as defined below) in the nucleic acid molecule of formula (IIIa) are at least one cytidine (cytosine) or an analogue thereof, more preferably a stretch of at least 2, 3, 4, 5, 6, 7, 8, 9, 10, 11, 12, 13, 14, 15, 16, 17, 18, 19 or even 20 or more cytidines (cytosines) or an analogue thereof. Likewise preferably, for formula (IIIa), when l or n>1, at least 60%, 70%, 80%, 90% or even 100% of the nucleotides of the core structure elements $C_l$ and/or $C_n$ are cytidine (cytosine) or an analogue thereof, as defined above. The remaining nucleotides (nucleosides) to 100% in the core structure elements $C_l$ and/or $C_n$ (when cytidine (cytosine) constitutes less than 100% of these nucleotides (nucleosides)) may then be uridine (uracil) or an analogue thereof, as defined hereinbefore.

X, particularly $X_m$, as a further core structure element in the immunostimulatory sequence according to formula (IIIa), is preferably as defined above for formula (III). The number of core structure element X in the nucleic acid molecule of formula (IIIa) is determined by m. m is an integer and is typically at least 3, 4, 5, 6, 7, 8, 9, 10, 11, 12, 13, 14, 15, 16, 17, 18, 19, 20, 20 to 30, 30 to 40, 40 to 50, 50 to 60, 60 to 70, 70 to 80, 80 to 90, 90 to 100, 100 to 150, 150 to 200, or even more, wherein when m=3, X is uridine (uracil) or an analogue thereof, and when m>3, at least 3 or more directly successive uridines (uracils) or an analogue thereof occur in the element X of formula (IIIa) above. Such a sequence of at least 3 or more directly successive uridines (uracils) is referred to in connection with this application as a "monotonic uridine (uracil) sequence". A monotonic uridine (uracil) sequence typically has a length of at least 3, 4, 5, 6, 7, 8, 9 or 10, 11, 12, 13, 14, 15, 16, 17, 18, 19, 20, 20 to 30, 30 to 40, 40 to 50, 50 to 60, 60 to 70, 70 to 80, 80 to 90, 90 to 100, 100 to 150, 150 to 200 uridines (uracils) or optionally analogues of uridine (uracil) as defined above. Such a monotonic uridine (uracil) sequence occurs at least once in the core structure element X of the nucleic acid molecule of formula (IIIa). It is therefore possible, for example, for 1, 2, 3, 4, 5 or more monotonic uridine (uracil) sequences having at least 3 or more uridines (uracils) or analogues thereof to occur, which monotonic uridine (uracil) sequences can be interrupted in the core structure element X by at least one guanosine (guanine), adenosine (adenine), thymidine (thymine), cytidine (cytosine) or an analogue thereof, preferably 2, 3, 4, 5 or more. For example, when m=3, $X_m$ is a UUU. When m=4, $X_m$ can be, for example, without implying any limitation, a UUUA, UUUG, UUUC, UUUU, AUUU, GUUU or CUUU, etc. When n=10, $X_m$ can be, for example, without implying any limitation, a UUUAAUUUUC (SEQ ID NO: 134), UUUUGUUUUA (SEQ ID NO: 135), UUUGUUUGUU (SEQ ID NO: 1361, UUGUUUUGUU (SEQ ID NO: 137), UUUUUUUUUU (SEQ ID NO: 138), etc. The nucleotides (nucleosides) of $X_m$ adjacent to $C_1$ or $C_n$ of the nucleic acid molecule of formula (IIIa) preferably comprise uridine (uracil) or analogues thereof. When m>3, typically at least 50%, preferably at least 60%, 70%, 80%, 90% or even 100%, of the nucleotides of $X_m$ are uridine (uracil) or an analogue thereof, as defined above. The remaining nucleotides (nucleosides) of $X_m$ to 100% (where there is less than 100% uridine (uracil) in the sequence $X_m$) may then be guanosine (guanine), uridine (uracil), adenosine (adenine), thymidine (thymine), cytidine (cytosine) or an analogue thereof, as defined above.

Likewise, the immunostimulatory sequence according formula (IIIa) above contains a bordering element N, particularly $N_u$ and/or $N_v$, wherein the bordering element N, particularly $N_u$ and/or $N_v$, as well as integers x and y are as defined above.

The element $N_uC_lX_mC_nN_v$ may occur as a repetitive element according to the immunostimulatory sequence of formula (IIIa) $(N_uC_lX_mC_nN_v)_a$, as defined above, wherein the number of repetitions of this element according to formula (IIIa) $(N_uC_lX_mC_nN_v)_a$ is determined by the integer a. Preferably, a is an integer from about 1 to 100, 1 to 50, 1 to 20, more preferably an integer from about 1 to 15, most preferably an integer from about 1 to 10. In this context, the repetitive elements $N_uC_lX_mC_nN_v$ may be equal or different from each other.

According to a particularly preferred embodiment, the immunostimulatory sequence of formula (IIIa) $(N_uC_lX_mC_nN_v)_a$, as defined above, comprises a core structure preferably selected from at least one of the following sequences of SEQ ID NOs: 81-83 as defined above:

The immunostimulatory sequence according to either formula (III) (or (IIIa)), particularly each single repetitive element $N_uG_lX_mG_nN_v$ (or $N_uC_lX_mC_nN_v$) thereof, may be single-stranded, double-stranded or partially double-stranded, etc. as defined for formula (III) in general.

If the immunostimulatory sequence according to either formula (III) (or (IIIa)) is a single-stranded nucleic acid molecule, the sequence is typically single-stranded over its entire length.

Likewise, if the immunostimulatory sequence according to either formula (III) (or (IIIa)) is a double-stranded nucleic acid molecule, the sequence is typically double-stranded over its entire length.

If the immunostimulatory sequence according to either formula (III) (or (IIIa)) is a partially double-stranded nucleic acid molecule, the nucleic acid sequence of a nucleic acid molecule of either formula (III) (or (IIIa)) may be single-stranded in the region outside the core structure $G_lX_mG_n$ (or $C_lX_mC_n$), and double-stranded in the region of said core structure, the core structure $G_lX_mG_n$ (or $C_lX_mC_n$), preferably being selected from at least one of the above defined sequences of SEQ ID NOs: 1-83. Even more preferably, the core structure $G_lX_mG_n$ (or $C_lX_mC_n$) of (either) formula (III) (or (IIIa)) may be double-stranded in such a region of the core structure, wherein a stretch of uridines (uracils) occurs, most preferably over the entire uridine (uracil) stretch or at least 60%, 70%, 80%, 90%, 95%, 98% or 99% thereof.

Alternatively or additionally, if the immunostimulatory sequence according to either formula (III) or (IIIa) is a partially double-stranded nucleic acid molecule, other parts (than the core structure $G_lX_mG_n$) of the immunostimulatory sequence according to formula (III) or (IIIa) as defined above may be double-stranded. E.g., the nucleic acid sequence of a nucleic acid molecule of either formula (III) or (IIIa) may be double-stranded in the region outside the core structure $G_lX_mG_n$ (or $C_lX_mC_n$), e.g. in the bordering elements $N_u$ and/or $N_v$, and single-stranded in the region of said core structure, the core structure $G_lX_mG_n$ (or $C_lX_mC_n$), preferably selected from at least one of the above defined sequences of SEQ ID NOs: 1-83. E.g. at least one of the bordering elements $N_v$ and/or $N_v$ may be double-stranded, whereas the remaining elements of either formula (III) or (IIIa), e.g. the core structure $G_lX_mG_n$ and/or other elements, may remain single-stranded.

Alternatively or additionally, the immunostimulatory sequence according to formula (III) may be selected from a mixture of a single-stranded nucleic acid molecule according to either formula (III) or (IIIa) and a (partially) double-stranded nucleic acid molecule according to either formula (III) (or (IIIa)), preferably in a ratio of about 1:10 to 10:1, more preferably in a ratio of 1:3 to 3:1.

According to a very particularly preferred embodiment, the immunostimulatory sequence according to formula (III) may be selected from e.g. any of the following sequences:

```
from SEQ ID NO: 84:
UAGCGAAGCU CUUGGACCUA GG UUUUU UUUUU UUUUU GGG

UGCGUUCCUA GAAGUACACG

or from SEQ ID NO: 85:
UAGCGAAGCU CUUGGACCUA GG UUUUU UUUUU UUUUU GGG

UGCGUUCCUA GAAGUACACG AUCGCUUCGA GAACCUGGAU

CC AAAAA AAAAA AAAAA CCC ACGCAAGGAU CUUCAUGUGC
```

or from SEQ ID NO: 114 (R820: $(N_{100})_2$)

```
GGGAGAAAGCUCAAGCUUGGAGCAAUGCCCGCACAUUGAGGAAACCGAGU

UGCAUAUCUCAGAGUAUUGGCCCCCGUGUAGGUUAUUCUUGACAGACAGU

GGAGCUUAUUCACUCCCAGGAUCCGAGUCGCAUACUACGGUACUGGUGAC

AGACCUAGGUCGUCAGUUGACCAGUCCGCCACUAGACGUGAGUCCGUCAA

AGCAGUUAGAUGUUACACUCUAUUAGAUC
```

or from SEQ ID NO: 115 (R719: $(N_{100})_5$)

```
GGGAGAAAGCUCAAGCUUGGAGCAAUGCCCGCACAUUGAGGAAACCGAGU

UGCAUAUCUCAGAGUAUUGGCCCCCGUGUAGGUUAUUCUUGACAGACAGU

GGAGCUUAUUCACUCCCAGGAUCCGAGUCGCAUACUACGGUACUGGUGAC

AGACCUAGGUCGUCAGUUGACCAGUCCGCCACUAGACGUGAGUCCGUCAA

AGCAGUUAGAUGUUACACUCUAUUAGAUCUCGGAUUACAGCUGGAAGGAG

CAGGAGUAGUGUUCUUGCUCUAAGUACCGAGUGUGCCCAAUACCCGAUCA

GCUUAUUAACGAACGGCUCCUCCUCUUAGACUGCAGCGUAAGUGCGGAAU

CUGGGGAUCAAAUUACUGACUGCCUGGAUUACCCUCGGACAUAUAACCUU

GUAGCACGCUGUUGCUGUAUAGGUGACCAACGCCCACUCGAGUAGACCAG

CUCUCUUAGUCCGGACAAUGAUAGGAGGCGCGGUCAAUCUACUUCUGGCU

AGUUAAGAAUAGGCUGCACCGACCUCUAUAAGUAGCGUGUCCUCUAG
```

or from SEQ ID NO: 116 (R720: $(N_{100})_{10}$)

```
GGGAGAAAGCUCAAGCUUGGAGCAAUGCCCGCACAUUGAGGAAACCGAGU

UGCAUAUCUCAGAGUAUUGGCCCCCGUGUAGGUUAUUCUUGACAGACAGU

GGAGCUUAUUCACUCCCAGGAUCCGAGUCGCAUACUACGGUACUGGUGAC

AGACCUAGGUCGUCAGUUGACCAGUCCGCCACUAGACGUGAGUCCGUCAA

AGCAGUUAGAUGUUACACUCUAUUAGAUCUCGGAUUACAGCUGGAAGGAG

CAGGAGUAGUGUUCUUGCUCUAAGUACCGAGUGUGCCCAAUACCCGAUCA

GCUUAUUAACGAACGGCUCCUCCUCUUAGACUGCAGCGUAAGUGCGGAAU

CUGGGGAUCAAAUUACUGACUGCCUGGAUUACCCUCGGACAUAUAACCUU
```

-continued

GUAGCACGCUGUUGCUGUAUAGGUGACCAACGCCCACUCGAGUAGACCAG

CUCUCUUAGUCCGGACAAUGAUAGGAGGCGCGGUCAAUCUACUUCUGGCU

AGUUAAGAAUAGGCUGCACCGACCUCUAUAAGUAGCGUGUCCUCUAGAGC

UACGCAGGUUCGCAAUAAAAGCGUUGAUUAGUGUGCAUAGAACAGACCUC

UUAUUCGGUGAAACGCCAGAAUGCUAAAUUCCAAUAACUCUUCCCAAAAC

GCGUACGGCCGAAGACGCGCUUAUCUUGUGUACGUUCUCGCACAUGGA

AGAAUCAGCGGGCAUGGUGGUAGGGCAAUAGGGGAGCUGGGUAGCAGCGA

AAAAGGGCCCCUGCGCACGUAGCUUCGCUGUUCGUCUGAAACAACCCGGC

AUCCGUUGUAGCGAUCCCGUUAUCAGUGUUAUUCUUGUGCGCACUAAGAU

UCAUGGUGUAGUCGACAAUAACAGCGUCUUGGCAGAUUCUGGUCACGUGC

CCUAUGCCCGGGCUUGUGCCUCUCAGGUGCACAGCGAUACUUAAAGCCUU

CAAGGUACUCGACGUGGGUACCGAUUCGUGACACUUCCUAAGAUUAUUCC

ACUGUGUUAGCCCCGCACCGCCGACCUAAACUGGUCCAAUGUAUACGCAU

UCGCUGAGCGGAUCGAUAAUAAAAGCUUGAAUU or from SEQ ID NO: 117 (R821: $(N_{40}U_{20}N_{40})_2$)

GGGAGAAAGCUCAAGCUUAUCCAAGUAGGCUGGUCACCUGUACAACGUAG

CCGGUAUUUUUUUUUUUUUUUUUUUUUUGACCGUCUCAAGGUCCAAGUUA

GUCUGCCUAUAAAGGUGCGGAUCCACAGCUGAUGAAAGACUUGUGCGGUA

CGGUUAAUCUCCCCUUUUUUUUUUUUUUUUUUUUUAGUAAAUGCGUCUAC

UGAAUCCAGCGAUGAUGCUGGCCCAGAUC or from SEQ ID NO: 118 (Seq. R722: $(N_{40}U_{20}N_{40})_5$)

GGGAGAAAGCUCAAGCUUAUCCAAGUAGGCUGGUCACCUGUACAACGUAG

CCGGUAUUUUUUUUUUUUUUUUUUUUUUGACCGUCUCAAGGUCCAAGUUA

GUCUGCCUAUAAAGGUGCGGAUCCACAGCUGAUGAAAGACUUGUGCGGUA

CGGUUAAUCUCCCCUUUUUUUUUUUUUUUUUUUUUAGUAAAUGCGUCUAC

UGAAUCCAGCGAUGAUGCUGGCCCAGAUCUUCGACCACAAGUGCAUAUAG

UAGUCAUCGAGGGUCGCCUUUUUUUUUUUUUUUUUUUUUUUGGCCCAGUU

CUGAGACUUCGCUAGAGACUACAGUUACAGCUGCAGUAGUAACCACUGCG

GCUAUUGCAGGAAAUCCCGUUCAGGUUUUUUUUUUUUUUUUUUUUUCCGC

UCACUAUGAUUAAGAACCAGGUGGAGUGUCACUGCUCUCGAGGUCUCACG

AGAGCGCUCGAUACAGUCCUUGGAAGAAUCUUUUUUUUUUUUUUUUUUUU

UUGUGCGACGAUCACAGAGAACUUCUAUUCAUGCAGGUCUGCUCUA or from SEQ ID NO: 119 (R723: $(N_{40}U_{20}N_{40})_{10}$):

GGGAGAAAGCUCAAGCUUAUCCAAGUAGGCUGGUCACCUGUACAACGUAG

CCGGUAUUUUUUUUUUUUUUUUUUUUUUGACCGUCUCAAGGUCCAAGUUA

GUCUGCCUAUAAAGGUGCGGAUCCACAGCUGAUGAAAGACUUGUGCGGUA

CGGUUAAUCUCCCCUUUUUUUUUUUUUUUUUUUUUAGUAAAUGCGUCUAC

UGAAUCCAGCGAUGAUGCUGGCCCAGAUCUUCGACCACAAGUGCAUAUAG

UAGUCAUCGAGGGUCGCCUUUUUUUUUUUUUUUUUUUUUUUGGCCCAGUU

CUGAGACUUCGCUAGAGACUACAGUUACAGCUGCAGUAGUAACCACUGCG

GCUAUUGCAGGAAAUCCCGUUCAGGUUUUUUUUUUUUUUUUUUUUUCCGC

UCACUAUGAUUAAGAACCAGGUGGAGUGUCACUGCUCUCGAGGUCUCACG

-continued

AGAGCGCUCGAUACAGUCCUUGGAAGAAUCUUUUUUUUUUUUUUUUUUUU

UUGUGCGACGAUCACAGAGAACUUCUAUUCAUGCAGGUCUGCUCUAGAAC

GAACUGACCUGACGCCUGAACUUAUGAGCGUGCGUAUUUUUUUUUUUUUU

UUUUUUUUUCCUCCCAACAAAUGUCGAUCAAUAGCUGGGCUGUUGGAGAC

GCGUCAGCAAAUGCCGUGGCUCCAUAGGACGUGUAGACUUCUAUUUUUUU

UUUUUUUUUUUUUUCCCGGGACCACAAAUAAUAUUCUUGCUUGGUUGGGC

GCAAGGGCCCCGUAUCAGGUCAUAAACGGGUACAUGUUGCACAGGCUCCU

UUUUUUUUUUUUUUUUUUUUUUCGCUGAGUUAUUCCGGUCUCAAAAGACG

GCAGACGUCAGUCGACAACACGGUCUAAAGCAGUGCUACAAUCUGCCGUG

UUCGUGUUUUUUUUUUUUUUUUUUUUGUGAACCUACACGGCGUGCACUGU

AGUUCGCAAUUCAUAGGGUACCGGCUCAGAGUUAUGCCUUGGUUGAAAAC

UGCCCAGCAUACUUUUUUUUUUUUUUUUUUUUCAUAUUCCCAUGCUAAGC

AAGGGAUGCCGCGAGUCAUGUUAAGCUUGAAUU

According to another very particularly preferred embodiment, the immunostimulatory sequence according to formula (IIIa) may be selected from e.g. any of the following sequences:

(SEQ ID NO: 86)

UAGCGAAGCU CUUGGACCUA CC UUUUU UUUUU UUUUU CCC

UGCGUUCCUA GAAGUACACG or (SEQ ID NO: 87)

UAGCGAAGCU CUUGGACCUA CC UUUUU UUUUU UUUUU CCC

UGCGUUCCUA GAAGUACACG AUCGCUUCGA GAACCUGGAU

GG AAAAA AAAAA AAAAA GGG ACGCAAGGAU CUUCAUGUGC

According to one preferred embodiment, the immunostimulatory sequence according to formula (III) (or (IIIa)) as defined above may be modified with a poly(X) sequence (modifying element). Such immunostimulatory sequences may comprise e.g. a nucleic acid molecule according to formula (IV):

$$poly(IV)_s(N_uG_lX_mG_nN_v)_apoly(IV)_t,$$

wherein the nucleic acid molecule of formula (IV) likewise has a length of at least 50 nucleotides, preferably of at least 100 nucleotides, more preferably of at least 150 nucleotides, even more preferably of at least 200 nucleotides and most preferably of at least 250 nucleotides.

In an immunostimulatory sequence according to formula (IV), the elements G, X and N, particularly, the core structure $G_lX_mG_n$, and the elements $N_u$ and $N_v$, as well as the integers a, l, m, n, u and v are as defined above for formula (III). In the context of the present invention, a modifying element poly(IV), particularly $poly(IV)_s$ and/or $poly(IV)_t$, of an immunostimulatory sequence according to formula (IV), is typically a single-stranded, a double-stranded or a partially double-stranded nucleic acid sequence, e.g a DNA or RNA sequence as defined above in general. Preferably, the modifying element poly(IV), particularly $poly(IV)_s$ and/or $poly(IV)_t$, is a homopolymeric stretch of nucleic acids, wherein X may be any nucleotide or deoxynucleotide or comprises a nucleoside as defined above for X of an immunostimulatory sequence according to formula (III) or (IIIa).

Preferably, X may selected independently for each poly(IV), particularly poly$(IV)_s$ and/or poly$(IV)_t$, from a nucleotide or deoxynucleotide or comprises a nucleoside, wherein the nucleotide (nucleoside) is selected from guanosine (guanine), uridine (uracil), adenosine (adenine), thymidine (thymine), cytidine (cytosine), inosine or an analogue of these nucleotides, e.g. from a single-stranded stretch of cytidines (cytosines) (poly(C)), of guanosine (guanine)s (poly(G)), of adenosine (adenine)s (poly(A)), of uridines (uracils) (poly (U)), of inosines (poly(III)), etc. or from a homopolymeric double-stranded stretch of inosines and cytidines (cytoines) (poly(III:C)), of adenosine (adenine) and uridines (uracils) (poly(A:U)), etc., wherein the homopolymeric sequence, particularly poly(III:C) and/or poly(A:U), may be coupled to the sequence $(N_uG_lX_mG_nN_v)_a$ of the nucleic acid molecule according to formula (IV) via any of its strands, e.g. either using the poly-C, the poly-I, the poly-A or the poly-U sequence. The length of modifying element poly(IV), particularly poly$(IV)_s$ and/or poly$(IV)_t$, of the immunostimulatory sequence of formula (IV) is determined by integers s and/or t, wherein s and/or t, independent from each other, may be an integer from about 5 to 100, preferably about 5 to 70, more preferably about 5 to 50, even more preferably about 5 to 30 and most preferably about 5 to 20.

According to a particularly preferred embodiment, a nucleic acid molecule according to formula (IV) as defined above, may specifically comprise e.g. a nucleic acid molecule according to formula (IVa), $$poly(X)(N_uG_lX_mG_nN_v)_a,$$

or a nucleic acid molecule according to formula (IVb), $$poly(X)(N_uG_lX_mG_nN_v)_a poly(X),$$

wherein any of these nucleic acid molecules of formulas (IVa) or (IVb) likewise has a length of at least 50 nucleotides, preferably of at least 100 nucleotides, more preferably of at least 150 nucleotides, even more preferably of at least 200 nucleotides and most preferably of at least 250 nucleotides. Similarly, all other definitions apply as set forth for formula (IV) or (III) above. Likewise, said formulas (IV), (IVa) and (IVb) may be defined on basis of a formula according to formula (IIIb), i.e. introducing the core structure $C_lX_mC_n$.

More preferably, poly(X) in an immunostimulatory sequence according to either formula (IV), (IVa) and/or (IVb) may be selected from a poly(IV) as defined above, more preferably from poly(I:C) and/or from poly(A:U). These modifying elements poly(X), particularly poly(I:C) and/or poly(A:U), may be coupled to the sequence according to formula (IV), (IVa) and/or (IVb) via any of its strands, e.g. either using the poly-C, the poly-G, the poly-I, the poly-A or the poly-U sequence.

Similarly as defined above for formula (III) or (IIIa), the immunostimulatory sequence according to either formula (IV), (IVa) and/or (IVb) may be a single-stranded, a double-stranded or a partially double-stranded nucleic acid molecule, as defined above.

If the immunostimulatory sequence according to formula (IV), (IVa) and/or (IVb) is a single-stranded nucleic acid molecule, the sequence is typically single-stranded over its entire length.

Likewise, if the immunostimulatory sequence according to either formula (IV), (IVa) and/or (IVb) is a double-stranded nucleic acid molecule, the sequence is typically double-stranded over its entire length.

If the immunostimulatory sequence according to either formula (IV), (IVa) and/or (IVb) is a partially double-stranded nucleic acid molecule, the nucleic acid sequence of a nucleic acid molecule of either formula (IV), (IVa) and/or (IVb) may be single-stranded in the region outside the core structure $G_lX_mG_n$, and double-stranded in the region of said core structure, the core structure $G_lX_mG_n$, preferably being selected from at least one of the above defined sequences of SEQ ID NOs: 1-80 or SEQ ID NOs: 81 to 83. Even more preferably, the core structure $G_lX_mG_n$ (or $C_lX_mC_n$) of either formula (III) (or (IIIa)) may be double-stranded in such a region of the core structure, wherein a stretch of uridines (uracils) occurs, most preferably over the entire uridine (uracil) stretch or at least 60%, 70%, 80%, 90%, 95%, 98 or 99% thereof.

Alternatively or additionally, if the immunostimulatory sequence according to either formula (IV), (IVa) and/or (IVb) is a partially double-stranded nucleic acid molecule, other parts (than the core structure $G_lX_mG_n$) of the immunostimulatory sequence according to either formula (IV), (IVa) and/or (IVb) as defined above may be double-stranded. E.g., the nucleic acid sequence of a nucleic acid molecule of either formula (IV), (IVa) and/or (IVb) may be double-stranded in the region outside the core structure $G_lX_mG_n$, e.g. in the bordering elements $N_u$ and/or $N_v$, and/or in the modifying element poly(X), e.g. poly(X), and or poly(X), (such as e.g. a poly(I:C) or poly(A:U) sequence), and e.g. single-stranded in the region of said core structure, the core structure $G_lX_mG_n$, preferably being selected from at least one of the above defined sequences of SEQ ID NOs: 1-83. E.g. at least one of the bordering elements $N_u$ and/or $N_v$, and/or at least one of the modifying elements poly(IV), e.g. poly$(IV)_s$ and or poly$(IV)_t$, may be double-stranded, whereas the remaining elements of either formula (IV), (IVa) and/or (IVb), e.g. the core structure $G_lX_mG_n$ and/or other elements, may remain single-stranded.

Alternatively or additionally a mixture of a single-stranded nucleic acid molecule according to either formula (IV), (IVa)) and/(IVb) and a (partially) double-stranded nucleic acid molecule according to either formula (IV), (IVa)) and/(IVb), preferably in a ratio of about 1:10 to 10:1, more preferably in a ratio of 1:3 to 3:1.

According to a particularly preferred embodiment, the immunostimulatory sequence according to either formula (IV), (IVa) and/or (IVb) may be selected from e.g. any of the following sequences:

```
                                              (SEQ ID NO: 88)
CCCCCCCCCC CCCCCCCCCC GG UUUUU UUUUU UUUUU GGG

                                              (SEQ ID NO: 89)
CCCCCCCCCC CCCCCCCCCC GG UUUUU UUUUU UUUUU GGG

IIIIIIIIII IIIIIIIIII

                                              (SEQ ID NO: 90)
CCCCCCCCCC CCCCCCCCCC GG UUUUU UUUUU UUUUU GGG

                         AAAAA AAAAA AAAAA

                                              (SEQ ID NO: 91)
CCCCCCCCCC CCCCCCCCCC GG UUUUU UUUUU UUUUU GGG

GGGGGGGGGG GGGGGGGGGG CC AAAAA AAAAA AAAAA CCC

                                              (SEQ ID NO: 92)
CCCCCCCCCC CCCCCCCCCC UAGCGAAGCU CUUGGACCUA GG

UUUUU UUUUU UUUUU GGG UGCGUUCCUA GAAGUACACG
```

-continued

```
CCCCCCCCCC CCCCCCCCCC GG UUUUU UUUUU UUUUU GGG

UGCGUUCCUA GAAGUACACG GGGGGGGGGG GGGGGGGGGG CC

AAAAA AAAAA AAAAA CCC ACGCAAGGAU CUUCAUGUGC

                                   (SEQ ID NO: 93)
UAGCGAAGCU CUUGGACCUA

AUCGCUUCGA GAACCUGGAU

CCCCCCCCCC CCCCCCCCCC GG UUUUU UUUUU UUUUU GGG

UGCGUUCCUA GAAGUACACG

              CC AAAAA AAAAA AAAAA CCC

ACGCAAGGAU CUUCAUGUGC

                                   (SEQ ID NO: 94)
UAGCGAAGCU CUUGGACCUA

AUCGCUUCGA GAACCUGGAU
```

An immunostimulatory sequence according to formula (III) (or (IIIa)) as defined above may also be modified by inserting a stem or a stem loop, e.g. leading to a nucleic acid molecule according to formula (Va), $(N_u \text{ stem1 } G_l X_m G_n \text{ stem2 } N_v)_a$, or to a nucleic acid molecule according to formula (Vb), $(N_u G_l X_m G_n N_v)_a \text{ stem1 } N_{w1} \text{ stem2 } N_{w2}$, wherein the nucleic acid molecule of either formula (Va) and/or (Vb) has a length of at least 100 nucleotides, more preferably of at least 150 nucleotides, even more preferably of at least 200 nucleotides and most preferably of at least 250 nucleotides. Likewise, said formulas (Va) and (Vb) may be defined on basis of formula (IIIb), i.e. by introducing the core structure $C_l X_m C_n$.

Particularly, the immunostimulatory sequences of either formula (Va) and/or (Vb) represent variants of formula (III) as defined above. In a nucleic acid according to any of formulas (Va) and/or (Vb), the bordering elements N, i.e. $N_u$ and/or $N_v$, bordering the core structure $G_l X_m G_n$, are further augmented by at least one stem or stem loop structure, preferably consisting of single stem loop elements stem1 and stem2. In the immunostimulatory sequences according to any of formulas (Va) and/or (Vb) as defined above, the elements G, X and N, particularly, the core structure $G_l X_m G_n$, and the integers a, l, m, n, u and v are as defined above. More preferably integer a=1. Optionally u and/or v may be 0. Additionally, elements $N_{w1}$ and $N_{w2}$, adjacent to stem loop elements stem1 and stem2, represent further bordering elements, which are defined as described above for bordering elements $N_u$ and/or $N_v$. Particularly, bordering element N in general is as described above for N in formula (III) above, and integers w1 and w2 are independently selected from each other and are defined as above in formula (III) for integers u and/or v.

In this context, a stem or stem loop structure is an intramolecular base pairing that can occur in single-stranded DNA or, more commonly, in RNA. The structure is also known as a hairpin or hairpin loop. It occurs when two regions of the same molecule, e.g. stem loop elements stem1 and stem2, usually palindromic sequence elements in nucleic acid sequences, form base-pairs with each other, leading to (a double helix that ends in) an unpaired loop. The unpaired loop thereby typically represents a region of the nucleic acid, which shows no or nearly no identity or homology with the sequence of either stem1 or stem2 and is thus not capable of base pairing with any of these stem loop elements. The resulting lollipop-shaped structure is a key building block of many RNA secondary structures. The formation of a stem-loop structure is thus dependent on the stability of the resulting helix and loop regions, wherein the first prerequisite is typically the presence of a sequence that can fold back on itself to form a paired double helix. The stability of paired stem loop elements is determined by the length, the number of mismatches or bulges it contains (a small number of mismatches is typically tolerable, especially in a long helix), and the base composition of the paired region. E.g., pairings between guanosine (guanine) and cytidine (cytosine) may be more preferred in such sequences, since they have three hydrogen bonds and are more stable compared to adenosine (adenine)-uridine (uracil) pairings, which have only two. In RNA, guanosine (guanine)-uridine (uracil) pairings featuring two hydrogen bonds may thus be favorable. The stability of the loop also influences the formation of the stem-loop structure. "Loops" (i.e. only the loop not containing stem loop elements stem1 and stem2) that are less than three bases long are sterically less preferable. However, stems, i.e. formations which show no (defined) loop but just an unpaired region between stem1 and stem2 may also be included. In the context of the present invention, optimal loop length tends to be about 4-100 bases long, more preferably 4 to 50 or even 4 to 30 or even 4 to 20 bases.

Hence, in the context of an immunostimulatory sequence according to any of formulas (Va) and/or (Vb), stem loop elements stem1 and stem2 typically represent parts of one stem or stem loop structure, wherein the stem or stem loop structure may be formed by stem loop elements stem1 and stem2, and a loop may be formed by a sequence, which is located between these stem loop elements. The stem or stem loop may have the form of a helix in the base-paired region. Each stem loop element stem1 and stem2, is preferably a nucleic acid as defined above, more preferably an RNA, and most preferably a single-stranded RNA, wherein any of nucleotides (nucleosides) or analogs as defined above for core structure element X may be used as a nucleotides (nucleosides) for either stem1 and/or stem2. Additionally, stem loop element stem1 represents a palindromic sequence of stem loop element stem2. Both sequences are therefore preferably capable of base pairing with each other and thus together form basis for a stem or stem loop.

Therefore, stem loop elements stem1 or stem2 may be selected pairwise from any nucleic acid sequence, provided that stem loop elements stem1 or stem2 are palindromic to each other, i.e. that one sequence is equal to the other (complementary) sequence read backwards or shows a identity or homology to this sequence of at least 90%, more preferably of at least 95%, and most preferably of at least 99% to the other sequence, when read backwards. Such palindromic sequences stem1 and stem2 may be formed each by a nucleic acid sequence having a length of about 5 to 50, more preferably about 5 to 40 and most preferably about 5 to 30 nucleic acids, selected from adenosine (adenine), guanosine (guanine), cytidine (cytosine), uridine (uracil), thymidine (thymine), or an analogue thereof as defined herein.

Exemplary sequences for stem loop elements stem1 and stem2 may include e.g.:

```
a) for stem1:
UAGCGAAGCUCUUGGACCUA      (SEQ ID NO: 95)

for stem2:
UAGGUCCAAGAGCUUCGCUA      (SEQ ID NO: 96)

b) for stem1:
UAGGUCCAAGAGCUUCGCUA      (SEQ ID NO: 96)
```

-continued

```
for stem2:
UAGCGAAGCUCUUGGACCUA      (SEQ ID NO: 95)

c) for stem1:
GCCGCGGGCCG               (SEQ ID NO: 97)

for stem2:
CGGCCCGCGGC               (SEQ ID NO: 98)

d) for stem1:
CGGCCCGCGGC               (SEQ ID NO: 98)

for stem2:
GCCGCGGGCCG               (SEQ ID NO: 97)

e) for stem1:
GACACGGUGC                (SEQ ID NO: 99)

for stem2:
GCACCGUGCA                (SEQ ID NO: 100)

f) for stem1:
GCACCGUGCA                (SEQ ID NO: 100)

for stem2:
GACACGGUGC                (SEQ ID NO: 99)

g) for stem1:
ACCUAGGU                  (SEQ ID NO: 101)

for stem2:
ACCUAGGU                  (SEQ ID NO: 101)

h) for stem1:
UGGAUCCA                  (SEQ ID NO: 102)

for stem2:
UGGAUCCA                  (SEQ ID NO: 102)

i) for stem1:
CCUGC                     (SEQ ID NO: 103)

for stem2:
GCAGG                     (SEQ ID NO: 104)

j) for stem1:
GCAGG                     (SEQ ID NO: 105)

for stem2:
CCUGC                     (SEQ ID NO: 106)
```

etc.

According to one first alternative, the core structure $G_lX_mG_n$ may be located within the stem loop structure, i.e. the core structure $G_lX_mG_n$ may be located between stem loop elements stem1 and stem2, thereby preferably forming a loop. Such a nucleic acid molecule is resembled by formula (Va), having the composition ($N_u$ stem1 $G_lX_mG_n$ stem2 $N_v$)$_a$, as defined above. When u and/or v=0, and a=1 formula (Va) may lead to a specific nucleic acid molecule "stem1 $G_lX_mG_n$ stem2", which is also incorporated by the present invention.

According to another alternative, the core structure $G_lX_mG_n$ may be located outside the stem loop structure, wherein likewise stem loop elements stem1 and stem2 may be separated from each other by a sequence, preferably a bordering element N, e.g. $N_{w1}$ or $N_{w2}$, which then may form a loop structure upon base pairing of stem loop elements stem1 and stem2. Additionally, stem loop elements 1 and/or 1, adjacent to the core structure $G_lX_mG_n$ may be separated from the core structure $G_lX_mG_n$ by a further bordering element, e.g. $N_{w1}$ or $N_{w2}$. According to the present invention, such a nucleic acid is resembled by formula (Vb), having the composition ($N_uG_lX_mG_n$ stem1 $N_{w1}$ stem2 $N_{w2}$, as defined above.

The immunostimulatory sequence according to either formula (Va) and/or (Vb) may be single-stranded, or partially double-stranded. If the immunostimulatory sequence according to either formula (Va) and/or (Vb) is a single-stranded nucleic acid molecule, the sequence is typically single-stranded over its entire length. If the immunostimulatory sequence according to either formula (Va) and/or (Vb) is a partially double-stranded nucleic acid molecule, the nucleic acid molecule of either formula (Va) and/or (Vb) preferably may be single-stranded in the region of the stem loop elements stems and stem2 and in the regions of the loop formed by either the core structure $G_lX_mG_n$ or by any other element, e.g. $N_{w1}$ or $N_{w2}$. Elements positioned outside the stem loop elements stem1 and stem2 and in the regions of the loop formed by either the core structure $G_lX_mG_n$ or by any other element, e.g. $N_{w1}$ or $N_{w2}$, may then be, independent from each other, single or double-stranded. Alternatively or additionally a mixture of a single-stranded or partially double-stranded nucleic acid molecule according to either formula (Va) or (Vb) and a (partially) double-stranded nucleic acid molecule according to either formula (Va) or (Vb), preferably in a ratio of about 1:10 to 10:1, more preferably in a ratio of 1:3 to 3:1.

According to a very particularly preferred embodiment, the immunostimulatory sequence according to either formula (Va) and/or (Vb), respectively, may be selected from e.g. any of the following sequences:

(SEQ ID NO: 107)
UAGCGAAGCU CUUGGACCUA GG UUUUU UUUUU UUUUU GGG
UAGGUCCAAG AGCUUCGCUA (SEQ ID NO: 108)
UAGCGAAGCU CUUGGACCUA GG UUUUU UUUUU UUUUU GGG
UGCGUUCCUA GAAGUACACG GCCGCGGGCCG UGCGUUCCUA
GAAGUACACG CGGCCCGCGGC UGCGUUCCUA GAAGUACACG (stem1 and stem2 are underlined, the core structure $G_lX_mG_n$ is written in bold);

The immunostimulatory sequence of formula (I), (II), (III), (IIIa), (IV), (IVa), (IVb), (Va) and/or (Vb) as defined above, is typically a nucleic acid, which may be in the form of any DNA or RNA, preferably, without being limited thereto, a circular or linear DNA or RNA, a single- or a double-stranded DNA or RNA (which may also be regarded as an DNA or RNA due to non-covalent association of two single-stranded DNAs or RNAs) or a partially double-stranded DNA or RNA (which is typically formed by a longer and at least one shorter single-stranded DNA or RNA molecule or by at least two single-stranded DNA or RNA-molecules, which are about equal in length, wherein one or more single-stranded DNA or RNA molecules are in part complementary to one or more other single-stranded DNA or RNA molecules and thus form a double-stranded RNA in this region), e.g. a (partially) single-stranded DNA or RNA, mixed with regions of a (partially) double-stranded DNA or RNA. Preferably, the nucleic acid molecule of formula (I), (II), (III), (IIIa), (IV), (IVa), (IVb), (Va) and/or (Vb) as defined above may be in the form of a single- or a double-stranded DNA or RNA, more preferably a partially double-stranded DNA or RNA. It is also preferred that the immunostimulatory sequence of formula (I), (II), (III), (IIIa), (IV), (IVa), (IVb), (Va) and/or (Vb) as defined above is in the form of a mixture of a single-stranded nucleic and double stranded DNA or RNA.

It is particularly advantageous, if the immunostimulatory sequence of formula (I), (II), (III), (IIIa), (IV), (IVa), (IVb), (Va) and/or (Vb) as defined above is a partially double-stranded nucleic acid molecule, since such a (partially double-stranded) immunostimulatory sequence according to formula (I), (II), (III), (IIIa), (IV), (IVa), (IVb), (Va) and/or (Vb) as defined above), can positively stimulate the innate immune response in a patient to be treated by addressing the PAMP-(pathogen associated molecular pattern) receptors for single-stranded RNA (TLR-7 and TLR-8) as well as the PAMP-receptors for double-stranded RNA (TLR-3, RIG-I and MDA-5). Receptors TLR-3, TLR-7 and TLR-8 are located in the endosome and are activated by RNA taken up by the endosome. In contrast, RIG-I and MDA-5 are cytoplasmic receptors, which are activated by RNA, which was directly taken up into the cytoplasm or which has been released from the endosomes (endosomal release or endosomal escape). Accordingly, any partially double-stranded immunostimulatory sequence of formula (I), (II), (III), (IIIa), (IV), (IVa), (IVb), (Va) and/or (Vb) as defined above is capable of activating different signal cascades of immunostimulation and thus leads to an innate immune response or enhances such a response significantly.

Nucleic acid molecules of either formula (I), (II), (III), (IIIa), (IV), (IVa), (IVb), (Va) and/or (Vb) as defined above, may be prepared using any method known in the art, including synthetic methods such as e.g. solid phase synthesis, as well as in vitro methods such as in vitro transcription reactions. Preferably, an in vitro transcription is used for preparation of the immunostimulatory sequences. As surprisingly found by the inventors of the present invention, nucleic acid molecules of either formula (I), (II), (III), (IIIa), (IV), (IVa), (IVb), (Va) and/or (Vb) as defined above show an even better stimulation of the innate immune system, when prepared by an in vitro transcription due to its 5'-phosphate, when compared to nucleic acid molecules of either formula (I), (II), (III), (IIIa), (IV), (IVa), (IVb), (Va) and/or (Vb) prepared by synthetic methods. Such a stimulation of the innate immune system is, without being bound thereto, contributed to the activation of the receptor RIG-1. Accordingly, nucleic acid molecules of either formula (I), (II), (III), (IIIa), (IV), (IVa), (IVb), (Va) and/or (Vb) as defined above are particularly preferred, when prepared by an in vitro transcription reaction.

Furthermore, (classes of) RNA molecules, which may be used for the at least one (m)RNA of the adjuvant component of the inventive immunostimulatory composition, may include any other RNA capable of eliciting an immune response. Without being limited thereto, such an immunostimulatory RNA may include ribosomal RNA (rRNA), transfer RNA (tRNA), messenger RNA (mRNA), and viral RNA (vRNA).

According to a third embodiment, the at least one (m)RNA of the adjuvant component of the inventive immunostimulatory composition may be an siRNA. An siRNA is of interest particularly in connection with the phenomenon of RNA interference. Attention was drawn to the phenomenon of RNA interference in the course of immunological research. In recent years, an RNA-based defence mechanism has been discovered, which occurs both in the kingdom of the fungi and in the plant and animal kingdom and acts as an “immune system of the genome”. The system was originally described in various species independently of one another, first in *C. elegans*, before it was possible to identify the underlying mechanisms of the processes as being identical: RNA-mediated virus resistance in plants, PTGS (posttranscriptional gene silencing) in plants, and RNA interference in eukaryotes are accordingly based on a common procedure. The in vitro technique of RNA interference (RNAi) is based on double-stranded RNA molecules (dsRNA), which trigger the sequence-specific suppression of gene expression (Zamore (2001) Nat. Struct. Biol. 9: 746-750; Sharp (2001) Genes Dev. 5:485-490: Hannon (2002) Nature 41: 244-251). In the transfection of mammalian cells with long dsRNA, the activation of protein kinase R and RnaseL brings about unspecific effects, such as, for example, an interferon response (Stark et al. (1998) Annu. Rev. Biochem. 67: 227-264; He and Katze (2002) Viral Immunol. 15: 95-119). Recently, dsRNA molecules have also been used in vivo (McCaffrey et al. (2002), Nature 418: 38-39; Xia et al. (2002), Nature Biotech. 20: 1006-1010; Brummelkamp et al. (2002), Cancer Cell 2: 243-247). Thus, an siRNA used for the at least one (m)RNA of the adjuvant component of the inventive immunostimulatory composition may be an immunostimulatory RNA, and typically comprises a (single- or) double stranded, preferably a double-stranded, RNA sequence with about 8 to 30 nucleotides, preferably 17 to 25 nucleotides, even more preferably from 20 to 25 and most preferably from 21 to 23 nucleotides. In principle, all the sections having a length of from 17 to 29, preferably from 19 to 25, most preferably from 21 to 23 base pairs that occur in the coding region of an RNA sequence as mentioned above can serve as target sequence for such an siRNA. Equally, siRNAs can also be directed against nucleotide sequences of a protein, particularly of regulatory proteins, which negatively regulate induction of an (innate or adaptive) immune response, that do not lie in the coding region, in particular in the 5' non-coding region of the RNA, for example, therefore, against non-coding regions of an RNA having a regulatory function. The target sequence of the siRNA, used as the at least one (m)RNA of the adjuvant component of the inventive immunostimulatory composition, can therefore lie in the translated and/or untranslated region of the nucleotide sequence of such a protein as defined above and/or in the region of its control elements. The target sequence of an siRNA as defined above can also lie in the overlapping region of untranslated and translated sequence; in particular, the target sequence can comprise at least one nucleotide upstream of the start triplet of the coding region of the RNA.

According to a fourth embodiment, the at least one (m)RNA of the adjuvant component of the inventive immunostimulatory composition may be an antisense RNA. In the context of the present invention, an antisense RNA is preferably a (single-stranded) RNA molecule transcribed off the coding, rather than the template, strand of a DNA, so that (preferably) the (entire) anti-sense mRNA sequence is complementary to the sense (messenger) RNA. An antisense RNA as defined herein typically forms a duplex between the sense and antisense RNA molecules and is thus capable to block transcription of the coding strand. An antisense RNA used as the at least one (m)RNA of the adjuvant component of the inventive immunostimulatory composition can be directed against the nucleotide sequences, e.g. a (naturally occurring) mRNA or genomic sequence encoding a protein or peptide, which may be selected from any protein or peptide sequence suitable for that purpose. Preferably, the antisense RNA used herein as at least one (m)RNA of the adjuvant component of the inventive immunostimulatory composition comprises a length as defined above in general for RNA molecules, more preferably a length of 1000 to 5000, of 500 to 5000, of 5 to 5000, or of 5 to 1000, 5 to 500, 5 to 250, of 5 to 100, of 5 to 50 or of 5 to 30 nucleotides.

According to a fifth embodiment, the at least one (m)RNA of the adjuvant component of the inventive immunostimulatory composition may be a coding RNA. Such a coding RNA may be any RNA as defined above. Preferably, such a coding RNA may be a single- or a double-stranded RNA, more preferably a single-stranded RNA, and/or a circular or linear RNA, more preferably a linear RNA. Even more preferably, the coding RNA may be a (linear) single-stranded RNA. Most preferably, the coding RNA may be a ((linear) single-stranded) messenger RNA (mRNA). The coding RNA used as the at least one (m)RNA of the adjuvant component of the inventive immunostimulatory composition may further encode a protein or a peptide, which may be selected, without being restricted thereto, e.g. from therapeutically active proteins or peptides, from antigens, e.g. tumor antigens, pathogenic antigens (e.g. selected from pathogenic proteins as defined above or from animal antigens, viral antigens, protozoal antigens, bacterial antigens, allergic antigens), autoimmune antigens, or further antigens, from allergens, from antibodies, from immunostimulatory proteins or peptides, from antigen-specific T-cell receptors, or from any other protein or peptide suitable for a specific (therapeutic) application, wherein the coding RNA used as the at least one (m)RNA of the adjuvant component of the inventive immunostimulatory composition may be transported into a cell, a tissue or an organism and the protein may be expressed subsequently in this cell, tissue or organism.

a) Therapeutically Active Proteins

In this context, therapeutically active proteins encoded by the at least one (m)RNA of the adjuvant component of the immunostimulatory composition may be selected from any naturally occurring recombinant or isolated proteins known to a skilled person from the prior art. Without being restricted thereto therapeutically active proteins may comprise proteins, capable of stimulating or inhibiting the signal transduction in the cell, e.g. cytokines, antibodies, etc. Therapeutically active proteins may thus comprise cytokines of class I of the family of cytokines, having 4 positionally conserved cysteine residues (CCCC) (SEQ ID NO: 139) and comprising a conserved sequence motif Trp-Ser-X-Trp-Ser (WSXWS) (SEQ ID NO: 140), wherein X is a non-conserved amino acid. Cytokines of class 1 of the family of cytokines comprise the GM-CSF subfamily, e.g. IL-3, IL-5, GM-CSF, the IL-6-subfamily, e.g. IL-6, IL-11, IL-12, or the IL-2-subfamily, e.g. IL-2, IL-4, IL-7, IL-9, IL-15, etc., or the cytokines IL-1alpha, IL-1beta, IL-10 etc. Therapeutically active proteins may also comprise cytokines of class II of the family of cytokines, which also comprise 4 positionally conserved cystein residues (CCCC) (SEQ ID NO: 139), but no conserved sequence motif Trp-Ser-X-Trp-Ser (WSXWS) (SEQ ID NO: 140). Cytokines of class II of the family of cytokines comprise e.g. IFN-alpha, IFN-beta, IFN-gamma, etc. Therapeutically active proteins may additionally comprise cytokines of the family of tumor necrose factors, e.g. TNF-alpha, TNF-beta, etc., or cytokines of the family of chemokines, which comprise 7 transmembrane helices and interact with G-protein, e.g. IL-8, MIP-1, RANTES, CCR5, CXR4, etc., or cytokine specific receptors, such as TNF-RI, TNF-RII, CD40, OX40 (CD134), Fas.

Therapeutically active proteins encoded by the at least one (m)RNA of the adjuvant component of the immunostimulatory composition may also be selected from any of the proteins given in the following: 0ATL3, 0FC3, 0PA3, 0PD2, 4-1BBL, 5T4, 6Ckine, 707-AP, 9D7, A2M, AA, AAAS, AACT, AASS, ABAT, ABCA1, ABCA4, ABCB1, ABCB11, ABCB2, ABCB4, ABCB7, ABCC2, ABCC6, ABCC8, ABCD1, ABCD3, ABCG5, ABCG8, ABL1, ABO, ABR ACAA1, ACACA, ACADL, ACADM, ACADS, ACADVL, ACAT1, ACCPN, ACE, ACHE, ACHM3, ACHM1, ACLS, ACPI, ACTA1, ACTC, ACTN4, ACVRL1, AD2, ADA, ADAMTS13, ADAMTS2, ADFN, ADH1B, ADH1C, ADLDH3A2, ADRB2, ADRB3, ADSL, AEZ, AFA, AFD1, AFP, AGA, AGL, AGMX2, AGPS, AGS1, AGT, AGTR1, AGXT, AH02, AHCY, AHDS, AHHR, AHSG, AIC, AIED, AIH2, AIH3, AIM-2, AIPL1, AIRE, AK1, ALAD, ALAS2, ALB, HPG1, ALDH2, ALDH3A2, ALDH4A1, ALDH5A1, ALDH1A1, ALDOA, ALDOB, ALMS1, ALPL, ALPP, ALS2, ALX4, AMACR, AMBP, AMCD, AMCD1, AMCN, AMELX, AMELY, AMGL, AMH, AMHR2, AMPD3, AMPD1, AMT, ANC, ANCR, ANK1, ANOP1, AOM, APOA4, AP0C2, AP0C3, AP3B1, APC, aPKC, APOA2, APOA1, APOB, AP0C3, AP0C2, APOE, APOH, APP, APRT, APS1, AQP2, AR, ARAF1, ARG1, ARHGEF12, ARMET, ARSA, ARSB, ARSC2, ARSE, ART-4, ARTC1/m, ARTS, ARVD1, ARX, AS, ASAH, ASAT, ASD1, ASL, ASMD, ASMT, ASNS, ASPA, ASS, ASSP2, ASSP5, ASSP6, AT3, ATD, ATHS, ATM, ATP2A1, ATP2A2, ATP2C1, ATP6B1, ATP7A, ATP7B, ATP8B1, ATPSK2, ATRx, ATXN1, ATXN2, ATXN3, AUTS1, AVMD, AVP, AVPR2, AVSD1, AXIN1, AXIN2, AZF2, B2M, B4GALT7, B7H4, BAGE, BAGE-1, BAX, BBS2, BBS3, BBS4, BCA225, BCAA, BCH, BCHE, BCKDHA, BCKDHB, BCL10, BCL2, BCL3, BCL5, BCL6, BCPM, BCR, BCR/ABL, BDC, BDE, BDMF, BDMR, BEST1, beta-Catenin/m, BF, BFHD, BFIC, BFLS, BFSP2, BGLAP, BGN, BHD, BHR1, BING-4, BIRC5, BJS, BLM, BLMH, BLNK, BMPR2, BPGM, BRAF, BRCA1, BRCA1/m, BRCA2, BRCA2/m, BRCD2, BRCD1, BRDT, BSCL, BSCL2, BTAA, BTD, BTK, BUB1, BWS, BZX, C0L2A1, C0L6A1, C1NH, C1QA, C1QB, C1QG, C1S, C2, C3, C4A, C4B, C5, C6, C7, C7orf2, C8A, C8B, C9, CA125, CA15-3/CA 27-29, CA195, CA19-9, CA72-4, CA2, CA242, CA50, CABYR, CACD, CACNA2D1, CACNA1A, CACNA1F, CACNA1S, CACNB2, CACNB4, CAGE, CA1, CALB3, CALCA, CALCR, CALM, CALR, CAM43, CAMEL, CAP-1, CAPN3, CARD15, CASP-5/m, CASP-8, CASP-8/m, CASR, CAT, CATM, CAV3, CB1, CBBM, CBS, CCA1, CCAL2, CCAL1, CCAT, CCL-1, CCL-11, CCL-12, CCL-13, CCL-14, CCL-15, CCL-16, CCL-17, CCL-18, CCL-19, CCL-2, CCL-20, CCL-21, CCL-22, CCL-23, CCL-24, CCL-25, CCL-27, CCL-3, CCL-4, CCL-5, CCL-7, CCL-8, CCM1, CCNB1, CCND1, CCO, CCR2, CCR5, CCT, CCV, CCZS, CD1, CD19, CD20, CD22, CD25, CD27, CD27L, cD3, CD30, CD30, CD30L, CD33, CD36, CD3E, CD3G, CD3Z, CD4, CD40, CD40L, CD44, CD44v, CD44v6, CD52, CD55, CD56, CD59, CD80, CD86, CDAN1, CDAN2, CDAN3, CDC27, CDC27/m, CDC2L1, CDH1, CDK4, CDK4/m, CDKN1C, CDKN2A, CDKN2A/m, CDKN1A, CDKN1C, CDL1, CDPD1, CDR1, CEA, CEACAM1, CEACAM5, CECR, CECR9, CEPA, CETP, CFNS, CFTR, CGF1, CHAC, CHED2, CHED1, CHEK2, CHM, CHML, CHR39c, CHRNA4, CHRNA1, CHRNB1, CHRNE, CHS, CHS1, CHST6, CHX10, CIAS1, CIDX, CKN1, CLA2, CLA3, CLA1, CLCA2, CLCN1, CLCN5, CLCNKB, CLDN16, CLP, CLN2, CLN3, CLN4, CLN5, CLN6, CLN8, C1QA, C1QB, C1QG, C1R, CLS, CMCWTD, CMDJ, CMD1A, CMD1B, CMH2, MH3, CMH6, CMKBR2, CMKBR5, CML28, CML66, CMM, CMT2B, CMT2D, CMT4A, CMT1A, CMTX2, CMTX3, C-MYC, CNA1, CND, CNGA3, CNGA1, CNGB3, CNSN, CNTF, COA-1/m, COCH, COD2, COD1, COH1, COL10A, C0L2A2, COL11A2, COL17A1, COL1A1, COL1A2, C0L2A1, COL3A1, COL4A3, COL4A4, COL4A5, COL4A6, COL5A1, COL5A2, C0L6A1, C0L6A2, C0L6A3, COL7A1, COL8A2, COL9A2, COL9A3, COL11A1, COL1A2, COL23A1, COL1A1, COLQ, COMP, COMT, CORDS, CORD1, COX10, COX-2, CP, CPB2, CPO, CPP, CPS1, CPT2, CPT1A, CPX, CRAT, CRB1, CRBM, CREBBP, CRH, CRHBP, CRS, CRV, CRX, CRYAB, CRYBA1, CRYBB2, CRYGA, CRYGC, CRYGD, CSA, CSE, CSF1R, CSF2RA, CSF2RB, CSF3R, CSF1R, CST3, CSTB, CT, CT7, CT-9/BRD6, CTAA1, CTACK, CTEN, CTH, CTHM, CTLA4, CTM, CTNNB1, CTNS, CTPA, CTSB, CTSC, CTSK, CTSL, CTS1, CUBN, CVD1, CX3CL1, CXCL1, CXCL10, CXCL11, CXCL12, CXCL13, CXCL16, CXCL2, CXCL3, CXCL4, CXCL5, CXCL6, CXCL7, CXCL8, CXCL9, CYB5, CYBA, CYBB, CYBB5, CYFRA 21-1, CYLD, CYLD1, CYMD, CYP11B1, CYP11B2, CYP17, CYP17A1, CYP19, CYP19A1, CYP1A2, CYP1B1, CYP21A2, CYP27A1, CYP27B1, CYP2A6, CYP2C, CYP2C19, CYP2C9, CYP2D, CYP2D6, CYP2D7P1, CYP3A4, CYP7B1, CYPB1, CYP11B1, CYP1A1, CYP1B1, CYRAA, D40, DADI, DAM, DAM-10/MAGE-B1, DAM-6/MAGE-B2, DAX1, DAZ, DBA, DBH, DBI, DBT, DCC, DC-CK1, DCK, DCR, DCX, DDB 1, DDB2, DDIT3, DDU, DECR1, DEK-CAN, DEM, DES, DF, DFN2, DFN4, DFN6, DFNA4, DFNA5, DFNB5, DGCR, DHCR7, DHFR, DHOF, DHS, DIA1, DIAPH2, DIAPH1, DIH1, DIO1, DISCI, DKCl, DLAT, DLD, DLL3, DLX3, DMBT1, DMD, DM1, DMPK, DMWD, DNAI1, DNASE1, DNMT3B, DPEP1, DPYD, DPYS, DRD2, DRD4, DRPLA, DSCR1, DSG1, DSP, DSPP, DSS, DTDP2, DTR, DURS1, DWS, DYS, DYSF, DYT2, DYT3, DYT4, DYT2, DYT1, DYX1, EBAF, EBM, EBNA, EBP, EBR3, EBS1, ECA1, ECB2, ECE1, ECGF1, ECT, ED2, ED4, EDA, EDAR, ECA1, EDN3, EDNRB, EEC1, EEF1A1L14, EEGV1, EFEMP1, EFTUD2/m, EGFR, EGFR/Her1, EGI, EGR2, EIF2AK3, eIF4G, EKV, EI IS, ELA2, ELF2, ELF2M, ELK1, ELN, ELONG, EMD, EML1, EMMPRIN, EMX2, ENA-78, ENAM, END3, ENG, ENO1, ENPP1, ENUR2, ENUR1, EOS, EP300, EPB41, EPB42, EPCAM, EPD, EphA1, EphA2, EphA3, EphrinA2, EphrinA3, EPHX1, EPM2A, EPO, EPOR, EPX, ERBB2, ERCC2 ERCC3, ERCC4, ERCC5, ERCC6, ERVR, ESR1, ETFA, ETFB, ETFDH, ETM1, ETV6-AML1, ETV1, EVC, EVR2, EVR1, EWSR1, EXT2, EXT3, EXT1, EYA1, EYCL2, EYCL3, EYCL1, EZH2, F10, F11, F12, F13A1, F13B, F2, F5, F5F8D, F7, F8, F8C, F9, FABP2, FACL6, FAH, FANCA, FANCB, FANCC, FANCD2, FANCF, FasL, FBN2, FBN1, FBP1, FCG3RA, FCGR2A, FCGR2B, FCGR3A, FCHL, FCMD, FCP1, FDPSL5, FECH, FEO, FEOM1, FES, FGA, FGB, FGD1, FGF2, FGF23, FGF5, FGFR2, FGFR3, FGFR1, FGG, FGS1, FH, FIC1, FIH, F2, FKBP6, FLNA, FLT4, FMO3, FMO4, FMR2, FMR1, FN, FN1/m, FOXC1, FOXE1, FOXL2, FOXO1A, FPDMM, FPF, Fra-1, FRAXF, FRDA, FSHB, FSHMD1A, FSHR, FTH1, FTHL17, FTL, FTZF1, FUCA1, FUT2, FUT6, FUT1, FY, G250, G250/CAIX, G6PC, G6PD, G6PT1, G6PT2, GAA, GABRA3, GAGE-1, GAGE-2, GAGE-3, GAGE-4, GAGE-5, GAGE-6, GAGE-7b, GAGE-8, GALC, GALE, GALK1, GALNS, GALT, GAMT, GAN, GAST, GASTRIN17, GATA3, GATA, GBA, GBE, GC, GCDH, GCGR, GCH1, GCK, GCP-2, GCS1, G-CSF, GCSH, GCSL, GCY, GDEP, GDF5, GDI1, GDNF, GDXY, GFAP, GFND, GGCX, GGT1, GH2, GH1, GHR, GHRHR, GHS, GIF, GINGF, GIP, GJA3, GJA8, GJB2, GJB3, GJB6, GJB1, GK, GLA, GLB, GLB1, GLC3B, GLC1B, GLC1C, GLDC, GLI3, GLP1, GLRA1, GLUD1, GM1 (fuc-GM1), GM2A, GM-CSF, GMPR, GNAI2, GNAS, GNAT1, GNB3, GNE, GNPTA, GNRH, GNRH1, GNRHR, GNS, GnT-V, gp100, GP1BA, GP1BB, GP9, GPC3, GPD2, GPDS1, GP1, GP1BA, GPN1LW, GPNMB/m, GPSC, GPX1, GRHPR, GRK1, GROα, GROβ, GROγ, GRPR, GSE, GSM1, GSN, GSR, GSS, GTD, GTS, GUCA1A, GUCY2D, GULOP, GUSB, GUSM, GUST, GYPA, GYPC, GYS1, GYS2, HOKPP2, HOMG2, HADHA, HADHB, HAGE, HAGH, HAL, HAST-2, HB 1, HBA2, HBA1, HBB, HBBP1, HBD, HBE1, HBG2, HBG1, HBHR, HBP1, HBQ1, HBZ, HBZP, HCA, HCC-1, HCC-4, HCF2, HCG, HCL2, HCL1, HCR, HCVS, HD, HPN, HER2, HER2/NEU, HER3, HERV-K-MEL, HESX1, HEXA, HEXB, HF1, HFE, HF1, HGD, HHC2, HHC3, HHG, HK1 HLA-A, HLA-A*0201-R170I , HLA-A11/m, HLA-A2/m, HLA-DPB1 HLA-DRA, HLCS, HLXB9, HMBS, HMGA2, HMGCL, HMI, HMN2, HMOX1, HMS1 HMW-MAA, HND, HNE, HNF4A, HOAC, HOMEOBOX NKX 3.1, HOM-TES-14/SCP-1, HOM-TES-85, HOXA1 HOXD13, HP, HPC1, HPD, HPE2, HPE1, HPFH, HPFH2, HPRT1, HPS1, HPT, HPV-E6, HPV-E7, HR, HRAS, HRD, HRG, HRPT2, HRPT1, HRX, HSD11B2, HSD17B3, HSD17B4, HSD3B2, HSD3B3, HSN1, HSP70-2M, HSPG2, HST-2, HTC2, HTC1, hTERT, HTN3, HTR2c, HVBS6, HVBS1, HVEC, HV1S, HYAL1, HYR, 1-309, IAB, IBGC1, IBM2, ICAM1, ICAM3, iCE, ICHQ, ICR5, ICR1, ICS1, IDDM2, IDDM1, IDS, IDUA, IF, IFNa/b, IFNGR1, IGAD1, IGER, IGF-1R, IGF2R, IGF1, IGH, IGHC, IGHG2, IGHG1, IGHM, IGHR, IGKC, 1HG1, IHH, IKBKG, IL1, IL-1 RA, IL10, IL-11, IL12, IL12RB1, IL13, IL-13Rα2, IL-15, IL-16, IL-17, IL18, IL-1a, IL-1α, IL-1b, IL-1β, IL1RAPL1, IL2, IL24, IL-2R, IL2RA, IL2RG, IL3, IL3RA, IL4, IL4R, IL4R, IL-5, IL6, IL-7, IL7R, IL-8, IL-9, Immature laminin receptor, IMMP2L, INDX, INFGR1, INFGR2, INFα, IFN, INFγ, INS, INSR, INVS, IP-10, IP2, IPF1, IP1, IRF6, IRS1, ISCW, ITGA2, ITGA2B, ITGA6, ITGA7, ITGB2, ITGB3, ITGB4, ITIH1, ITM2B, IV, IVD, JAG1, JAK3, JBS, JBTS1, JMS, JPD, KAL1, KAL2, KALI, KLK2, KLK4, KCNA1, KCNE2, KCNE1, KCNH2, KCNJ1, KCNJ2, KCNJ1, KCNQ2, KCNQ3, KCNQ4, KCNQ1, KCS, KERA, KFM, KFS, KFSD, KHK, ki-67, KIAA0020, KIAA0205, KIAA0205/m, KIF1B, KIT, KK-LC-1, KLK3, KLKB1, KM-HN-1, KMS, KNG, KNO, K-RAS/m, KRAS2, KREV1, KRT1, KRT10, KRT12, KRT13, KRT14, KRT14L1, KRT14L2, KRT14L3, KRT16, KRT16L1, KRT16L2, KRT17, KRT18, KRT2A, KRT3, KRT4, KRT5, KRT6 A, KRT6B, KRT9, KRTHB1, KRTHB6, KRT1, KSA, KSS, KWE, KYNU, LOH19CR1, L1CAM, LAGE, LAGE-1, LALL, LAMA2, LAMA3, LAMB3, LAMB1, LAMC2, LAMP2, LAP, LCA5, LCAT, LCCS, LCCS1, LCFS2, LCS1, LCT, LDHA, LDHB, LDHC, LDLR, LDLR/FUT, LEP, LEWISY, LGCR, LGGF-PBP, LGI1, LGMD2H, LGMD1A, LGMD1B, LHB, LHCGR, LHON, LHRH, LHX3, LIF, LIG1, LIMM, LIMP2, LIPA, LIPA, LIPB, LIPC, LIVIN, L1CAM, LMAN1, LMNA, LMX1B, LOLR, LOR, LOX, LPA, LPL, LPP, LQT4, LRP5, LRS1, LSFC, LT-13, LTBP2, LTC4S, LYL1, XCL1, LYZ, M344, MA50, MAA, MADH4, MAFD2, MAFD1, MAGE, MAGE-A1, MAGE-A10, MAGE-A12, MAGE-A2, MAGE-A3, MAGE-A4, MAGE-A6, MAGE-A9, MAGEB1, MAGE-B10, MAGE-B16, MAGE-B17, MAGE-B2, MAGE-B3, MAGE-B4, MAGE-B5, MAGE-B6, MAGE-C1, MAGE-C2, MAGE-C3, MAGE-D1, MAGE-D2, MAGE-D4, MAGE-E1, MAGE-E2, MAGE-F1, MAGE-H1, MAGEL2, MGB1, MGB2, MAN2A1, MAN2B1, MANBA, MANBB, MAOA, MAOB, MAPK8IP1, MAPT, MART-1, MART-2, MART2/m, MAT1A, MBL2, MBP, MBS1, MC1R, MC2R, MC4R, MCC, MCCC2, MCCC1, MCDR1, MCF2, MCKD, MCL1, MC1R, MCOLN1, MCOP, MCOR, MCP-1, MCP-2, MCP-3, MCP-4, MCPH2, MCPH1, MCS, M-CSF, MDB, MDCR, MDM2, MDRV, MDS 1, ME1, ME1/m, ME2, ME20, ME3, MEAX, MEB, MEC CCL-28, MECP2, MEFV, MELANA, MELAS, MEN1 MSLN, MET, MF4, MG50, MG50/PXDN, MGAT2, MGAT5, MGC1 MGCR, MGCT, MGI, MGP, MHC2TA, MHS2, MHS4, MIC2, MICS, MIDI, MIF, MIP, MIP-5/HCC-2, MITE, MJD, MKI67, MKKS, MKS1, MLH1, MLL, MLLT2, MLLT3, MLLT7, MLLT1, MLS, MLYCD, MMA1a, MMP 11, MMVP1, MN/CA IX-Antigen, MNG1, MN1, MOC31, MOCS2, MOCS1, MOG, MORC, MOS, MOV18, MPD1, MPE, MPFD, MPI, MPIF-1, MPL, MPO, MPS3C, MPZ, MRE11A, MROS, MRP1, MRP2, MRP3, MRSD, MRx14, MRx2, MRx20, MRx3, MRx40, MRXA, MRx1, MS, MS4A2, MSD, MSH2, MSH3, MSH6, MSS, MSSE, MSX2, MSX1, MTATP6, MTC03, MTCO1, MTCYB, MTHFR, MTM1, MTMR2, MTND2, MTND4, MTND5, MTND6, MTND1, MTP, MTR, MTRNR2, MTRNR1, MTRR, MTTE, MTTG, MITI, MTTK, MTTL2, MTTL1, MTTN, MTTP, MTTS1, MUC1, MUC2, MUC4, MUC5AC, MUM-1, MUM-1/m, MUM-2, MUM-2/m, MUM-3, MUM-3/m, MUT, mutant p21 ras, MUTYH, MVK, MX2, MXI1, MY05A, MYB, MYBPC3, MYC, MYCL2, MYH6, MYH7, MYL2, MYL3, MYMY, MYO15A, MYO1G, MYO5A, MYO7A, MYOC, Myosin/m, MYP2, MYP1, NA88-A, N-acetylglucosaminyltransferase-V, NAGA, NAGLU, NAMSD, NAPB, NAT2, NAT, NBIA1, NBS1, NCAM, NCF2, NCF1, NDN, NDP, NDUFS4, NDUFS7, NDUFS8, NDUFV1, NDUFV2, NEB, NEFH, NEM1, Neo-PAP, neo-PAP/m, NEU1, NEUROD1, NF2, NF1, NFYC/m, NGEP, NHS, NKS1, NKX2E, NM, NME1, NMP22, NMTC, NODAL, NOG, NOS3, NOTCH3, NOTCH1, NP, NPC2, NPC1, NPHL2, NPHP1, NPHS2, NPHS1, NPM/ALK, NPPA, NQO1, NR2E3, NR3C1, NR3C2, NRAS, NRAS/m, NRL, NROB1, NRTN, NSE, NSX, NTRK1, NUMA1, NXF2, NY-CO1, NY-ESO1, NY-ESO-B, NY-LU-12, ALDOA, NYS2, NYS4, NY-SAR-35, NYS1, NYX, OA3, OA1, OAP, OASD, 0AT, OCA1, OCA2, OCD1, OCRL, OCRL1, OCT, ODDD, ODT1, OFC1, OFD1, OGDH, OGT, OGT/m, OPA2, OPA1, OPD1, OPEM, OPG, OPN, OPN1LW, OPN1MW, OPN1SW, OPPG, OPTB1, TTD, ORM1, ORP1, OS-9, OS-9/m, OSM LIF, OTC, OTOF, OTSC1, OXCT1, OYTES1, P15, P190 MINOR BCR-ABL, P2RY12, P3, P16, P40, P4HB, P-501, P53, P53/m, P97, PABPN1, PAFAH1B1, PAFAH1P1, PAGE-4, PAGE-5, PAH, PAI-1, PAI-2, PAK3, PAP, PAPPA, PARK2, PART-1, PATE, PAX2, PAX3, PAX6, PAX7, PAX8, PAX9, PBCA, PBCRA1, PBT, PBX1, PBXP1, PC, PCBD, PCCA, PCCB, PCK2, PCK1, PCLD, PCOS1, PCSK1, PDB1, PDCN, PDE6A, PDE6B, PDEF, PDGFB, PDGFR, PDGFRL, PDHA1, PDR, PDX1, PECAM1, PEE1, PEO1, PEPD, PEX10, PEX12, PEX13, PEX3, PEX5, PEX6, PEX7, PEX1, PF4, PFBI, PFC, PFKFB1, PFKM, PGAM2, PGD, PGK1, PGK1P1, PGL2, PGR, PGS, PHA2A, PHB, PHEX, PHGDH, PHKA2, PHKA1, PHKB, PHKG2, PHP, PHYH, PI, PI3, PIGA, PIM1-KINASE, PIN1, PIP5K1B, PITX2, PITX3, PKD2, PKD3, PKD1, PKDTS, PKHD1, PKLR, PKP1, PKU1, PLA2G2A, PLA2G7, PLAT, PLEC1, PLG, PLI, PLOD, PLP1, PMEL17, PML, PML/RARα, PMM2, PMP22, PMS2, PMS1, PNKD, PNLIP, POF1, POLA, POLH, POMC, PON2, PON1, PORC, POTE, POU1F1, POU3F4, POU4F3, POU1F1, PPAC, PPARG, PPCD, PPGB, PPH1, PPKB, PPMX, PPDX, PPP1R3A, PPP2R2B, PPT1, PRAME, PRB, PRB3, PRCA1, PRCC, PRD, PRDX5/m, PRF1, PRG4, PRKAR1A, PRKCA, PRKDC, PRKWNK4, PRNP, PROC, PRODH, PROM1, PROP1, PROS1, PRST, PRP8, PRPF31, PRPF8, PRPH2, PRPS2, PRPS1, PRS, PRSS7, PRSS1, PRTN3, PRX, PSA, PSAP, PSCA, PSEN2, PSEN1, PSG1, PSGR, PSM, PSMA, PSORS1, PTC, PTCH, PTCH1, PTCH2, PTEN, PTGS1, PTH, PTHR1, PTLAH, PTOS1, PTPN12, PTPNI I, PTPRK, PTPRK/m, PTS, PUJO, PVR, PVRL1, PWCR, PXE, PXMP3, PXR1, PYGL, PYGM, QDPR, RAB27A, RAD54B, RAD54L, RAG2, RAGE, RAGE-1, RAG1, RAP1, RARA, RASA1, RBAF600/m, RB1, RBP4, RBP4, RBS, RCA1, RCAS1, RCCP2, RCD1, RCV1, RDH5, RDPA, RDS, RECQL2, RECQL3, RECQL4, REG1A, REHOBE, REN, RENBP, RENS1, RET, RFX5, RFXANK, RFXAP, RGR, RHAG, RHAMM/CD168, RHD, RHO, Rip-1, RLBP1, RLN2, RLN1, RLS, RMD1, RMRP, ROM1, ROR2, RP, RP1, RP14, RP17, RP2, RP6, RP9, RPD1, RPE65, RPGR, RPGRIP1, RP1, RP10, RPS19, RPS2, RPS4X, RPS4Y, RPS6KA3, RRAS2, RS1, RSN, RSS, RU1, RU2, RUNX2, RUNXl, RWS, RYR1, S-100, SAA1, SACS, SAG, SAGE, SALL1, SARDH, SART1, SART2, SART3, SAS, SAX1, SCA2, SCA4, SCA5, SCA7, SCA8, SCA1, SCC, SCCD, SCF, SCLC1, SCN1A, SCN1B, SCN4A, SCN5A, SCNN1A, SCNN1B, SCNN1G, SCO2, SCP1, SCZD2, SCZD3, SCZD4, SCZD6, SCZD1, SDF-1α/β, SDHA, SDHD, SDYS, SEDL, SERPENA7, SERPINA3, SERPINA6, SERPINA1, SERPINC1, SERPIND1, SERPINE1, SERPINF2, SERPING1, SERPINI1, SFTPA1, SFTPB, SFTPC, SFTPD, SCCA, SGCB, SGCD, SGCE, SGM1, SGSH, SGY-1, SH2D1A, SHBG, SHFM2, SHFM3, SHFM1, SHH, SHOX, SI, SIAL, SIALYL LEWISX, SIASD, S11, SIM1, SIRT2/m, SIX3, SJS1, SKP2, SLC10A2, SLC12A1, SLC12A3, SLC17A5, SLC19A2, SLC22A1L, SLC22A5, SLC25A13, SLC25A15, SLC25A20, SLC25A4, SLC25A5, SLC25A6, SLC26A2, SLC26A3, SLC26A4, SLC2A1, SLC2A2, SLC2A4, SLC3A1, SLC4A1, SLC4A4, SLC5A1, SLC5A5, SLC6A2, SLC6A3, SLC6A4, SLC7A7, SLC7A9, SLC11A1, SLOS, SMA, SMAD1, SMAL, SMARCB1, SMAX2, SMCR, SMCY, SM1, SMN2, SMN1, SMPD1, SNCA, SNRPN, SOD2, SOD3, SOD1, SOS1, SOST, SOX9, SOX10, Sp17, SPANXC, SPG23, SPG3A, SPG4, SPG5A, SPG5B, SPG6, SPG7, SPINK1, SPINK5, SPPK, SPPM, SPSMA, SPTA1, SPTB, SPTLC1, SRC, SRD5A2, SRPX, SRS, SRY, βhCG, SSTR2, SSX1, SSX2 (HOM-MEL-40/SSX2), SSX4, ST8, STAMP-1, STAR, STARP1, STATH, STEAP, STK2, STK11, STn/KLH, STO, STOM, STS, SUOX, SURF1, SURVIVIN-2B, SYCP1, SYM1, SYN1, SYNS1, SYP, SYT/SSX, SYT-SSX-1, SYT-SSX-2, TA-90, TAAL6, TACSTD1, TACSTD2, TAG72, TAF7L, TAF1, TAGE, TAG-72, TALI, TAM, TAP2, TAP1, TAPVR1, TARC, TARP, TAT, TAZ, TBP, TBX22, TBX3, TBX5, TBXA2R, TBXAS1, TCAP, TCF2, TCF1, TCIRG1, TCL2, TCL4, TCL1A, TCN2, TCOF1, TCR, TCRA, TDD, TDFA, TDRD1, TECK, TECTA, TEK, TEL/AML1, TELAB1, TEX15, TF, TFAP2B, TFE3, TFR2, TG, TGFA, TGF-β, TGFBI, TGFB1, TGFBR2, TGFBRE, TGFβ, TGFβRII, TGIF, TGM-4, TGM1, TH, THAS, THBD, THC, THC2, THM, THPO, THRA, THRB, TIMM8A, TIMP2, TIMP3, TIMP1, TITF1, TKCR, TKT, TLP, TLR1, TLR10, TLR2, TLR3, TLR4, TLR4, TLR5, TLR6, TLR7, TLR8, TLR9, TLX1, TM4SF1, TM4SF2, TMC1, TMD, TMIP, TNDM, TNF, TNFRSF11A, TNFRSF1A, TNFRSF6, TNFSF5, TNFSF6, TNFα, TNFβ, TNNI3, TNNT2, TOC, TOP2A, TOP1, TP53, TP63, TPA, TPBG, TPI, TPI/m, TPI1, TPM3, TPM1, TPMT, TPO, TPS, TPTA, TRA, TRAG3, TRAPPC2, TRC8, TREH, TRG, TRH, TRIM32, TRIM37, TRP1, TRP2, TRP-2/6b, TRP-2/INT2, Trp-p8, TRPS1, TS, TSC2, TSC3, TSC1, TSG101, TSHB, TSHR, TSP-180, TST, TTGA2B, TTN, TTPA, TTR, TU M2-PK, TULP1, TWIST, TYH, TYR, TYROBP, TYROBP, TYRP1, TYS, UBE2A, UBE3A, UBE1, UCHL1, UFS, UGT1A, ULR, UMPK, UMPS, UOX, UPA, UQCRC1, URO5, UROD, UPK1B, UROS, USH2A, USH3A, USH1A, USH1C, USP9Y, UV24, VBCH, VCF, VDI, VDR, VEGF, VEGFR-2, VEGFR-1, VEGFR-2/FLK-1, VHL, VIM, VMD2, VMD1, VMGLOM, VNEZ, VNF, VP, VRNI, VWF, VWS, WAS, WBS2, WFS2, WFS1, WHCR, WHN, WISP3, WMS, WRN, WS2A, WS2B, WSN, WSS, WT2, WT3, WT1, WTS, WWS, XAGE, XDH, XIC, XIST, XK, XM, XPA, XPC, XRCC9, XS, ZAP70, ZFHX1B, ZFX, ZFY, ZIC2, ZIC3, ZNF145, ZNF261, ZNF35, ZNF41, ZNF6, ZNF198, ZWS1.

Therapeutically active proteins may further be selected from apoptotic factors or apoptosis related proteins including AlF, Apaf e.g. Apaf-1, Apaf-2, Apaf-3, oder APO-2 (L), APO-3 (L), Apopain, Bad, Bak, Bax, Bcl-2, Bcl-$x_L$, Bcl-$x_S$, bik, CAD, Calpain, Caspase e.g. Caspase-1, Caspase-2, Caspase-3, Caspase-4, Caspase-5, Caspase-6, Caspase-7, Caspase-8, Caspase-9, Caspase-10, Caspase-11, ced-3, ced-9, c-Jun, c-Myc, crm A, cytochrom C, CdR1, DcR1, DD, DED, DISC, DNA-$PK_{CS}$, DR3, DR4, DR5, FADD/MORT-1, FAK, Fas (Fas-ligand CD95/fas (receptor)), FLICE/MACH, FLIP, fodrin, fos, G-Actin, Gas-2, gelsolin, granzyme A/B, ICAD, ICE, JNK, Iamin A/B, MAP, MCL-1, Mdm-2, MEKK-1, MORT-1, NEDD, NF-$_{kappa}$B, NuMa, p53, PAK-2, PARP, perforin, PITSLRE, PKCdelta, pRb, presenilin, prICE, RAIDD, Ras, RIP, sphingomyelinase, thymidinkinase from herpes simplex, TRADD, TRAF2, TRAIL-R1, TRAIL-R2, TRAIL-R3, transglutaminase, etc.

A therapeutically active protein, which may be encoded by the at least one (m)RNA of the adjuvant component of the inventive immunostimulatory composition, can also be an adjuvant protein. In this context, an adjuvant protein is preferably to be understood as any protein, which is capable to elicit an innate immune response as defined herein. Preferably, such an innate immune response comprises activation of a pattern recognition receptor, such as e.g. a receptor selected from the Toll-like receptor (TLR) family, including e.g. a Toll like receptor selected from human TLR1 to TLR10 or from murine Toll like receptors TLR1 to TLR13. Preferably, an innate immune response is elicited in a mammal as defined above. More preferably, the adjuvant protein is selected from human adjuvant proteins or from pathogenic adjuvant proteins, in particular from bacterial adjuvant proteins. In addition, mRNA encoding human proteins involved in adjuvant effects may be used as well.

Human adjuvant proteins, which may be encoded by the at least one (m)RNA of the adjuvant component of the inventive immunostimulatory composition, typically comprise any human protein, which is capable of eliciting an innate immune response (in a mammal), e.g. as a reaction of the binding of an exogenous TLR ligand to a TLR. More preferably, human adjuvant proteins encoded by the at least one modified (m)RNA of the inventive immunostimulatory composition are selected from the group consisting of, without being limited thereto, cytokines which induce or enhance an innate immune response, including IL-2, IL-12, IL-15, IL-18, IL-21CCL21, GM-CSF and TNF-alpha; cytokines which are released from macrophages, including IL-1, IL-6, IL-8, IL-12 and TNF-alpha; from components of the complement system including C1q, MBL, C1r, C1s, C2b, Bb, D, MASP-1, MASP-2, C4b, C3b, C5a, C3a, C4a, C5b, C6, C7, C8, C9, CR1, CR2, CR3, CR4, C1qR, C1INH, C4bp, MCP, DAF, H, I, P and CD59; from proteins which are components of the signalling networks of the pattern recognition receptors including TLR and IL-1R1, whereas the components are ligands of the pattern recognition receptors including IL-1alpha, IL-1beta, Beta-defensin, heat shock proteins, such as HSP10, HSP60, HSP65, HSP70, HSP75 and HSP90, gp96, Fibrinogen, TypIII repeat extra domain A of fibronectin; the receptors, including IL-1RI, TLR1, TLR2, TLR3, TLR4, TLR5, TLR6, TLR7, TLR8, TLR9, TLR10, TLR11; the signal transducers including components of the Small-GTPases signalling (RhoA, Ras, Rac1, Cdc42 etc.), components of the PIP signalling (PI3K, Src-Kinases, etc.), components of the MyD88-dependent signalling (MyD88, IRAK1, IRAK2, etc.), components of the MyD88-independent signalling (TICAM1, TICAM2 etc.); activated transcription factors including e.g. NF-κB, c-Fos, c-Jun, c-Myc; and induced target genes including e.g. IL-1 alpha, IL-1 beta, Beta-Defensin, IL-6, IFN gamma, IFN alpha and IFN beta; from costimulatory molecules, including CD28 or CD40-ligand or PD1; protein domains, including LAMP; cell surface proteins; or human adjuvant proteins including CD80, CD81, CD86, trif, flt-3 ligand, thymopentin, Gp96 or fibronectin, etc., or any species homolog of any of the above human adjuvant proteins.

Pathogenic adjuvant proteins, which may be encoded by the at least one (m)RNA of the adjuvant component of the inventive immunostimulatory composition, typically comprise any pathogenic (adjuvant) protein, which is capable of eliciting an innate immune response (in a mammal), more preferably selected from pathogenic (adjuvant) proteins derived from bacteria, protozoa, viruses, or fungi, animals, etc., and even more preferably from pathogenic adjuvant proteins selected from the group consisting of, without being limited thereto, bacterial proteins, protozoan proteins (e.g. profilin—like protein of *Toxoplasma gondii*), viral proteins, or fungal proteins, animal proteins, etc.

In this context, bacterial (adjuvant) proteins, which may be encoded by the at least one (m)RNA of the adjuvant component of the inventive immunostimulatory composition, may comprise any bacterial protein, which is capable of eliciting an innate immune response (preferably in a mammal) or shows an adjuvant character. More preferably, such bacterial (adjuvant) proteins are selected from the group consisting of bacterial heat shock proteins or chaperons, including Hsp60, Hsp70, Hsp90, Hsp100; OmpA (Outer membrane protein) from gram-negative bacteria; bacterial porins, including OmpF; bacterial toxins, including pertussis toxin (PT) from *Bordetella pertussis*, pertussis adenylate cyclase toxin CyaA and CyaC from *Bordetella pertussis*, PT-9K/129G mutant from pertussis toxin, pertussis adenylate cyclase toxin CyaA and CyaC from *Bordetella pertussis*, tetanus toxin, cholera toxin (CT), cholera toxin B-subunit, CTK63 mutant from cholera toxin, CTE112K mutant from CT, *Escherichia coli* heat-labile enterotoxin (LT), B subunit from heat-labile enterotoxin (LTB) *Escherichia coli* heat-labile enterotoxin mutants with reduced toxicity, including LTK63, LTR72; phenol-soluble modulin; neutrophil-activating protein (HP-NAP) from *Helicobacter pylori*; Surfactant protein D; Outer surface protein A lipoprotein from *Borrelia burgdofferi*, Ag38 (38 kDa antigen) from *Mycobacterium tuberculosis*; proteins from bacterial fimbriae; Enterotoxin CT of *Vibrio cholerae*, Pilin from pili from gram negative bacteria, and Surfactant protein A; etc., or any species homolog of any of the above bacterial (adjuvant) proteins.

Bacterial (adjuvant) proteins, which may be encoded by the at least one (m)RNA of the adjuvant component of the inventive immunostimulatory composition, may also be selected from bacterial adjuvant proteins, even more preferably selected from the group consisting of, without being limited thereto, bacterial flagellins, including flagellins from organisms including *Agrobacterium, Aquifex, Azospirillum, Bacillus, Bartonella, Bordetella, Borrelia, Burkholderia, Campylobacter, Caulobacte, Clostridium, Escherichia, Helicobacter, Lachnospiraceae, Legionella, Listeria, Pro-*

*teus, Pseudomonas, Rhizobium, Rhodobacter, Roseburia, Salmonella, Serpulina, Serratia, Shigella, Treponema, Vibrio, Wolinella, Yersinia*, more preferably flagellins from the species, without being limited thereto, *Agrobacterium tumefaciens, Aquifex pyrophilus, Azospirillum brasilense, Bacillus subtilis, Bacillus thuringiensis, Bartonella bacilliformis, Bordetella bronchiseptica, Borrelia burgdorferi, Burkholderia cepacia, Campylobacter jejuni, Caulobacter crescentus, Clostridium botulinum* strain Bennett clone 1, *Escherichia coli, Helicobacter pylori, Lachnospiraceae bacterium, Legionella pneumophila, Listeria monocytogenes, Proteus mirabilis, Pseudomonas aeroguinosa, Pseudomonas syringae, Rhizobium meliloti, Rhodobacter sphaeroides, Roseburia cecicola, Roseburis hominis, Salmonella typhimurium, Salmonella bongori, Salmonella typhi, Salmonella enteritidis, Serpulina hyodysenteriae, Serratia marcescens, Shigella boydii, Treponema phagedenis, Vibrio alginolyticus, Vibrio cholerae, Vibrio parahaemolyticus, Wolinella succinogenes* and *Yersinia enterocolitica.*

Bacterial flagellins, which may be encoded by the at least one (m)RNA of the adjuvant component of the inventive immunostimulatory composition, even more preferably comprise a sequence selected from the group comprising any of the following sequences as referred to their accession numbers:

| organism | species | gene name | accession No | GI No |
|---|---|---|---|---|
| *Agrobacterium* | *Agrobacterium tumefaciens* | FlaD (flaD)<br>FlhB (flhB)<br>FliG (fliG)<br>FliN (fliN)<br>FliM (fliM)<br>MotA (motA)<br>FlgF (flgF)<br>FliI (fliI)<br>FlgB (flgB)<br>FlgC (flgC)<br>FliE (fliE)<br>FlgG (flgG)<br>FlgA (flgA)<br>FlgI (flgI)<br>FlgH (flgH)<br>FliL (fliL)<br>FliP (fliP)<br>FlaA (flaA)<br>FlaB (flaB)<br>FlaC (flaC) | U95165 | GI:14278870 |
| *Aquifex* | *Aquifex pyrophilus* | | U17575 | GI:596244 |
| *Azospirillum* | *Azospirillum brasilense* | Laf1 | U26679 | GI:1173509 |
| *Bacillus* | *Bacillus subtilis* | hag | AB033501 | GI:14278870 |
| *Bacillus* | *Bacillus thuringiensis* | flab | X67138 | GI:46019718 |
| *Bartonella* | *Bartonella bacilliformis* | | L20677 | GI:304184 |
| *Bordetella* | *Bordetella bronchiseptica* | flaA | L13034 | GI:289453 |
| *Borrelia* | *Borrelia burgdorferi* | | X16833 | GI:39356 |
| *Burkholderia* | *Burkholderia cepacia* | fliC | AF011370 | GI:2935154 |
| *Campylobacter* | *Campylobacter jejuni* | flaA<br>flaB | J05635 | GI:144197 |
| *Caulobacter* | *Caulobacter crescentus* | | J01556 | GI:144239 |
| *Clostridium* | *Clostridium botulinum* strain Bennett clone 1 | FlaA | DQ845000 | GI:114054886 |
| *Escherichia* | *Escherichia coli* | hag | M14358<br>AJ 884569<br>(EMBL-SVA) | GI:146311 |
| *Helicobacter* | *Helicobacter pylori* | flaA | X60746 | GI:43631 |
| *Lachnospiraceae* | *Lachnospiraceae bacterium* | | DQ789131 | GI:113911615 |
| *Legionella* | *Legionella pneumophila* | flaA | X83232 | GI:602877 |
| *Listeria* | *Listeria monocytogenes* | flaA | X65624 | GI:44097 |
| *Proteus* | *Proteus mirabilis* | FlaD (flaD)<br>FlaA (flaA)<br>FlaB (flaB)<br>FliA (fliA)<br>FliZ (fliZ) | AF221596 | GI:6959881 |
| *Pseudomonas* | *Pseudomonas aeroguinosa* | flaA | M57501 | GI:151225 |
| *Pseudomonas* | *Pseudomonas syringae* | fliC | EF544882 | GI:146335619 |

-continued

| organism | species | gene name | accession No | GI No |
|---|---|---|---|---|
| *Rhizobium* | *Rhizobium meliloti* | flaA flaB | M24526 | GI:152220 |
| *Rhodobacter* | *Rhodobacter sphaeroides* | fliC | AF274346 | GI:10716972 |
| *Roseburia* | *Roseburia cecicola* | | M20983 | GI:152535 |
| *Roseburia* | *Roseburis hominis* | Fla2 | DQ789141 | GI:113911632 |
| *Salmonella* | *Salmonella typhimurium* | | D13689 (NCBI ID) | GI:217062 |
| *Salmonella* | *Salmonella bongori* | fliC | AY603412 | GI:51342390 |
| *Salmonella* | *Salmonella typhi* | flag | L21912 | GI:397810 |
| *Salmonella* | *Salmonella enteritidis* | fliC | M84980 | GI:154015 |
| *Serpulina* | *Serpulina hyodysenteriae* | flaB2 | X63513 | GI:450669 |
| *Serratia* | *Serratia marcescens* | hag | M27219 | GI:152826 |
| *Shigella* | *Shigella boydii* | fliC-SB | D26165 | GI:442485 |
| *Treponema* | *Treponema phagedenis* | flaB2 | M94015 | GI:155060 |
| *Vibrio* | *Vibrio alginolyticus* | flaA | EF125175 | GI:119434395 |
| *Vibrio s* | *Vibrio parahaemolyticus* | | AF069392 | GI:7327274 |
| *Wolinella* | *Wolinella succinogenes* | flag | M82917 | GI:155337 |
| *Yersinia* | *Yersinia enterocolitica* | | L33467 | GI:496295 |

Protozoan proteins, which may also be encoded by the at least one (m)RNA of the adjuvant component of the inventive immunostimulatory composition, may be selected from any protozoan protein showing adjuvant character, more preferably, from the group consisting of, without being limited thereto, Tc52 from *Trypanosoma cruzi*, PFTG from *Trypanosoma gondii*, Protozoan heat shock proteins, LelF from *Leishmania* spp., profilin-like protein from *Toxoplasma gondii*, etc.

Viral proteins, which may be encoded by the at least one (m)RNA of the adjuvant component of the inventive immunostimulatory composition, may be selected from any viral protein showing adjuvant character, more preferably, from the group consisting of, without being limited thereto, Respiratory Syncytial Virus fusion glycoprotein (F-protein), envelope protein from MMT virus, mouse leukemia virus protein, Hemagglutinin protein of wild-type measles virus, etc.

Fungal proteins, which may be encoded by the at least one (m)RNA of the adjuvant component of the inventive immunostimulatory composition, may be selected from any fungal protein showing adjuvant character, more preferably, from the group consisting of, without being limited thereto, fungal immunomodulatory protein (FIP; LZ-8), etc.

Finally, pathogenic adjuvant proteins, which may be encoded by the at least one (m)RNA of the adjuvant component of the inventive immunostimulatory composition, may finally be selected from any further pathogenic protein showing adjuvant character, more preferably, from the group consisting of, without being limited thereto, Keyhole limpet hemocyanin (KLH), OspA, etc.

b) Antigens

The at least one (m)RNA of the adjuvant component of the immunostimulatory composition may alternatively encode an antigen. According to the present invention, the term "antigen" refers to a substance which is recognized by the immune system and is capable of triggering an antigen-specific immune response, e.g. by formation of antibodies as part of an adaptive immune response or antigen-specific T-cells. In this context, the first step of an adaptive immune response is the activation of naïve antigen-specific T cells by antigen-presenting cells. This occurs in the lymphoid tissues and organs through which naïve T cells are constantly passing. The three cell types that can serve as antigen-presenting cells are dendritic cells, macrophages, and B cells. Each of these cells has a distinct function in eliciting immune responses. Tissue dendritic cells take up antigens by phagocytosis and macropinocytosis and are stimulated by infection to migrate to the local lymphoid tissue, where they differentiate into mature dendritic cells. Macrophages ingest particulate antigens such as bacteria and are induced by infectious agents to express MHC class II molecules. The unique ability of B cells to bind and internalize soluble protein antigens via their receptors may be important to induce T cells. By presenting the antigen on MHC molecules leads to activation of T cells which induces their proliferation and differentiation into armed effector T cells. The most important function of effector T cells is the killing of infected cells by CD8 cytotoxic T cells and the activation of macrophages by TH1 cells which together make up cell-mediated immunity, and the activation of B cells by both TH2 and TH1 cells to produce different classes of antibody, thus driving the humoral immune response. T cells recognize an antigen by their T cell receptors which does not recognize and bind antigen directly, but instead recognize short peptide fragments e.g. of pathogens' protein antigens, which are bound to MHC molecules on the surfaces of other cells.

T cells fall into two major classes that have different effector functions. The two classes are distinguished by the expression of the cell-surface proteins CD4 and CD8. These two types of T cells differ in the class of MHC molecule that they recognize. There are two classes of MHC molecule—MHC class I and MHC class II—which differ in their structure and expression pattern on tissues of the body. CD4 T cells bind to the MHC class II molecule and CD8 T cells to the MHC class I molecule. MHC class I and MHC class II have distinct distributions among cells that reflect the different effector functions of the T cells that recognize them. MHC class I molecules present peptides from pathogens, commonly viruses to CD8 T cells, which differentiate into cytotoxic T cells that are specialized to kill any cell that they specifically recognize. Almost all cells express MHC class I molecules, although the level of constitutive expression varies from one cell type to the next. But not only pathogenic peptides from viruses are presented by MHC class I molecules, also self-antigens like tumour antigens are presented by them. MHC class I molecules bind peptides from proteins degraded in the cytosol and transported in the endoplasmic reticulum. Thereby MHC class I molecules on the surface of cells infected with viruses or other cytosolic pathogens display peptides from these pathogen. The CD8 T cells that recognize MHC classI:peptide complexes are specialized to kill any cells displaying foreign peptides and so rid the body of cells infected with viruses and other cytosolic pathogens. The main function of CD4 T cells (CD4 helper T cells) that recognize MHC class II molecules is to activate other effector cells of the immune system. Thus MHC class II molecules are normally found on B lymphocytes, dendritic cells, and macrophages, cells that participate in immune responses, but not on other tissue cells. Macrophages, for example, are activated to kill the intravesicular pathogens they harbour, and B cells to secrete immunoglobulins against foreign molecules. MHC class II molecules are prevented from binding to peptides in the endoplasmic reticulum and thus MHC class II molecules bind peptides from proteins which are degraded in endosomes. They can capture peptides from pathogens that have entered the vesicular system of macrophages, or from antigens internalized by immature dendritic cells or the immunoglobulin receptors of B cells. Pathogens that accumulate in large numbers inside macrophage and dendritic cell vesicles tend to stimulate the differentiation of TH1 cells, whereas extracellular antigens tend to stimulate the production of TH2 cells. TH1 cells activate the microbicidal properties of macrophages and induce B cells to make IgG antibodies that are very effective of opsonising extracellular pathogens for ingestion by phagocytic cells, whereas TH2 cells initiate the humoral response by activating naïve B cells to secrete IgM, and induce the production of weakly opsonising antibodies such as IgG1 and IgG3 (mouse) and IgG2 and IgG4 (human) as well as IgA and IgE (mouse and human).

In the context of the present invention, antigens as encoded by the at least one (m)RNA of the adjuvant component of the inventive immunostimulatory composition typically comprise any antigen, falling under the above definition, more preferably protein and peptide antigens, e.g. tumor antigens, allergy antigens, auto-immune self-antigens, pathogenic antigens, etc. In accordance with the invention, antigens as encoded by the at least one (m)RNA of the adjuvant component of the inventive immunostimulatory composition may be antigens generated outside the cell, more typically antigens not derived from the host organism (e.g. a human) itself (i.e. non-self antigens) but rather derived from host cells outside the host organism, e.g. viral antigens, bacterial antigens, fungal antigens, protozoological antigens, animal antigens (preferably selected from animals or organisms as disclosed herein), allergy antigens, etc. Allergy antigens are typically antigens, which cause an allergy in a human and may be derived from either a human or other sources. Antigens as encoded by the at least one (m)RNA of the adjuvant component of the inventive immunostimulatory composition may be furthermore antigens generated inside the cell, the tissue or the body, e.g. by secretion of proteins, their degradation, metabolism, etc. Such antigens include antigens derived from the host organism (e.g. a human) itself, e.g. tumor antigens, self-antigens or auto-antigens, such as auto-immune self-antigens, etc., but also (non-self) antigens as defined above, which have been originally been derived from host cells outside the host organism, but which are fragmented or degraded inside the body, tissue or cell, e.g. by (protease) degradation, metabolism, etc. Pathogenic antigens particularly comprise e.g. antigens from influenza, including hemagglutinin (HA), neuroamidase (NA), matrix protein 1 (M1), ion channel protein M2 (M2), nucleoprotein (NP), etc; or e.g. antigens from respiratory syncytial virus (RSV), including F-protein, G-protein, etc.

Antigens as encoded by the at least one (m)RNA of the adjuvant component of the inventive immunostimulatory composition may furthermore comprise fragments of such antigens as mentioned herein, particularly of protein or peptide antigens. Fragments of such antigens in the context of the present invention may comprise fragments preferably having a length of about 6 to about 20 or even more amino acids, e.g. fragments as processed and presented by MHC class I molecules, preferably having a length of about 8 to about 10 amino acids, e.g. 8, 9, or 10, (or even 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T-cells in form of a complex consisting of the peptide fragment and an MHC molecule, i.e. the fragments are typically not recognized in their naïve form.

Fragments of antigens as defined herein may also comprise epitopes of those antigens. Epitopes (also called "antigen determinants") are typically fragments located on the outer surface of (naïve) protein or peptide antigens as defined herein, preferably having 5 to 15 amino acids, more preferably having 5 to 12 amino acids, even more preferably having 6 to 9 amino acids, which may be recognized by antibodies, i.e. in their naïve form.

One class of antigens as encoded by the at least one (m)RNA of the adjuvant component of the inventive immunostimulatory composition comprises tumor antigens. "Tumor antigens" are preferably located on the surface of the (tumor) cell. Tumor antigens may also be selected from proteins, which are overexpressed in tumor cells compared to a normal cell. Furthermore, tumor antigens also includes antigens expressed in cells which are (were) not themselves (or originally not themselves) degenerate but are associated with the supposed tumor. Antigens which are connected with tumor-supplying vessels or (re)formation thereof, in particular those antigens which are associated with neovascularization, e.g. growth factors, such as VEGF, bFGF etc., are also included herein. Antigens connected with a tumor furthermore include antigens from cells or tissues, typically embedding the tumor. Further, some substances (usually proteins or peptides) are expressed in patients suffering (knowingly or not-knowingly) from a cancer disease and they occur in increased concentrations in the body fluids of said patients. These substances are also referred to as "tumor antigens", however they are not antigens in the stringent meaning of an immune response inducing substance. The class of tumor antigens can be divided further into tumor-specific antigens (TSAs) and tumor-associated-antigens (TAAs). TSAs can only be presented by tumor cells and never by normal "healthy" cells. They typically result from a tumor specific mutation. TAAs, which are more common, are usually presented by both tumor and healthy cells. These antigens are recognized and the antigen-presenting cell can be destroyed by cytotoxic T cells. Additionally, tumor antigens can also occur on the surface of the tumor in the form of, e.g., a mutated receptor. In this case, they can be recognized by antibodies.

Examples of tumor antigens as encoded by the at least one (m)RNA of the adjuvant component of the inventive immunostimulatory composition are shown in Tables 1 and 2 below. These tables illustrate specific (protein) antigens (i.e. "tumor antigens") with respect to the cancer disease, they are associated with. According to the invention, the terms "cancer diseases" and "tumor diseases" are used synonymously herein.

TABLE 1

Antigens expressed in cancer diseases

| Tumor antigen | Name of tumor antigen | Cancers or cancer diseases related thereto |
|---|---|---|
| 5T4 | | colorectal cancer, gastric cancer, ovarian cancer |
| 707-AP | 707 alanine proline | Melanoma |
| 9D7 | | renal cell carcinoma |
| AFP | alpha-fetoprotein | hepatocellular carcinoma, gallbladder cancer, testicular cancer ovarian cancer, bladder cancer |
| AlbZIP HPG1 | | prostate cancer |
| alpha5beta1-Integrin | | |
| alpha5beta6-Integrin | | colon cancer |
| alpha-methylacyl-coenzyme A racemase | | prostate cancer |
| ART-4 | adenocarcinoma antigen recognized by T cells 4 | lung cancer, head and neck cancer, leukemia, esophageal cancer, gastric cancer, cervical cancer, ovarian cancer, breast cancer, squamous cell carcinoma |
| B7H4 | | ovarian cancer |
| BAGE-1 | B antigen | bladder cancer, head and neck cancer, lung cancer, melanoma, squamous cell carcinoma |
| BCL-2 | | leukemia |
| BING-4 | | melanoma |
| CA 15-3/CA 27-29 | | breast cancer, ovary cancer, lung cancer, prostate cancer |
| CA 19-9 | | gastric cancer, pancreatic cancer, liver cancer, breast cancer, gallbladder cancer, colon cancer, ovary cancer, lung cancer |
| CA 72-4 | | ovarian cancer |
| CA125 | | ovarian cancer, colorectal cancer, gastric cancer, liver cancer, pancreatic cancer, uterus cancer, cervix carcinoma, colon cancer, breast cancer, lung cancer |
| calreticulin | | bladder cancer |
| CAMEL | CTL-recognized antigen on melanoma | melanoma |
| CASP-8 | caspase-8 | head and neck cancer |
| cathepsin B | | breast cancer |
| cathepsin L | | breast cancer |
| CD19 | | B-cell malignancies |
| CD20 | | |
| CD22 | | |
| CD25 | | |
| CD30 | | |
| CD33 | | |
| CD4 | | |
| CD52 | | |
| CD55 | | |
| CD56 | | |
| CD80 | | |
| CEA | carcinoembryonic antigen | gut carcinoma, colorectal cancer, colon cancer, hepatocellular cancer, lung cancer, breast cancer, thyroid cancer, pancreatic cancer, liver cancer cervix cancer, bladder cancer, melanoma |
| CLCA2 | calcium-activated chloride channel-2 | lung cancer |
| CML28 | | leukemia |
| Coactosin-like protein | | pancreatic cancer |
| Collagen XXIII | | prostate cancer |
| COX-2 | | ovarian cancer, breast cancer, colorectal cancer |

TABLE 1-continued

| Antigens expressed in cancer diseases | | |
|---|---|---|
| Tumor antigen | Name of tumor antigen | Cancers or cancer diseases related thereto |
| CT-9/BRD6 | bromodomain testis-specific protein | |
| Cten | C-terminal tensin-like protein | prostate cancer |
| cyclin B1 | | |
| cyclin D1 | | ovarian cancer |
| cyp-B | cyclophilin B | bladder cancer, lung cancer, T-cell leukemia, squamous cell carcinoma, |
| CYPB1 | cytochrom P450 1B1 | leukemia |
| DAM-10/MAGE-B1 | differentiation antigen melanoma 10 | melanoma, skin tumors, ovarian cancer, lung cancer |
| DAM-6/MAGE-B2 | differentiation antigen melanoma 6 | melanoma, skin tumors, ovarian cancer, lung cancer |
| EGFR/Her1 | | lung cancer, ovarian cancer, head and neck cancer, colon cancer, pancreatic cancer, breast cancer |
| EMMPRIN | tumor cell-associated extracellular matrix metalloproteinase inducer/ | lung cancer, breast cancer, bladder cancer, ovarian cancer, brain cancer, lymphoma |
| EpCam | epithelial cell adhesion molecule | ovarian cancer, breast cancer, colon cancer, lung cancer |
| EphA2 | ephrin type-A receptor 2 | glioma |
| EphA3 | ephrin type-A receptor 2 | melanoma, sarcoma, lung cancer |
| ErbB3 | | breast cancer |
| EZH2 | (enhancer of Zeste homolog 2) | endometrium cancer, melanoma, prostate cancer, breast cancer |
| FGF-5 | fibroblast growth factor-5 | renal cell carcinoma, breast cancer, prostate cancer |
| FN | fibronectin | melanoma |
| Fra-1 | Fos-related antigen-1 | breast cancer, esophageal cancer, renal cell carcinoma, thyroid cancer |
| G250/CAIX | glycoprotein 250 | leukemia, renal cell carcinoma, head and neck cancer, colon cancer, ovarian cancer, cervical cancer |
| GAGE-1 | G antigen 1 | bladder cancer, lung cancer, sarcoma, melanoma, head and neck cancer |
| GAGE-2 | G antigen 2 | bladder cancer, lung cancer, sarcoma, melanoma, head and neck cancer |
| GAGE-3 | G antigen 3 | bladder cancer, lung cancer, sarcoma, melanoma, head and neck cancer |
| GAGE-4 | G antigen 4 | bladder cancer, lung cancer, sarcoma, melanoma, head and neck cancer |
| GAGE-5 | G antigen 5 | bladder cancer, lung cancer, sarcoma, melanoma, head and neck cancer |
| GAGE-6 | G antigen 6 | bladder cancer, lung cancer, sarcoma, melanoma, head and neck cancer |
| GAGE-7b | G antigen 7b | bladder cancer, lung cancer, sarcoma, melanoma, head and neck cancer |
| GAGE-8 | G antigen 8 | bladder cancer, lung cancer, sarcoma, melanoma, head and neck cancer |
| GDEP | gene differentially expressed in prostate | prostate cancer |
| GnT-V | N-acetylglucosaminyltransferase V | glioma, melanoma |
| gp100 | glycoprotein 100 kDa | melanoma |
| GPC3 | glypican 3 | hepatocellular carcinoma, melanoma |
| HAGE | helicase antigen | bladder cancer |
| HAST-2 | human signet ring tumor-2 | |
| hepsin | | prostate |
| Her2/neu/ErbB2 | human epidermal receptor-2/neurological | breast cancer, bladder cancer, melanoma, ovarian cancer, pancreas cancer, gastric cancer |
| HERV-K-MEL | | melanoma |
| HNE | human neutrophil elastase | leukemia |
| homeobox NKX 3.1 | | prostate cancer |

TABLE 1-continued

| Antigens expressed in cancer diseases | | |
|---|---|---|
| Tumor antigen | Name of tumor antigen | Cancers or cancer diseases related thereto |
| HOM-TES-14/SCP-1 | | ovarian cancer |
| HOM-TES-85 | | |
| HPV-E6 | | cervical cancer |
| HPV-E7 | | cervical cancer |
| HST-2 | | gastric cancer |
| hTERT | human telomerase reverse transcriptase | breast cancer, melanoma, lung cancer, ovarian cancer, sarcoma, Non-Hodgkin-lymphoma, acute leukemia |
| iCE | intestinal carboxyl esterase | renal cell carcinoma |
| IGF-1R | | colorectal cancer |
| IL-13Ra2 | interleukin 13 receptor alpha 2 chain | glioblastoma |
| IL-2R | | colorectal cancer |
| IL-5 | | |
| immature laminin receptor | | renal cell carcinoma |
| kallikrein 2 | | prostate cancer |
| kallikrein 4 | | prostate cancer |
| Ki67 | | prostate cancer, breast cancer, Non-Hodgkin-lymphoma, melanoma |
| KIAA0205 | | bladder cancer |
| KK-LC-1 | Kita-kyushu lung cancer antigen 1 | lung cancer |
| KM-HN-1 | | tongue cancer, hepatocellular carcinomas, melanoma, gastric cancer, esophageal, colon cancer, pancreatic cancer |
| LAGE-1 | L antigen | bladder cancer, head and neck cancer, melanoma |
| livin | | bladder cancer, melanoma |
| MAGE-A1 | melanoma antigen-A1 | bladder cancer, head and neck cancer, melanoma, colon cancer, lung cancer, sarcoma, leukemia |
| MAGE-A10 | melanoma antigen-A10 | bladder cancer, head and neck cancer, melanoma, colon cancer, lung cancer, sarcoma, leukemia |
| MAGE-A12 | melanoma antigen-A12 | bladder cancer, head and neck cancer, melanoma, colon cancer, lung cancer, sarcoma, leukemia, prostate cancer, myeloma, brain tumors |
| MAGE-A2 | melanoma antigen-A2 | bladder cancer, head and neck cancer, melanoma, colon cancer, lung cancer, sarcoma, leukemia |
| MAGE-A3 | melanoma antigen-A3 | bladder cancer, head and neck cancer, melanoma, colon cancer, lung cancer, sarcoma, leukemia |
| MAGE-A4 | melanoma antigen-A4 | bladder cancer, head and neck cancer, melanoma, colon cancer, lung cancer, sarcoma, leukemia |
| MAGE-A6 | melanoma antigen-A6 | bladder cancer, head and neck cancer, melanoma, colon cancer, lung cancer, sarcoma, leukemia |
| MAGE-A9 | melanoma-antigen-A9 | bladder cancer, head and neck cancer, melanoma, colon cancer, lung cancer, sarcoma, leukemia |
| MAGE-B1 | melanoma-antigen-B1 | melanoma |
| MAGE-B10 | melanoma-antigen-B10 | melanoma |
| MAGE-B16 | melanoma-antigen-B16 | melanoma |
| MAGE-B17 | melanoma-antigen-B17 | melanoma |
| MAGE-B2 | melanoma-antigen-B2 | melanoma |
| MAGE-B3 | melanoma-antigen-B3 | melanoma |
| MAGE-B4 | melanoma-antigen-B4 | melanoma |
| MAGE-B5 | melanoma-antigen-B5 | melanoma |
| MAGE-B6 | melanoma-antigen-B6 | melanoma |
| MAGE-C1 | melanoma-antigen-C1 | bladder cancer, melanoma |
| MAGE-C2 | melanoma-antigen-C2 | melanoma |
| MAGE-C3 | melanoma-antigen-C3 | melanoma |
| MAGE-D1 | melanoma-antigen-D1 | melanoma |
| MAGE-D2 | melanoma-antigen-D2 | melanoma |
| MAGE-D4 | melanoma-antigen-D4 | melanoma |
| MAGE-E1 | melanoma-antigen-E1 | bladder cancer, melanoma |
| MAGE-E2 | melanoma-antigen-E2 | melanoma |
| MAGE-F1 | melanoma-antigen-F1 | melanoma |

TABLE 1-continued

| Antigens expressed in cancer diseases | | |
|---|---|---|
| Tumor antigen | Name of tumor antigen | Cancers or cancer diseases related thereto |
| MAGE-H1 | melanoma-antigen-H1 | melanoma |
| MAGEL2 | MAGE-like 2 | melanoma |
| mammaglobin A | | breast cancer |
| MART-1/Melan-A | melanoma antigen recognized by T cells-1/melanoma antigen A | melanoma |
| MART-2 | melanoma antigen recognized by T cells-2 | melanoma |
| matrix protein 22 | | bladder cancer |
| MC1R | melanocortin 1 receptor | melanoma |
| M-CSF | macrophage colony-stimulating factor gene | ovarian cancer |
| mesothelin | | ovarian cancer |
| MG50/PXDN | | breast cancer, glioblastoma, melanoma |
| MMP 11 | M-phase phosphoprotein 11 | leukemia |
| MN/CA IX-antigen | | renal cell carcinoma |
| MRP-3 | multidrug resistance-associated protein 3 | lung cancer |
| MUC1 | mucin 1 | breast cancer |
| MUC2 | mucin 2 | breast cancer, ovarian cancer, pancreatic cancer |
| NA88-A | NA cDNA clone of patient M88 | melanoma |
| N-acetylglucos-aminyltransferase-V | | |
| Neo-PAP | Neo-poly(A) polymerase | |
| NGEP | | prostate cancer |
| NMP22 | | bladder cancer |
| NPM/ALK | nucleophosmin/anaplastic lymphoma kinase fusion protein | |
| NSE | neuron-specific enolase | small cell cancer of lung, neuroblastoma, Wilm' tumor, melanoma, thyroid cancer, kidney cancer, testicle cancer, pancreas cancer |
| NY-ESO-1 | New York esophageous 1 | bladder cancer, head and neck cancer, melanoma, sarcoma, B-lymphoma, hepatoma, pancreatic cancer, ovarian cancer, breast cancer |
| NY-ESO-B | | |
| OA1 | ocular albinism type 1 protein | melanoma |
| OFA-iLRP | oncofetal antigen-immature laminin receptor | leukemia |
| OGT | O-linked N-acetylglucosamine transferase gene | |
| OS-9 | | |
| osteocalcin | | prostate cancer |
| osteopontin | | prostate cancer, breast cancer, ovarian cancer |
| p15 | protein 15 | |
| p15 | | melanoma |
| p190 minor bcr-abl | | |
| p53 | | |
| PAGE-4 | prostate GAGE-like protein-4 | prostate cancer |
| PAI-1 | plasminogen acitvator inhibitor 1 | breast cancer |
| PAI-2 | plasminogen acitvator inhibitor 2 | breast cancer |
| PAP | prostate acic phosphatase | prostate cancer |
| PART-1 | | prostate cancer |
| PATE | | prostate cancer |
| PDEF | | prostate cancer |
| Pim-1-Kinase | | |
| Pin1 | Propyl isomerase | prostate cancer |
| POTE | | prostate cancer |
| PRAME | preferentially expressed antigen of melanoma | melanoma, lung cancer, leukemia, head and neck cancer, renal cell carcinoma, sarcoma |
| prostein | | prostate cancer |
| proteinase-3 | | |
| PSA | prostate-specific antigen | prostate cancer |
| PSCA | | prostate cancer |
| PSGR | | prostate cancer |
| PSM | | |

TABLE 1-continued

| Antigens expressed in cancer diseases | | |
|---|---|---|
| Tumor antigen | Name of tumor antigen | Cancers or cancer diseases related thereto |
| PSMA | prostate-specific membrane antigen | prostate cancer |
| RAGE-1 | renal antigen | bladder cancer, renal cancer, sarcoma, colon cancer |
| RHAMM/CD168 | receptor for hyaluronic acid mediated motility | leukemia |
| RU1 | renal ubiquitous 1 | bladder cancer, melanoma, renal cancer |
| RU2 | renal ubiquitous 1 | bladder cancer, melanoma, sarcoma brain tumor, esophagel cancer, renal cancer, colon cancer, breast cancer |
| S-100 | | melanoma |
| SAGE | sarcoma antigen | |
| SART-1 | squamous antigen rejecting tumor 1 | esophageal cancer, head and neck cancer, lung cancer, uterine cancer |
| SART-2 | squamous antigen rejecting tumor 1 | head and neck cancer, lung cancer, renal cell carcinoma, melanoma, brain tumor |
| SART-3 | squamous antigen rejecting tumor 1 | head and neck cancer, lung cancer, leukemia, melanoma, esophageal cancer |
| SCC | squamous cell carcinoma antigen | lung cancer |
| Sp17 | sperm protein 17 | multiple myeloma |
| SSX-1 | synovial sarcoma X breakpoint 1 | hepatocellular cell carcinom, breast cancer |
| SSX-2/HOM-MEL-40 | synovial sarcoma X breakpoint 2 | breast cancer |
| SSX-4 | synovial sarcoma X breakpoint 4 | bladder cancer, hepatocellular cell carcinoma, breast cancer |
| STAMP-1 | | prostate cancer |
| STEAP | six transmembrane epithelial antigen prostate | prostate cancer |
| survivin | | bladder cancer |
| survivin-2B | intron 2-retaining survivin | bladder cancer |
| TA-90 | | melanoma |
| TAG-72 | | prostate carcinoma |
| TARP | | prostate cancer |
| TGFb | TGFbeta | |
| TGFbRII | TGFbeta receptor II | |
| TGM-4 | prostate-specific transglutaminase | prostate cancer |
| TRAG-3 | taxol resistant associated protein 3 | breast cancer, leukemia, and melanoma |
| TRG | testin-related gene | |
| TRP-1 | tyrosine related protein 1 | melanoma |
| TRP-2/6b | TRP-2/novel exon 6b | melanoma, glioblastoma |
| TRP-2/INT2 | TRP-2/intron 2 | melanoma, glioblastoma |
| Trp-p8 | | prostate cancer |
| Tyrosinase | | melanoma |
| UPA | urokinase-type plasminogen activator | breast cancer |
| VEGF | vascular endothelial growth factor | |
| VEGFR-2/FLK-1 | vascular endothelial growth factor receptor-2 | |
| WT1 | Wilm' tumor gene | gastric cancer, colon cancer, lung cancer, breast cancer, ovarian cancer, leukemia |

TABLE 2

| Mutant antigens expressed in cancer diseases | | |
|---|---|---|
| Mutant antigen | Name of mutant antigen | Cancers or cancer diseases related thereto |
| alpha-actinin-4/m | | lung carcinoma |
| ARTC1/m | | melanoma |
| bcr/abl | breakpoint cluster region-Abelson fusion protein | CML |
| beta-Catenin/m | beta-Catenin | melanoma |
| BRCA1/m | | breast cancer |
| BRCA2/m | | breast cancer |

TABLE 2-continued

| Mutant antigens expressed in cancer diseases | | |
|---|---|---|
| Mutant antigen | Name of mutant antigen | Cancers or cancer diseases related thereto |
| CASP-5/m | | colorectal cancer, gastric cancer, endometrial carcinoma |
| CASP-8/m | | head and neck cancer, squamous cell carcinoma |
| CDC27/m | cell-division-cycle 27 | |
| CDK4/m | cyclin-dependent kinase 4 | melanoma |
| CDKN2A/m | | melanoma |
| CML66 | | CML |
| COA-1/m | | colorectal cancer |
| DEK-CAN | fusion protein | AML |
| EFTUD2/m | | melanoma |
| ELF2/m | Elongation factor 2 | lung squamous cell carcinoma |
| ETV6-AML1 | Ets variant gene6/acute myeloid leukemia 1 gene fusion protein | ALL |
| FN1/m | fibronectin 1 | melanoma |
| GPNMB/m | | melanoma |
| HLA-A*0201-R170I | arginine to isoleucine exchange at residue 170 of the alpha-helix of the alpha2-domain in the HLA-A2 gene | renal cell carcinoma |
| HLA-A11/m | | melanoma |
| HLA-A2/m | | renal cell carcinoma |
| HSP70-2M | heat shock protein 70-2 mutated | renal cell carcinoma, melanoma, neuroblastoma |
| KIAA0205/m | | bladder tumor |
| K-Ras/m | | pancreatic carcinoma, colorectal carcinoma |
| LDLR-FUT | LDR-Fucosyltransferase fusion protein | melanoma |
| MART2/m | | melanoma |
| ME1/m | | non-small cell lung carcinoma |
| MUM-1/m | melanoma ubiquitous mutated 1 | melanoma |
| MUM-2/m | melanoma ubiquitous mutated 2 | melanoma |
| MUM-3/m | melanoma ubiquitous mutated 3 | melanoma |
| Myosin class I/m | | melanoma |
| neo-PAP/m | | melanoma |
| NFYC/m | | lung squamous cell carcinoma |
| N-Ras/m | | melanoma |
| OGT/m | | colorectal carcinoma |
| OS-9/m | | melanoma |
| p53/m | | |
| Pml/RARa | promyelocytic leukemia/retinoic acid receptor alpha | APL, PML |
| PRDX5/m | | melanoma |
| PTPRK/m | receptor-type protein-tyrosine phosphatase kappa | melanoma |
| RBAF600/m | | melanoma |
| SIRT2/m | | melanoma |
| SYT-SSX-1 | synaptotagmin I/synovial sarcoma X fusion protein | sarcoma |
| SYT-SSX-2 | synaptotagmin I/synovial sarcoma X fusion protein | sarcoma |
| TEL-AML1 | translocation Ets-family leukemia/acute myeloid leukemia 1 fusion protein | AML |
| TGFbRII | TGFbeta receptor II | colorectal carcinoma |
| TPI/m | triosephosphate isomerase | Melanoma |

In a preferred embodiment according to the present invention, the tumor antigens as encoded by the at least one (m)RNA of the adjuvant component of the inventive immunostimulatory composition are selected from the group consisting of 5T4, 707-AP, 9D7, AFP, AlbZIP HPG1, alpha-5-beta-1-integrin, alpha-5-beta-6-integrin, alpha-actinin-4/m, alpha-methylacyl-coenzyme A racemase, ART-4, ARTC1/m, B7H4, BAGE-1, BCL-2, bcr/abl, beta-catenin/m, BING-4, BRCA1/m, BRCA2/m, CA 15-3/CA 27-29, CA 19-9, CA72-4, CA125, calreticulin, CAMEL, CASP-8/m, cathepsin B, cathepsin L, CD19, CD20, CD22, CD25, CDE30, CD33, CD4, CD52, CD55, CD56, CD80, CDC27/m, CDK4/m, CDKN2A/m, CEA, CLCA2, CML28, CML66, COA-1/m, coactosin-like protein, collage XXIII, COX-2, CT-9/BRD6, Cten, cyclin B1, cyclin D1, cyp-B, CYPB1, DAM-10, DAM-6, DEK-CAN, EFTUD2/m, EGFR, ELF2/m, EMMPRIN, EpCam, EphA2, EphA3, ErbB3, ETV6-AML1, EZH2, FGF-5, FN, Frau-1, G250, GAGE-1, GAGE-2, GAGE-3, GAGE-4, GAGE-5, GAGE-6, GAGE7b, GAGE-8, GDEP, GnT-V, gp100, GPC3, GPNMB/m, HAGE, HAST-2, hepsin, Her2/neu, HERV-K-MEL, HLA-A*0201-R171, HLA-A11/m, HLA-A2/m, HNE, homeobox NKX3.1, HOM-TES-14/SCP-1, HOM-TES-85, HPV-E6, HPV-E7, HSP70-2M, HST-2, hTERT, iCE, IGF-1R, IL-13Ra2, IL-2R, IL-5, immature laminin receptor, kallikrein-2, kallikrein-4, Ki67, KIAA0205, KIAA0205/m, KK-LC-1, K-Ras/m, LAGE-A1, LDLR-FUT, MAGE-A1, MAGE-A2, MAGE-A3, MAGE-A4, MAGE-A6, MAGE-A9, MAGE-A10, MAGE-A12, MAGE-B1, MAGE-B2, MAGE-B3, MAGE-B4, MAGE-B5, MAGE-B6, MAGE-B10, MAGE-B16, MAGE-B17, MAGE-C1, MAGE-C2, MAGE-C3, MAGE-D1, MAGE-D2, MAGE-D4, MAGE-E1, MAGE-E2, MAGE-F1, MAGE-H1, MAGEL2, mammaglobin A, MART-1/melan-A, MART-2, MART-2/m, matrix protein 22, MC1R, M-CSF, ME1/m, mesothelin, MG50/PXDN, MMP11, MN/CA IX-antigen, MRP-3, MUC-1, MUC-2, MUM-1/m, MUM-2/m, MUM-3/m, myosin class I/m, NA88-A, N-acetylglucosaminyltransferase-V, Neo-PAP, Neo-PAP/m, NFYC/m, NGEP, NMP22, NPM/ALK, N-Ras/m, NSE, NY-ESO-1, NY-ESO-B, OA1, OFA-iLRP, OGT, OGT/m, OS-9, OS-9/m, osteocalcin, osteopontin, p15, p190 minor bcr-abl, p53, p53/m, PAGE-4, PAI-1, PAI-2, PART-1, PATE, PDEF, Pim-1-Kinase, Pin-1, Pml/PARalpha, POTE, PRAME, PRDX5/m, prostein, proteinase-3, PSA, PSCA, PSGR, PSM, PSMA, PTPRK/m, RAGE-1, RBAF600/m, RHAMM/CD168, RU1, RU2, S-100, SAGE, SART-1, SART-2, SART-3, SCC, SIRT2/m, Sp17, SSX-1, SSX-2/HOM-MEL-40, SSX-4, STAMP-1, STEAP, survivin, survivin-2B, SYT-SSX-1, SYT-SSX-2, TA-90, TAG-72, TARP, TEL-AML1, TGFbeta, TGFbetaR11, TGM-4, TPI/m, TRAG-3, TRG, TRP-1, TRP-2/6b, TRP/INT2, TRP-p8, tyrosinase, UPA, VEGF, VEGFR-2/FLK-1, and WT1.

In a particularly preferred embodiment, the tumor antigens as encoded by the at least one (m)RNA of the adjuvant component of the inventive immunostimulatory composition are selected from the group consisting of MAGE-A1 (e.g. MAGE-A1 according to accession number M77481), MAGE-A2, MAGE-A3, MAGE-A6 (e.g. MAGE-A6 according to accession number NM_005363), MAGE-C1, MAGE-C2, melan-A (e.g. melan-A according to accession number NM_005511), GP100 (e.g. GP100 according to accession number M77348), tyrosinase (e.g. tyrosinase according to accession number NM_000372), survivin (e.g. survivin according to accession number AF077350), CEA (e.g. CEA according to accession number NM_004363), Her-2/neu (e.g. Her-2/neu according to accession number M11730), WT1 (e.g. WT1 according to accession number NM_000378), PRAME (e.g. PRAME according to accession number NM_006115), EGFR1 (epidermal growth factor receptor 1) (e.g. EGFR1 (epidermal growth factor receptor 1) according to accession number AF288738), MUC1, mucin-1 (e.g. mucin-1 according to accession number NM_002456), SEC61 G (e.g. SEC61G according to accession number NM_014302), hTERT (e.g. hTERT accession number NM_198253), 5T4 (e.g. 5T4 according to accession number NM_006670), NY-Eso-1 (e.g. NY-Eso1 according to accession number NM_001327), TRP-2 (e.g. TRP-2 according to accession number NM_001922), STEAP, PCA, PSA, PSMA, etc.

According to a further particularly preferred embodiment, the tumor antigens as encoded by the at least one (m)RNA of the adjuvant component of the inventive immunostimulatory composition may form a cocktail of antigens, e.g. in an active (immunostimulatory) composition or a kit of parts (wherein preferably each antigen is contained in one part of the kit), preferably for eliciting an (adaptive) immune response for the treatment of prostate cancer (PCa), preferably of neoadjuvant and/or hormone-refractory prostate cancers, and diseases or disorders related thereto. For this purpose, the at least one (m)RNA of the adjuvant component of the inventive immunostimulatory composition is preferably at least one RNA, more preferably at least one mRNA, which may encode at least one, preferably two, three or even four (preferably different) antigens of the following group of antigens:

PSA (Prostate-Specific Antigen)=KLK3 (Kallikrein-3),
PSMA (Prostate-Specific Membrane Antigen),
PSCA (Prostate Stem Cell Antigen),
STEAP (Six Transmembrane Epithelial Antigen of the Prostate).

According to another particularly preferred embodiment, the tumor antigens as encoded by the at least one (m)RNA of the adjuvant component of the inventive immunostimulatory composition may form a cocktail of antigens, e.g. in an active (immunostimulatory) composition or a kit of parts (wherein preferably each antigen is contained in one part of the kit), preferably for eliciting an (adaptive) immune response for the treatment of non-small cell lung cancers (NSCLC), preferably selected from the three main sub-types squamous cell lung carcinoma, adenocarcinoma and large cell lung carcinoma, or of disorders related thereto. For this purpose, the at least one (m)RNA of the adjuvant component of the inventive immunostimulatory composition is preferably at least one mRNA, which may encode at least one, preferably two, three, four, five, six, seven, eight, nine, ten eleven or twelve (preferably different) antigens of the following group of antigens:

hTERT,
WT1,
MAGE-A2,
5T4,
MAGE-A3,
MUC1,
Her-2/neu,
NY-ESO-1,
CEA,
Survivin,
MAGE-C1, and/or
MAGE-C2, wherein any combination of these antigens is possible.

According to a further particularly preferred embodiment, the tumor antigens as encoded by the at least one (m)RNA of the adjuvant component of the inventive immunostimulatory composition may form a cocktail of antigens, e.g. in an active (immunostimulatory) composition or a kit of parts (wherein preferably each antigen is contained in one part of the kit), preferably for eliciting an (adaptive) immune response for the treatment of non-small cell lung cancers (NSCLC), preferably selected from the three main sub-types squamous cell lung carcinoma, adenocarcinoma and large cell lung carcinoma, or of disorders related thereto. For this purpose, the at least one (m)RNA of the adjuvant component of the inventive immunostimulatory composition is preferably at least one RNA, more preferably at least one mRNA, which may encode at least two (preferably different) antigens, a) wherein at least one, preferably at least two, three, four, five or even six, of these at least two antigens is (are) selected from:
   5T4
   NY-ESO-1,
   MAGE-A2,
   MAGE-A3,
   MAGE-C1, and/or
   MAGE-C2, and
b) wherein the further antigen(s) is (are) selected from at least one antigen as defined herein, preferably in any of the herein mentioned combinations, groups or subgroups of antigens, e.g. the further antigen(s) is (are) selected from, e.g.:

hTERT,
WT1,
MAGE-A2,
5T4,
MAGE-A3,
MUC1,
Her-2/neu,
NY-ESO-1,
CEA,
Survivin,
MAGE-C1, and/or
MAGE-C2.

In the above embodiments, each of the above defined proteins, e.g. therapeutically active proteins, antibodies, antigens, etc., as defined herein may be encoded by one (monocistronic) RNA, preferably one (monocistronic) mRNA. In other words, the at least one (m)RNA of the adjuvant component of the inventive immunostimulatory composition may comprise at least two (monocistronic) RNAs, preferably mRNAs, wherein each of these at least two (monocistronic) RNAs, preferably mRNAs, may encode, e.g. just one (preferably different) protein, e.g. an antigen, preferably selected from one of the above mentioned antigen combinations.

According to another particularly preferred embodiment, the at least one (m)RNA of the adjuvant component of the inventive immunostimulatory composition may comprise (at least) one bi- or even multicistronic RNA, preferably mRNA, i.e. (at least) one RNA which carries, e.g. two or even more of the coding sequences of at least two (preferably different) proteins, e.g. antigens, preferably selected from one of the above mentioned antigen combinations. Such coding sequences, e.g. of the at least two (preferably different) proteins, e.g. antigens, of the (at least) one bi- or even multicistronic RNA may be separated by at least one IRES (internal ribosomal entry site) sequence, as defined below. Thus, the term “encoding at least two (preferably different) proteins” may mean, without being limited thereto, that the (at least) one (bi- or even multicistronic) RNA, preferably an mRNA, may encode e.g. at least two, three, four, five, six, seven, eight, nine, ten, eleven or twelve or more (preferably different) proteins, e.g. antigens of the above mentioned group(s) of antigens, or their fragments or variants, therapeutically active proteins, antibodies, adjuvant proteins, etc. More preferably, without being limited thereto, the (at least) one (bi- or even multicistronic) RNA, preferably mRNA, may encode e.g. at least two, three, four, five or six or more (preferably different) proteins, e.g. antigens of the above mentioned subgroup(s) of antigens, or their fragments or variants within the above definitions. In this context, a so-called IRES (internal ribosomal entry site) sequence as defined herein can function as a sole ribosome binding site, but it can also serve to provide a bi- or even multicistronic RNA as defined herein which codes for several proteins, which are to be translated by the ribosomes independently of one another. Examples of IRES sequences which can be used according to the invention are those from picornaviruses (e.g. FMDV), pestiviruses (CFFV), polioviruses (PV), encephalomyocarditis viruses (ECMV), foot and mouth disease viruses (FMDV), hepatitis C viruses (HCV), classical swine fever viruses (CSFV), mouse leukoma virus (MLV), simian immunodeficiency viruses (SIV) or cricket paralysis viruses (CrPV).

According to a further particularly preferred embodiment, the at least one (m)RNA of the adjuvant component of the inventive immunostimulatory composition may comprise a mixture of at least one monocistronic RNA, preferably mRNA, as defined herein, and at least one bi- or even multicistronic RNA, preferably mRNA, as defined herein. The at least one monocistronic RNA and/or the at least one bi- or even multicistronic RNA preferably encode different proteins, e.g. antigens, or their fragments or variants, the antigens preferably being selected from one of the above mentioned groups or subgroups of antigens, more preferably in one of the above mentioned combinations. However, the at least one monocistronic RNA and the at least one bi- or even multicistronic RNA may preferably also encode (in part) identical proteins as defined herein, e.g. antigens selected from one of the above mentioned groups or subgroups of antigens, preferably in one of the above mentioned combinations, provided that the at least one (m)RNA of the adjuvant component of the inventive immunostimulatory composition as a whole provides at least two (preferably different) proteins, e.g. antigens, as defined herein. Such an embodiment may be advantageous e.g. for a staggered, e.g. time dependent, administration of one or several of the at least one (m)RNA of the adjuvant component of the inventive immunostimulatory composition, e.g. as a pharmaceutical composition, to a patient in need thereof. The components of such a pharmaceutical composition of the present invention, particularly the different complexed RNAs encoding the at least two (preferably different) proteins, may be e.g. contained in (different parts of) a kit of parts composition or may be e.g. administered separately as components of different pharmaceutical compositions according to the present invention.

One further class of antigens as encoded by the at least one (m)RNA of the adjuvant component of the inventive immunostimulatory composition comprises allergy antigens. Such allergy antigens may be selected from antigens derived from different sources, e.g. from animals, plants, fungi, bacteria, etc. Allergens in this context include e.g. grasses, pollens, molds, drugs, or numerous environmental triggers, etc. Allergy antigens typically belong to different classes of compounds, such as nucleic acids and their fragments, proteins or peptides and their fragments, carbohydrates, polysaccharides, sugars, lipids, phospholipids, etc. Of particular interest in the context of the present invention are antigens, which are encoded by the at least one (m)RNA of the adjuvant component of the inventive immunostimulatory composition, i.e. protein or peptide antigens and their fragments or epitopes, or nucleic acids and their fragments, particularly nucleic acids and their fragments, encoding such protein or peptide antigens and their fragments or epitopes.

Particularly preferred, antigens derived from animals, which are encoded by the at least one (m)RNA of the adjuvant component of the inventive immunostimulatory composition, may include antigens derived from, without being limited thereto, insects, such as mite (e.g. house dust mites), mosquito, bee (e.g. honey bee, bumble bee), cockroache, tick, moth (e.g. silk moth), midge, bug, flea, wasp, caterpillar, fruit fly, migratory locust, grasshopper, ant aphide, from crustaceans, such as shrimps, crab, krill, lobster, prawn, crawfish, scampi, from birds, such as duck, goose, seagull, turkey, ostrich, chicken, from fishes, such as eel, herring, carp, seabream, codfish, halibut, catfish, beluga, salmon, flounder, mackerel, cuttlefish, perch, form molluscs, such as scallop, octopus, abalone, snail, whelk, squid, clam, mussel, from spiders, from mammals, such as cow, rabbit, sheep, lion, jaguar, leopard, rat, pig, buffalo, dog, loris, hamster, guinea pig, fallow deer, horse, cat, mouse, ocelot, serval, from arthropod, such as spider, or silverfish, from worms, such as nematodes, from *trichinella* species, or roundworm, from amphibians, such as frogs, or from sea squirt, etc.

Antigens derived from plants, which are encoded by the at least one (m)RNA of the adjuvant component of the inventive immunostimulatory composition, may include antigens derived from, without being limited thereto, fruits, such as kiwi, pineapple, jackfruit, papaya, lemon, orange, mandarin, melon, sharon fruit, strawberry, lychee, apple, cherry paradise apple, mango, passion fruit, plum, apricot, nectarine, pear, passion fruit, raspberry, grape, from vegetables, such as garlic, onion, leek, soya bean, celery, cauliflower, turnip, paprika, chickpea, fennel, zucchini, cucumber, carrot, yam, bean, pea, olive, tomato, potato, lentil, lettuce, avocado, parsley, horseradish, chirimoya, beet, pumkin, spinach, from spices, such as mustard, coriander, saffron, pepper, aniseed, from crop, such as oat, buckwheat, barley, rice, wheat, maize, rapeseed, sesame, from nuts, such as cashew, walnut, butternut, pistachio, almond, hazelnut, peanut, brazil nut, pecan, chestnut, from trees, such as alder, hornbeam, cedar, birch, hazel, beech, ash, privet, oak, plane tree, cypress, palm, from flowers, such as ragweed, carnation, forsythia, sunflower, lupine, chamomile, lilac, passion flower, from grasses, such as quack grass, common bent, brome grass, Bermuda grass, sweet vernal grass, rye grass, or from other plants, such as opium poppy, pellitory, ribwort, tobacco, asparagus, mugwort, cress, etc.

Antigens derived from fungi, which are encoded by the at least one (m)RNA of the adjuvant component of the inventive immunostimulatory composition, may include antigens derived from, without being limited thereto, e.g. *Alternia* sp., *Aspergillus* sp., *Beauveria* sp., *Candida* sp., *Cladosporium* sp., *Endothia* sp., *Curcularia* sp., *Embellisia* sp., *Epicoccum* sp., *Fusarium* sp., *Malassezia* sp., *Penicillum* sp., *Pleospora* sp., *Saccharomyces* sp., etc.

Antigens derived from bacteria, which are encoded by the at least one (m)RNA of the adjuvant component of the inventive immunostimulatory composition, may include antigens derived from, without being limited thereto, e.g. *Bacillus tetani, Staphylococcus aureus, Streptomyces griseus*, etc.

c) Antibodies

According to a further embodiment, the at least one (m)RNA of the adjuvant component of the inventive immunostimulatory composition may encode an antibody. According to the present invention, such an antibody may be selected from any antibody, e.g. any recombinantly produced or naturally occurring antibodies, known in the art, in particular antibodies suitable for therapeutic, diagnostic or scientific purposes, or antibodies which have been identified in relation to specific cancer diseases. Herein, the term "antibody" is used in its broadest sense and specifically covers monoclonal and polyclonal antibodies (including agonist, antagonist, and blocking or neutralizing antibodies) and antibody species with polyepitopic specificity. According to the invention, "antibody" typically comprises any antibody known in the art (e.g. IgM, IgD, IgG, IgA and IgE antibodies), such as naturally occurring antibodies, antibodies generated by immunization in a host organism, antibodies which were isolated and identified from naturally occurring antibodies or antibodies generated by immunization in a host organism and recombinantly produced by biomolecular methods known in the art, as well as chimeric antibodies, human antibodies, humanized antibodies, bispecific antibodies, intrabodies, i.e. antibodies expressed in cells and optionally localized in specific cell compartments, and fragments and variants of the aforementioned antibodies. In general, an antibody consists of a light chain and a heavy chain both having variable and constant domains. The light chain consists of an N-terminal variable domain, $V_L$, and a C-terminal constant domain, $C_L$. In contrast, the heavy chain of the IgG antibody, for example, is comprised of an N-terminal variable domain, $V_H$, and three constant domains, $C_H1$, $C_H2$ and $C_H3$. Single chain antibodies may be encoded by the RNA of the modified (m)RNA of the invention as well, preferably by a single-stranded RNA, more preferably by an mRNA.

According to a first alternative, the at least one (m)RNA of the adjuvant component of the inventive immunostimulatory composition may encode a polyclonal antibody. In this context, the term, "polyclonal antibody" typically means mixtures of antibodies directed to specific antigens or immunogens or epitopes of a protein which were generated by immunization of a host organism, such as a mammal, e.g. including goat, cattle, swine, dog, cat, donkey, monkey, ape, a rodent such as a mouse, hamster and rabbit. Polyclonal antibodies are generally not identical, and thus usually recognize different epitopes or regions from the same antigen. Thus, in such a case, typically a mixture (a composition) of different RNAs will be used as the at least one (m)RNA of the adjuvant component of the inventive immunostimulatory composition, each RNA encoding a specific (monoclonal) antibody being directed to specific antigens or immunogens or epitopes of a protein.

According to a further alternative, the at least one (m)RNA of the adjuvant component of the inventive immunostimulatory composition may encode a monoclonal antibody. The term "monoclonal antibody" herein typically refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed to a single antigenic site. Furthermore, in contrast to conventional (polyclonal) antibody preparations which typically include different antibodies directed to different determinants (epitopes), each monoclonal antibody is directed to a single determinant on the antigen. For example, monoclonal antibodies as defined above may be made by the hybridoma method first described by Kohler and Milstein, Nature, 256:495 (1975), or may be made by recombinant DNA methods, e.g. as described in U.S. Pat. No. 4,816,567. "Monoclonal antibodies" may also be isolated from phage libraries generated using the techniques described in McCafferty et al., Nature, 348:552-554 (1990), for example. According to Kohler and Milstein, an immunogen (antigen) of interest is injected into a host such as a mouse and B-cell lymphocytes produced in response to the immunogen are harvested after a period of time. The B-cells are combined with myeloma cells obtained from mouse and introduced into a medium which permits the B-cells to fuse with the myeloma cells, producing hybridomas. These fused cells (hybridomas) are then placed into separate wells of microtiter plates and grown to produce monoclonal antibodies. The monoclonal antibodies are tested to determine which of them are suitable for detecting the antigen of interest. After being selected, the monoclonal antibodies can be grown in cell cultures or by injecting the hybridomas into mice. However, for the purposes of the present invention, the peptide sequences of these monoclonal antibodies have to be sequenced and the RNA sequences encoding these antibodies can be used as the at least one (m)RNA of the adjuvant component of the inventive immunostimulatory composition, which can be prepared according to procedures well known in the art.

For therapeutical purposes in humans, non-human monoclonal or polyclonal antibodies, such as murine antibodies may also be encoded by the at least one (m)RNA of the adjuvant component of the inventive immunostimulatory composition. However, such antibodies are typically only of limited use, since they generally induce an immune response by production of human antibodies directed to the said non-human antibodies, in the human body. Therefore, a particular non-human antibody can only be administered once to the human. To solve this problem, chimeric, humanized non-human and human antibodies are also envisaged encoded by the at least one (m)RNA of the adjuvant component of the inventive immunostimulatory composition. “Chimeric” antibodies, which may be encoded by the at least one (m)RNA of the adjuvant component of the inventive immunostimulatory composition, are preferably antibodies in which the constant domains of an antibody described above are replaced by sequences of antibodies from other organisms, preferably human sequences. “Humanized” (non-human) antibodies, which may be also encoded by the at least one (m)RNA of the adjuvant component of the inventive immunostimulatory composition, are antibodies in which the constant and variable domains (except for the hypervariable domains) described above of an antibody are replaced by human sequences. According to another alternative, the at least one (m)RNA of the adjuvant component of the inventive immunostimulatory composition may encode human antibodies, i.e. antibodies having only human sequences. Such human antibodies can be isolated from human tissues or from immunized non-human host organisms which are transgene for the human IgG gene locus, and RNA sequences may be prepared according to procedures well known in the art. Additionally, human antibodies can be provided by the use of a phage display.

In addition, the at least one (m)RNA of the adjuvant component of the inventive immunostimulatory composition may encode bispecific antibodies. “Bispecific” antibodies in context of the invention are preferably antibodies which act as an adaptor between an effector and a respective target by two different $F_{a/b}$-domains, e.g. for the purposes of recruiting effector molecules such as toxins, drugs, cytokines etc., targeting effector cells such as CTL, NK cells, makrophages, granulocytes, etc. (see for review: Kontermann R. E., Acta Pharmacol. Sin, 2005, 26(1): 1-9). Bispecific antibodies as described herein are, in general, configured to recognize by two different $F_{a/b}$-domains, e.g. two different antigens, immunogens, epitopes, drugs, cells (or receptors on cells), or other molecules (or structures) as described above. Bispecificity means herewith that the antigen-binding regions of the antibodies are specific for two different epitopes. Thus, different antigens, immunogens or epitopes, etc. can be brought close together, what, optionally, allows a direct interaction of the two components. For example, different cells such as effector cells and target cells can be connected via a bispecific antibody. Encompassed, but not limited, by the present invention are antibodies or fragments thereof which bind, on the one hand, a soluble antigen as described herein, and, on the other hand, an antigen or receptor on the surface of a tumor cell.

According to the invention, the at least one (m)RNA of the adjuvant component of the inventive immunostimulatory composition may also encode intrabodies, wherein these intrabodies may be antibodies as defined above. Since these antibodies are intracellular expressed antibodies, i.e. antibodies which are encoded by nucleic acids localized in specific areas of the cell and also expressed there, such antibodies may be termed intrabodies.

Antibodies as encoded by the at least one (m)RNA of the adjuvant component of the inventive immunostimulatory composition may preferably comprise full-length antibodies, i.e. antibodies composed of the full heavy and full light chains, as described above. However, derivatives of antibodies such as antibody fragments, variants or adducts may also be encoded by the at least one (m)RNA of the adjuvant component of the inventive immunostimulatory composition.

The at least one (m)RNA of the adjuvant component of the inventive immunostimulatory composition may also encode antibody fragments selected from Fab, Fab', $F(ab')_2$, Fc, Facb, pFc', Fd and Fv fragments of the aforementioned (full-length) antibodies. In general, antibody fragments are known in the art. For example, an Fab (“fragment, antigen binding”) fragment is composed of one constant and one variable domain of each of the heavy and the light chain. The two variable domains bind the epitope on specific antigens. The two chains are connected via a disulfide linkage. An scFv (“single chain variable fragment”) fragment, for example, typically consists of the variable domains of the light and heavy chains. The domains are linked by an artificial linkage, in general a polypeptide linkage such as a peptide composed of 15-25 glycine, proline and/or serine residues.

As a second component, the inventive immunostimulatory composition comprises at least one free mRNA, encoding at least one therapeutically active protein or peptide as defined herein, at least one antigen as defined herein, e.g. tumor antigens, pathogenic antigens (e.g. selected from pathogenic proteins as defined above or from animal antigens, viral antigens, protozoal antigens, bacterial antigens, allergic antigens), autoimmune antigens, or further antigens, at least one allergen as defined herein, at least one antibody as defined herein, at least one antigen-specific T-cell receptor as defined herein, or at least one other protein or peptide suitable for a specific (therapeutic) application as defined herein. This second component is added (according to a second step of preparation of the inventive immunostimulatory composition) to the above prepared “adjuvant component” to form the inventive immunostimulatory composition. Prior to addition, the at least one free mRNA is not complexed and will preferably not undergo any detectable or significant complexation reaction upon the addition of the adjuvant component. This is due to the strong binding of the cationic or polycationic compound to the above described at least one (m)RNA in the adjuvant component. In other words, when the at least one free mRNA, encoding the therapeutically active protein, is added to the “adjuvant component”, preferably no free or substantially no free cationic or polycationic compound is present, which may form a complex with the at least one free mRNA. Accordingly, an efficient translation of the at least one free mRNA of the inventive composition is possible in vivo.

The at least one free mRNA, which is the second component of the inventive immunostimulatory composition, is a messenger RNA, encoding at least one therapeutically active protein or peptide as defined herein, at least one antigen as defined herein, e.g. tumor antigens, pathogenic antigens (e.g. selected from pathogenic proteins as defined above or from animal antigens, viral antigens, protozoal antigens, bacterial antigens, allergic antigens), autoimmune antigens, or further antigens, at least one allergen as defined herein, at least one antibody as defined herein, at least one antigen-specific T-cell receptor as defined herein, or at least one other protein or peptide suitable for a specific (therapeutic) application as defined herein. In this context, an mRNA is in general defined as above for the adjuvant component as an RNA, which is composed of several structural elements, e.g. an optional 5'-UTR region, an upstream positioned ribosomal binding site followed by a coding region, an optional 3'-UTR region, which may be followed by a poly-A tail (and/or a poly-C-tail). The at least one free mRNA may occur as a mono-, di-, or even multicistronic RNA, i.e. an RNA which carries the coding sequences of one, two or more proteins. Such coding sequences in di-, or even multicistronic mRNA may be separated by at least one IRES sequence, e.g. as defined herein.

The at least one free mRNA, provided as a second component of the inventive immunostimulatory composition, may encode at least one therapeutically active protein. In the context of the present invention, such a therapeutically active protein preferably may be any protein or peptide, suitable for a therapeutic purpose, more preferably may be selected from any recombinant or isolated protein known to a skilled person from the prior art and even more preferably may be selected from any therapeutically active protein as defined above for the adjuvant component of the inventive immunostimulatory composition. Such therapeutically active proteins as defined above include, without being limited thereto, e.g. proteins, capable of stimulating or inhibiting the signal transduction in the cell, e.g. cytokines, antibodies, etc., apoptotic factors or apoptosis related proteins, adjuvant proteins, e.g. selected from human adjuvant proteins or from pathogenic adjuvant proteins, in particular from bacterial adjuvant proteins, etc.

The at least one free mRNA, provided as a second component of the inventive immunostimulatory composition, may furthermore encode at least one antibody or antibody fragment. In this context, the at least one free mRNA, provided as a second component of the inventive immunostimulatory composition, may encode any antibody or antibody fragment as defined above for the adjuvant component of the inventive immunostimulatory composition.

Finally, the at least one free mRNA, provided as a second component of the inventive immunostimulatory composition, may also encode at least one antigen as defined above. In this context, a (tumor) antigen or in general the term "antigen" is defined as described above for the adjuvant component of the inventive immunostimulatory composition and typically refers to a substance which is recognized by the immune system and is capable of triggering an antigen-specific immune response, e.g. by formation of antibodies as part of an adaptive immune response. According to a preferred embodiment, the at least one free mRNA, provided as a second component of the inventive immunostimulatory composition, may encode any antigen as defined above for the adjuvant component of the inventive immunostimulatory composition. According to an even more preferred embodiment, such antigens may be selected from tumor antigens as defined above for the adjuvant component of the inventive immunostimulatory composition, e.g. tumor-specific antigens (TSAs) and tumor-associated-antigens (TAAs) as defined above, etc.

The at least one free mRNA, which is provided as a second component of the inventive immunostimulatory composition, may be identical or different to the at least one (m)RNA of the adjuvant component of the inventive immunostimulatory composition, dependent on the specific requirements of therapy. Even more preferably, the at least one free mRNA, which is provided as a second component of the inventive immunostimulatory composition, is identical to the at least one (m)RNA of the adjuvant component of the inventive immunostimulatory composition.

The ratio of the first component (i.e. the adjuvant component comprising or consisting of at least one (m)RNA complexed with a cationic or polycationic compound) and the second component (i.e. the at least one free mRNA) may be selected in the inventive immunostimulatory composition according to the specific requirements of a particular therapy, e.g. a cancer therapy, etc. Typically, the ratio of adjuvant component and the at least one free mRNA (adjuvant component:free mRNA) of the inventive immunostimulatory composition is selected such that a significant stimulation of the innate immune system is elicited due to the adjuvant component. In parallel, the ratio is selected such that a significant amount of the at least one free mRNA can be provided in vivo leading to an efficient translation and concentration of the expressed protein in vivo. e.g. the at least one antibody, antigen and/or therapeutically active protein, etc. as defined above. Preferably the ratio of adjuvant component:free mRNA in the inventive immunostimulatory composition is selected from a range of about 5:1 (w/w) to about 1:10 (w/w), more preferably from a range of about 4:1 (w/w) to about 1:8 (w/w), even more preferably from a range of about 3:1 (w/w) to about 1:5 (w/w) or 1:3 (w/w), and most preferably the ratio of adjuvant component: free mRNA in the inventive immunostimulatory composition is selected from a ratio of about 1:1 (w/w).

Additionally or alternatively, the ratio of the first component (i.e. the adjuvant component comprising or consisting of at least one (m)RNA complexed with a cationic or polycationic compound) and the second component (i.e. the at least one free mRNA) may be calculated on the basis of the nitrogen/phosphate ratio (N/P-ratio) of the entire RNA complex. In the context of the present invention, an N/P-ratio is preferably in the range of about 0.1-10, preferably in a range of about 0.3-4 and most preferably in a range of about 0.5-2 or 0.7-2 regarding the ratio of RNA:peptide in the complex, and most preferably in the range of about 0.7-1.5.

Additionally or alternatively, the ratio of the first component (i.e. the adjuvant component comprising or consisting of at least one (m)RNA complexed with a cationic or polycationic compound) and the second component (i.e. the at least one free mRNA) may also be selected in the inventive immunostimulatory composition on the basis of the molar ratio of both RNAs to each other, i.e. the (m)RNA of the adjuvant component, being complexed with a cationic or polycationic compound) and the at least one free mRNA of the second component. Typically, the molar ratio of the (m)RNA of the adjuvant component to the at least one free mRNA of the second component may be selected such, that the molar ratio suffices the above (w/w) and/or N/P-definitions. More preferably, the molar ratio of the (m)RNA of the adjuvant component to the at least one free mRNA of the second component may be selected e.g. from a molar ratio of about 0.001:1, 0.01:1, 0.1:1, 0.2:1, 0.3:1, 0.4:1, 0.5:1, 0.6:1, 0.7:1, 0.8:1, 0.9:1, 1:1, 1:0.9, 1:0.8, 1:0.7, 1:0.6, 1:0.5, 1:0.4, 1:0.3, 1:0.2, 1:0.1, 1:0.01, 1:0.001, etc. or from any range formed by any two of the above values, e.g. a range selected from about 0.001:1 to 1:0.001, including a range of about 0.01:1 to 1:0.001, 0.1:1 to 1:0.001, 0.2:1 to 1:0.001, 0.3:1 to 1:0.001, 0.4:1 to 1:0.001, 0.5:1 to 1:0.001, 0.6:1 to 1:0.001, 0.7:1 to 1:0.001, 0.8:1 to 1:0.001, 0.9:1 to 1:0.001, 1:1 to 1:0.001, 1:0.9 to 1:0.001, 1:0.8 to 1:0.001, 1:0.7 to 1:0.001, 1:0.6 to 1:0.001, 1:0.5 to 1:0.001, 1:0.4 to 1:0.001, 1:0.3 to 1:0.001, 1:0.2 to 1:0.001, 1:0.1 to 1:0.001, 1:0.01 to 1:0.001, or a range of about 0.01:1 to 1:0.01, 0.1:1 to 1:0.01, 0.2:1 to 1:0.01, 0.3:1 to 1:0.01, 0.4:1 to 1:0.01, 0.5:1 to 1:0.01, 0.6:1 to 1:0.01, 0.7:1 to 1:0.01, 0.8:1 to 1:0.01, 0.9:1 to 1:0.01, 1:1 to 1:0.01, 1:0.9 to 1:0.01, 1:0.8 to 1:0.01, 1:0.7 to 1:0.01, 1:0.6 to 1:0.01, 1:0.5 to 1:0.01, 1:0.4 to 1:0.01, 1:0.3 to 1:0.01, 1:0.2 to 1:0.01, 1:0.1 to 1:0.01, 1:0.01 to 1:0.01, or including a range of about 0.001:1 to 1:0.01, 0.001:1 to 1:0.1, 0.001:1 to 1:0.2, 0.001:1 to 1:0.3, 0.001:1 to 1:0.4, 0.001:1 to 1:0.5, 0.001:1 to 1:0.6, 0.001:1 to 1:0.7, 0.001:1 to 1:0.8, 0.001:1 to 1:0.9, 0.001:1 to 1:1, 0.001 to 0.9:1, 0.001 to 0.8:1, 0.001 to 0.7:1, 0.001 to 0.6:1, 0.001 to 0.5:1, 0.001 to 0.4:1, 0.001 to 0.3:1, 0.001 to 0.2:1, 0.001 to 0.1:1, or a range of about 0.01:1 to 1:0.01, 0.01:1 to 1:0.1, 0.01:1 to 1:0.2, 0.01:1 to 1:0.3, 0.01:1 to 1:0.4, 0.01:1 to 1:0.5, 0.01:1 to 1:0.6, 0.01:1 to 1:0.7, 0.01:1 to 1:0.8, 0.01:1 to 1:0.9, 0.01:1 to 1:1, 0.001 to 0.9:1, 0.001 to 0.8:1, 0.001 to 0.7:1, 0.001 to 0.6:1, 0.001 to 0.5:1, 0.001 to 0.4:1, 0.001 to 0.3:1, 0.001 to 0.2:1, 0.001 to 0.1:1, etc.

Even more preferably, the molar ratio of the (m)RNA of the adjuvant component to the at least one free mRNA of the second component may be selected e.g. from a range of about 0.01:1 to 1:0.01. Most preferably, the molar ratio of the (m)RNA of the adjuvant component to the at least one free mRNA of the second component may be selected e.g. from a molar ratio of about 1:1. Any of the above definitions with regard to (w/w) and/or N/P ratio may also apply.

According to the present invention, the at least one (m)RNA of the adjuvant component and/or the at least one free mRNA of the inventive immunostimulatory composition as defined above, encoding a protein, e.g. a therapeutically active protein, antibody and/or antigen, may also encode fragments and/or variants of the aforementioned proteins, wherein the fragments and/or variants may have a sequence identity to one of the aforementioned proteins of at least 5%, 10%, 20%, 30%, 40%, 50%, 60%, 70%, 80% or 85%, preferably at least 90%, more preferably at least 95% and most preferably at least 99% over the whole length of the (coding) nucleic acid sequences encoding these proteins. In the context of the present invention a fragment of such a protein is to be understood as a truncated protein thereof, i.e. an amino acid sequence, which is N-terminally, C-terminally and/or intrasequentially truncated compared to the amino acid sequence of the original (native) protein. Especially, fragments including an antigenic epitope are preferred. In this context, fragments and epitopes are preferably as specifically defined above for antigens.

A "variant" in the context of the present invention refers to a protein as defined above, e.g. a therapeutically active protein, adjuvant protein, antigen or antibody as defined above (or its encoding mRNA or (m)RNA sequence), wherein nucleic acids of the at least one (m)RNA of the adjuvant component of the inventive immunostimulatory composition or nucleic acids of the at least one free mRNA of the inventive immunostimulatory composition, encoding e.g. a therapeutically active protein, antibody and/or antigen, etc., are exchanged. Thereby, a therapeutically active protein, adjuvant protein, antigen or antibody is generated, having an amino acid sequence which differs from the original sequence in one or more mutation(s), such as one or more substituted, inserted and/or deleted amino acid(s). Preferably, the fragments and/or variants have the same biological function or specific activity compared to the full-length native proteins, e.g. therapeutically active proteins, antigens or antibodies. Such "biological function" include e.g. the specific binding capacity (e.g. of particular antigens), catalytic activity of these proteins, e.g. of therapeutically active proteins, etc. In this context, the term "biological function" of antibodies as described herein also comprises neutralization of antigens, complement activation or opsonization. Thereby, antibodies typically recognize either native epitopes on the cell surface or free antigens. Antibodies as defined above can interact with the cell-presenting antigens and initiate different defense mechanisms. On the one hand, the antibody can initiate signaling mechanisms in the targeted cell that leads to the cell's self-destruction (apoptosis). On the other hand, it can mark the cell in such a way that other components or effector cells of the body's immune system can recognize and attack. The attack mechanisms are referred to as antibody-dependent complement-mediated cytotoxicity (CMC) and antibody-dependent cellular cytotoxicity (ADCC). ADCC involves a recognition of the antibody by immune cells that engage the antibody-marked cells and either through their direct action, or through the recruitment of other cell types, lead to the tagged-cell's death. CMC is a process where a cascade of different complement proteins becomes activated, usually when several antibodies are in close proximity to each other, either resulting in cell lysis or attracting other immune cells to this location for effector cell function. In the neutralization of an antigen, the antibody can bind an antigen and neutralize the same. Such neutralization reaction, in turn, leads in general to blocking of the antibody. Thus, the antibody can bind only one antigen, or, in case of a bispecific antibody, two antigens. In particular, scFv antibody fragments are useful for neutralization reactions because they don't contain the functionalities of the constant domain of an antibody. In the complement activation, the complex system of complement proteins can be activated via binding of an antibody which is independent of the Fc part of an antibody. End products of the complement cascade result in lysis of the cell and generation of an inflammatory milieu. In the opsonization, pathogens or other non-cellular particles are made accessible to phagocytes via binding the constant domain of an antibody. Alternatively, cells recognized as foreign can be lysed via antibody-dependent cell-mediated cytotoxicity (ADCC). In particular, NK-cells can display lysis functions by activating Fc receptors.

In order to determine the percentage to which two sequences are identical, particularly the at least one (m)RNA of the adjuvant component of the inventive immunostimulatory composition and/or the at least one free mRNA of the inventive immunostimulatory composition, the sequences can be aligned in order to be subsequently compared to one another. Therefore, as an example, e.g. gaps can be inserted into the sequence of the first sequence (e.g. (m)RNA or mRNA) and the component at the corresponding position of the second sequence (e.g. (m)RNA or mRNA) can be compared. If a position in the first sequence (e.g. (m)RNA or mRNA) sequence is occupied by the same component as is the case at a position in the second sequence (e.g. (m)RNA or mRNA), the two sequences are identical at this position. The percentage to which two (m)RNA (or mRNA) sequences are identical is a function of the number of identical positions divided by the total number of positions. The same, of course also applies accordingly to DNA sequences or the encoded amino acid sequences.

The percentage to which two sequences, such as the at least one (m)RNA of the adjuvant component of the inventive immunostimulatory composition and/or the at least one free mRNA of the inventive immunostimulatory composition, or their encoded amino acid sequences, are identical can be determined using a mathematical algorithm. A preferred, but not limiting, example of a mathematical algorithm which can be used is the algorithm of Karlin et al. (1993), PNAS USA, 90:5873-5877 or Altschul et al. (1997), Nucleic Acids Res, 25:3389-3402. Such an algorithm is integrated in the BLAST or NBLAST program. Sequences which are identical to the sequences of the at least one (m)RNA of the adjuvant component of the inventive immunostimulatory composition or of the at least one free mRNA of the inventive immunostimulatory composition (or to the coding regions thereof) to a certain extent can be identified by these programmes.

RNA sequences corresponding to the at least one (m)RNA of the adjuvant component or the at least one free mRNA of the inventive immunostimulatory composition encoding amino acid sequences, which have (a) conservative substitution(s) compared to the physiological, i.e. native and non-modified, sequence in particular fall under the term "variants". Substitutions in which encoded amino acids which originate from the same class are exchanged for one another are called conservative substitutions. In particular, these are encoded amino acids, encoded aliphatic side chains, positively or negatively charged side chains, aromatic groups in the side chains or encoded amino acids, the side chains of which can enter into hydrogen bridges, e.g. side chains which have a hydroxyl function. This means that e.g. an amino acid having a polar side chain is replaced by another amino acid having a likewise polar side chain, or, for example, an amino acid characterized by a hydrophobic side chain is substituted by another amino acid having a likewise hydrophobic side chain (e.g. serine (threonine) by threonine (serine) or leucine (isoleucine) by isoleucine (leucine)). Insertions and substitutions are possible, in particular, at those sequence positions which cause no modification of the three-dimensional structure or do not affect the binding region or the catalytic domain. Modifications of the three-dimensional structure by insertion(s) or deletion(s) can easily be determined e.g. using CD spectra (circular dichroism spectra) (Urry, 1985, Absorption, Circular Dichroism and ORD of Polypeptides, in: Modern Physical Methods in Biochemistry, Neuberger et al. (ed.), Elsevier, Amsterdam).

Those RNA sequences corresponding to the at least one (m)RNA of the adjuvant component of the inventive immunostimulatory composition or to the at least one free mRNA of the inventive immunostimulatory composition, which encode amino acid sequences as defined above, may occur as a mono-, di-, or even multicistronic RNA, i.e. an RNA which carries the coding sequences of one, two or more proteins as defined above, e.g. therapeutically active proteins, adjuvant proteins, (protein) antigens or antibodies as defined above. If an RNA sequence corresponding to the at least one (m)RNA of the adjuvant component and/or the at least one free mRNA of the inventive immunostimulatory composition within the above definition, encodes at least one protein as defined above, e.g. two, three or more of a therapeutically active protein, adjuvant protein, antigen or antibody as defined above, each of these proteins may be selected from the same or a (preferably) different protein as defined above. In any case, each protein encoded by an RNA sequence corresponding to the at least one (m)RNA of the adjuvant component of the inventive immunostimulatory composition and/or the at least one free mRNA of the inventive immunostimulatory composition, may be selected independently.

According to another particularly preferred embodiment, the inventive immunostimulatory composition of the present invention, may comprise as the at least one free mRNA or as the at least one (m)RNA of the adjuvant component at least one bi- or even multicistronic RNA sequence as defined above. Each coding sequence in these bi- or even multicistronic RNA sequences as defined above may be separated by at least one so-called IRES (internal ribosomal entry site) sequence. In this context, an IRES sequence can function as a sole ribosome binding site, but it can also serve to provide a bi- or even multicistronic RNA sequence as defined above which encodes several proteins which are to be translated by the ribosomes independently of one another. Examples of IRES sequences which can be used according to the invention are those from picornaviruses (e.g. FMDV), pestiviruses (CFFV), polioviruses (PV), encephalomyocarditis viruses (ECMV), foot and mouth disease viruses (FMDV), hepatitis C viruses (HCV), classical swine fever viruses (CSFV), mouse leukoma virus (MLV), simian immunodeficiency viruses (SIV) or cricket paralysis viruses (CrPV).

According to a particularly preferred embodiment, the immunostimulatory composition of the present invention may also comprise as the at least one (m)RNA of the adjuvant component and/or the at least one free mRNA, a mixture of different RNA sequences, wherein the mixture comprises e.g. at least one monocistronic mRNA encoding a protein as defined above, and/or at least one bi- or even multicistronic mRNA, encoding the same or different proteins as defined above, e.g. a therapeutically active protein, an adjuvant protein, an antigen and/or an antibody as defined above.

According to another specific embodiment, the at least one (m)RNA of the adjuvant component of the inventive immunostimulatory composition and/or the at least one free mRNA of the inventive immunostimulatory composition, may be provided as a "stabilized RNA", preferably a stabilized mRNA, that is to say as an RNA that is essentially resistant to in vivo degradation by various approaches (e.g. by an exo- or endo-nuclease). It is known in the art that instability and (fast) degradation of mRNA or of RNA in vivo in general may represent a serious problem in the application of RNA based compositions. This instability of RNA is typically due to RNA-degrading enzymes, "RNAases" (ribonucleases), wherein contamination with such ribonucleases may sometimes completely degrade RNA in solution. Accordingly, the natural degradation of RNA in the cytoplasm of cells is very finely regulated and RNase contaminations may be generally removed by special treatment prior to use of said compositions, in particular with diethyl pyrocarbonate (DEPC). A number of mechanisms of natural degradation are known in this connection in the prior art, which may be utilized as well. E.g., the terminal structure is typically of critical importance for an mRNA in vivo. As an example, at the 5' end of naturally occurring mRNAs there is usually a so-called "cap structure" (a modified guanosine nucleotide), and at the 3' end is typically a sequence of up to 200 adenosine nucleotides (the so-called poly-A tail).

According to a particularly preferred embodiment, the at least one (m)RNA of the adjuvant component of the inventive immunostimulatory composition and/or the at least one free mRNA of the inventive immunostimulatory composition, particularly if provided as an mRNA, can therefore be stabilized against degradation by RNases by the addition of a so-called "5' cap" structure. Particular preference is given in this connection to an m7G(5')ppp (5'(A,G(5')ppp(5')A or G(5')ppp(5')G as the 5' cap" structure. However, such a modification is introduced only if a modification, particularly as defined herein, has not already been introduced at the 5' end of the at least one (m)RNA and/or mRNA as defined above, or if the modification does not interfere with the immunogenic properties of the at least one (m)RNA and/or mRNA as defined above.

According to another particularly preferred embodiment, the at least one (m)RNA of the adjuvant component of the inventive immunostimulatory composition and/or the at least one free mRNA of the inventive immunostimulatory composition, may contain, especially if the RNA is in the form of an mRNA, a poly-A tail at its 3' terminus of typically about 10 to 200 adenosine nucleotides, preferably about 10 to 100 adenosine nucleotides, more preferably about 20 to 100 adenosine nucleotides or even more preferably about 40 to 80 adenosine nucleotides.

According to a further particularly preferred embodiment, the at least one (m)RNA of the adjuvant component of the inventive immunostimulatory composition and/or the at least one free mRNA of the inventive immunostimulatory composition, may contain, especially if the RNA is in the form of an mRNA, a poly-C tail at its 3' terminus of typically about 10 to 200 cytosine nucleotides, preferably about 10 to 100 cytosine nucleotides, more preferably about 20 to 70 cytosine nucleotides or even more preferably about 20 to 60 or even 10 to 40 cytosine nucleotides.

According to another embodiment, the at least one (m)RNA of the adjuvant component of the inventive immunostimulatory composition and/or the at least one free mRNA of the inventive immunostimulatory composition may furthermore be GC-modified or modified in another form. Some modifications of the RNA may be, dependent on the type of RNA, more suitable for an RNA in general, or, e.g. in the case of GC-modified (m)RNA or mRNA sequences, be more suitable for a coding RNA, preferably an (m)RNA and/or mRNA as defined above. Such further modifications as defined herein preferably lead to a stabilized (m)RNA and/or mRNA as defined above.

According to one specific embodiment, such a stabilized RNA may be prepared by modifying the G/C content of the coding region of the RNA sequences mentioned herein, e.g. an RNA sequence corresponding to the at least one (m)RNA of the adjuvant component and/or to the at least one free mRNA of the inventive immunostimulatory composition.

In a particularly preferred embodiment of the present invention, the G/C content of the coding region of the at least one (m)RNA of the adjuvant component and/or the at least one free mRNA of the inventive immunostimulatory composition is altered, preferably increased, compared to the G/C content of the coding region of the corresponding non-modified RNA (in the following "native RNA"). In this context, the encoded amino acid sequence of this G/C-increased RNA sequence corresponding to the at least one (m)RNA of the adjuvant component or the at least one free mRNA of the inventive immunostimulatory composition is preferably not altered compared to the corresponding native RNA. Such alteration of the GC-sequence may be termed in the following GC-stabilization.

This G/C-stabilization of the at least one (m)RNA of the adjuvant component of the inventive immunostimulatory composition and/or of the at least one free mRNA of the inventive immunostimulatory composition is based on the fact that the sequence of any RNA region to be translated is important for efficient translation of that RNA. Thus, the sequence of various nucleotides is important. In particular, sequences having an increased G (guanosine)/C (cytosine) content are more stable than sequences having an increased A (adenosine)/U (uracil) content. According to the invention, the codons the at least one (m)RNA of the adjuvant component of the inventive immunostimulatory composition or of the at least one free mRNA of the inventive immunostimulatory composition are therefore varied compared to its native RNA sequence, while retaining the translated amino acid sequence, such that they include an increased amount of G/C nucleotides. In respect to the fact that several codons code for one and the same amino acid (so-called degeneration of the genetic code), the most favorable codons for the stability can be determined (so-called alternative codon usage).

Depending on the amino acid to be encoded by the at least one (m)RNA of the adjuvant component of the inventive immunostimulatory composition and/or the at least one free mRNA of the inventive immunostimulatory composition, there are various possibilities for G/C-modification of the RNA sequence, compared to its native sequence. In the case of amino acids which are encoded by codons which contain exclusively G or C nucleotides, no G/C-modification of the codon is necessary. Thus, the codons for Pro (CCC or CCG), Arg (CGC or CGG), Ala (GCC or GCG) and Gly (GGC or GGG) require no G/C-modification, since no A or U is present.

In contrast, codons which contain A and/or U nucleotides can be G/C-modified by substitution of other codons which code for the same amino acids but contain no A and/or U. Examples of these are:

the codons for Pro can be G/C-modified from CCU or CCA to CCC or CCG;

the codons for Arg can be G/C-modified from CGU or CGA or AGA or AGG to CGC or CG G;

the codons for Ala can be G/C-modified from GCU or GCA to GCC or GCG;

the codons for Gly can be G/C-modified from GGU or GGA to GGC or GGG.

In other cases, although A or U nucleotides cannot be eliminated from the codons, it is however possible to decrease the A and U content by using codons which contain a lower content of A and/or U nucleotides. Examples of these are:

the codons for Phe can be G/C-modified from UUU to UUC;

the codons for Leu can be G/C-modified from UUA, UUG, CUU or CUA to CUC or CUG;

the codons for Ser can be G/C-modified from UCU or UCA or AGU to UCC, UCG or AGC;

the codon for Tyr can be G/C-modified from UAU to UAC;

the codon for Cys can be G/C-modified from UGU to UGC;

the codon for His can be G/C-modified from CAU to CAC;

the codon for Gln can be G/C-modified from CAA to CAG;

the codons for Ile can be G/C-modified from AUU or AUA to AUC;

the codons for Thr can be G/C-modified from ACU or ACA to ACC or ACG;

the codon for Asn can be G/C-modified from AAU to AAC;

the codon for Lys can be G/C-modified from AAA to AAG;

the codons for Val can be G/C-modified from GUU or GUA to GUC or GUG;

the codon for Asp can be G/C-modified from GAU to GAC;

the codon for Glu can be G/C-modified from GAA to GAG;

the stop codon UAA can be G/C-modified to UAG or UGA.

In the case of the codons for Met (AUG) and Trp (UGG), on the other hand, there is no possibility of sequence modification.

The substitutions listed above can be used either individually or in all possible combinations to increase the G/C content of the at least one (m)RNA of the adjuvant component of the inventive immunostimulatory composition and/or the at least one free mRNA of the inventive immunostimulatory composition compared to its particular native RNA (i.e. the non-modified sequence). Thus, for example, all codons for Thr occurring in the native sequence can be G/C-modified to ACC (or ACG). Preferably, however, for example, combinations of the above substitution possibilities are used:

substitution of all codons coding for Thr in the non-modified sequence (native RNA) to ACC (or ACG) and
substitution of all codons originally coding for Ser to UCC (or UCG or AGC);

substitution of all codons coding for Ile in the original sequence to AUC and
substitution of all codons originally coding for Lys to AAG and
substitution of all codons originally coding for Tyr to UAC;

substitution of all codons coding for Val in the original sequence to GUC (or GUG) and
substitution of all codons originally coding for Glu to GAG and
substitution of all codons originally coding for Ala to GCC (or GCG) and
substitution of all codons originally coding for Arg to CGC (or CGG);

substitution of all codons coding for Val in the original sequence to GUC (or GUG) and
substitution of all codons originally coding for Glu to GAG and
substitution of all codons originally coding for Ala to GCC (or GCG) and
substitution of all codons originally coding for Gly to GGC (or GGG) and
substitution of all codons originally coding for Asn to AAC;

substitution of all codons coding for Val in the original sequence to GUC (or GUG) and
substitution of all codons originally coding for Phe to UUC and
substitution of all codons originally coding for Cys to UGC and
substitution of all codons originally coding for Leu to CUG (or CUC) and
substitution of all codons originally coding for Gln to CAG and
substitution of all codons originally coding for Pro to CCC (or CCG); etc.

Preferably, the G/C content of the coding region of an RNA sequence corresponding to the at least one (m)RNA of the adjuvant component and/or the at least one free mRNA of the inventive immunostimulatory composition is increased by at least 7%, more preferably by at least 15%, particularly preferably by at least 20%, compared to the G/C content of the coding region of the native RNA which codes for a protein. According to a specific embodiment at least 60%, more preferably at least 70%, even more preferably at least 80% and most preferably at least 90%, 95% or even 100% of the substitutable codons in the region coding for a protein or the whole sequence of the native RNA sequence are substituted, thereby increasing the GC/content of said sequence.

In this context, it is particularly preferable to increase the G/C content of the native RNA of the at least one (m)RNA of the adjuvant component of the inventive immunostimulatory composition and/or the at least one free mRNA of the inventive immunostimulatory composition, to the maximum (i.e. 100% of the substitutable codons of the native RNA), in particular in the region coding for a protein.

According to the invention, a further preferred modification of the at least one (m)RNA of the adjuvant component of the inventive immunostimulatory composition and/or the at least one free mRNA of the inventive immunostimulatory composition is based on the finding that the translation efficiency is also determined by a different frequency in the occurrence of tRNAs in cells. Thus, if so-called "rare codons" are present in a native RNA sequence to an increased extent, the corresponding G/C-stabilized or native RNA sequence may be translated to a significantly poorer degree than in the case, where codons coding for relatively "frequent" tRNAs are present.

According to the invention, the region in the at least one (m)RNA of the adjuvant component of the inventive immunostimulatory composition and/or the at least one free mRNA of the inventive immunostimulatory composition, which code for a protein, is preferably GC-stabilized compared to the corresponding region of the respective native RNA such that at least one codon of the native sequence which codes for a tRNA which is relatively rare in the cell is exchanged for a codon which codes for a tRNA which is relatively frequent in the cell and carries the same amino acid as the relatively rare tRNA. By this modification, the native RNA sequences are GC-stabilized such that codons for which frequently occurring tRNAs are available are inserted. In other words, according to the invention, by this modification all codons of the native sequence which code for a tRNA which is relatively rare in the cell can in each case be exchanged for a codon which codes for a tRNA which is relatively frequent in the cell and which, in each case, carries the same amino acid as the relatively rare tRNA.

Which tRNAs occur relatively frequently in the cell and which, in contrast, occur relatively rarely is known to a person skilled in the art; cf. e.g. Akashi, Curr. Opin. Genet. Dev. 2001, 11(6): 660-666. The codons which use for the particular amino acid the tRNA which occurs the most frequently, e.g. the Gly codon, which uses the tRNA which occurs the most frequently in the (human) cell, are particularly preferred.

According to the invention, it is particularly preferable to link the sequential G/C content which is increased, in particular maximized, in the GC-stabilized RNA sequence of the at least one (m)RNA of the adjuvant component and/or the at least one free mRNA of the inventive immunostimulatory composition, with the "frequent" codons without modifying the amino acid sequence of the protein encoded by the coding region of the native RNA. This preferred embodiment allows provision of a particularly efficiently translated and GC-stabilized RNA sequence of the at least one (m)RNA of the inventive immunostimulatory composition of the adjuvant component and/or the at least one free mRNA of the inventive immunostimulatory composition.

The determination of the necessary (and/or possible) GC modification of the at least one (m)RNA of the adjuvant component of the inventive immunostimulatory composition and/or the at least one free mRNA of the inventive immunostimulatory composition, as described above (increased G/C content; exchange of tRNAs), can be carried out using the computer program as explained in WO 02/098443—the disclosure content of which is included in its full scope in the present invention. Using this computer program, the nucleotide sequence of any desired coding RNA as defined above can be GC-stabilized with the aid of the genetic code or the degenerative nature thereof such that a maximum G/C content results. In combination with the use of codons which code for tRNAs occurring as frequently as possible in the cell, the amino acid sequence coded by the GC-stabilized RNA sequence of the at least one (m)RNA of the adjuvant component and/or the at least one free mRNA of the inventive immunostimulatory composition is preferably not further modified compared to their native RNA sequence. Alternatively, it is also possible to modify only the G/C content or only the codon usage compared to the original sequence. The source code in Visual Basic 6.0 (development environment used: Microsoft Visual Studio Enterprise 6.0 with Servicepack 3) is also described in WO 02/098443.

According to another specific embodiment, the at least one (m)RNA of the adjuvant component of the inventive immunostimulatory composition and/or the at least one free mRNA of the inventive immunostimulatory composition, may be provided as a stabilized RNA, that is essentially resistant to in vivo degradation (e.g. by an exo- or endo-nuclease), by modifying the phosphate backbone of this (these) RNA sequence(s) as defined herein. Nucleotides that may be preferably used in this connection contain a phosphorothioate-modified phosphate backbone, preferably at least one of the phosphate oxygens contained in the phosphate backbone being replaced by a sulfur atom. A stabilized RNA sequence as defined herein, may further include, for example: non-ionic phosphate analogues, such as, for example, alkyl and aryl phosphonates, in which the charged phosphonate oxygen is replaced by an alkyl or aryl group, or phosphodiesters and alkylphosphotriesters, in which the charged oxygen residue is present in alkylated form. In more detail, the phosphate moieties may preferably be substituted by, e.g., phosphoramidates, phosphorothioates, peptide nucleotides, methylphosphonates etc.

According to another embodiment, an RNA sequence as defined herein, preferably the at least one (m)RNA of the adjuvant component of the inventive immunostimulatory composition and/or the at least one free mRNA of the inventive immunostimulatory composition, can likewise be modified (and preferably stabilized) by introducing modified nucleotides containing modifications of their ribose or base moieties into the RNA sequence. Generally, an RNA sequence as defined herein, preferably the at least one (m)RNA of the adjuvant component of the inventive immunostimulatory composition and/or the at least one free mRNA of the inventive immunostimulatory composition, may contain any native (=naturally occurring) nucleotide, e.g. guanosine, uracil, adenosine, thymidine and/or cytosine or an analogue thereof. In this connection, nucleotide analogues are defined as non-natively occurring variants of naturally occurring nucleotides. Accordingly, analogues are chemically derivatized nucleotides with non-natively occurring functional groups, which are preferably added to or deleted from the naturally occurring nucleotide or which substitute the naturally occurring functional groups of a nucleotide. Accordingly, each component of the naturally occurring nucleotide may be modified, namely the base component, the sugar (ribose) component and/or the phosphate component forming the backbone of the RNA sequence to be modified. Analogues of guanosine, uracil, adenosine, and cytosine include, without implying any limitation, any naturally occurring or non-naturally occurring guanosine, uracil, adenosine, thymidine or cytosine that has been altered chemically, for example by acetylation, methylation, hydroxylation, etc., including 1-methyl-adenosine, 1-methyl-guanosine, 1-methyl-inosine, 2,2-dimethyl-guanosine, 2,6-diaminopurine, 2'-Amino-2'-deoxyadenosine, 2'-Amino-2'-deoxycytidine, 2'-Amino-2'-deoxyguanosine, 2'-Amino-2'-deoxyuridine, 2-Amino-6-chloropurineriboside, 2-Aminopurine-riboside, 2'-Araadenosine, 2'-Aracytidine, 2'-Arauridine, 2'-Azido-2'-deoxyadenosine, 2'-Azido-2'-deoxycytidine, 2'-Azido-2'-deoxyguanosine, 2'-Azido-2'-deoxyuridine, 2-Chloroadenosine, 2'-Fluoro-2'-deoxyadenosine, 2'-Fluoro-2'-deoxycytidine, 2'-Fluoro-2'-deoxyguanosine, 2'-Fluoro-2'-deoxyuridine, 2'-Fluorothymidine, 2-methyl-adenosine, 2-methyl-guanosine, 2-methyl-thio-N6-isopenenyl-adenosine, 2'-O-Methyl-2-aminoadenosine, 2'-O-Methyl-2'-deoxyadenosine, 2'-O-Methyl-2'-deoxycytidine, 2'-O-Methyl-2'-deoxyguanosine, 2'-O-Methyl-2'-deoxyuridine, 2'-O-Methyl-5-methyluridine, 2'-O-Methylinosine, 2'-O-Methylpseudouridine, 2-Thiocytidine, 2-thio-cytosine, 3-methyl-cytosine, 4-acetyl-cytosine, 4-Thiouridine, 5-(carboxyhydroxymethyl)-uracil, 5,6-Dihydrouridine, 5-Aminoallylcytidine, 5-Aminoallyl-deoxy-uridine, 5-Bromouridine, 5-carboxymethylaminomethyl-2-thio-uracil, 5-carboxymethylamonomethyl-uracil, 5-Chloro-Ara-cytosine, 5-Fluoro-uridine, 5-Iodouridine, 5-methoxycarbonylmethyl-uridine, 5-methoxy-uridine, 5-methyl-2-thio-uridine, 6-Azacytidine, 6-Azauridine, 6-Chloro-7-deaza-guanosine, 6-Chloropurineriboside, 6-Mercapto-guanosine, 6-Methyl-mercaptopurine-riboside, 7-Deaza-2'-deoxy-guanosine, 7-Deazaadenosine, 7-methyl-guanosine, 8-Azaadenosine, 8-Bromo-adenosine, 8-Bromo-guanosine, 8-Mercapto-guanosine, 8-Oxoguanosine, Benzimidazole-riboside, Beta-D-mannosyl-queosine, Dihydro-uracil, Inosine, N1-Methyladenosine, N6-([6-Aminohexyl]carbamoylmethyl)-adenosine, N6-isopentenyl-adenosine, N6-methyl-adenosine, N7-Methyl-xanthosine, N-uracil-5-oxyacetic acid methyl ester, Puromycin, Queosine, Uracil-5-oxyacetic acid, Uracil-5-oxyacetic acid methyl ester, Wybutoxosine, Xanthosine, and Xylo-adenosine. The preparation of such analogues is known to a person skilled in the art, for example from U.S. Pat. No. 4,373,071, U.S. Pat. No. 4,401,796, U.S. Pat. No. 4,415,732, U.S. Pat. No. 4,458,066, U.S. Pat. No. 4,500,707, U.S. Pat. No. 4,668,777, U.S. Pat. No. 4,973,679, U.S. Pat. No. 5,047,524, U.S. Pat. No. 5,132,418, U.S. Pat. No. 5,153,319, U.S. Pat. No. 5,262,530 and U.S. Pat. No. 5,700,642. In the case of an analogue as described above, particular preference is given according to the invention to those analogues that increase the immunogenity of an RNA sequence as defined herein, preferably the at least one (m)RNA of the adjuvant component of the inventive immunostimulatory composition and/or the at least one free mRNA of the inventive immunostimulatory composition, and/or do not interfere with a further modification of the RNA that has been introduced.

An RNA sequence of the inventive immunostimulatory composition as defined herein, preferably the at least one (m)RNA of the adjuvant component and/or the at least one free mRNA of the inventive immunostimulatory composition, may contain backbone modifications. A backbone modification in connection with the present invention is a modification in which phosphates of the backbone of the nucleotides contained in the RNA are chemically modified. Such backbone modifications typically include, without implying any limitation, modifications from the group consisting of methylphosphonates, phosphoramidates and phosphorothioates (e.g. cytidine-5'-O-(1-thiophosphate)).

The RNA sequence of the inventive immunostimulatory composition as defined herein, preferably the at least one (m)RNA of the adjuvant component and/or the at least one free mRNA of the inventive immunostimulatory composition, may additionally or alternatively also contain sugar modifications. A sugar modification in connection with the present invention is a chemical modification of the sugar of the nucleotides present and typically includes, without implying any limitation, sugar modifications selected from the group consisting of 2'-deoxy-2'-fluoro-oligoribonucleotide (2'-fluoro-2'-deoxycytidine-5'-triphosphate, 2'-fluoro-2'-deoxyuridine-5'-triphosphate), 2'-deoxy-2'-deamine oligoribonucleotide (2'-amino-2'-deoxycytidine-5'-triphosphate, 2'-amino-2'-deoxyuridine-5'-triphosphate), 2'-O-alkyl oligoribonucleotide, 2'-deoxy-2'-C-alkyl oligoribonucleotide (2'-O-methylcytidine-5'-triphosphate, 2'-methyluridine-5'-triphosphate), 2'-C-alkyl oligoribonucleotide, and isomers thereof (2'-aracytidine-5'-triphosphate, 2'-arauridine-5'-triphosphate), or azidotriphosphate (2'-azido-2'-deoxycytidine-5'-triphosphate, 2'-azido-2'-deoxyuridine-5'-triphosphate).

The RNA sequence of the inventive immunostimulatory composition as defined herein, preferably the at least one (m)RNA of the adjuvant component and/or the at least one free mRNA of the inventive immunostimulatory composition, may additionally or alternatively also contain at least one base modification, which is preferably suitable for increasing the expression of the protein coded for by the RNA sequence, preferably the at least one (m)RNA of the adjuvant component, significantly as compared with the unaltered, i.e. natural (=native), RNA sequence. Significant in this case means an increase in the expression of the protein compared with the expression of the native RNA sequence by at least 20%, preferably at least 30%, 40%, 50% or 60%, more preferably by at least 70%, 80%, 90% or even 100% and most preferably by at least 150%, 200% or even 300%. In connection with the present invention, a nucleotide having a base modification is preferably selected from the group of the base-modified nucleotides consisting of 2-amino-6-chloropurineriboside-5'-phosphate, 2-aminoadenosine-5'-triphosphate, 2-thiocytidine-5'-triphosphate, 2-thiouridine-5'-triphosphate, 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-iodocytidine-5'-triphosphate, 5-iodouridine-5'-triphosphate, 5-methylcytidine-5'-triphosphate, 5-methyluridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate, or puromycin-5'-triphosphate, xanthosine-5'-triphosphate. Particular preference is given to nucleotides for base modifications selected from the group of base-modified nucleotides consisting of 5-methylcytidine-5'-triphosphate, 7-deazaguanosine-5'-triphosphate, 5-bromocytidine-5'-triphosphate, and pseudouridine-5'-triphosphate.

According to a particularly specific embodiment, an RNA sequence as defined herein, preferably the at least one (m)RNA of the adjuvant component of the inventive immunostimulatory composition and/or the at least one free mRNA of the inventive immunostimulatory composition comprises between 0.1% and 100% (modified) nucleotides selected from (modified) nucleotides as defined above with respect to the non-modified, i.e. native RNA sequence, wherein preferably between 0.1% and 100% of each natively occurring non-modified ATP, GTP, CTP, UTP (and/or TTP) nucleotide of an RNA sequence as defined herein, preferably of the at least one (m)RNA of the adjuvant component of the inventive immunostimulatory composition and/or of the at least one free mRNA of the inventive immunostimulatory composition, or of its corresponding DNA-template, may be modified using a corresponding modified nucleotide as defined above, more preferably between 0.1% and 20%, between 10% and 30%, between 20% and 40%, between 30% and 50%, between 40% and 60%, between 50% and 70%, between 60% and 80%, between 70% and 90%, or between 80% and 100% or at least 10%, more preferably at least 30%, more preferably at least 40%, more preferably at least 60%, more preferably at least 70%, more preferably at least 80% and more preferably at least 90% and most preferably 100% of each natively occurring non-modified ATP, GTP CTP, UTP (and/or TTP) nucleotide of the non-modified RNA.

In a further preferred embodiment of the present invention, the A/U content in the environment of the ribosome binding site of an (optionally already GC-stabilized) RNA sequence as defined herein, preferably the at least one (m)RNA of the adjuvant component of the inventive immunostimulatory composition and/or the at least one free mRNA of the inventive immunostimulatory composition, is increased compared to the A/U content in the environment of the ribosome binding site of its particular native RNA sequence. This modification (an increased A/U content around the ribosome binding site) increases the efficiency of ribosome binding to the RNA sequence. An effective binding of the ribosomes to the ribosome binding site (Kozak sequence: GCCGCCACCAUGG (SEQ ID NO: 122), the AUG forms the start codon) in turn has the effect of an efficient translation of the RNA sequence as defined herein.

According to a further embodiment of the present invention an RNA sequence as defined herein, preferably the at least one (m)RNA of the adjuvant component of the inventive immunostimulatory composition and/or the at least one free mRNA of the inventive immunostimulatory composition, may be further modified with respect to potentially destabilizing sequence elements. Particularly, the coding region and/or the 5' and/or 3' untranslated region of the RNA sequence as defined herein may be further modified compared to the particular native RNA sequence such that is contains no destabilizing sequence elements, the coded amino acid sequence of the RNA sequence as defined herein preferably not being modified compared to its particular native RNA. It is known that, for example, in sequences of eukaryotic RNAs destabilizing sequence elements (DSE) occur, to which signal proteins bind and regulate enzymatic degradation of RNA in vivo. For further stabilization of the RNA sequence as defined herein, optionally in the region which encodes for a protein, one or more such further modifications compared to the corresponding region of the native RNA can therefore be carried out, so that no or substantially no destabilizing sequence elements are contained therein. According to the invention, DSEs present in the untranslated regions (3'- and/or 5'-UTR) can also be eliminated from an RNA sequence as defined herein, preferably from the at least one (m)RNA of the adjuvant component of the inventive immunostimulatory composition and/or from the at least one free mRNA of the inventive immunostimulatory composition, by such further modifications.

Such destabilizing sequences are e.g. AU-rich sequences (AURES), which occur in 3'-UTR sections of numerous unstable RNAs (Caput et al., Proc. Natl. Acad. Sci. USA 1986, 83: 1670 to 1674). An RNA sequence as defined herein, preferably the at least one (m)RNA of the adjuvant component of the inventive immunostimulatory composition and/or the at least one free mRNA of the inventive immunostimulatory composition, is therefore preferably (further) modified compared to the native RNA such that the modified RNA contains no such destabilizing sequences.

This also applies to those sequence motifs which are recognized by possible endonucleases, e.g. the sequence GAACAAG, which is contained in the 3'-UTR segment of the gene which codes for the transferrin receptor (Binder et al., EMBO). 1994, 13: 1969 to 1980). These sequence motifs are also preferably removed according to the invention in the RNA sequence as defined herein, preferably the at least one (m)RNA of the adjuvant component of the inventive immunostimulatory composition and/or the at least one free mRNA of the inventive immunostimulatory composition.

Also preferably according to the invention, an RNA sequence as defined herein, preferably the at least one (m)RNA of the adjuvant component of the inventive immunostimulatory composition and/or the at least one free mRNA of the inventive immunostimulatory composition, has, in a further modified form at least one IRES as defined above and/or at least one 5' and/or 3' stabilizing sequence, e.g. to enhance ribosome binding or to allow expression of different encoded proteins, e.g., antibodies, therapeutically active proteins or antigens, as defined above, located on an at least one (bi- or even multicistronic) RNA as defined above.

According to the invention, an RNA sequence as defined herein, preferably the at least one (m)RNA of the adjuvant component of the inventive immunostimulatory composition and/or the at least one free mRNA of the inventive immunostimulatory composition, furthermore preferably may have at least one 5' and/or 3' stabilizing sequence. These stabilizing sequences in the 5' and/or 3' untranslated regions have the effect of increasing the half-life of the RNA as defined herein in the cytosol. These stabilizing sequences can have 100% sequence homology to naturally occurring sequences which occur in viruses, bacteria and eukaryotes, but can also be partly or completely synthetic. The untranslated sequences (UTR) of the globin gene, e.g. from *Homo sapiens* or *Xenopus laevis* may be mentioned as an example of stabilizing sequences which can be used in the present invention for a further stabilized RNA sequence as defined herein, preferably a further stabilized at least one (m)RNA of the adjuvant component of the inventive immunostimulatory composition and/or a further stabilized at least one free mRNA of the inventive immunostimulatory composition. Another example of a stabilizing sequence has the general formula (C/U)CCAN$_x$CCC(U/A)Py$_x$UC(C/U)CC (SEQ ID NO: 123), which is contained in the 3'UTR of the very stable RNA which codes for globin, (I)-collagen, 15-lipoxygenase or for tyrosine hydroxylase (cf. Holcik et al., Proc. Natl. Acad. Sci. USA 1997, 94: 2410 to 2414). Such stabilizing sequences can of course be used individually or in combination with one another and also in combination with other stabilizing sequences known to a person skilled in the art. An RNA sequence as defined herein, preferably the at least one (m)RNA of the adjuvant component of the inventive immunostimulatory composition and/or the at least one free mRNA of the inventive immunostimulatory composition, is therefore preferably present as globin UTR (untranslated regions)-stabilized RNA.

Any of the above modifications may be applied to an RNA sequence as defined herein, preferably the at least one (m)RNA of the adjuvant component of the inventive immunostimulatory composition and/or the at least one free mRNA of the inventive immunostimulatory composition, and further to any RNA as used in the context of the present invention and may be, if suitable or necessary, be combined with each other in any combination, provided, these combinations of modifications do not interfere with each other in the respective modified RNA. A person skilled in the art will be able to take his choice accordingly.

According to the invention, an RNA sequence as defined herein, preferably the at least one (m)RNA of the adjuvant component of the inventive immunostimulatory composition and/or the at least one free mRNA of the inventive immunostimulatory composition, may be prepared using any naturally or synthetic DNA or RNA sequence available in the art as a template, i.e. any suitable (desoxy)ribonucleic acid. Such naturally or synthetic DNA or RNA sequences may be obtained from any synthetic or naturally occurring source, which is available to a skilled person, e.g. may be derived from a protein or peptide library or may be transcribed from a nucleic acid library, such as a cDNA library, or may be obtained from any living or dead tissue, from a sample obtained from e.g. a human, animal or bacterial source. Alternatively, an RNA sequence as defined herein, preferably the at least one (m)RNA of the adjuvant component of the inventive immunostimulatory composition and/or the at least one free mRNA of the inventive immunostimulatory composition, may be prepared synthetically by methods known to a person skilled in the art, e.g., by solid phase synthesis or any other suitable method for preparing nucleic acid sequences, particularly RNA sequences. Furthermore, substitutions, additions or eliminations of nucleotides or bases in these sequences are preferably carried out using a DNA matrix for preparation of the RNA as defined herein or by techniques of the well known site directed mutagenesis or with an oligonucleotide ligation strategy (see e.g. Maniatis et al, Molecular Cloning: A Laboratory Manual, Cold Spring Harbor Laboratory Press, 3rd ed., Cold Spring Harbor, N.Y., 2001). The modification(s) of an RNA sequence as defined herein, preferably the at least one (m)RNA of the adjuvant component of the inventive immunostimulatory composition and/or the at least one free mRNA of the inventive immunostimulatory composition, can also be introduced into the RNA by means of further methods known to a person skilled in the art. Suitable methods are, for example, synthesis methods using (automatic or semi-automatic) oligonucleotide synthesis devices, biochemical methods, such as, for example, in vitro transcription methods, etc. In this connection there can preferably be used in the case of (relatively short) sequences, whose length generally does not exceed from 50 to 100 nucleotides, synthesis methods using (automatic or semi-automatic) oligonucleotide synthesis devices as well as in vitro transcription methods. In the case of (relatively long) sequences, for example sequences having a length of more than 50 to 100 nucleotides, biochemical methods are preferably suitable, such as, for example, in vitro transcription methods. However, even longer base-modified RNA molecules may be synthesized synthetically by coupling various synthesized fragments covalently.

As defined above, the inventive immunostimulatory composition comprises a) an adjuvant component and b) at least one free mRNA. According to another embodiment, the inventive immunostimulatory composition may comprise an additional adjuvant, i.e. an adjuvant which is contained in the inventive immunostimulatory composition additional to the adjuvant component defined above. In this context, an adjuvant may be understood as any compound, which is suitable to support administration and optionally delivery of the inventive immunostimulatory composition according to the invention. Furthermore, such an adjuvant may, without being bound thereto, initiate or increase an immune response of the innate immune system, i.e. a non-specific immune response. With other words, when administered, the inventive immunostimulatory composition typically elicits an innate immune response due to the adjuvant component, comprising or consisting of the at least one (m)RNA complexed with a cationic or polycationic compound as defined above. However, such an innate immune response may be enhanced by adding an additional adjuvant, as defined in the following. Such an additional adjuvant may be selected from any adjuvant known to a skilled person and suitable for the present case, i.e. supporting the induction of an innate immune response in a mammal, except of cationic or polycationic compounds as defined above in order to prevent complexation of the at least one free mRNA. Preferably, the adjuvant may be selected from the group consisting of, without being limited thereto, including chitosan, TDM, MDP, muramyl dipeptide, pluronics, alum solution, aluminium hydroxide, ADJUMER™ (polyphosphazene); aluminium phosphate gel; glucans from algae; algammulin; aluminium hydroxide gel (alum); highly protein-adsorbing aluminium hydroxide gel; low viscosity aluminium hydroxide gel; AF or SPT (emulsion of squalane (5%), Tween 80 (0.2%), Pluronic L121 (1.25%), phosphate-buffered saline, pH 7.4); AVRIDINE™ (propanediamine); BAY R1005™ ((N-(2-deoxy-2-L-leucylamino-b-D-glucopyranosyl)-N-octadecyl-dodecanoyl-amide hydroacetate); CALCITRIOL™ (1-alpha,25-dihydroxy-vitamin D3); calcium phosphate gel; CAPTM (calcium phosphate nanoparticles); cholera holotoxin, cholera-toxin-A1-protein-A-D-fragment fusion protein, sub-unit B of the cholera toxin; CRL 1005 (block copolymer P1205); cytokine-containing liposomes; DDA (dimethyldioctadecylammonium bromide); DHEA (dehydroepiandrosterone); DMPC (dimyristoylphosphatidylcholine); DMPG (dimyristoylphosphatidylglycerol); DOC/alum complex (deoxycholic acid sodium salt); Freund's complete adjuvant; Freund's incomplete adjuvant; gamma inulin; Gerbu adjuvant (mixture of: i) N-acetylglucosaminyl-(P1-4)-N-acetylmuramyl-L-alanyl-D-glutamine (GMDP), ii) dimethyldioctadecylammonium chloride (DDA), iii) zinc-L-proline salt complex (ZnPro-8); GM-CSF); GMDP(N-acetylglucosaminyl-(b1-4)-N-acetylmuramyl-L-alanyl-D-isoglutamine); imiquimod (1-(2-methypropyl)-1H-imidazo [4,5-c]quinoline-4-amine); ImmTher™ (N-acetylglucosaminyl-N-acetylmuramyl-L-Ala-D-isoGlu-L-Ala-glycerol dipalmitate); DRVs (immunoliposomes prepared from dehydration-rehydration vesicles); interferon-gamma; interleukin-1beta; interleukin-2; interleukin-7; interleukin-12; ISCOMS™; ISCOPREP 7.0.3.™; liposomes; LOXORIBINE™ (7-allyl-8-oxoguanosine); LT oral adjuvant (*E. coli* labile enterotoxin-protoxin); microspheres and microparticles of any composition; MF59™; (squalene-water emulsion); MONTANIDE ISA 51™ (purified incomplete Freund's adjuvant); MONTANIDE ISA 720™ (metabolisable oil adjuvant); MPL™ (3-Q-desacyl-4'-monophosphoryl lipid A); MTP-PE and MTP-PE liposomes ((N-acetyl-L-alanyl-D-isoglutaminyl-L-alanine-2-(1,2-dipalmitoyl-sn-glycero-3-(hydroxyphosphoryloxy))-ethylamide, monosodium salt); MURAMETIDE™ (Nac-Mur-L-Ala-D-Gln-$OCH_3$); MURAPALMITINE™ and D-MURAPALMITINE™ (Nac-Mur-L-Thr-D-isoGln-sn-glyceroldipalmitoyl); NAGO (neuraminidase-galactose oxidase); nanospheres or nanoparticles of any composition; NISVs (non-ionic surfactant vesicles); PLEURAN™ (β-glucan); PLGA, PGA and PLA (homo- and co-polymers of lactic acid and glycolic acid; microspheres/nanospheres); PLURONIC L121™; PMMA (polymethyl methacrylate); PODDS™ (proteinoid microspheres); polyethylene carbamate derivatives; poly-rA: poly-rU (polyadenylic acid-polyuridylic acid complex); polysorbate 80 (Tween 80); protein cochleates (Avanti Polar Lipids, Inc., Alabaster, Ala.); STIMULON™ (QS-21); Quil-A (Quil-A saponin); S-28463 (4-amino-otec-dimethyl-2-ethoxymethyl-1H-imidazo[4,5-c]quinoline-1-ethanol); SAF-1™ ("Syntex adjuvant formulation"); Sendai proteoliposomes and Sendai-containing lipid matrices; Span-85 (sorbitan trioleate); Specol (emulsion of Marcol 52, Span 85 and Tween 85); squalene or Robane® (2,6,10,15,19,23-hexamethyltetracosan and 2,6,10,15,19,23-hexamethyl-2,6,10,14,18,22-tetracosahexane); stearyltyrosine (octadecyltyrosine hydrochloride); Theramid® (N-acetylglucosaminyl-N-acetylmuramyl-L-Ala-D-isoGlu-L-Ala-dipalmitoxypropylamide); Theronyl-MDP (Termurtide™ or [thr 1]-MDP; N-acetylmuramyl-L-threonyl-D-isoglutamine); Ty particles (Ty-VLPs or virus-like particles); Walter-Reed liposomes (liposomes containing lipid A adsorbed on aluminium hydroxide), and lipopeptides, including Pam3Cys, in particular aluminium salts, such as Adju-phos, Alhydrogel, Rehydragel; emulsions, including CFA, SAF, IFA, MF59, Provax, TiterMax, Montanide, Vaxfectin; copolymers, including Optivax (CRL1005), L121, Poloaxmer4010), etc.; liposomes, including Stealth, cochleates, including BIORAL; plant derived adjuvants, including QS21, Quil A, Iscomatrix, ISCOM; adjuvants suitable for costimulation including Tomatine, biopolymers, including PLG, PMM, Inulin, microbe derived adjuvants, including Romurtide, DETOX, MPL, CWS, Mannose, CpG nucleic acid sequences, CpG7909, ligands of human TLR 1-10, ligands of murine TLR 1-13, ISS-1018, IC31, Imidazoquinolines, Ampligen, Ribi529, IMOxine, IRIVs, VLPs, cholera toxin, heat-labile toxin, Pam3Cys, Flagellin, GPI anchor, LNFPIII/Lewis X, antimicrobial peptides, UC-1V150, RSV fusion protein, cdiGMP; and adjuvants suitable as antagonists including CGRP neuropeptide. Suitable adjuvants may furthermore be selected from lipid modified nucleic acids or from any of the immunostimulatory sequences of formula (I), (II), (III), (IIIa), (IV), (IVa), (IVb), (Va) and/or (Vb) as defined above.

According to a further embodiment, the present invention also provides a pharmaceutical composition, comprising the inventive immunostimulatory composition as defined above and optionally a pharmaceutically acceptable carrier and/or vehicle.

As a first ingredient, the inventive pharmaceutical composition comprises the inventive immunostimulatory composition as defined above, i.e. an a) adjuvant component, comprising or consisting of at least one (m)RNA, complexed with a cationic or polycationic compound, and b) at least one free mRNA, encoding at least one therapeutically active protein, antigen and/or antibody, wherein the immunostimulatory composition is capable to elicit or enhance an innate and optionally an adaptive immune response in a mammal. Accordingly, the inventive pharmaceutical composition typically supports an innate immune response and optionally an adaptive immune response of the immune system of a patient to be treated.

Furthermore, the inventive pharmaceutical composition may comprise a pharmaceutically acceptable carrier and/or vehicle. In the context of the present invention, a pharmaceutically acceptable carrier typically includes the liquid or non-liquid basis of the inventive pharmaceutical composition. If the inventive pharmaceutical composition is provided in liquid form, the carrier will typically be pyrogen-free water; isotonic saline or buffered (aqueous) solutions, e.g phosphate, citrate etc. buffered solutions. Particularly for injection of the inventive pharmaceutical composition, water or preferably a buffer, more preferably an aqueous buffer, may be used, containing a sodium salt, preferably at least 50 mM of a sodium salt, a calcium salt, preferably at least 0.01 mM of a calcium salt, and optionally a potassium salt, preferably at least 3 mM of a potassium salt. According to a preferred embodiment, the sodium, calcium and, optionally, potassium salts may occur in the form of their halogenides, e.g. chlorides, iodides, or bromides, in the form of their hydroxides, carbonates, hydrogen carbonates, or sulfates, etc. Without being limited thereto, examples of sodium salts include e.g. NaCl, NaI, NaBr, $Na_2CO_3$, $NaHCO_3$, $Na_2SO_4$, examples of the optional potassium salts include e.g. KCl, KI, KBr, $K_2CO_3$, $KHCO_3$, $K_2SO_4$, and examples of calcium salts include e.g. $CaCl_2$, $CaI_2$, $CaBr_2$, $CaCO_3$, $CaSO_4$, $Ca(OH)_2$. Furthermore, organic anions of the aforementioned cations may be contained in the buffer. According to a more preferred embodiment, the buffer suitable for injection purposes as defined above, may contain salts selected from sodium chloride (NaCl), calcium chloride ($CaCl_2$) and optionally potassium chloride (KCl), wherein further anions may be present additional to the chlorides. $CaCl_2$ can also be replaced by another salt like KCl. Typically, the salts in the injection buffer are present in a concentration of at least 50 mM sodium chloride (NaCl), at least 3 mM potassium chloride (KCl) and at least 0.01 mM calcium chloride ($CaCl_2$). The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person. Ringer or Ringer-Lactate solution is particularly preferred as a liquid basis.

However, one or more compatible solid or liquid fillers or diluents or encapsulating compounds may be used as well for the inventive pharmaceutical composition, which are suitable for administration to a patient to be treated. The term "compatible" as used here means that these constituents of the inventive pharmaceutical composition are capable of being mixed with an RNA sequence as defined herein, preferably the at least one (m)RNA of the adjuvant component of the inventive immunostimulatory composition complexed with a cationic or polycationic compound, and the at least one free mRNA of the inventive immunostimulatory composition, in such a manner that no interaction occurs which would substantially reduce the pharmaceutical effectiveness of the inventive pharmaceutical composition under typical use conditions. Pharmaceutically acceptable carriers, fillers and diluents must, of course, have sufficiently high purity and sufficiently low toxicity to make them suitable for administration to a person to be treated. Some examples of compounds which can be used as pharmaceutically acceptable carriers, fillers or constituents thereof are sugars, such as, for example, lactose, glucose and sucrose; starches, such as, for example, corn starch or potato starch; cellulose and its derivatives, such as, for example, sodium carboxymethylcellulose, ethylcellulose, cellulose acetate; powdered tragacanth; malt; gelatin; tallow; solid glidants, such as, for example, stearic acid, magnesium stearate; calcium sulfate; vegetable oils, such as, for example, groundnut oil, cottonseed oil, sesame oil, olive oil, corn oil and oil from *theobroma*; polyols, such as, for example, polypropylene glycol, glycerol, sorbitol, mannitol and polyethylene glycol; alginic acid.

The inventive pharmaceutical composition may be administered orally, parenterally, by inhalation spray, topically, rectally, nasally, buccally, vaginally or via an implanted reservoir. The term parenteral as used herein includes subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, and sublingual injection or infusion techniques.

Preferably, the inventive pharmaceutical composition may be administered by parenteral injection, more preferably by subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, and sublingual injection or via infusion techniques. Sterile injectable forms of the inventive pharmaceutical compositions may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation of the inventive pharmaceutical composition.

The inventive pharmaceutical composition as defined above may also be administered orally in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient, i.e. the at least one (m)RNA of the adjuvant component of the inventive immunostimulatory composition and/or the at least one free mRNA of the inventive immunostimulatory composition forming part of the inventive pharmaceutical composition as defined above, is combined with emulsifying and suspending agents. If desired, certain sweetening, flavoring or coloring agents may also be added.

The inventive pharmaceutical composition may also be administered topically, especially when the target of treatment includes areas or organs readily accessible by topical application, e.g. including diseases of the skin or of any other accessible epithelial tissue. Suitable topical formulations are readily prepared for each of these areas or organs. For topical applications, the inventive pharmaceutical composition may be formulated in a suitable ointment, containing the inventive immunostimulatory composition, particularly its components as defined above, suspended or dissolved in one or more carriers. Carriers for topical administration include, but are not limited to, mineral oil, liquid petrolatum, white petrolatum, propylene glycol, polyoxyethylene, polyoxypropylene compound, emulsifying wax and water. Alternatively, the inventive pharmaceutical composition can be formulated in a suitable lotion or cream. In the context of the present invention, suitable carriers include, but are not limited to, mineral oil, sorbitan monostearate, polysorbate 60, cetyl esters wax, cetearyl alcohol, 2-octyldodecanol, benzyl alcohol and water.

The inventive pharmaceutical composition typically comprises a "safe and effective amount" of the components of the inventive pharmaceutical composition, particularly of the at least one (m)RNA of the adjuvant component of the inventive immunostimulatory composition complexed with a cationic or polycationic compound, and/or of the at least one free mRNA of the inventive immunostimulatory composition. As used herein, a "safe and effective amount" means an amount of the at least one (m)RNA of the adjuvant component of the inventive immunostimulatory composition complexed with a cationic or polycationic compound, and/or of the at least one free mRNA of the inventive immunostimulatory composition, that is sufficient to significantly induce a positive modification of a disease or disorder as defined herein. At the same time, however, a "safe and effective amount" is small enough to avoid serious side-effects, that is to say to permit a sensible relationship between advantage and risk. The determination of these limits typically lies within the scope of sensible medical judgment. A "safe and effective amount" of the components of the inventive pharmaceutical composition, particularly of the at least one (m)RNA of the adjuvant component of the inventive immunostimulatory composition complexed with a cationic or polycationic compound, and/or of the at least one free mRNA of the inventive immunostimulatory composition, herein will furthermore vary in connection with the particular condition to be treated and also with the age and physical condition of the patient to be treated, the body weight, general health, sex, diet, time of administration, rate of excretion, drug combination, the activity of the specific (m)RNA or mRNA as defined herein employed, the severity of the condition, the duration of the treatment, the nature of the accompanying therapy, of the particular pharmaceutically acceptable carrier used, and similar factors, within the knowledge and experience of the accompanying doctor. The inventive pharmaceutical composition may be used for human and also for veterinary medical purposes, preferably for human medical purposes, as a pharmaceutical composition in general or as a vaccine.

According to a specific embodiment, the inventive pharmaceutical composition may be provided as a vaccine. Such an inventive vaccine is typically composed like the inventive pharmaceutical composition and preferably supports at least an innate immune response of the immune system of a patient to be treated. Additionally, the inventive vaccine furthermore may also elicit an adaptive immune response, preferably, if the (at least one (m)RNA of the adjuvant component of the inventive immunostimulatory composition complexed with a cationic or polycationic compound, and/or preferably the) at least one free mRNA of the inventive immunostimulatory composition encodes any of the above mentioned antigens (or antibodies), which elicit an adaptive immune response.

The inventive vaccine may also comprise a pharmaceutically acceptable carrier, adjuvant, and/or vehicle as defined above for the inventive pharmaceutical composition. In the specific context of the inventive vaccine, the choice of a pharmaceutically acceptable carrier is determined in principle by the manner in which the inventive vaccine is administered. The inventive vaccine can be administered, for example, systemically or locally. Routes for systemic administration in general include, for example, transdermal, oral, parenteral routes, including subcutaneous, intravenous, intramuscular, intraarterial, intradermal and intraperitoneal injections and/or intranasal administration routes. Routes for local administration in general include, for example, topical administration routes but also intradermal, transdermal, subcutaneous, or intramuscular injections or intralesional, intracranial, intrapulmonal, intracardial, and sublingual injections. More preferably, vaccines may be administered by an intradermal, subcutaneous, or intramuscular route. Inventive vaccines are therefore preferably formulated in liquid (or sometimes in solid) form. The suitable amount of the inventive vaccine to be administered can be determined by routine experiments with animal models. Such models include, without implying any limitation, rabbit, sheep, mouse, rat, dog and non-human primate models. Preferred unit dose forms for injection include sterile solutions of water, physiological saline or mixtures thereof. The pH of such solutions should be adjusted to about 7.4. Suitable carriers for injection include hydrogels, devices for controlled or delayed release, polylactic acid and collagen matrices. Suitable pharmaceutically acceptable carriers for topical application include those which are suitable for use in lotions, creams, gels and the like. If the inventive vaccine is to be administered orally, tablets, capsules and the like are the preferred unit dose form. The pharmaceutically acceptable carriers for the preparation of unit dose forms which can be used for oral administration are well known in the prior art. The choice thereof will depend on secondary considerations such as taste, costs and storability, which are not critical for the purposes of the present invention, and can be made without difficulty by a person skilled in the art.

The inventive vaccine can additionally contain one or more auxiliary substances in order to further increase its immunogenicity. A synergistic action of the at least one (m)RNA of the adjuvant component of the inventive immunostimulatory composition complexed with a cationic or polycationic compound, and/or of the at least one free mRNA of the inventive immunostimulatory composition, as defined above, and of an auxiliary substance, which may be optionally contained in the inventive vaccine as described above, is preferably achieved thereby. Depending on the various types of auxiliary substances, various mechanisms can come into consideration in this respect. For example, compounds that permit the maturation of dendritic cells (DCs), for example lipopolysaccharides, TNF-alpha or CD40 ligand, form a first class of suitable auxiliary substances. In general, it is possible to use as auxiliary substance any agent that influences the immune system in the manner of a "danger signal" (LPS, GP96, etc.) or cytokines, such as GM-CFS, which allow an immune response produced by the immune-stimulating adjuvant according to the invention to be enhanced and/or influenced in a targeted manner. Particularly preferred auxiliary substances are cytokines, such as monokines, lymphokines, interleukins or chemokines, that further promote the innate immune response, such as IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, INF-alpha, IFN-beta, INF-gamma, GM-CSF, G-CSF, M-CSF, LT-beta or TNF-alpha, growth factors, such as hGH.

Further additives which may be included in the inventive vaccine are emulsifiers, such as, for example, Tween®; wetting agents, such as, for example, sodium lauryl sulfate; colouring agents; taste-imparting agents, pharmaceutical carriers; tablet-forming agents; stabilizers; antioxidants; preservatives.

The inventive vaccine can also additionally contain any further compound, which is known to be immune-stimulating due to its binding affinity (as ligands) to human Toll-like receptors TLR1, TLR2, TLR3, TLR4, TLR5, TLR6, TLR7, TLR8, TLR9, TLR10, or due to its binding affinity (as ligands) to murine Toll-like receptors TLR1, TLR2, TLR3, TLR4, TLR5, TLR6, TLR7, TLR8, TLR9, TLR10, TLR11, TLR12 or TLR13.

Another class of compounds, which may be added to an inventive vaccine in this context, may be CpG nucleic acids, in particular CpG-RNA or CpG-DNA. A CpG-RNA or CpG-DNA can be a single-stranded CpG-DNA (ss CpG-DNA), a double-stranded CpG-DNA (dsDNA), a single-stranded CpG-RNA (ss CpG-RNA) or a double-stranded CpG-RNA (ds CpG-RNA). The CpG nucleic acid is preferably in the form of CpG-RNA, more preferably in the form of single-stranded CpG-RNA (ss CpG-RNA). The CpG nucleic acid preferably contains at least one or more (mitogenic) cytosine/guanine dinucleotide sequence(s) (CpG motif(s)). According to a first preferred alternative, at least one CpG motif contained in these sequences, that is to say the C (cytosine) and the G (guanine) of the CpG motif, is unmethylated. All further cytosines or guanines optionally contained in these sequences can be either methylated or unmethylated. According to a further preferred alternative, however, the C (cytosine) and the G (guanine) of the CpG motif can also be present in methylated form.

According to a further preferred object of the present invention, the inventive immunostimulatory composition, preferably the components of the inventive immunostimulatory composition, i.e. the at least one (m)RNA of the adjuvant component of the inventive immunostimulatory composition complexed with a cationic or polycationic compound, together with the at least one free mRNA of the inventive immunostimulatory composition, may be used for the preparation of a pharmaceutical composition or a vaccine, preferably all as defined herein, for the prophylaxis, treatment and/or amelioration of any of the diseases and disorders as defined herein.

Accordingly, the inventive immunostimulatory composition, the inventive pharmaceutical composition or the inventive vaccine, or the at least one (m)RNA of the adjuvant component of the inventive immunostimulatory composition complexed with a cationic or polycationic compound, together with the at least one free mRNA of the inventive immunostimulatory composition, may be used for (the preparation of a medicament for) the prophylaxis, treatment and/or amelioration of e.g. cancer or tumor diseases, preferably selected from melanomas, malignant melanomas, colon carcinomas, lymphomas, sarcomas, blastomas, renal carcinomas, gastrointestinal tumors, gliomas, prostate tumors, bladder cancer, rectal tumors, stomach cancer, oesophageal cancer, pancreatic cancer, liver cancer, mammary carcinomas (=breast cancer), uterine cancer, cervical cancer, acute myeloid leukaemia (AML), acute lymphoid leukaemia (ALL), chronic myeloid leukaemia (CML), chronic lymphocytic leukaemia (CLL), hepatomas, various virus-induced tumors such as, for example, papilloma virus-induced carcinomas (e.g. cervical carcinoma=cervical cancer), adenocarcinomas, herpes virus-induced tumors (e.g. Burkitt's lymphoma, EBV-induced B-cell lymphoma), heptatitis B-induced tumors (hepatocell carcinomas), HTLV-1- and HTLV-2-induced lymphomas, acoustic neuroma, lung carcinomas (=lung cancer=bronchial carcinoma), small-cell lung carcinomas, pharyngeal cancer, anal carcinoma, glioblastoma, rectal carcinoma, astrocytoma, brain tumors, retinoblastoma, basalioma, brain metastases, medulloblastomas, vaginal cancer, pancreatic cancer, testicular cancer, Hodgkin's syndrome, meningiomas, Schneeberger disease, hypophysis tumor, Mycosis fungoides, carcinoids, neurinoma, spinalioma, Burkitt's lymphoma, laryngeal cancer, renal cancer, thymoma, corpus carcinoma, bone cancer, non-Hodgkin's lymphomas, urethral cancer, CUP syndrome, head/neck tumors, oligodendroglioma, vulval cancer, intestinal cancer, colon carcinoma, oesophageal carcinoma (=Oesophageal cancer), wart involvement, tumors of the small intestine, craniopharyngeomas, ovarian carcinoma, genital tumors, ovarian cancer (=Ovarian carcinoma), pancreatic carcinoma (=pancreatic cancer), endometrial carcinoma, liver metastases, penile cancer, tongue cancer, gall bladder cancer, leukaemia, plasmocytoma, lid tumor, prostate cancer (=prostate tumors), etc.

Furthermore, the inventive immunostimulatory composition, the inventive pharmaceutical composition or the inventive vaccine, or the at least one (m)RNA of the adjuvant component of the inventive immunostimulatory composition complexed with a cationic or polycationic compound, together with the at least one free mRNA of the inventive immunostimulatory composition, may be used for (the preparation of a medicament for) the prophylaxis, treatment, and/or amelioration of e.g. infectious diseases, preferably (viral, bacterial or protozoological) infectious diseases. Such infectious diseases, preferably to (viral, bacterial or protozoological) infectious diseases, are typically selected from influenza, malaria, SARS, yellow fever, AIDS, Lyme borreliosis, Leishmaniasis, anthrax, meningitis, viral infectious diseases such as AIDS, Condyloma acuminata, hollow warts, Dengue fever, three-day fever, Ebola virus, cold, early summer meningoencephalitis (FSME), flu, shingles, hepatitis, herpes simplex type I, herpes simplex type II, Herpes zoster, influenza, Japanese encephalitis, Lassa fever, Marburg virus, measles, foot-and-mouth disease, mononucleosis, mumps, Norwalk virus infection, Pfeiffer's glandular fever, smallpox, polio (childhood lameness), pseudo-croup, fifth disease, rabies, warts, West Nile fever, chickenpox, cytomegalic virus (CMV), bacterial infectious diseases such as miscarriage (prostate inflammation), anthrax, appendicitis, borreliosis, botulism, *Camphylobacter, Chlamydia trachomatis* (inflammation of the urethra, conjunctivitis), cholera, diphtheria, donavanosis, epiglottitis, typhus fever, gas gangrene, gonorrhoea, rabbit fever, *Heliobacter pylori*, whooping cough, climatic bubo, osteomyelitis, Legionnaire's disease, leprosy, listeriosis, pneumonia, meningitis, bacterial meningitis, anthrax, otitis media, *Mycoplasma hominis*, neonatal sepsis (Chorioamnionitis), noma, paratyphus, plague, Reiter's syndrome, Rocky Mountain spotted fever, *Salmonella paratyphus, Salmonella typhus*, scarlet fever, syphilis, tetanus, tripper, tsutsugamushi disease, tuberculosis, typhus, vaginitis (colpitis), soft chancre, and infectious diseases caused by parasites, protozoa or fungi, such as amoebiasis, bilharziosis, Chagas disease, *Echinococcus*, fish tapeworm, fish poisoning (Ciguatera), fox tapeworm, athlete's foot, canine tapeworm, candidosis, yeast fungus spots, scabies, cutaneous Leishmaniosis, lambliasis (giardiasis), lice, malaria, microscopy, onchocercosis (river blindness), fungal diseases, bovine tapeworm, schistosomiasis, porcine tapeworm, toxoplasmosis, trichomoniasis, trypanosomiasis (sleeping sickness), visceral Leishmaniosis, nappy/diaper dermatitis or miniature tapeworm.

Likewise, the inventive immunostimulatory composition, the inventive pharmaceutical composition or the inventive vaccine, or the at least one (m)RNA of the adjuvant component of the inventive immunostimulatory composition complexed with a cationic or polycationic compound, together with the at least one free mRNA of the inventive immunostimulatory composition, may be used for (the preparation of a medicament for) the prophylaxis, treatment, and/or amelioration of e.g. autoimmune diseases. Autoimmune diseases can be broadly divided into systemic and organ-specific or localised autoimmune disorders, depending on the principal clinico-pathologic features of each disease. Autoimmune diseases may be divided into the categories of systemic syndromes, including systemic lupus erythematosus (SLE), Sjögren's syndrome, Scleroderma, Rheumatoid Arthritis and polymyositis or local syndromes which may be endocrinologic (type I diabetes (Diabetes mellitus Type 1), Hashimoto's thyroiditis, Addison's disease etc.), dermatologic (pemphigus vulgaris), haematologic (autoimmune haemolytic anaemia), neural (multiple sclerosis) or can involve virtually any circumscribed mass of body tissue. The autoimmune diseases to be treated may be selected from the group consisting of type I autoimmune diseases or type II autoimmune diseases or type III autoimmune diseases or type IV autoimmune diseases, such as, for example, multiple sclerosis (MS), rheumatoid arthritis, diabetes, type I diabetes (Diabetes mellitus Type 1), chronic polyarthritis, Basedow's disease, autoimmune forms of chronic hepatitis, colitis ulcerosa, type I allergy diseases, type II allergy diseases, type III allergy diseases, type IV allergy diseases, fibromyalgia, hair kiss, Bechterew's disease, Crohn's disease, Myasthenia gravis, neurodermitis, Polymyalgia rheumatica, progressive systemic sclerosis (PSS), Reiter's syndrome, rheumatic arthritis, psoriasis, vasculitis, etc, or type II diabetes. While the exact mode as to why the immune system induces a immune reaction against autoantigens has not been elucidated so far, there are several findings with regard to the etiology. Accordingly, the autoreaction may be due to a T-Cell bypass. A normal immune system requires the activation of B-cells by T-cells before the former can produce antibodies in large quantities. This requirement of a T-cell can be by-passed in rare instances, such as infection by organisms producing super-antigens, which are capable of initiating polyclonal activation of B-cells, or even of T-cells, by directly binding to the β-subunit of T-cell receptors in a non-specific fashion. Another explanation deduces autoimmune diseases from a Molecular Mimicry. An exogenous antigen may share structural similarities with certain host antigens; thus, any antibody produced against this antigen (which mimics the self-antigens) can also, in theory, bind to the host antigens and amplify the immune response. The most striking form of molecular mimicry is observed in Group A beta-haemolytic streptococci, which shares antigens with human myocardium, and is responsible for the cardiac manifestations of rheumatic fever.

Additionally, the inventive immunostimulatory composition, the inventive pharmaceutical composition or the inventive vaccine, or the at least one (m)RNA of the adjuvant component of the inventive immunostimulatory composition complexed with a cationic or polycationic compound, together with the at least one free mRNA of the inventive immunostimulatory composition, may be used for (the preparation of a medicament for) the prophylaxis, treatment, and/or amelioration of allergies or allergic diseases, i.e. diseases related to allergies. Allergy is a condition that typically involves an abnormal, acquired immunological hypersensitivity to certain foreign antigens or allergens, such as the allergy antigens as defined above. Such allergy antigens or allergens may be selected from allergy antigens as defined above antigens derived from different sources, e.g. from animals, plants, fungi, bacteria, etc. Allergens in this context include e.g. grasses, pollens, molds, drugs, or numerous environmental triggers, etc. Allergies normally result in a local or systemic inflammatory response to these antigens or allergens and lead to an immunity in the body against these allergens. Without being bound to theory, several different disease mechanisms are supposed to be involved in the development of allergies. According to a classification scheme by P. Gell and R. Coombs the word "allergy" was restricted to type I hypersensitivities, which are caused by the classical IgE mechanism. Type I hypersensitivity is characterised by excessive activation of mast cells and basophils by IgE, resulting in a systemic inflammatory response that can result in symptoms as benign as a runny nose, to life-threatening anaphylactic shock and death. Well known types of allergies include, without being limited thereto, allergic asthma (leading to swelling of the nasal mucosa), allergic conjunctivitis (leading to redness and itching of the conjunctiva), allergic rhinitis ("hay fever"), anaphylaxis, angiodema, atopic dermatitis (eczema), urticaria (hives), eosinophilia, respiratory, allergies to insect stings, skin allergies (leading to and including various rashes, such as eczema, hives (urticaria) and (contact) dermatitis), food allergies, allergies to medicine, etc. With regard to the present invention, the inventive immunostimulatory composition, the inventive pharmaceutical composition or the inventive vaccine, or the at least one (m)RNA of the adjuvant component of the inventive immunostimulatory composition complexed with a cationic or polycationic compound, together with the at least one free mRNA of the inventive immunostimulatory composition, may be used for the treatment of such allergic disorders or diseases, preferably by desensitizing the immune reaction which triggers a specific immune response. Such a desensitizing may be carried out by administering an effective amount of the allergen or allergic antigen encoded by a RNA of the inventive immunostimulatory composition, preferably the at least one free mRNA, to induce a slight immune reaction. The amount of the allergen or allergic antigen may then be raised step by step in subsequent administrations until the immune system of the patient to be treated tolerates a specific amount of allergen or allergic antigen.

In the context of the above, the invention furthermore relates also to the use of the inventive immunostimulatory composition, the inventive pharmaceutical composition or the inventive vaccine, or the at least one (m)RNA of the adjuvant component of the inventive immunostimulatory composition complexed with a cationic or polycationic compound, together with the at least one free mRNA of the inventive immunostimulatory composition, for the prophylaxis, treatment, and/or amelioration of diseases or disorders as mentioned herein. It also includes in particular the use of the inventive immunostimulatory composition, the inventive pharmaceutical composition or the inventive vaccine, or the at least one (m)RNA of the adjuvant component of the inventive immunostimulatory composition complexed with a cationic or polycationic compound, together with the at least one free mRNA of the inventive immunostimulatory composition for inoculation or the use of these components as an inoculant. According to one particularly preferred embodiment of the present invention, such a method for prophylaxis, treatment, and/or amelioration of the above-mentioned diseases or disorders, or an inoculation method for preventing the above-mentioned diseases, typically comprises administering the described pharmaceutical composition to a patient in need thereof (e.g. suffering from any of the above diseases or showing symptoms thereof), in particular to a human being, preferably in a "safe and effective amount" and in one of the above formulations as described above for inventive pharmaceutical compositions. The administration mode also may be as described above for inventive pharmaceutical compositions or vaccines.

The present invention relates also to an in vitro transcription method for the preparation of the at least one (m)RNA, to be complexed with a cationic or polycationic compound, or the at least one free mRNA, respectively, encoding at least one therapeutically active protein, antigen and/or antibody, both as defined above, comprising the following steps:

a) preparation/provision of a (desoxy)ribonucleic acid as a template for the inventive at least one (m)RNA, to be complexed with a cationic or polycationic compound, or the at least one free mRNA, respectively, encoding at least one therapeutically active protein, antigen and/or antibody, both as described above;
b) addition of the (desoxy)ribonucleic acid to an in vitro transcription medium comprising a RNA polymerase, a suitable buffer, a nucleotide mix, the nucleotide mix optionally comprising one or more nucleotides with chemically modified nucleosides selected from the chemically modified nucleosides as defined above as replacement (partially or completely) for one or more of the naturally occurring nucleosides A, G, U and/or C, and optionally one or more naturally occurring nucleosides A, G, U and/or C if not all of the naturally occurring nucleosides A, G, U and/or C are to be replaced, and optionally an RNase inhibitor;
c) incubation of the (desoxy)ribonucleic acid in the in vitro transcription medium and in vitro transcription of the (desoxy)ribonucleic acid; and
d) optionally purification and removal of the unincorporated nucleotides from the in vitro transcription medium.

A (desoxy)ribonucleic acid as described in step a) of the inventive in vitro transcription method can be any nucleic acid as described above that may be used as a template for the preparation of the at least one (m)RNA, to be complexed with a cationic or polycationic compound, and/or the at least one free mRNA, respectively, encoding at least one therapeutically active protein, antigen and/or antibody. For this purpose typically DNA sequences are used, for example genomic DNA or fragments thereof, or plasmids, or RNA sequences (corresponding thereto), for example mRNA sequences, preferably in linearized form. The in vitro transcription reaction can usually be carried out using a vector having a RNA polymerase binding site. To this end there can be used any vectors known in the art, for example commercially available vectors (see above). Preference is given, for example, to those vectors that have a SP6 or a T7 or T3 binding site upstream and/or downstream of the cloning site. Accordingly, the (desoxy)ribonucleic acid sequences used can be transcribed later, as desired, depending on the chosen RNA polymerase. A (desoxy)ribonucleic acid sequence used for in vitro transcription and coding for a protein as defined above, e.g. a therapeutically active protein, an antigen or an antibody, is typically cloned into a vector, for example via a multiple cloning site of the vector used. Prior to transcription, the plasmid is typically cleaved with restriction enzymes at the site at which the future 3' end of the at least one (m)RNA of the adjuvant component as defined above or the at least one free mRNA as defined above is to be located, using a suitable restriction enzyme, and the fragment is purified. This prevents the future at least one (m)RNA of the adjuvant component as defined above or the at least one free mRNA as defined above, from containing vector sequences, and a defined length may be obtained.

Alternatively, it is also possible to prepare the (desoxy) ribonucleic acid as transcription template by polymerase chain reaction (PCR). To this end, one of the primers used for PCR typically contains the sequence of a RNA polymerase binding site. It is further preferred for the 5' end of the primer to have a length of approximately 10 to 50 further nucleotides, more preferably 15 to 30 further nucleotides and most preferably of approximately 20 nucleotides.

Prior to the in vitro transcription reaction, the (desoxy) ribonucleic acid, e.g., the specific DNA or RNA template, is typically purified and free of RNase in order to ensure a high yield. Purification can be carried out by any process known in the art, for example with a caesium chloride gradient or ion-exchange process.

According to method step b) of the inventive in vitro transcription method, the (desoxy)ribonucleic acid is added to an in vitro transcription medium. A suitable in vitro transcription medium first contains a (desoxy)ribonucleic acid as prepared under step a), for example approximately from about 0.1 to about 10 μg, preferably approximately from about 1 to about 5 μg, more preferably about 2.5 μg and most preferably approximately about 1 μg, of such a nucleic acid. A suitable in vitro transcription medium further optionally contains a reducing agent, e.g. DTT, more preferably approximately from about 1 to about 20 μl of about 50 mM DTT, yet more preferably approximately about 5 μl of about 50 mM DTT. The in vitro transcription medium further contains nucleotides (AMP, GMP, UMP and/or CMP), for example a nucleotide mix. In the case of the present invention the nucleotides preferably comprise chemically modified nucleosides as defined above. Such (chemically modified) nucleotides may serve as replacement for one or more of the naturally occurring nucleotides AMP, GMP, UMP and/or CMP, and optionally one or more naturally occurring nucleotides AMP, GMP, UMP and/or CMP, if not all of the naturally occurring nucleotides AMP, GMP, UMP and/or CMP are to be replaced. The nucleotides AMP, GMP, UMP and/or CMP are typically present in the nucleotide mix in a concentration of typically approximately from 0.1 to 10 mM per nucleotide, preferably from 0.1 to 1 mM per nucleotide, preferably approximately 4 mM in total. (Chemically) modified nucleotides as described above (approximately 1 mM per nucleotide, preferably approximately 4 mM in total), are typically added in such an amount that the native nucleotide is replaced completely by the (modified) nucleotide(s) comprising a chemically modified nucleoside as defined above. It is, however, also possible to use mixtures of one or more modified nucleotides as defined above and one or more naturally occurring nucleotides instead of a particular nucleotide, that is to say one or more chemically modified nucleotides as described above can occur as a replacement for one or more of the naturally occurring nucleotides AMP, GMP, UMP and/or CMP, and optionally additionally one or more naturally occurring nucleotides AMP, GMP, UMP and/or CMP may be contained, if not all the naturally occurring nucleotides AMP, GMP, UMP and/or CMP are to be replaced. By selective addition of the desired base to the in vitro transcription medium, the content, that is to say the occurrence and amount, of the desired nucleotide modification in the transcribed inventive at least one (m)RNA, to be complexed with a cationic or polycationic compound, or the at least one free mRNA, encoding at least one therapeutically active protein, antigen and/or antibody, can therefore be controlled. A suitable in vitro transcription medium likewise contains a RNA polymerase, e.g. T7-RNA polymerase (e.g. T7-Opti mRNA Kit, CureVac, Tubingen, Germany), T3-RNA polymerase or SP6, typically approximately from 10 to 500 U, preferably approximately from 25 to 250 U, more preferably approximately from 50 to 150 U, and most preferably approximately 100 U of RNA polymerase. The in vitro transcription medium is further preferably kept free of RNase in order to avoid degradation of the transcribed (m)RNA. A suitable in vitro transcription medium therefore optionally contains in addition an RNase inhibitor.

In a step c) of the inventive in vitro transcription method, the (desoxy)ribonucleic acid of step b) is incubated and transcribed in the in vitro transcription medium, typically for approximately 30 to 120 minutes, preferably for approximately 40 to 90 minutes and most preferably for approximately 60 minutes, at approximately 30 to 45° C., preferably at 37 to 42° C. The incubation temperature is governed by the RNA polymerase that is used, for example in the case of T7 RNA polymerase it is approximately 37° C. The nucleic acid obtained by the transcription is preferably the at least one (m)RNA, to be complexed with a cationic or polycationic compound, or the at least one free mRNA, encoding at least one therapeutically active protein, antigen and/or antibody, respectively, both as defined herein.

Subsequent to incubation according to method step c) above, purification of the reaction can optionally take place in step d) of the in vitro transcription method according to the invention. To this end, any suitable process known in the art can be used, for example chromatographic purification processes, e.g. affinity chromatography, gel filtration, etc. By means of the purification, non-incorporated, i.e. excess, nucleotides can be removed from the in vitro transcription medium. Any suitable method known in the prior art, e.g. chromatographic purification methods, e.g. affinity chromatography, gel filtration etc., can be used for this. By such a purification, a clean transcribed RNA of an RNA sequence as defined herein, e.g. of an at least one (m)RNA, to be complexed with a cationic or polycationic compound, or of the at least one free mRNA, encoding at least one therapeutically active protein, antigen and/or antibody, respectively, can be obtained. For example, after the transcription the reaction mixture containing the transcribed RNA can typically be digested with DNase in order to remove the DNA template still contained in the reaction mixture. The transcribed RNA can be subsequently or alternatively precipitated with LiCl. Purification of the transcribed RNA can then take place via ion-pair reversed phase (IP RP)-HPLC. This renders it possible in particular to separate longer and shorter fragments from one another effectively. Preferably, in this context the purification takes place via a method for purification of the RNA on a preparative scale, which is distinguished in that the RNA as defined herein, particularly the at least one (m)RNA, to be complexed with a cationic or polycationic compound, or the at least one free mRNA, encoding at least one therapeutically active protein, antigen and/or antibody, respectively, is purified by means of HPLC using a porous reverse phase as the stationary phase (PURE Messenger). For example, for the purification in step d) of the inventive in vitro transcription method, a reverse phase can be employed as the stationary phase for the HPLC purification. For the chromatography with reverse phases, a non-polar compound typically serves as stationary phase, and a polar solvent, such as mixtures of water, which is usually employed in the form of buffers, with acetonitrile and/or methanol, serves as the mobile phase for the elution. Preferably, the porous reverse phase has a particle size of 8.0±2 μm, preferably ±1 μm, more preferably +/−0.5 μm. The reverse phase material can be in the form of beads. The purification can be carried out in a particularly favourable manner with a porous reverse phase having this particle size, optionally in the form of beads, particularly good separation results being obtained. The reverse phase employed is preferably porous since with stationary reverse phases which are not porous, such as are described, e.g., by Azarani A. and Hecker K. H., pressures which are too high are built up, so that preparative purification of the RNA as defined herein, particularly the at least one (m)RNA, to be complexed with a cationic or polycationic compound, or the at least one free mRNA, encoding at least one therapeutically active protein, antigen and/or antibody, respectively, is possible, if at all, only with great difficulty. The reverse phase preferably has a pore size of from 200 Å to 5,000 Å, in particular a pore size of from 300 Å to 4,000 Å. Particularly preferred pore sizes for the reverse phases are 200 Å-400 Å, 800 Å-1,200 Å and 3,500 Å-4,500 Å. With a reverse phase having these pore sizes, particularly good results are achieved in respect of the purification of the RNA as defined herein in process step d). The material for the reverse phase is preferably a polystyrene-divinylbenzene, and non-alkylated polystyrene-divinylbenzenes can be employed in particular. Stationary phases with polystyrene-divinylbenzene are known per se. For the purification in method step d), the polystyrene-divinylbenzenes which are known per se and already employed for HPLC methods and are commercially obtainable can be used. A non-alkylated porous polystyrene-divinylbenzene which in particular has a particle size of 8.0±0.5 μm and a pore size of 250 Å-300 Å, 900 Å-1,100 Å or 3,500 Å-4,500 Å is very particularly preferably used for the purification in method step d). The advantages described above can be achieved in a particularly favourable manner with this material for the reverse phases. The HPLC purification can be carried out by the ion pair method, an ion having a positive charge being added to the mobile phase as a counter-ion to the negatively charged RNA. An ion pair having a lipophilic character, which is slowed down by the non-polar stationary phase of the reverse phase system, is formed in this manner. In practices, the precise conditions for the ion pair method must be worked out empirically for each concrete separation problem. The size of the counter-ion, its concentration and the pH of the solution contribute greatly towards the result of the separation. In a favourable manner, alkylammonium salts, such as triethylammonium acetate and/or tetraalkylammonium compounds, such as tetrabutylammonium, are added to the mobile phase. Preferably, 0.1 M triethylammonium acetate is added and the pH is adjusted to about 7. The choice of mobile phase depends on the nature of the desired separation. This means that the mobile phase found for a specific separation, such as can be known, for example, from the prior art, cannot be transferred readily to another separation problem with adequate prospect of success. The ideal elution conditions, in particular the mobile phase used, must be determined for each separation problem by empirical experiments. A mixture of an aqueous solvent and an organic solvent can be employed as the mobile phase for elution of the RNA as defined herein, particularly the at least one (m)RNA, complexed with a cationic or polycationic compound, or the at least one free mRNA, encoding at least one therapeutically active protein, antigen and/or antibody, respectively, by the HPLC method. In this context, it is favourable if a buffer which has, in particular, a pH of about 7, for example 6.5-7.5, e.g. 7.0, is used as the aqueous solvent; preferably, the buffer triethylammonium acetate is used, particularly preferably a 0.1 M triethylammonium acetate buffer which, as described above, also acts as a counter-ion to RNA as defined herein in the ion pair method. The organic solvent employed in the mobile phase can be acetonitrile, methanol or a mixture of these two, very particularly preferably acetonitrile. The purification of the RNA as defined herein in method step d) using an HPLC method as described, particularly purification of the at least one (m)RNA, to be complexed with a cationic or polycationic compound, or of the at least one free mRNA, encoding at least one therapeutically active protein, antigen and/or antibody, respectively, is carried out in a particularly favourable manner with these organic solvents. The mobile phase is particularly preferably a mixture of 0.1 M triethylammonium acetate, pH 7, and acetonitrile. It has emerged to be likewise particularly favourable if the mobile phase contains 5.0 vol. % to 20.0 vol. % of organic solvent, based on the mobile phase, and the remainder to make up 100 vol. % is the aqueous solvent. It is very particularly favourable for the method according to the invention if the mobile phase contains 9.5 vol. % to 14.5 vol. % of organic solvent, based on the mobile phase, and the remainder to make up 100 vol. % is the aqueous solvent. Elution of the RNA as defined herein, particularly the at least one (m)RNA, to be complexed with a cationic or polycationic compound, or the at least one free mRNA, encoding at least one therapeutically active protein, antigen and/or antibody, respectively, can subsequently be carried out isocratically or by means of a gradient separation. In the case of an isocratic separation, elution of the RNA as defined herein is carried out with a single eluting agent or a mixture of several eluting agents which remains constant, it being possible for the solvents described above in detail to be employed as the eluting agent.

The present patent application also provides a method of transfecting and optionally administering the inventive immunostimulatory composition or its components as defined above, the inventive pharmaceutical composition or the inventive vaccine, as defined above, comprising the following steps:

(a) collection of blood cells, professional antigen presenting cells (APCs), especially dendritic cells (DCs), and
(b) transfection of the blood cells, professional antigen presenting cells (APCs), especially dendritic cells (DCs), in vitro with the inventive immunostimulatory composition or its components, the inventive pharmaceutical composition or the inventive vaccine.

In the context of the present invention, "blood cells" are preferably understood according to the invention as meaning a mixture or an enriched to substantially pure population of red blood cells, granulocytes, mononuclear cells (PBMCs) and/or blood platelets from whole blood, blood serum or another source, e.g. from the spleen or lymph nodes, only a small proportion of professional APCs being present. Preferably, blood cells in the present invention are typically characterized in that they contain a small proportion of well-differentiated professional antigen presenting cells (APCs), especially dendritic cells (DCs). The blood cells as used according to the present invention may be preferably fresh blood cells, i.e. the period between collection of the blood cells (especially blood withdrawal) and transfection being only short, e.g. less than 12 h, preferably less than 6 h, particularly preferably less than 2 h and very particularly preferably less than 1 h. However, the blood cells as used according to the present invention may also be blood cells obtained upon withdrawal of blood prior to need, e.g. an operation or a treatment as defined herein, and which are stored subsequently until use.

Blood cells may be collected from an animal or human patient by standard methods, for example. Thus whole blood can easily be obtained by puncturing a suitable vessel. Serum is obtained in known manner by coagulating the solid blood constituents. PBMCs may be mentioned as an example of an enriched partial population of blood cells. These are conventionally isolated by a method first described by Bøyum (Nature 204, 793-794, 1964; Scan. J. Lab. Clin. Invest. Suppl. 97, 1967). This is generally done by withdrawing blood from the individual and adding it e.g. to a solution of density 1.077 g/ml (25° C.), conventionally containing Ficoll and sodium diatrizoate, for density gradient centrifugation. During careful centrifugation at room temperature, the PBMCs collect at the Ficoll/blood interface whereas the red blood cells and the remaining white blood cells are sedimented. The interface with the PBMCs is recovered and conventionally washed with a suitable buffer, e.g. sterile PBS. The PBMCs are preferably subjected to a short isotonic treatment with an aqueous solution of e.g. ammonium chloride. Finally, the PBMCs are washed a further one or more times with a buffer such as PBS (sterile). The cells obtained can then optionally be stored under suitable conditions, conventionally at −70° C., until further use.

According to one preferred embodiment, the blood cells immediately prior to transfection are fresh blood cells, i.e. there is only a short period between the collection of blood cells (especially blood withdrawal) in step (a) and the transfection according to step (b), e.g. less than 12 h, preferably less than 6 h, particularly preferably less than 2 h and very particularly preferably less than 1 h.

In the context of the present invention, dendritic cells (DCs), as used in the above mentioned inventive method of transfection and optionally administration, are typically potent antigen presenting cells (APCs) that typically possess the ability to stimulate naïve T cells. They comprise a system of leukocytes widely distributed in all tissues, especially in those that provide an environmental interface. DCs posses a heterogeneous haemopoietic lineage, in that subsets from different tissues have been shown to posses a differential morphology, phenotype and function. The ability to stimulate naïve T cell proliferation appears to be shared between these various DC subsets. It has been suggested that the so-called myeloid and lymphoid-derived subsets of DCs perform specific stimulatory or tolerogenic function, respectively. DCs are derived from bone marrow progenitors and circulate in the blood as immature precursors prior to migration into peripheral tissues. Within different tissues, DCs differentiate and become active in the taking up and processing of antigens, and their subsequent presentation on the cell surface linked to major histocompatibility (MHC) molecules. Upon appropriate stimulation, DCs undergo further maturation and migrate to secondary lymphoid tissues where they present antigens to T cells and induce an immune response. DCs are receiving increasing scientific and clinical interest due to their key role in anti-cancer host responses and potential use as biological adjuvants in tumour vaccines, as well as their involvement in the immunobiology of tolerance and autoimmunity. Dendritic cells (DCs), however, may also be used in the context of the present invention, if no or a lower immune response is required or envisaged. Such dendritic cells (DCs), as defined above, may be isolated from different tissues as mentioned above or from blood, particularly from blood samples as described above.

Preferably, the blood cells, professional antigen presenting cells (APCs), especially dendritic cells (DCs), used for the inventive method of transfection and optionally administration pharmaceutical composition or the vaccine according to the invention originate from the actual patient who will be treated with the pharmaceutical composition of the present invention (autologous cells). The pharmaceutical composition or the vaccine according to the invention therefore preferably contain autologous blood cells, professional antigen presenting cells (APCs), especially dendritic cells (DCs).

The transfection of the blood cells, professional antigen presenting cells (APCs), especially dendritic cells (DCs), is likewise carried out by common methods, e.g. by means of electroporation or chemical methods, especially lipofection, preferably only by administration of the inventive composition without further transfection reagents.

The RNA as defined herein, particularly the at least one (m)RNA, complexed with a cationic or polycationic compound, and the at least one free mRNA, encoding at least one therapeutically active protein, antigen and/or antibody, respectively, used for the in vitro transfection according to step (b) is prepared by methods known to those skilled in the art, especially by chemical synthesis or particularly preferably by means of molecular biological methods which have already been mentioned above.

As defined above, there may be the need to transfect the blood cells, professional antigen presenting cells (APCs), especially dendritic cells (DCs), used for the inventive method of transfection and optionally administration, with an RNA as defined herein, particularly the inventive immunostimulatory composition or its components, or the inventive pharmaceutical composition or vaccine. Furthermore, administration of such transfected cells to a patient, to living tissues and/or organisms in vivo, particularly retransplantation into the host organism in the case of autologous cells, may be envisaged as well and carried out as an optional step c) of the above mentioned method. In this context, an organism (or a being) typically means mammals, selected from, without being restricted thereto, the group comprising humans, and animals, including e.g. pig, goat, cattle, swine, dog, cat, donkey, monkey, ape or rodents, including mouse, hamster and rabbit. Furthermore, living tissues as mentioned above, are preferably derived from these organisms. Administration of the transfected cells to those living tissues and/or organisms may occur via any suitable administration route, e.g. systemically, and include e.g. intra- or transdermal, oral, parenteral, including subcutaneous, intramuscular or intravenous injections, topical and/or intranasal routes as defined above.

According to another embodiment, the present invention also provides a method for the preparation of the inventive immunostimulatroy composition, comprising following steps:

a) preparing an "adjuvant component" comprising or consisting of at least one (m)RNA as defined above, complexed with a cationic or polycationic compound, as defined above, preferably by mixing the at least one (m)RNA as defined above in a specific ratio with the cationic or polycationic compound, as defined above; and
b) preparing the inventive immunostimulatory composition by adding in a specific ratio as defined above the at least one free mRNA as defined above to the adjuvant component prepared according to step a), wherein the at least one free mRNA as defined above, encodes at least one therapeutically active protein, antigen and/or antibody as defined above.

The so called "adjuvant component" is prepared according to a step a) of the inventive method of preparation by complexing the at least one (m)RNA of the adjuvant component with a cationic or polycationic compound preferably in a specific ratio to form a stable complex. As defined above, it is important, that no free cationic or polycationic compound or only a neclectably small amount remains in the adjuvant component after complexing the (m)RNA. Accordingly, the ratio of the (m)RNA and the cationic or polycationic compound in the adjuvant component is typically selected such that the (m)RNA is entirely complexed and no free cationic or polycationic compound or only a neclectably small amount remains in the composition. Preferably the ratio of the adjuvant component, i.e. the ratio of the (m)RNA to the cationic or polycationic compound is selected in a range of about 6:1 (w/w) to about 0.25:1 (w/w), more preferably from about 5:1 (w/w) to about 0.5:1 (w/w), even more preferably of about 4:1 (w/w) to about 1:1 (w/w) or of about 3:1 (w/w) to about 1:1 (w/w), and most preferably a ratio of about 3:1 (w/w) to about 2:1 (w/w).

Additionally or alternatively, the ratio of the first component (i.e. the adjuvant component comprising or consisting of at least one (m)RNA complexed with a cationic or polycationic compound) and the second component (i.e. the at least one free mRNA) may be calculated on the basis of the nitrogen/phosphate ratio (N/P-ratio) of the entire RNA complex. In the context of the present invention, an N/P-ratio is preferably in the range of about 0.1-10, preferably in a range of about 0.3-4 and most preferably in a range of about 0.5-2 or 0.7-2 regarding the ratio of RNA:peptide in the complex, and most preferably in the range of about 0.7-1.5.

Additionally or alternatively, the ratio of the first component (i.e. the adjuvant component comprising or consisting of at least one (m)RNA complexed with a cationic or polycationic compound) and the second component (i.e. the at least one free mRNA) may also be selected in the inventive immunostimulatory composition on the basis of the molar ratio of both RNAs to each other, i.e. the (m)RNA of the adjuvant component, being complexed with a cationic or polycationic compound) and the at least one free mRNA of the second component. Typically, the molar ratio of the (m)RNA of the adjuvant component to the at least one free mRNA of the second component may be selected such, that the molar ratio suffices the above (w/w) and/or N/P-definitions. More preferably, the molar ratio of the (m)RNA of the adjuvant component to the at least one free mRNA of the second component may be selected e.g. from a molar ratio of as defined above, e.g. a molar ratio of about 0.001:1, 0.01:1, 0.1:1, 0.2:1, 0.3:1, 0.4:1, 0.5:1, 0.6:1, 0.7:1, 0.8:1, 0.9:1, 1:1, 1:0.9, 1:0.8, 1:0.7, 1:0.6, 1:0.5, 1:0.4, 1:0.3, 1:0.2, 1:0.1, 1:0.01, 1:0.001, etc. or from any range formed by any two of the above values, e.g. a range selected from about 0.001:1 to 1:0.001, 0.01:1 to 1:0.001, 0.1:1 to 1:0.001, 1:1 to 1:0.001, 0.001:1 to 1:0.01, 0.001:1 to 1:0.1, 0.001:1 to 1:1, 0.01:1 to 1:0.01, 0.1:1 to 1:0.1, 1:1, etc.

Even more preferably, the molar ratio of the (m)RNA of the adjuvant component to the at least one free mRNA of the second component may be selected e.g. from a range of about 0.01:1 to 1:0.01. Most preferably, the molar ratio of the (m)RNA of the adjuvant component to the at least one free mRNA of the second component may be selected e.g. from a molar ratio of about 1:1. In this particular embodiment, any of the above definitions with regard to (w/w) and/or N/P ratio may also apply.

In the context of the present inventive method, the cationic or polycationic compound is preferably selected from a cationic or polycationic compound as defined above, suitable for complexing and thereby stabilizing a nucleic acid, particularly an (m)RNA, e.g. by associating the nucleic acid with the cationic or polycationic compound. Association or complexing the modified (m)RNA of the inventive immunostimulatory composition with cationic or polycationic compounds as defined above preferably provides adjuvant properties to the (m)RNA and confers a stabilizing effect to the (m)RNA of the adjuvant component by complexation. The procedure for stabilizing the modified (m)RNA is in general described in EP-A-1083232, the disclosure of which is incorporated by reference into the present invention in its entirety, but also may be carried out by any suitable procedure known in the art.

According to step b) of the inventive method of preparation as described above, the inventive immunostimulatory composition is obtained by adding in a specific ratio an at least one free mRNA as defined above to the adjuvant component prepared according to step a), wherein the at least one free mRNA as defined above encodes at least one therapeutically active protein, antigen and/or antibody, as defined above. As further described above, the ratio of the adjuvant component (comprising at least one (m)RNA complexed with a cationic or polycationic compound) and the second component (at least one free mRNA) in the inventive immunostimulatory composition may be selected according to the specific requirements of a particular therapy, e.g. a cancer or anti-tumor therapy, a gene therapy, an anti-allergy therapy (desensitizing), prophylactic or therapeutic vaccination, etc. Typically, the ratio of the adjuvant component and the second component of the inventive immunostimulatory composition is selected such that a significant stimulation of the innate immune system is elicited due to the adjuvant component. In parallel, the ratio is selected such that a significant amount of the at least one free mRNA can be provided in vivo leading to an efficient translation of the expressed protein in vivo. Preferably the ratio of adjuvant component:free mRNA in the inventive immunostimulatory composition is selected from a range as defined above, e.g. of about 5:1 (w/w) to about 1:10 (w/w), more preferably from a range of about 4:1 (w/w) to about 1:8 (w/w), even more preferably from a range of about 3:1 (w/w) to about 1:5 (w/w) or 1:3 (w/w), and most preferably the ratio of adjuvant component:free mRNA in the inventive immunostimulatory composition is selected from a ratio of about 1:1 (w/w).

Optionally, further components as defined above may be added to the inventive immunostimulatory composition, in one or more additional steps.

According to a final embodiment, the present invention also provides kits, particularly kits of parts, comprising as components alone or in combination, the inventive immunostimulatroy composition or its components, i.e. the at least one (m)RNA, complexed with a cationic or polycationic compound, and the at least one free mRNA, encoding at least one therapeutically active protein, antigen and/or antibody, respectively, and/or an inventive pharmaceutical composition or vaccine, and optionally technical instructions with information on the administration and dosage of these components. Such kits, preferably kits of parts, may be applied, e.g., for any of the above mentioned applications or uses.

FIGURES

The following Figures are intended to illustrate the invention further. They are not intended to limit the subject matter of the invention thereto.

FIG. 1: depicts the results of the expression of luciferase after intradermal injection of mRNA encoding luciferase in vivo, wherein a composition comprising an amount of 10 μg free mRNA coding for luciferase (Pp Luc) with or without combination with LacZ-mRNA (wt LacZ) complexed with protamine (2:1 and 1:1) were prepared and injected intradermally into the ear pinna. As can be seen, LacZ-mRNA: protamine complexes, which have been formulated in a ratio of 1:1 or 2:1, respectively, had no negative influence on the expression of luciferase, i.e. no free protamine was present in the solution or only a very small amount, which had nor negative influence on the translation. Accordingly, no complex formation between protamine and ppLuc mRNA was possible, which indicates the stability of the already formed LacZ-mRNA:protamine complexes.

Figure 2:
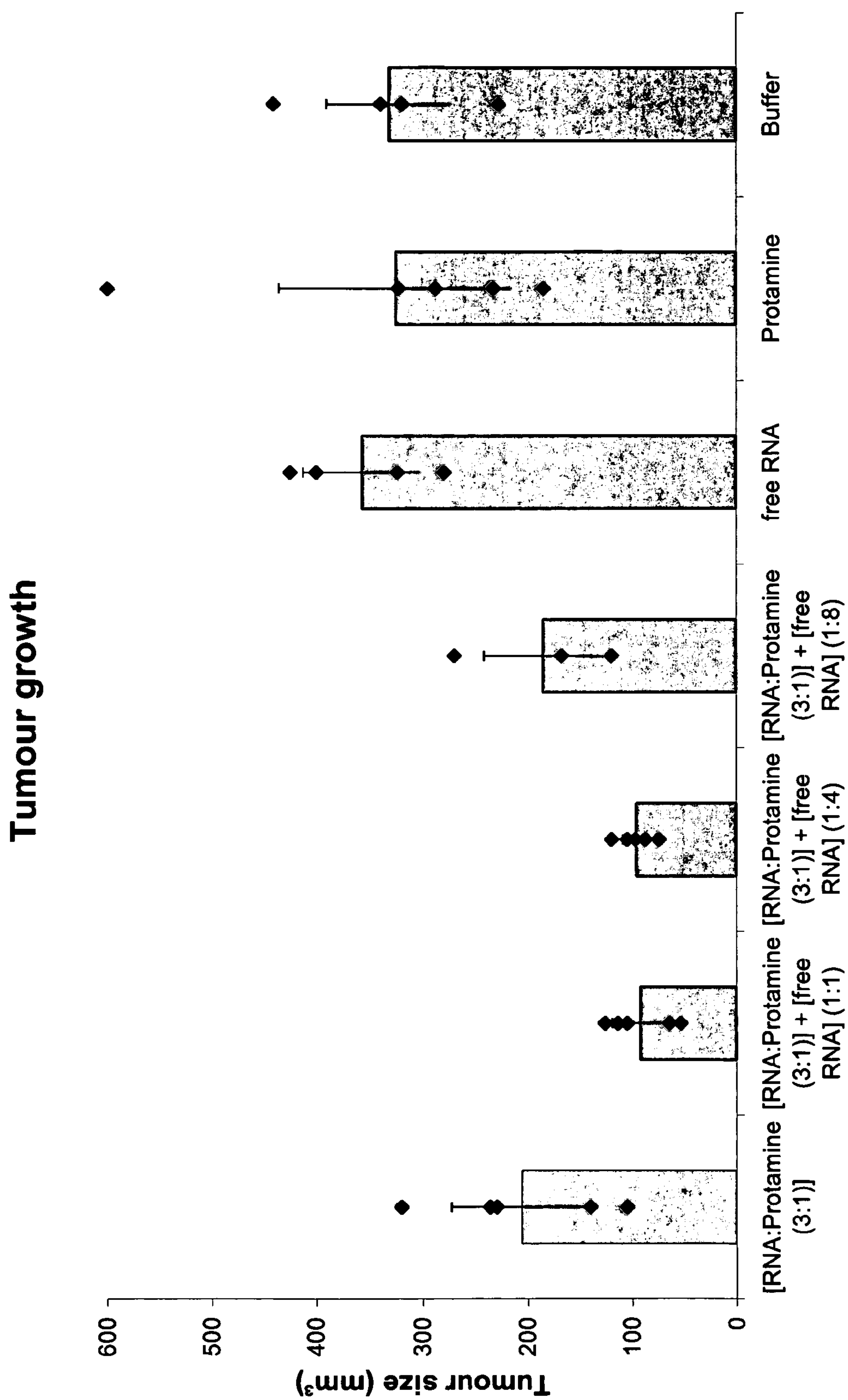

FIG. 2: shows the results of a vaccination reaction in the E.G7-OVA-model for therapeutic purposes. For the experiment, 300,000 E.G7-OVA tumor cells were implanted in C57 BL/6 mice and the mice were vaccinated 8 times within 2 weeks with the inventive immunostimulatory composition comprising 20 μg GC-enriched mRNA coding for *Gallus gallus* Ovalbumin. In a first experiment, either an RNA was used, which was entirely complexed with protamine in a ratio of 3:1 or an RNA, wherein the complexed RNA was mixed with free RNA in a ratio of 1:1, 1:4 and 1:8 (w/w). As can be seen in FIG. 2, free RNA as well as protamine alone do not exhibit any effect on tumor growth in comparison to the buffer control (Ringer-lactate solution). Surprisingly, a vaccination with a protamine complexed RNA in a ratio of 3:1 (RNA:protamine) significantly reduces tumor growth. Addition of free RNA enhances the tumor response even further, wherein a ratio of more than 1:8 (complexed RNA: free RNA), e.g. 1:4 or even 1:1, has been proven to be particularly advantageous.

Figure 3:
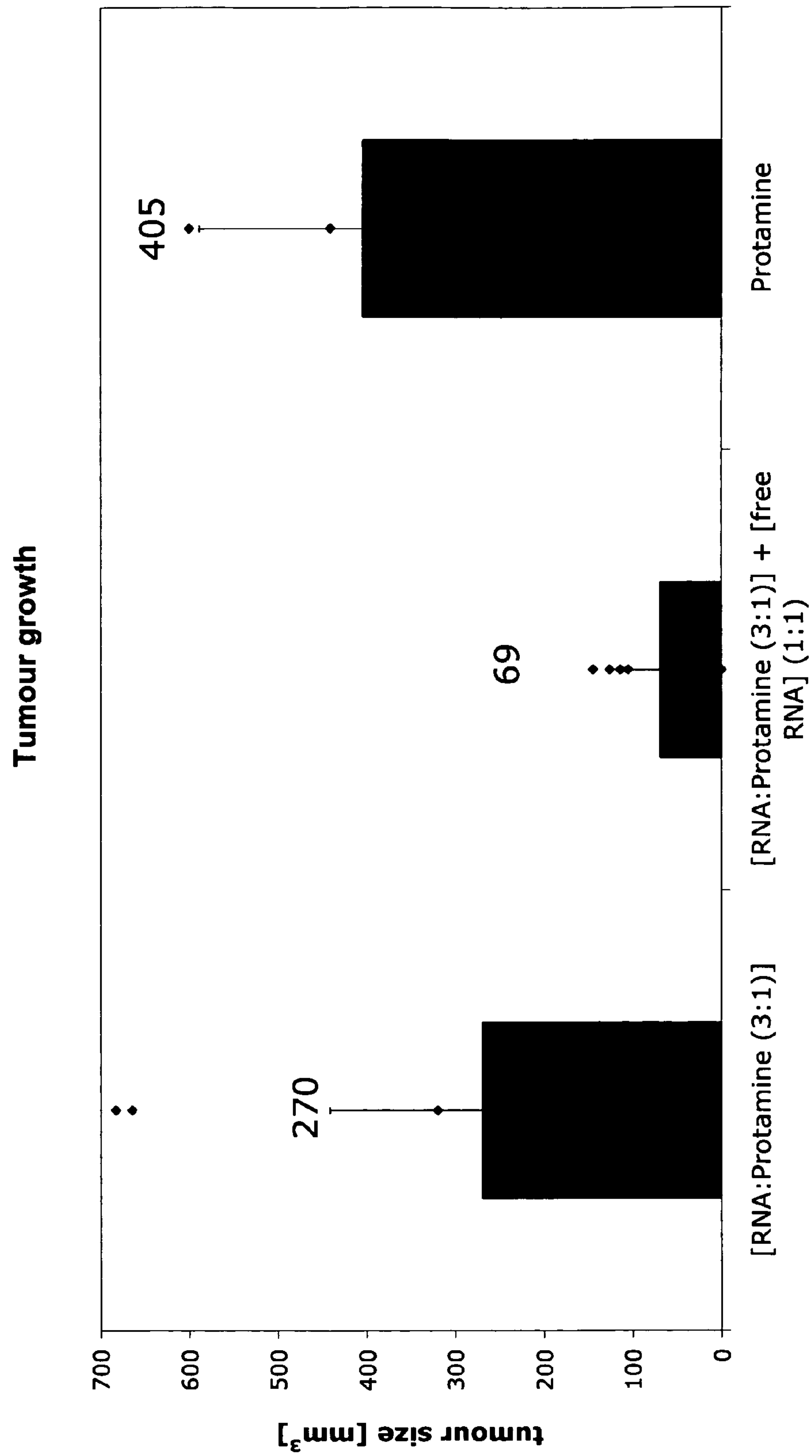

FIG. 3: describes the results of a vaccination reaction in the E.G7-OVA-model for therapeutic purposes similar to the Experiment in FIG. 2. For this second experiment either an RNA was used, which was entirely complexed with protamine in a ratio of 3:1 or an RNA according to an improved protocol, wherein the complexed RNA was mixed with free RNA in a ratio of RNA:protamine 3:1+free RNA (1:1)). As can be seen in FIG. 3, the combination of complexed RNA and free RNA, particular in the described ratios, leads to an improved tumor defense.

Figure 4:
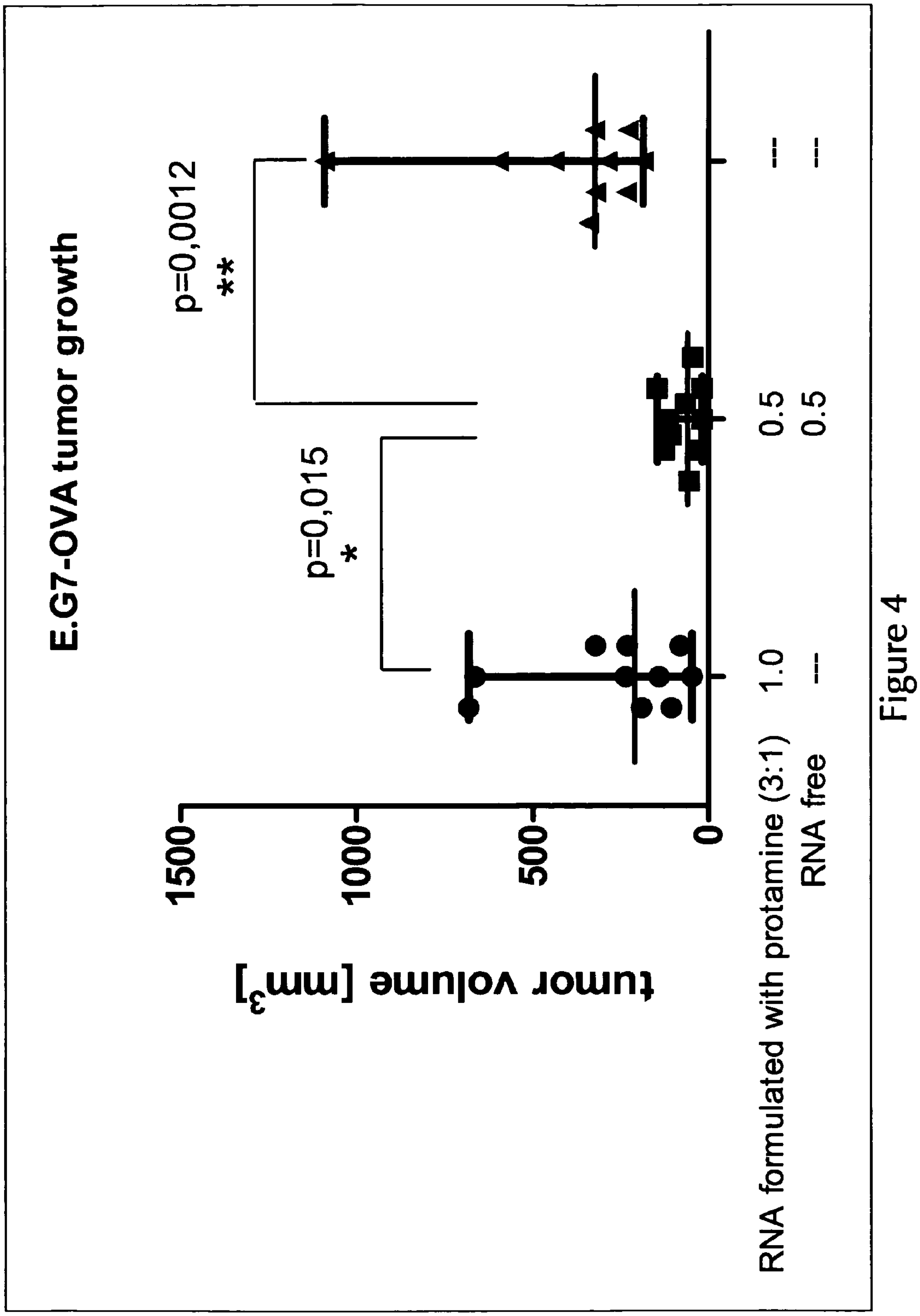

FIG. 4: shows the statistical (mathematical) analysis of the experiment according to FIG. 3. FIG. 4 particularly shows that the difference between the groups are significant. The statistical (mathematical) analysis was carried out with the GraphPad Prism Software and the p values were determined using the Mann Whitney test. The analysis underlines the results shown in FIG. 3.

Figure 5:
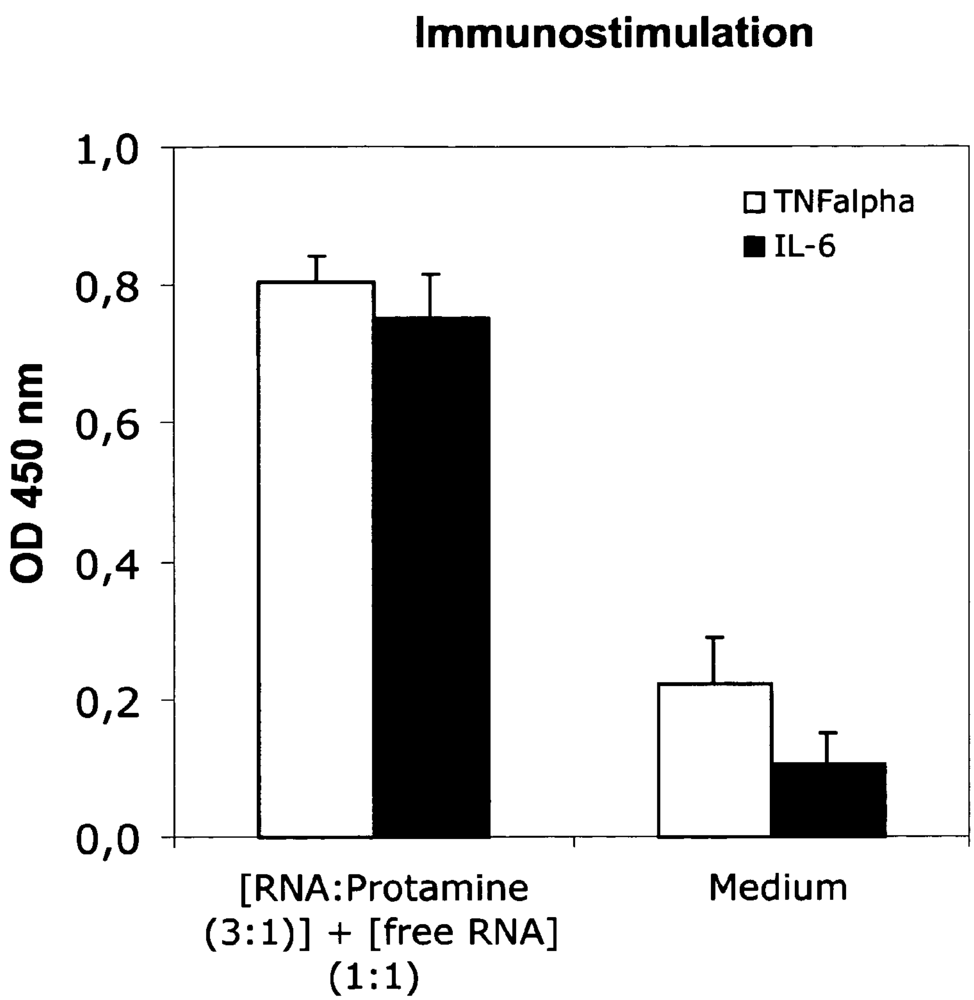

FIG. 5: depicts the results of the detection of immunostimulatory properties and the stimulation of hPBMC with mRNA (CAP-GgOva(GC)-muag-A70-C30) ("A70" and "C30" disclosed as SEQ ID NOS 141-142, respectively). For this experiment $2\times10^5$ hPBMCs were seeded in 200 μl medium per well in 96 well plates and 50 μl of the inventive composition, comprising 10 μg mRNA coding for *Gallus*

*gallus* ovalbumin were added to stimulate cytokine release over night at 37° C. The secretion of cytokines (TNFalpha and IL6) in hPBMCs with compositions comprising complexed and free RNA, showed a significant elevation in an ELISA detection indicating good immunostimulatory properties.

Figure 6:
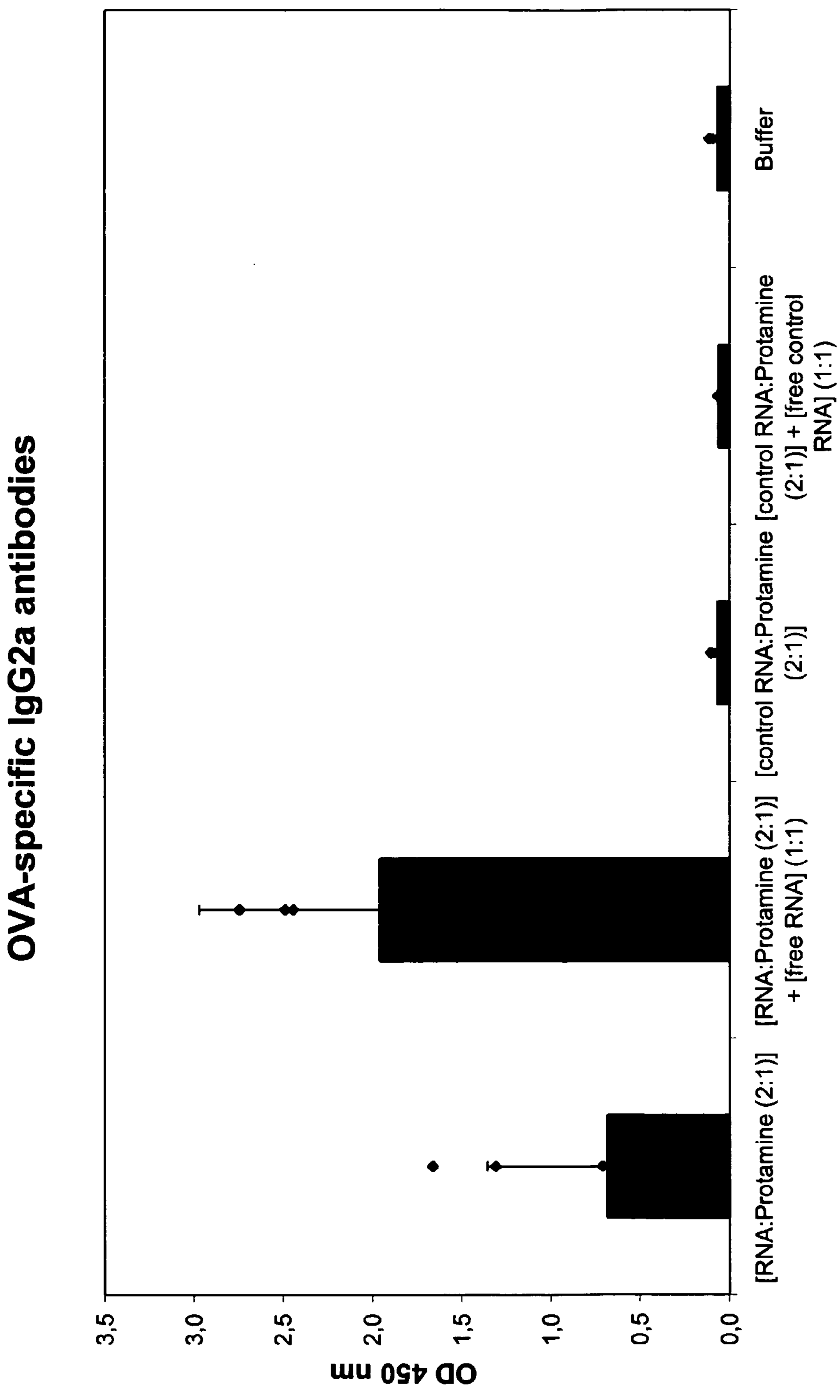

FIG. 6: describes the results of the induction of a humoral immune response in vivo, wherein C57 BL/6 mice were vaccinated 8-times with each 16 μg GC-enriched mRNA (CAP-GgOva(GC)-muag-A70-C30) ("A70" and "C30" disclosed as SEQ ID NOS 141-142, respectively) coding for *Gallus gallus* Ovalbumin or an "irrelevant" control RNA (pB-Luc RNA). As can be seen in FIG. 6, the combination of a complexed RNA with a free RNA, particularly in a ratio of (1:1) leads to an elevated humoral immune response compared to the vaccination with an entirely complexed RNA.

FIG. 7: shows the mRNA sequence according to SEQ ID NO: 120, which exhibits a length of 1365 nucleotides and was termed "CAP-GgOva(GC)-muag-A70-C30" ("A70" and "C30" disclosed as SEQ ID NOS 141-142, respectively). The mRNA sequence CAP-GgOva(GC)-muag-A70-C30 ("A70" and "C30" disclosed as SEQ ID NOS 141-142, respectively) contained following sequence elements:

GC-optimized sequence for a better codon usage and stabilization muag (mutated alpha-globin-3'-UTR)

70×adenosine at the 3'-terminal end (poly-A-tail) (SEQ ID NO: 141),

30×cytosine at the 3'-terminal end (poly-C-tail) (SEQ ID NO: 142).

The ORF is indicated in italic letters, muag (mutated alpha-globin-3'-UTR is indicated with a dotted line, the poly-A-tail is underlined with a single line and the poly-C-tail is underlined with a double line.

FIG. 8: depicts the mRNA sequence according to SEQ ID NO: 121, which exhibits a length of 1816 nucleotides and was termed "T7TS-Ppluc(wt)-A70" ("A70" disclosed as SEQ ID NO: 141). The coding sequence (CDS) of the entire mRNA sequence is indicated in italic letters, the poly-A-tail is underlined with a single line.

Figure 9:
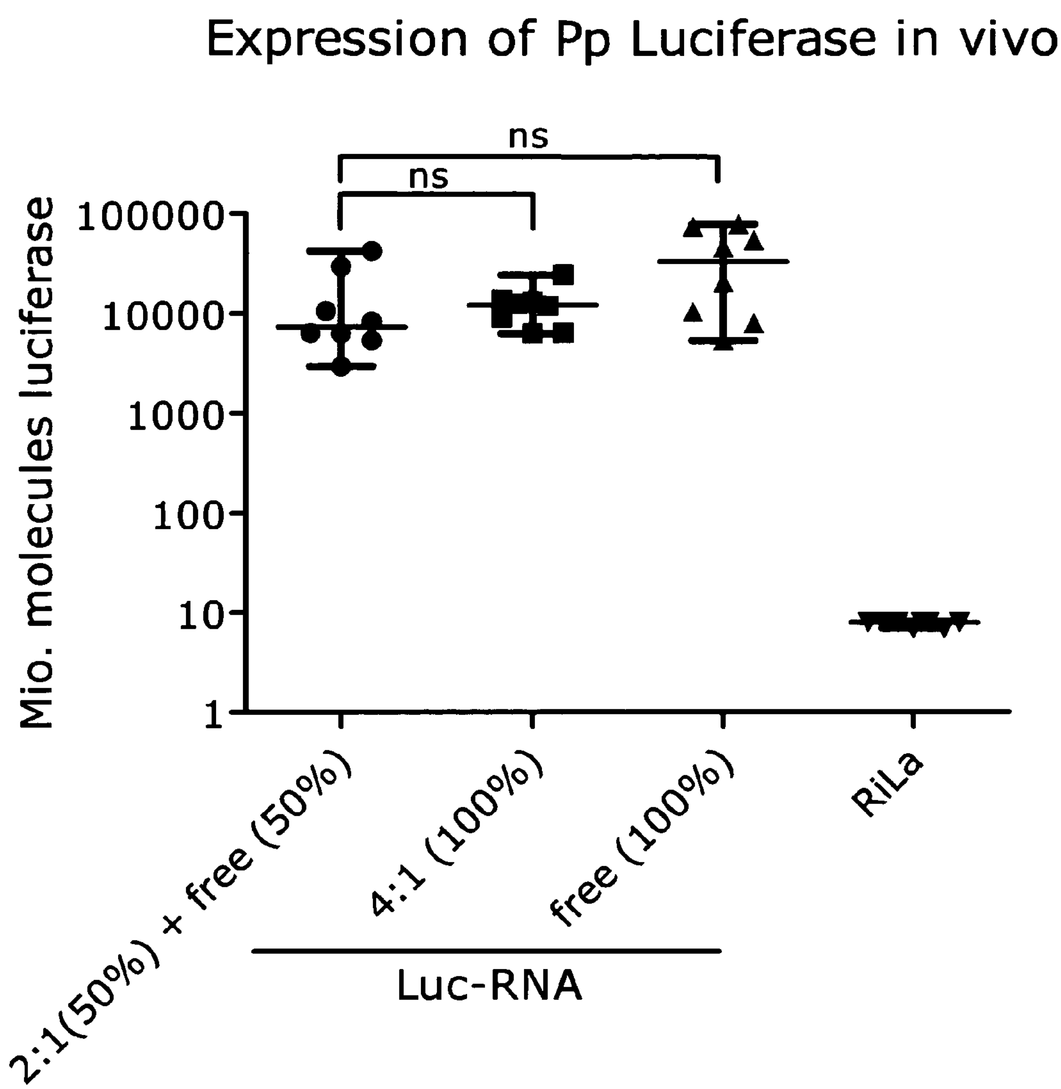

FIG. 9: shows the statistical analysis of the expression of luciferase in Balb/c mice. The statistical analysis was carried out with the GraphPad Prism Software and the p values were determined using the Mann Whitney test. The results in FIG. 9 show that the RNA complexed according to the invention (2:1 (50%)+free (50%) exhibits the same expression when compared to naked RNA and RNA which is complexed in the ratio of 4:1 with protamine. As can be seen, differences between the relevant groups are not significant (ns). Thus, an immune stimulation can be efficiently provided with the inventive complexed RNA wherein expression level is maintained compared to naked RNA and RNA which is complexed in the ratio of 4:1 with protamine (see also FIG. 10).

Figure 10:
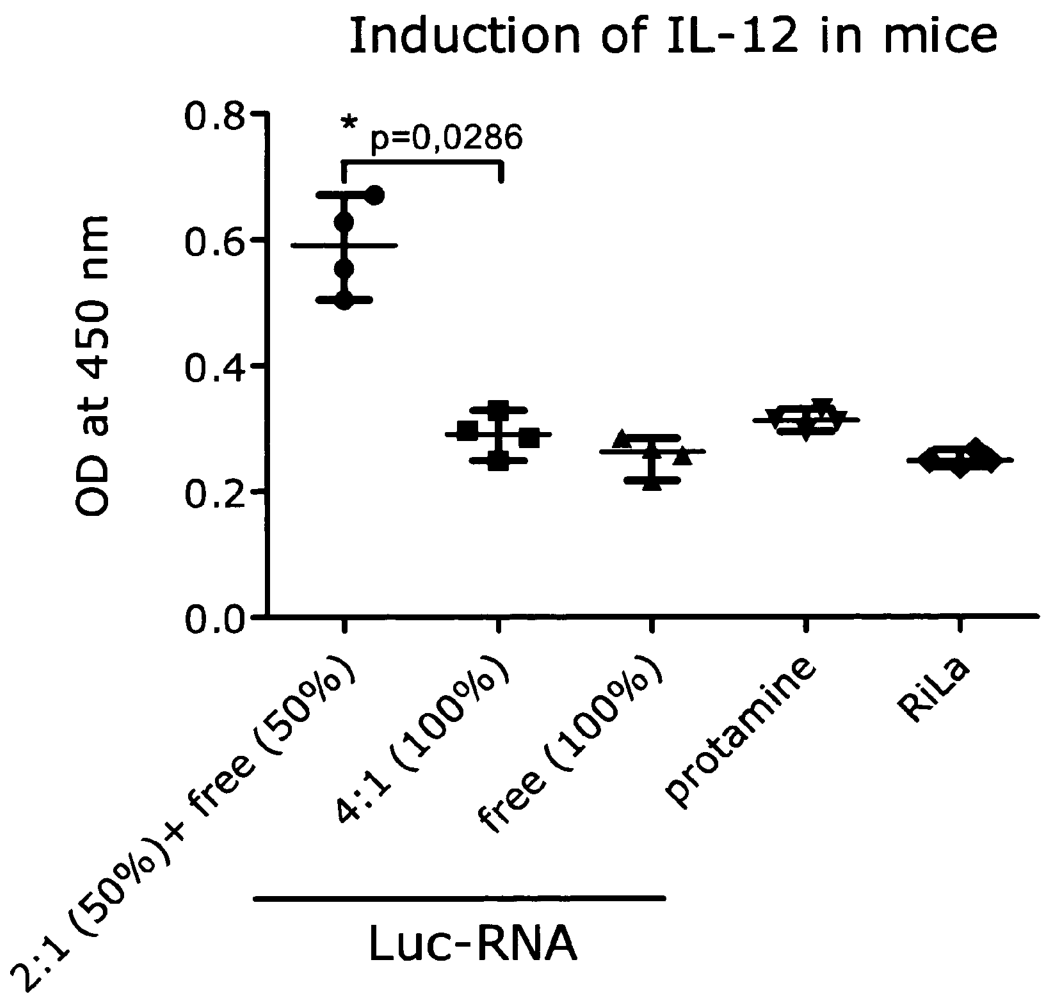

FIG. 10: depicts the statistical analysis of induction of IL-12 in Balb/c mice. The statistical analysis was carried out with the GraphPad Prism Software and the p values were determined using the Mann Whitney test. The results show that the difference between the inventive complexed RNA (2:1 (50%+free (50%)) and the group 4:1 (100%) which comprises the same amount of RNA and protamine is significant. Thus, an immune stimulation can be efficiently provided with the inventive complexed RNA wherein expression level is maintained compared to naked RNA and RNA which is complexed in the ratio of 4:1 with protamine (see also FIG. 9).

Figure 11:
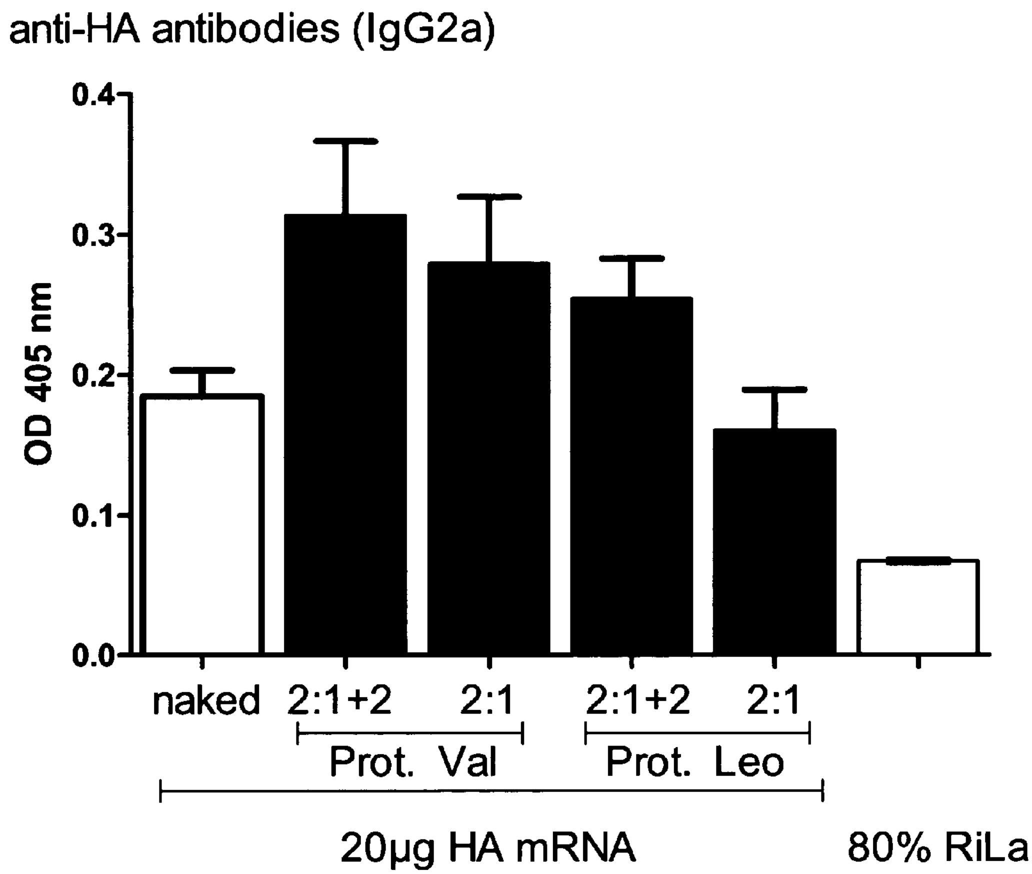

FIG. 11: shows the induction of IgG2a antibodies against the Influenza antigen hemagglutinin (HA). Therefore mice were vaccinated 2 times with 20 μg GC-enriched mRNA coding for hemagglutinin (HA) naked or formulated with protamine hydrochloride (Prot. Val) or protamine sulphate (Prot. Leo) as indicated. As can be seen in FIG. 11, the combination of a complexed RNA with free RNA leads to an elevated humoral immune response compared to the vaccination with an entirely complexed RNA. Compared to naked RNA, complexed RNA leads to higher IgG2a antibody titers, an indicator of the Th1 driven response. Complexation of RNA with protamine hydrochloride (Protamine Valeant) has a stronger effect than complexation with protamine sulphate.

Figure 12:
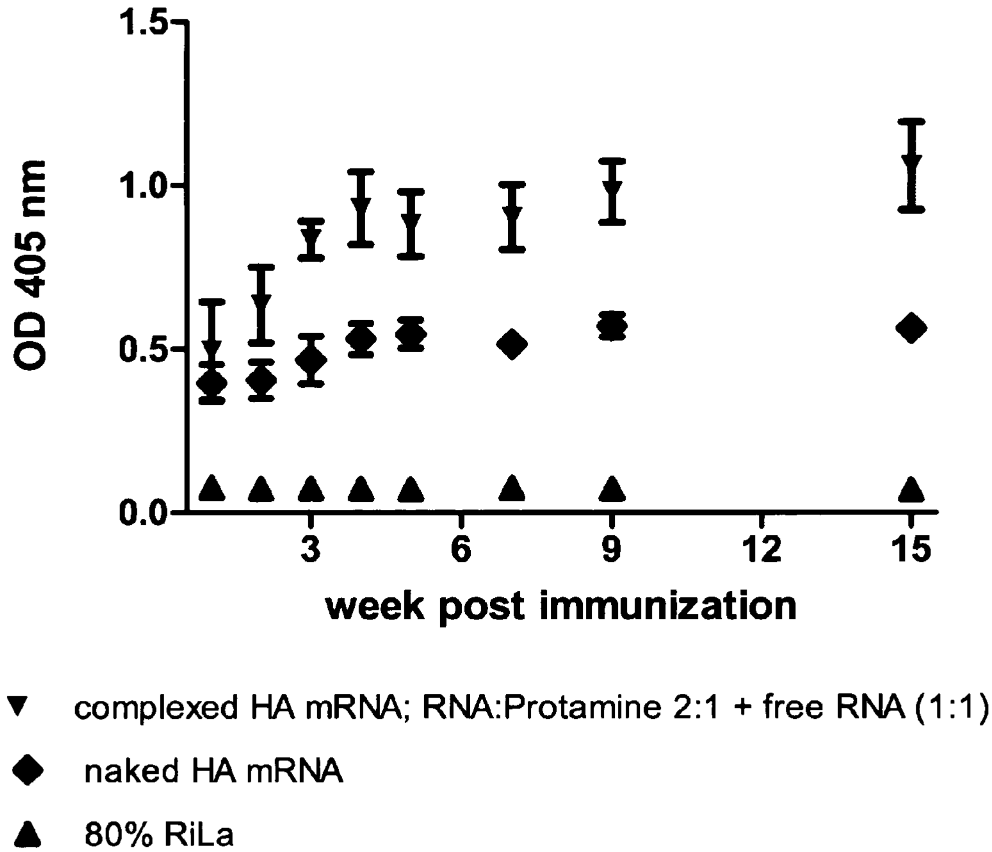

FIG. 12: illustrates the induction of IgG2a-specific antibodies against the Influenza antigen HA over 15 weeks after immunization. Therefore mice were vaccinated 2 times with 20 μg GC-enriched mRNA coding for hemagglutinin (HA) naked or complexed with protamine (RNA:Protamine 2:1+free RNA (1:1) (w/w)) and IgG2a antibodies were measured at the indicated time points. Sera from different time points after immunization were analysed by ELISA. Hemagglutinin-specific antibody titers of the IgG2a subtype are plotted for the groups treated with buffer (80% RiLa), naked or complexed HA mRNA.

Figure 13:
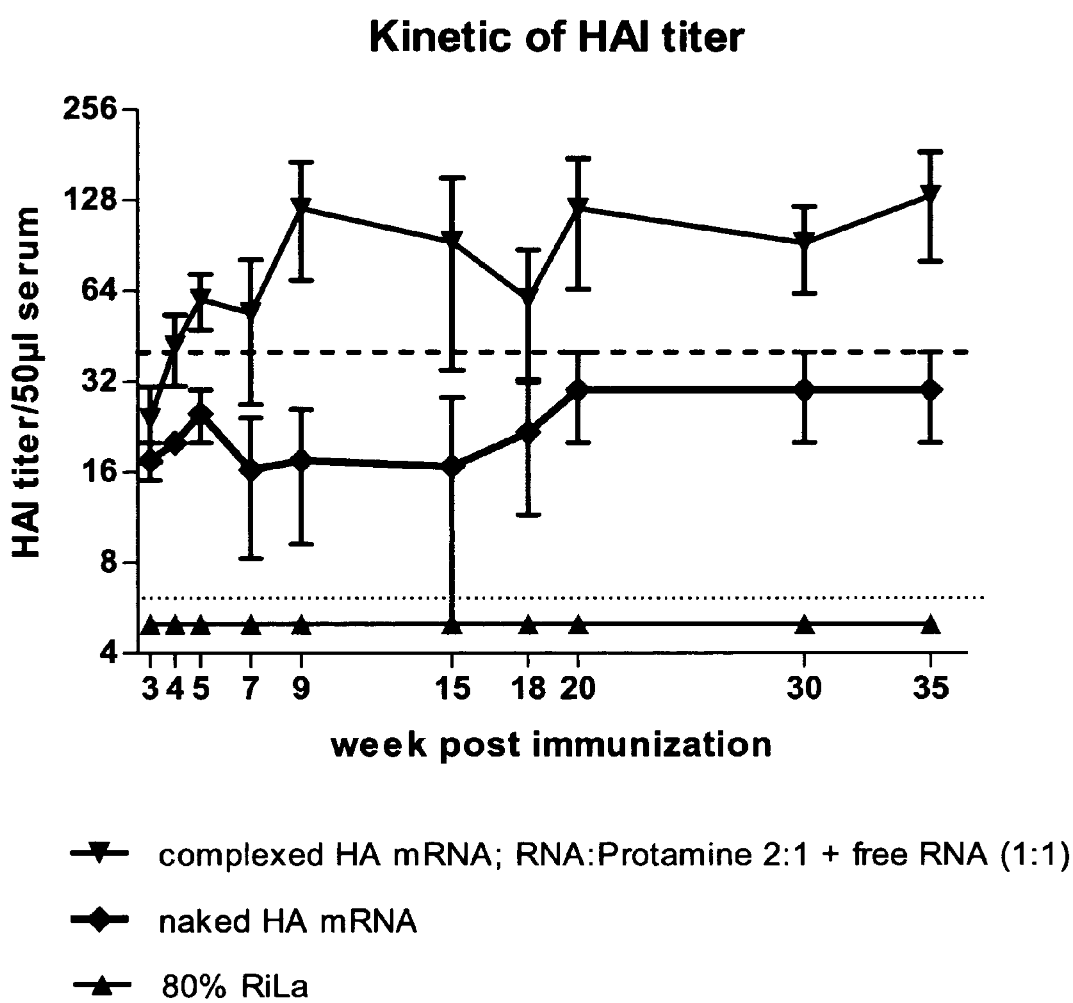

FIG. 13: depicts the induction of antibodies against the influenza antigen HA by HAI assay. Therefore mice were vaccinated 2 times with 20 μg GC-enriched mRNA coding for hemagglutinin (HA) naked or formulated with protamine (RNA:Protamine 2:1+free RNA (1:1) (w/w)) and the HAI assay was performed at the indicated time points.

FIG. 14: shows the mRNA sequence (SEQ ID NO: 124) encoding the pathogenic antigen hemagglutinin (HA) from influenza virus.

EXAMPLES

The following examples are intended to illustrate the invention further. They are not intended to limit the subject matter of the invention thereto.

Example 1

Preparation of mRNA Construct Encoding Pp Luciferase (*Photinus pyralis*)

For the following experiments a DNA sequence, encoding Pp luciferase (*Photinus pyralis*) and corresponding to the respective mRNA encoding Pp luciferase sequences as used herein, was prepared and used for subsequent transfection and vaccination experiments. Thereby, the DNA sequence corresponding to the native Pp Luciferase encoding mRNA was modified with a poly-A-tag (A70) (SEQ ID NO: 141) leading to SEQ ID NO: 121 (see FIG. 8). The final construct had a length of 1816 nucleotides and was termed "T7TS-Ppluc(wt)-A70" ("A70" disclosed as SEQ ID NO: 141).

Example 2

Preparation of mRNA Construct Encoding *Gallus gallus* Ovalbumin

For the following experiments a further DNA sequence, encoding *Gallus gallus* Ovalbumin and corresponding to the respective mRNA sequences, was prepared and used for subsequent transfection and vaccination experiments. Thereby, the DNA sequence corresponding to the native

*Gallus gallus* Ovalbumin encoding mRNA was GC-optimized for a better codon-usage and stabilization. Then, the DNA sequence corresponding to the coding *Gallus gallus* Ovalbumin mRNA sequence was transferred into an RNActive construct, which has been modified with a poly-A-tag and a poly-C-tag (A70-C30) ("A70" and "C30" disclosed as SEQ ID NOS 141-142, respectively). The final construct had a length of 1365 nucleotides and was termed "CAP-GgOva (GC)-muag-A70-C30" ("A70" and "C30" disclosed as SEQ ID NOS 141-142, respectively). It contained following sequence elements:

- GC-optimized sequence for a better codon usage and stabilization
- muag (mutated alpha-globin-3'-UTR)
- 70×adenosine at the 3'-terminal end (poly-A-tail) (SEQ ID NO: 141),
- 30×cytosine at the 3'-terminal end (poly-C-tail) (SEQ ID NO: 142).

The corresponding mRNA sequence is shown in FIG. 7 (see SEQ ID NO: 120).

Example 3

In Vitro-Transcription Experiments

The recombinant plasmid DNA was linearized and subsequently in vitro transcribed using the T7 RNA polymerase. The DNA template was then degraded by DNAseI digestion. The RNA was recovered by LiCl precipitation and further cleaned by HPLC extraction (PUREMessenger®, CureVac GmbH, Tubingen, Germany).

Example 4

Making of the Inventive Composition

The mRNA used in the experiments below was complexed with protamine by addition of protamine to the mRNA in the indicated ratios (1:1-1:4) (w/w). After incubation for 10 min, the free RNA was added.

Example 5

Expression of Luciferase after Intradermal Injection of mRNA Encoding Luciferase In Vivo In this experiment the influence of compositions comprising readily prepared mRNA:protamine complexes and/or free mRNA on the translation was investigated. Therefore, a composition comprising an amount of 10 μg free mRNA coding for luciferase (Pp Luc) with or without combination with LacZ-mRNA complexed with protamine (2:1 and 1:1) were prepared and injected intradermally into the ear pinna.

The mRNA encoding Pp Luciferase was prepared as described above. The composition to be administered contained either no further complexed RNA, lacZ-mRNA: protamine in a concentration of 2:1 or lacZ-mRNA: protamine in a concentration of 1:1. As a control, a composition was administered containing no mRNA encoding Pp Luciferase (*Photinus pyralis*). Protamine was used as a control. In order to prepare these compositions, lacZ-mRNA was formulated in a first step with protamine in different amounts and ratios (2:1 and 1:1 (w/w)) and added as a first component. Then, free Pp Luc mRNA was added 10 minutes later to the composition.

After 24 h the ear pinna were removed and frozen in liquid nitrogen. For homogenization, the samples were placed in a TissueLyser for 3 min at 30 $s^{-1}$. Then 800 μl lysis-buffer (25 mM Tris-HCl pH (7.5-7.8); 2 mM EDTA; 10% (w/v) Glycerol; 1% (w/v) Triton-X-100; 2 mM DTT; 1 mM PMSF) is added and samples are placed again in the TissueLyser for 6 min at 30 $s^{-1}$. Samples are centrifuged for 10 min at 13500 rpm and 4° C. The supernatant is removed and stored at −80° C. until luciferase measurement. Supernatants were mixed with Luciferin Buffer (25 mM Glycylglycin, 15 mM $MgSO_4$, 5 mM ATP, 62.5 μM Luciferin) and the luminescence was measured with a luminometer (Lumat LB 9507; Berthold Technologies, Bad Wildbad, Germany).

As a result (see FIG. 1), LacZ-mRNA:protamine complexes, which have been formulated in a ratio of 1:1 or 2:1, respectively, had no negative influence on the expression of luciferase, i.e. no free protamine was present in the solution or only a very small amount, which had no negative influence on the translation. Accordingly, no complex formation between protamine and ppLuc mRNA was possible, which indicates the stability of the already formed LacZ-mRNA: protamine complexes.

Example 6

Vaccination in the E.G7-OVA-Model for Therapeutic Purposes

General Method:

300000 E.G7-OVA tumor cells were implanted in C57 BL/6 mice. In the following 3 weeks the mice were vaccinated 8 times within 3 weeks with the inventive composition comprising 20 μg GC-enriched mRNA coding for *Gallus gallus* Ovalbumine. The tumor size was measured 18 days after the implantation of the tumor cells.

A) First Experiment

300000E.G7-OVA tumor cells were implanted into C57 BL/6-mice. Within the following two weeks the mice were vaccinated 8-times with each 20 μg GC-enriched mRNA encoding *Gallus gallus* Ovalbumin. For this experiment, either an RNA was used, which was entirely complexed with protamine in a ratio of 3:1 or an RNA, wherein the complexed RNA was mixed with free RNA in a ratio of 1:1, 1:4 and 1:8 (w/w).

The results are shown in FIG. 2. As can be seen in FIG. 2, free RNA as well as protamine alone does not exhibit any little effect on tumor growth in comparison to the buffer control (Ringer-lactate solution). Surprisingly, a vaccination with a protamine complexed RNA in a ratio of 3:1 (RNA:protamine) significantly reduces tumor growth. Addition of free RNA enhances the tumor response even further, wherein a ratio of more than 1:8 (complexed RNA: free RNA), e.g. 1:4 or even 1:1, has been proven to be particularly advantageous.

B) Second Experiment

300000E.G7-OVA tumor cells were implanted into C57 BL/6-mice. Within the following three weeks the mice were vaccinated 8-times with each 20 μg GC-enriched mRNA encoding *Gallus gallus* Ovalbumin. For this experiment, either an RNA was used, which was entirely complexed with protamine in a ratio of 3:1 or an RNA according to an improved protocol, wherein the complexed RNA was mixed with free RNA in a ratio of RNA:Protamin 3:1+free RNA (1:1)).

The results of this experiment are depicted in FIG. 3. As can be seen in FIG. 3, the combination of complexed RNA and free RNA, particular in the described ratios, leads to an improved tumor defense.

The statistical (mathematical) analysis was carried out with the GraphPad Prism Software. The p values were determined using the Mann Whitney test (see FIG. 4).

Example 7

Detection of Immunostimulatory Properties, and Stimulation of hPBMC with mRNA For this experiment hPBMC were isolated by centrifugation on Ficoll (20 min at 2000 rpm) and subsequently washed two times in PBS. hPBMC were then resuspended in FCS, 10% DMSO at a density of $5\times10^7$/ml. 1 ml aliquots were frozen and stored at −80° C.

Prior to the experiment, hPBMc were thawed by resuspending in PBS, followed by two washes in PBS. hPBMC were then suspended in X-Vivo 15, 1% glutamine, 1% Pen/Strep at a density of $1\times10^6$/ml. After seeding hPBMCs at $2\times10^5$ per well in 96 well plates, 50 μl of the inventive composition, comprising 8 μg mRNA coding for *Gallus gallus* ovalbumin were added to stimulate cytokine release over night at 37° C.

Therefore, human PBMCs were incubated for 20 hours with RNA, encoding *Gallus gallus* Ovalbumin (OVA), complexed with protamine (3:1) plus 50% free RNA (formulated as follows: RNA:protamine 3:1+free RNA (1:1) (w/w)). The secretion of cytokines (TNFalpha and IL6) was measured and detected in the supernatant using Standard ELISA.

For the TNFalpha and IL6 quantification (ELISA) Maxisorb plates were coated over night (4° C.) with capture antibody (1 μg/ml) and subsequently blocked with 1% BSA for 1 hour at room temperature (RT). After three washes with 0.05% Tween, 50 μl (TNFα) or 50 μl (IL-6) hPBMC supernatant, adjusted with blocking buffer 15 to 100 μl, were added to the wells. Binding was allowed to proceed for two hours (RT). The plate was then washed and 100 μl streptavidin-conjugated horseradish peroxidise was added. After incubation for 30 minutes and washing a colorimetric substrate (TMB, Perbio Science) was added. Optical densities were measured at 450 nm using a Tecan ELISA plate reader. All incubations were performed at room temperature and washing steps include at least 3 steps using PBS/Tween20 (0.05% v/v).

100 μl/well of a mixture of Strept-HRP (diluted 1/1000) and biotinylated detection antibody (0.5 μg/ml) were added. Incubation for one hour at RT was followed by three washes with 0.05% Tween. Finally, 100 μl/well of Amplex Red HRP substrate (50 μM), 0.014% $H_2O_2$ were added. Fluorescence was measured in a Spectramax Gemini plate reader (Ex 540 nm, Em 590 nm, cutoff 590 nm).

The results are shown in FIG. 5. As can be seen in FIG. 5, the compositions comprising complexed and free RNA exhibit an immunostimulatory property, which is reflected by a significant secretion of TNFalpha and IL-6 in hPBMCs.

Example 8

Induction of a Humoral Immune Response

C57 BL/6 mice were vaccinated 8-times with each 16 μg GC-enriched mRNA coding for *Gallus gallus* Ovalbumine or an "irrelevant" control RNA (pB-Luc RNA). Thereby, the RNA was either formulated entirely with protamine in a ratio of 2:1 or the ratio was according to an improved protocol RNA:Protamin 2:1+freie RNA (1:1) (w/w))). 2 weeks after the last vaccination blood samples were collected and expression of Ovalbumin-specific antibodies was determined.

For the detection of antigen-specific antibodies MaxiSorb plates (Nalgene Nunc International) were coated with Antigen (Ovalbumine, recombinant protein). After blocking with 1×PBS, 0.05% Tween and 1% BSA the plates were incubated with sera of the mice for 4 hours at room temperature. Subsequently the biotin-coupled secondary antibody was added. After washing the plate was incubated with horseradish peroxidise and the enzyme activity was determined by measuring the conversion of the substrate (2,2'-azino-bis (3-ethyl-benzthiazoline-6-sulfonsäure) (OD 450 nm). Optical densities were measured at 450 nm using a Tecan ELISA plate reader.

The results are shown in FIG. 6. As can be seen in FIG. 6, the combination of a complexed RNA with a free RNA leads to an elevated humoral immune response compared to the vaccination with an entirely complexed RNA.

Example 9

Statistical Analysis of the Expression of Luciferase in Balb/c Mice

In this experiment the influence of different formulation strategies with protamine on the translation of luciferase was investigated. Per group 2 mice were injected on 4 different sites intradermally with (1) a composition comprising 50% protamine-complexed (2:1) Luc-RNA in combination with 50% free RNA,
(2) a composition comprising Luc-RNA complexed with protamine in the ration 4:1,
(3) 100% free Luc-RNA, or
(4) Ringer-Lactate buffer as control.

Each sample comprised 10 μg mRNA coding for luciferase (Luc-RNA, i.e. the above described construct "T7TS-Ppluc(wt)-A70" according to SEQ ID NO: 121) ("A70" disclosed as SEQ ID NO: 141) in 50 μl Ringer-Lactate buffer. The first and the second group comprised also the same amount of protamine, but they were different formulated. The immunostimulatory composition of group (1) was prepared according to the invention.

The results are shown in FIG. 9. FIG. 9 shows the statistical analysis of the expression of luciferase in Balb/c mice. The statistical analysis was carried out with the GraphPad Prism Software and the p values were determined using the Mann Whitney test. The results in FIG. 9 show that the RNA complexed according to the invention (2:1 (50%)+free (50%), group (1)) exhibits the same expression when compared to naked RNA and RNA which is complexed in the ratio of 4:1 with protamine (groups (2) and (3)). As can be seen, differences between the relevant groups are not significant (ns). Thus, an immune stimulation can be efficiently provided with the inventive immunostimulatory composition wherein expression level is maintained compared to naked RNA and RNA which is complexed in the ratio of 4:1 with protamine (see also FIG. 10).

Example 10

Statistical Analysis of Induction of IL-12 in Balb/c Mice

For this experiment 40 μg mRNA coding for Luciferase (Luc-RNA, i.e. the above described construct "TITS-Ppluc (w0-A70" according to SEQ ID NO: 121) ("A70" disclosed as SEQ ID NO: 141) in the following compositions:

(1) 2:1 (50%)+free (50%) comprised 20 μg Luc-RNA complexed with protamine (2:1) (w/w) and 20 μg free Luc-RNA (i.e. an inventive immunostimulatory composition),
(2) 4:1 (100%) comprised 40 μg Luc-RNA complexed with protamin (4:1) (w/w),
(3) 40 μg free Luc-RNA,
(4) 10 μg protamine, and
(5) 800 μl RiLa (all samples were dissolved in Ringer-Lactate buffer to a final volume of 800 μl)

were intravenously injected into the tail vein of Balb/c mice (4 mice per group). After 4 hours, blood was taken by puncture of the retro-orbital veins and serum was used for cytokine (IL-2) ELISA. The ELISA was carried out as described for Example 7.

The results are shown in FIG. 10. FIG. 10 depicts the statistical analysis of induction of IL-12 in Balb/c mice according to Example 10. The statistical analysis was carried out with the GraphPad Prism Software and the p values were determined using the Mann Whitney test. The results show that the difference between the inventive immunostimulatory composition (2:1 (50%)+free (50%)) and the group 4:1 (100%), which comprises the same amount of RNA and protamine, is in fact significant. Thus, an immune stimulation can be efficiently provided with the inventive immunostimulatory composition wherein expression level is maintained compared to naked RNA and RNA, which is complexed in the ratio of 4:1 with protamine (see also FIG. 9).

Example 11

Induction of a Humoral Immune Response Against a Viral Antigen

Vaccination:

BALB/c mice were vaccinated twice with 20 μg GC-enriched mRNA coding for hemagglutinin (HA) of Influenza A/Puerto Rico/8/34 (PR8) or injection buffer (80% Ringer Lactate). Thereby, the RNA was either formulated entirely with protamine in a ratio of 2:1 or the ratio was according to the invention RNA:Protamin 2:1+free RNA (1:1) (w/w). For formulations, two different protamines were tested, protamine hydrochloride (Protamin Valeant) and protamine sulphate (Protamin LEO).

Detection of Specific Antibodies:

At different time points after last vaccination blood samples were collected and expression of hemagglutinin-specific antibodies was determined by ELISA (FIGS. 11 and 12) or hemagglutination inhibition assay (HAI) (FIG. 13).

Detection of Antigen-Specific Antibodies by ELISA:

For the detection of antigen-specific antibodies by ELISA, MaxiSorb plates (Nalgene Nunc International) were coated with antigen (inactivated PR8). After blocking with 1×PBS, 0.05% Tween and 1% BSA the plates were incubated with sera of the mice for 4 hours at room temperature. Subsequently the biotin-coupled secondary antibody was added. After washing the plate was incubated with horseradish peroxidise and the enzyme activity was determined by measuring the conversion of the substrate (2,2'-azino-bis (3-ethyl-benzthiazoline-6-sulfonic acid) (OD 405 nm). Optical densities were measured at 405 nm using a Tecan ELISA plate reader. The results of analysis of sera obtained two weeks after immunization are shown in FIG. 11. As can be seen in FIG. 11, the combination of a complexed RNA with free RNA leads to an elevated humoral immune response compared to the vaccination with an entirely complexed RNA. Compared to naked RNA, complexed RNA leads to higher IgG2a antibody titers, an indicator of the Th1 driven response. Complexation of RNA with protamine hydrochloride (Protamine Valeant) has a stronger effect than complexation with protamine sulphate.

In FIG. 12, sera from different time points after immunization were analysed by ELISA. Hemagglutinin-specific antibody titers of the IgG2a subtype are plotted for the groups treated with buffer (80% RiLa), naked or complexed HA mRNA. The complexation was done with Protamin Valeant following improved protocol RNA:Protamin 2:1+free RNA (1:1) (w/w).

Detection of Antigen-Specific Antibodies by HAI Assay:

Sera of immunized mice were also analysed by HAI assay. In an HAI assay, antibodies that neutralize the virus by blocking the interaction of the viral hemagglutinin and the sialic acid on the host cell are detected.

Sera were inactivated at 56° C. for 10 min to destroy complement and HAI inhibitors. Sera were further incubated with kaolin for 20 min and preadsorbed to chicken red blood cells for 30 min to remove unspecific factors that influence hemagglutination. Pre-treated serum samples were added to a 96 well, U-bottom plate in serial dilution and duplicates. 25 μl containing 4 hemagglutinating units of inactivated PR8 in PBS and 50 μl of 0.5% chicken red blood cells were then added and incubated at room temperature for 45 min. Endpoint HAI titers were defined as the reciprocal of the highest serum dilution that completely inhibited hemagglutination of the red blood cells. Titers of sera from different time points after immunization are plotted for the groups treated with buffer (80% RiLa), naked or complexed HA mRNA. The complexation was done with Protamin Valeant and the improved protocol RNA:Protamin 2:1+free RNA (1:1) (w/w). A titre of 40 is assumed to be protective in case of influenza infection. Mice immunized with complexed HA RNA show an enduring HAI titer of more than 40, whereas naked HA mRNA led to titers in average lower than the protective titer of 40.

The invention claimed is:

1. An immunostimulatory composition comprising:

a) an adjuvant component, comprising at least one mRNA, complexed with protamine wherein the weight ratio of the at least one mRNA to protamine in the adjuvant component is 2:1 to 3:1; and b) at least one free mRNA, encoding at least one antigen, wherein the molar ratio of the RNA of the adjuvant component to the at least one free mRNA of the second component b) is 1:1 to 1:4.

2. The immunostimulatory composition according to claim 1, wherein the at least one free mRNA and the at least one mRNA of the adjuvant component are identical to each other.

3. The immunostimulatory composition according to claim 1, wherein the at least one free mRNA and the at least one mRNA of the adjuvant component are different from each other.

4. The immunostimulatory composition according to claim 1, wherein the N/P ratio of the mRNA to the protamine in the adjuvant component is in the range of 0.1-10.

5. The immunostimulatory composition according to claim 1, wherein the at least one free mRNA and/or the at least one mRNA of the adjuvant component are GC-stabilized.

6. The immunostimulatory composition according to claim 5, wherein the G/C content of the coding region of the GC-stabilized RNA is increased compared with the G/C content of the coding region of the native RNA, the coded amino acid sequence of the GC-stabilized modified RNA not being altered compared with the encoded amino acid sequence of the native modified RNA.

7. The immunostimulatory composition according to claim 1, wherein the at least one free mRNA encodes an antigen, selected from 5T4, 707-AP, 9D7, AFP, AlbZIP HPG1, alpha5beta1-Integrin, alpha5beta6-Integrin, alpha-methylacyl-coenzyme A racemase, ART-4, B7H4, BAGE-1, BCL-2, BING-4, CA 15-3/CA 27-29, CA 19-9, CA 72-4, CA125, calreticulin, CAMEL, CASP-8, cathepsin B, cathepsin L, CD19, CD20, CD22, CD25, CD30, CD33, CD4, CD52, CD55, CD56, CD80, CEA, CLCA2, CML28, Coactosin-like protein, Collagen XXIII, COX-2, CT-9/BRD6, Cten, cyclin B1, cyclin D1, cyp-B, CYPB1, DAM-10/MAGE-B1, DAM-6/MAGE-B2, EGFR/Her1, EMMPRIN, EpCam, EphA2, EphA3, ErbB3, EZH2, FGF-5, FN, Fra-1, G250/CAIX, GAGE-1, GAGE-2, GAGE-3, GAGE-4, GAGE-5, GAGE-6, GAGE-7b, GAGE-8, GDEP, GnT-V, gp100, GPC3, HAGE, HAST-2, hepsin, Her2/neu/ErbB2, HERV-K-MEL, HNE, homeobox NKX 3.1, HOM-TES-14/SCP-1, HOM-TES-85, HPV-E6, HPV-E7, HST-2, hTERT, iCE, IGF-1R, IL-13Ra2, IL-2R, IL-5, immature laminin receptor, kallikrein 2, kallikrein 4, Ki67, KIAA0205, KK-LC-1, KM-HN-1, LAGE-1, Livin, MAGE-A1, MAGE-A10, MAGE-A12, MAGE-A2, MAGE-A3, MAGE-A4, MAGE-A6, MAGE-A9, MAGE-B1, MAGE-B10, MAGE-B16, MAGE-B17, MAGE-B2, MAGE-B3, MAGE-B4, MAGE-B5, MAGE-B6, MAGE-C1, MAGE-C2, MAGE-C3, MAGE-D1, MAGE-D2, MAGE-D4, MAGE-E1, MAGE-E2, MAGE-F1, MAGE-H1, MAGEL2, mammaglobin A, MART-1/Melan-A, MART-2, matrix protein 22, MC1R, M-CSF, Mesothelin, MG50/PXDN, MMP 11, MN/CA IX-antigen, MRP-3, MUC1, MUC2, NA88-A, N-acetylglucosaminyltransferase-V, Neo-PAP, NGEP, NMP22, NPM/ALK, NSE, NY-ESO-1, NY-ESO-B, OA1, OFA-iLRP, OGT, OS-9, osteocalcin, osteopontin, p15, p15, p190 minor bcr-abl, p53, PAGE-4, PAI-1, PAI-2, PAP, PART-1, PATE, PDEF, Pim-1-Kinase, Pin1, POTE, PRAME, prostein, proteinase-3, PSA, PSCA, PSGR, PSM, PSMA, RAGE-1, RHAMM/CD168, RU1, RU2, 8400, SAGE, SART-1, SART-2, SART-3, SCC, Sp17, SSX-1, SSX-2/HOM-MEL-40, SSX-4, STAMP-1, STEAP, survivin, survivin-213, TA-90, TAG-72, TARP, TGFb, TGFbR11, TGM-4, TRAG-3, TRG, TRP-1, TRP-2/6b, TRP-2/INT2, Trp-p8, Tyrosinase, UPA, VEGF, VEGFR-2/FLK-1, WT1; alpha-actinin-4/m, ARTC1/m, bcr/abl, beta-Catenin/m, BRCA1/m, BRCA2/m, CASP-5/m, CASP-8/m, CDC27/m, CDK4/m, CDKN2A/m, CML66, COA-1/m, DEK-CAN, EFTUD2/m, ELF2/m, ETV6-AML1, FN1/m, GPNMB/m, HLA-A*0201-R170I, HLA-A11/m, HLA-A2/m, HSP70-2M, KIAA0205/m, K-Ras/m, LDLR-FUT, MART2/m, ME1/m, MUM-1/m, MUM-2/m, MUM-3/m, Myosin class 1/m, neo-PAP/m, NFYC/m, N-Ras/m, OGT/m, OS-9/m, p53/m, Pml/RARa, PRDX5/m, PTPRX/m, RBAF600/m, SIRT2/m, SYT-SSX-1, SYT-SSX-2, TEL-AML1, TGFbRII, and TPI/m.

8. The immunostimulatory composition according to claim 1, wherein the at least one free mRNA encodes: (i) at least one, two, three or four different antigens of the following group of antigens: (1) PSA (Prostate-Specific Antigen)=KLK3 (Kallikrein-3), (2) PSMA (Prostate-Specific Membrane Antigen), (3) PSCA (Prostate Stem Cell Antigen), (4) STEAP (Six Transmembrane Epithelial Antigen of the Prostate), or (ii) at least one, two, three, four, five, six, seven, eight, nine, ten eleven or twelve different antigens of the following group of antigens: hTERT, WT1, MAGE-A2, 5T4, MAGE-A3, MUC1, Her-2/neu, NY-ESO-1, CEA, Survivin, MAGE-C1, and/or MAGE-C2, or a combination thereof.

9. A pharmaceutical composition, comprising an immunostimulatory composition according to claim 1 and optionally a pharmaceutically acceptable carrier, adjuvant, and/or vehicle.

10. A pharmaceutical composition according to claim 9, wherein the pharmaceutical composition is formulated to provide immune stimulation.

11. A method for preparing an immunostimulatory composition as defined according to claim 1, comprising following steps: (i) preparing the adjuvant component by mixing in a specific ratio the at least one mRNA and the protamine; and (ii) preparing the immunostimulatory composition by adding in a specific ratio of the at least one free mRNA to the adjuvant component prepared according to step (i).

12. A kit comprising the immunostimulatory composition according to claim 1, and a pharmaceutically acceptable carrier and technical instructions with information on the administration and dosage of the immunostimulatory composition and/or the pharmaceutically acceptable carrier.

13. The immunostimulatory composition according to claim 1, wherein the molar ratio of the mRNA of the adjuvant component to the at least one free mRNA of the second component b) is 1:1 and 1:3.

14. The immunostimulatory composition according to claim 1, wherein the molar ratio of the mRNA of the adjuvant component to the at least one free mRNA of the second component b) is 1:2 and 1:4.

15. The immunostimulatory composition according to claim 1, wherein the at least one free mRNA encodes an antigen selected from a cancer cell antigen, an autoimmune antigen, an infectious disease antigen or an allergic antigen.

16. The immunostimulatory composition according to claim 15, wherein the at least one free mRNA encodes an infectious disease antigen selected from a viral antigen, a protozoal antigen, or a bacterial antigen.

17. The immunostimulatory composition according to claim 1, wherein the weight ratio of the at least one mRNA to protamine in the adjuvant component is 2:1.

18. The immunostimulatory composition according to claim 1, wherein the weight ratio of the at least one mRNA to protamine in the adjuvant component is 3:1.

19. The immunostimulatory composition according to claim 4, wherein the N/P ratio of the mRNA to the protamine in the adjuvant component is 0.3 to 4.

20. The immunostimulatory composition according to claim 1, wherein the N/P ratio of the mRNA to the protamine in the adjuvant component is 0.5 to 2.

21. The immunostimulatory composition according to claim 1, wherein the N/P ratio of the mRNA to the protamine in the adjuvant component is 0.7 to 2.

22. The immunostimulatory composition according to claim 1, wherein the at least one free mRNA encodes a cancer cell antigen.

* * * * *

SEQUENCE LISTING

<160> NUMBER OF SEQ ID NOS: 142

<210> SEQ ID NO 1
<211> LENGTH: 20
<212> TYPE: RNA
<213> ORGANISM: Artificial Sequence
<220> FEATURE:
<223> OTHER INFORMATION: Description of Artificial Sequence: Synthetic
exemplary core structure "GlXmGn" oligonucleotide

<400> SEQUENCE: 1
gguuuuuuuu uuuuuuuggg 20

<210> SEQ ID NO 2
<211> LENGTH: 20
<212> TYPE: RNA
<213> ORGANISM: Artificial Sequence
<220> FEATURE:
<223> OTHER INFORMATION: Description of Artificial Sequence: Synthetic
exemplary core structure "GlXmGn" oligonucleotide

<400> SEQUENCE: 2
gggggguuuu uuuuuggggg 20

<210> SEQ ID NO 3
<211> LENGTH: 40
<212> TYPE: RNA
<213> ORGANISM: Artificial Sequence
<220> FEATURE:
<223> OTHER INFORMATION: Description of Artificial Sequence: Synthetic
exemplary core structure "GlXmGn" oligonucleotide

<400> SEQUENCE: 3
gggggguuuu uuuuuuuuuu uuuuuuuuuu uuuuuggggg 40

<210> SEQ ID NO 4
<211> LENGTH: 39
<212> TYPE: RNA
<213> ORGANISM: Artificial Sequence
<220> FEATURE:
<223> OTHER INFORMATION: Description of Artificial Sequence: Synthetic
exemplary core structure "GlXmGn" oligonucleotide

<400> SEQUENCE: 4
gugugugugu guuuuuuuuu uuuuuuugug ugugugugu 39

<210> SEQ ID NO 5
<211> LENGTH: 39
<212> TYPE: RNA
<213> ORGANISM: Artificial Sequence
<220> FEATURE:
<223> OTHER INFORMATION: Description of Artificial Sequence: Synthetic
exemplary core structure "GlXmGn" oligonucleotide

<400> SEQUENCE: 5
gguugguugg uuuuuuuuuu uuuuuuuggu ugguugguu 39

<210> SEQ ID NO 6
<211> LENGTH: 20
<212> TYPE: RNA
<213> ORGANISM: Artificial Sequence
<220> FEATURE:
<223> OTHER INFORMATION: Description of Artificial Sequence: Synthetic
exemplary core structure "GlXmGn" oligonucleotide

<400> SEQUENCE: 6
gggggggggu uugggggggg 20

<210> SEQ ID NO 7
<211> LENGTH: 20
<212> TYPE: RNA
<213> ORGANISM: Artificial Sequence
<220> FEATURE:
<223> OTHER INFORMATION: Description of Artificial Sequence: Synthetic
exemplary core structure "GlXmGn" oligonucleotide -continued

<400> SEQUENCE: 7
gggggggguu uugggggggg 20

<210> SEQ ID NO 8
<211> LENGTH: 20
<212> TYPE: RNA
<213> ORGANISM: Artificial Sequence
<220> FEATURE:
<223> OTHER INFORMATION: Description of Artificial Sequence: Synthetic
exemplary core structure "GlXmGn" oligonucleotide

<400> SEQUENCE: 8 gggggggguuu uuuggggggg 20

<210> SEQ ID NO 9
<211> LENGTH: 20
<212> TYPE: RNA
<213> ORGANISM: Artificial Sequence
<220> FEATURE:
<223> OTHER INFORMATION: Description of Artificial Sequence: Synthetic
exemplary core structure "GlXmGn" oligonucleotide

<400> SEQUENCE: 9 gggggggguuu uuuuggggggg 20

<210> SEQ ID NO 10
<211> LENGTH: 20
<212> TYPE: RNA
<213> ORGANISM: Artificial Sequence
<220> FEATURE:
<223> OTHER INFORMATION: Description of Artificial Sequence: Synthetic
exemplary core structure "GlXmGn" oligonucleotide

<400> SEQUENCE: 10 ggggggguuuu uuuugggggg 20

<210> SEQ ID NO 11
<211> LENGTH: 20
<212> TYPE: RNA
<213> ORGANISM: Artificial Sequence
<220> FEATURE:
<223> OTHER INFORMATION: Description of Artificial Sequence: Synthetic
exemplary core structure "GlXmGn" oligonucleotide

<400> SEQUENCE: 11 ggggggguuuu uuuuuggggg 20

<210> SEQ ID NO 12
<211> LENGTH: 20
<212> TYPE: RNA
<213> ORGANISM: Artificial Sequence
<220> FEATURE:
<223> OTHER INFORMATION: Description of Artificial Sequence: Synthetic
exemplary core structure "GlXmGn" oligonucleotide

<400> SEQUENCE: 12 ggggggguuuu uuuuuugggg 20

<210> SEQ ID NO 13
<211> LENGTH: 20
<212> TYPE: RNA
<213> ORGANISM: Artificial Sequence
<220> FEATURE:
<223> OTHER INFORMATION: Description of Artificial Sequence: Synthetic
exemplary core structure "GlXmGn" oligonucleotide

<400> SEQUENCE: 13
ggggguuuuu uuuuuugggg 20

<210> SEQ ID NO 14
<211> LENGTH: 20
<212> TYPE: RNA
<213> ORGANISM: Artificial Sequence
<220> FEATURE:
<223> OTHER INFORMATION: Description of Artificial Sequence: Synthetic
exemplary core structure “GlXmGn” oligonucleotide

<400> SEQUENCE: 14
ggggguuuuu uuuuuuuggg 20

<210> SEQ ID NO 15
<211> LENGTH: 20
<212> TYPE: RNA
<213> ORGANISM: Artificial Sequence
<220> FEATURE:
<223> OTHER INFORMATION: Description of Artificial Sequence: Synthetic
exemplary core structure “GlXmGn” oligonucleotide

<400> SEQUENCE: 15
gggguuuuuu uuuuuuuggg 20

<210> SEQ ID NO 16
<211> LENGTH: 20
<212> TYPE: RNA
<213> ORGANISM: Artificial Sequence
<220> FEATURE:
<223> OTHER INFORMATION: Description of Artificial Sequence: Synthetic
exemplary core structure “GlXmGn” oligonucleotide

<400> SEQUENCE: 16
gggguuuuuu uuuuuuuugg 20

<210> SEQ ID NO 17
<211> LENGTH: 20
<212> TYPE: RNA
<213> ORGANISM: Artificial Sequence
<220> FEATURE:
<223> OTHER INFORMATION: Description of Artificial Sequence: Synthetic
exemplary core structure “GlXmGn” oligonucleotide

<400> SEQUENCE: 17
gguuuuuuuu uuuuuuuugg 20

<210> SEQ ID NO 18
<211> LENGTH: 20
<212> TYPE: RNA
<213> ORGANISM: Artificial Sequence
<220> FEATURE:
<223> OTHER INFORMATION: Description of Artificial Sequence: Synthetic
exemplary core structure “GlXmGn” oligonucleotide

<400> SEQUENCE: 18
guuuuuuuuu uuuuuuuuug 20

<210> SEQ ID NO 19
<211> LENGTH: 22
<212> TYPE: RNA
<213> ORGANISM: Artificial Sequence
<220> FEATURE:
<223> OTHER INFORMATION: Description of Artificial Sequence: Synthetic
exemplary core structure “GlXmGn” oligonucleotide

<400> SEQUENCE: 19
gggggggggg uuugggggggg gg 22

<210> SEQ ID NO 20
<211> LENGTH: 22
<212> TYPE: RNA
<213> ORGANISM: Artificial Sequence
<220> FEATURE:
<223> OTHER INFORMATION: Description of Artificial Sequence: Synthetic exemplary core structure “GlXmGn” oligonucleotide

<400> SEQUENCE: 20 ggggggggggu uuugggggggg gg 22

<210> SEQ ID NO 21
<211> LENGTH: 22
<212> TYPE: RNA
<213> ORGANISM: Artificial Sequence
<220> FEATURE:
<223> OTHER INFORMATION: Description of Artificial Sequence: Synthetic exemplary core structure “GlXmGn” oligonucleotide

<400> SEQUENCE: 21 ggggggggguu uuuugggggg gg 22

<210> SEQ ID NO 22
<211> LENGTH: 22
<212> TYPE: RNA
<213> ORGANISM: Artificial Sequence
<220> FEATURE:
<223> OTHER INFORMATION: Description of Artificial Sequence: Synthetic exemplary core structure “GlXmGn” oligonucleotide

<400> SEQUENCE: 22 ggggggggguu uuuuuggggg gg 22

<210> SEQ ID NO 23
<211> LENGTH: 22
<212> TYPE: RNA
<213> ORGANISM: Artificial Sequence
<220> FEATURE:
<223> OTHER INFORMATION: Description of Artificial Sequence: Synthetic exemplary core structure “GlXmGn” oligonucleotide

<400> SEQUENCE: 23 gggggggguuu uuuuuggggg gg 22

<210> SEQ ID NO 24
<211> LENGTH: 22
<212> TYPE: RNA
<213> ORGANISM: Artificial Sequence
<220> FEATURE:
<223> OTHER INFORMATION: Description of Artificial Sequence: Synthetic exemplary core structure “GlXmGn” oligonucleotide

<400> SEQUENCE: 24 gggggggguuu uuuuuugggg gg 22

<210> SEQ ID NO 25
<211> LENGTH: 22
<212> TYPE: RNA
<213> ORGANISM: Artificial Sequence
<220> FEATURE:
<223> OTHER INFORMATION: Description of Artificial Sequence: Synthetic exemplary core structure “GlXmGn” oligonucleotide

<400> SEQUENCE: 25 gggggggguuu uuuuuuuggg gg 22

-continued

<210> SEQ ID NO 26
<211> LENGTH: 22
<212> TYPE: RNA
<213> ORGANISM: Artificial Sequence
<220> FEATURE:
<223> OTHER INFORMATION: Description of Artificial Sequence: Synthetic
exemplary core structure “GlXmGn” oligonucleotide

<400> SEQUENCE: 26
gggggguuuu uuuuuuuggg gg 22

<210> SEQ ID NO 27
<211> LENGTH: 22
<212> TYPE: RNA
<213> ORGANISM: Artificial Sequence
<220> FEATURE:
<223> OTHER INFORMATION: Description of Artificial Sequence: Synthetic
exemplary core structure “GlXmGn” oligonucleotide

<400> SEQUENCE: 27
gggggguuuu uuuuuuuugg gg 22

<210> SEQ ID NO 28
<211> LENGTH: 22
<212> TYPE: RNA
<213> ORGANISM: Artificial Sequence
<220> FEATURE:
<223> OTHER INFORMATION: Description of Artificial Sequence: Synthetic
exemplary core structure “GlXmGn” oligonucleotide

<400> SEQUENCE: 28
ggggguuuuu uuuuuuuugg gg 22

<210> SEQ ID NO 29
<211> LENGTH: 22
<212> TYPE: RNA
<213> ORGANISM: Artificial Sequence
<220> FEATURE:
<223> OTHER INFORMATION: Description of Artificial Sequence: Synthetic
exemplary core structure “GlXmGn” oligonucleotide

<400> SEQUENCE: 29
ggggguuuuu uuuuuuuuug gg 22

<210> SEQ ID NO 30
<211> LENGTH: 22
<212> TYPE: RNA
<213> ORGANISM: Artificial Sequence
<220> FEATURE:
<223> OTHER INFORMATION: Description of Artificial Sequence: Synthetic
exemplary core structure “GlXmGn” oligonucleotide

<400> SEQUENCE: 30
ggguuuuuuu uuuuuuuuug gg 22

<210> SEQ ID NO 31
<211> LENGTH: 22
<212> TYPE: RNA
<213> ORGANISM: Artificial Sequence
<220> FEATURE:
<223> OTHER INFORMATION: Description of Artificial Sequence: Synthetic
exemplary core structure “GlXmGn” oligonucleotide

<400> SEQUENCE: 31
gguuuuuuuu uuuuuuuuuu gg 22

<210> SEQ ID NO 32
<211> LENGTH: 24
<212> TYPE: RNA
<213> ORGANISM: Artificial Sequence
<220> FEATURE:
<223> OTHER INFORMATION: Description of Artificial Sequence: Synthetic
      exemplary core structure "GlXmGn" oligonucleotide

<400> SEQUENCE: 32
gggggggggg guuuggggggg gggg 24

<210> SEQ ID NO 33
<211> LENGTH: 24
<212> TYPE: RNA
<213> ORGANISM: Artificial Sequence
<220> FEATURE:
<223> OTHER INFORMATION: Description of Artificial Sequence: Synthetic
      exemplary core structure "GlXmGn" oligonucleotide

<400> SEQUENCE: 33
gggggggggg uuuuggggggg gggg 24

<210> SEQ ID NO 34
<211> LENGTH: 24
<212> TYPE: RNA
<213> ORGANISM: Artificial Sequence
<220> FEATURE:
<223> OTHER INFORMATION: Description of Artificial Sequence: Synthetic
      exemplary core structure "GlXmGn" oligonucleotide

<400> SEQUENCE: 34
gggggggggu uuuuuggggg gggg 24

<210> SEQ ID NO 35
<211> LENGTH: 24
<212> TYPE: RNA
<213> ORGANISM: Artificial Sequence
<220> FEATURE:
<223> OTHER INFORMATION: Description of Artificial Sequence: Synthetic
      exemplary core structure "GlXmGn" oligonucleotide

<400> SEQUENCE: 35
gggggggggu uuuuuugggg gggg 24

<210> SEQ ID NO 36
<211> LENGTH: 24
<212> TYPE: RNA
<213> ORGANISM: Artificial Sequence
<220> FEATURE:
<223> OTHER INFORMATION: Description of Artificial Sequence: Synthetic
      exemplary core structure "GlXmGn" oligonucleotide

<400> SEQUENCE: 36 ggggggggguu uuuuuugggg gggg 24

<210> SEQ ID NO 37
<211> LENGTH: 24
<212> TYPE: RNA
<213> ORGANISM: Artificial Sequence
<220> FEATURE:
<223> OTHER INFORMATION: Description of Artificial Sequence: Synthetic
      exemplary core structure "GlXmGn" oligonucleotide

<400> SEQUENCE: 37 ggggggggguu uuuuuuuggg gggg 24

-continued

<210> SEQ ID NO 38
<211> LENGTH: 24
<212> TYPE: RNA
<213> ORGANISM: Artificial Sequence
<220> FEATURE:
<223> OTHER INFORMATION: Description of Artificial Sequence: Synthetic
exemplary core structure "GlXmGn" oligonucleotide

<400> SEQUENCE: 38
gggggggguu uuuuuuuugg gggg 24

<210> SEQ ID NO 39
<211> LENGTH: 24
<212> TYPE: RNA
<213> ORGANISM: Artificial Sequence
<220> FEATURE:
<223> OTHER INFORMATION: Description of Artificial Sequence: Synthetic
exemplary core structure "GlXmGn" oligonucleotide

<400> SEQUENCE: 39
ggggggguuu uuuuuuuugg gggg 24

<210> SEQ ID NO 40
<211> LENGTH: 24
<212> TYPE: RNA
<213> ORGANISM: Artificial Sequence
<220> FEATURE:
<223> OTHER INFORMATION: Description of Artificial Sequence: Synthetic
exemplary core structure "GlXmGn" oligonucleotide

<400> SEQUENCE: 40
ggggggguuu uuuuuuuuug gggg 24

<210> SEQ ID NO 41
<211> LENGTH: 24
<212> TYPE: RNA
<213> ORGANISM: Artificial Sequence
<220> FEATURE:
<223> OTHER INFORMATION: Description of Artificial Sequence: Synthetic
exemplary core structure "GlXmGn" oligonucleotide

<400> SEQUENCE: 41
gggggguuuu uuuuuuuuug gggg 24

<210> SEQ ID NO 42
<211> LENGTH: 24
<212> TYPE: RNA
<213> ORGANISM: Artificial Sequence
<220> FEATURE:
<223> OTHER INFORMATION: Description of Artificial Sequence: Synthetic
exemplary core structure "GlXmGn" oligonucleotide

<400> SEQUENCE: 42
gggggguuuu uuuuuuuuuu gggg 24

<210> SEQ ID NO 43
<211> LENGTH: 24
<212> TYPE: RNA
<213> ORGANISM: Artificial Sequence
<220> FEATURE:
<223> OTHER INFORMATION: Description of Artificial Sequence: Synthetic
exemplary core structure "GlXmGn" oligonucleotide

<400> SEQUENCE: 43
gggguuuuuu uuuuuuuuuu gggg 24

<210> SEQ ID NO 44

<211> LENGTH: 24
<212> TYPE: RNA
<213> ORGANISM: Artificial Sequence
<220> FEATURE:
<223> OTHER INFORMATION: Description of Artificial Sequence: Synthetic exemplary core structure "GlXmGn" oligonucleotide

<400> SEQUENCE: 44
gggguuuuuu uuuuuuuuuu uggg 24

<210> SEQ ID NO 45
<211> LENGTH: 32
<212> TYPE: RNA
<213> ORGANISM: Artificial Sequence
<220> FEATURE:
<223> OTHER INFORMATION: Description of Artificial Sequence: Synthetic exemplary core structure "GlXmGn" oligonucleotide

<400> SEQUENCE: 45
guuuuuuuuu uuuuuuuuuu uuuuuuuuuu ug 32

<210> SEQ ID NO 46
<211> LENGTH: 34
<212> TYPE: RNA
<213> ORGANISM: Artificial Sequence
<220> FEATURE:
<223> OTHER INFORMATION: Description of Artificial Sequence: Synthetic exemplary core structure "GlXmGn" oligonucleotide

<400> SEQUENCE: 46
gguuuuuuuu uuuuuuuuuu uuuuuuuuuu uugg 34

<210> SEQ ID NO 47
<211> LENGTH: 36
<212> TYPE: RNA
<213> ORGANISM: Artificial Sequence
<220> FEATURE:
<223> OTHER INFORMATION: Description of Artificial Sequence: Synthetic exemplary core structure "GlXmGn" oligonucleotide

<400> SEQUENCE: 47
ggguuuuuuu uuuuuuuuuu uuuuuuuuuu uuuggg 36

<210> SEQ ID NO 48
<211> LENGTH: 37
<212> TYPE: RNA
<213> ORGANISM: Artificial Sequence
<220> FEATURE:
<223> OTHER INFORMATION: Description of Artificial Sequence: Synthetic exemplary core structure "GlXmGn" oligonucleotide

<400> SEQUENCE: 48 ggggguuuuuu uuuuuuuuuu uuuuuuuuuu uuuuggg 37

<210> SEQ ID NO 49
<211> LENGTH: 39
<212> TYPE: RNA
<213> ORGANISM: Artificial Sequence
<220> FEATURE:
<223> OTHER INFORMATION: Description of Artificial Sequence: Synthetic exemplary core structure "GlXmGn" oligonucleotide

<400> SEQUENCE: 49 gggggguuuuu uuuuuuuuuu uuuuuuuuuu uuuuugggg 39

<210> SEQ ID NO 50
<211> LENGTH: 41

-continued

<212> TYPE: RNA
<213> ORGANISM: Artificial Sequence
<220> FEATURE:
<223> OTHER INFORMATION: Description of Artificial Sequence: Synthetic
      exemplary core structure "GlXmGn" oligonucleotide

<400> SEQUENCE: 50
gggggguuuu uuuuuuuuuu uuuuuuuuuu uuuuuugggg g 41

<210> SEQ ID NO 51
<211> LENGTH: 43
<212> TYPE: RNA
<213> ORGANISM: Artificial Sequence
<220> FEATURE:
<223> OTHER INFORMATION: Description of Artificial Sequence: Synthetic
      exemplary core structure "GlXmGn" oligonucleotide

<400> SEQUENCE: 51
ggggggguuu uuuuuuuuuu uuuuuuuuuu uuuuuuuggg ggg 43

<210> SEQ ID NO 52
<211> LENGTH: 45
<212> TYPE: RNA
<213> ORGANISM: Artificial Sequence
<220> FEATURE:
<223> OTHER INFORMATION: Description of Artificial Sequence: Synthetic
      exemplary core structure "GlXmGn" oligonucleotide

<400> SEQUENCE: 52
gggggggguu uuuuuuuuuu uuuuuuuuuu uuuuuuuugg ggggg 45

<210> SEQ ID NO 53
<211> LENGTH: 47
<212> TYPE: RNA
<213> ORGANISM: Artificial Sequence
<220> FEATURE:
<223> OTHER INFORMATION: Description of Artificial Sequence: Synthetic
      exemplary core structure "GlXmGn" oligonucleotide

<400> SEQUENCE: 53
gggggggggu uuuuuuuuuu uuuuuuuuuu uuuuuuuuug ggggggg 47

<210> SEQ ID NO 54
<211> LENGTH: 7
<212> TYPE: RNA
<213> ORGANISM: Artificial Sequence
<220> FEATURE:
<223> OTHER INFORMATION: Description of Artificial Sequence: Synthetic
      exemplary core structure "GlXmGn" oligonucleotide

<400> SEQUENCE: 54 gguuugg 7

<210> SEQ ID NO 55
<211> LENGTH: 8
<212> TYPE: RNA
<213> ORGANISM: Artificial Sequence
<220> FEATURE:
<223> OTHER INFORMATION: Description of Artificial Sequence: Synthetic
      exemplary core structure "GlXmGn" oligonucleotide

<400> SEQUENCE: 55 gguuuugg 8

<210> SEQ ID NO 56
<211> LENGTH: 9
<212> TYPE: RNA

<213> ORGANISM: Artificial Sequence
<220> FEATURE:
<223> OTHER INFORMATION: Description of Artificial Sequence: Synthetic
exemplary core structure “GlXmGn” oligonucleotide

<400> SEQUENCE: 56 gguuuuugg 9

<210> SEQ ID NO 57
<211> LENGTH: 10
<212> TYPE: RNA
<213> ORGANISM: Artificial Sequence
<220> FEATURE:
<223> OTHER INFORMATION: Description of Artificial Sequence: Synthetic
exemplary core structure “GlXmGn” oligonucleotide

<400> SEQUENCE: 57
gguuuuuugg 10

<210> SEQ ID NO 58
<211> LENGTH: 11
<212> TYPE: RNA
<213> ORGANISM: Artificial Sequence
<220> FEATURE:
<223> OTHER INFORMATION: Description of Artificial Sequence: Synthetic
exemplary core structure “GlXmGn” oligonucleotide

<400> SEQUENCE: 58
gguuuuuuug g 11

<210> SEQ ID NO 59
<211> LENGTH: 12
<212> TYPE: RNA
<213> ORGANISM: Artificial Sequence
<220> FEATURE:
<223> OTHER INFORMATION: Description of Artificial Sequence: Synthetic
exemplary core structure “GlXmGn” oligonucleotide

<400> SEQUENCE: 59
gguuuuuuuu gg 12

<210> SEQ ID NO 60
<211> LENGTH: 13
<212> TYPE: RNA
<213> ORGANISM: Artificial Sequence
<220> FEATURE:
<223> OTHER INFORMATION: Description of Artificial Sequence: Synthetic
exemplary core structure “GlXmGn” oligonucleotide

<400> SEQUENCE: 60
gguuuuuuuu ugg 13

<210> SEQ ID NO 61
<211> LENGTH: 14
<212> TYPE: RNA
<213> ORGANISM: Artificial Sequence
<220> FEATURE:
<223> OTHER INFORMATION: Description of Artificial Sequence: Synthetic
exemplary core structure “GlXmGn” oligonucleotide

<400> SEQUENCE: 61
gguuuuuuuu uugg 14

<210> SEQ ID NO 62
<211> LENGTH: 15
<212> TYPE: RNA
<213> ORGANISM: Artificial Sequence -continued
<220> FEATURE:
<223> OTHER INFORMATION: Description of Artificial Sequence: Synthetic
      exemplary core structure “GlXmGn” oligonucleotide

<400> SEQUENCE: 62
gguuuuuuuu uuugg 15

<210> SEQ ID NO 63
<211> LENGTH: 16
<212> TYPE: RNA
<213> ORGANISM: Artificial Sequence
<220> FEATURE:
<223> OTHER INFORMATION: Description of Artificial Sequence: Synthetic
      exemplary core structure “GlXmGn” oligonucleotide

<400> SEQUENCE: 63
gguuuuuuuu uuuugg 16

<210> SEQ ID NO 64
<211> LENGTH: 17
<212> TYPE: RNA
<213> ORGANISM: Artificial Sequence
<220> FEATURE:
<223> OTHER INFORMATION: Description of Artificial Sequence: Synthetic
      exemplary core structure “GlXmGn” oligonucleotide

<400> SEQUENCE: 64
gguuuuuuuu uuuuugg 17

<210> SEQ ID NO 65
<211> LENGTH: 18
<212> TYPE: RNA
<213> ORGANISM: Artificial Sequence
<220> FEATURE:
<223> OTHER INFORMATION: Description of Artificial Sequence: Synthetic
      exemplary core structure “GlXmGn” oligonucleotide

<400> SEQUENCE: 65
gguuuuuuuu uuuuuugg 18

<210> SEQ ID NO 66
<211> LENGTH: 19
<212> TYPE: RNA
<213> ORGANISM: Artificial Sequence
<220> FEATURE:
<223> OTHER INFORMATION: Description of Artificial Sequence: Synthetic
      exemplary core structure “GlXmGn” oligonucleotide

<400> SEQUENCE: 66
gguuuuuuuu uuuuuuugg 19

<210> SEQ ID NO 67
<211> LENGTH: 9
<212> TYPE: RNA
<213> ORGANISM: Artificial Sequence
<220> FEATURE:
<223> OTHER INFORMATION: Description of Artificial Sequence: Synthetic
      exemplary core structure “GlXmGn” oligonucleotide

<400> SEQUENCE: 67 ggguuuggg 9

<210> SEQ ID NO 68
<211> LENGTH: 10
<212> TYPE: RNA
<213> ORGANISM: Artificial Sequence
<220> FEATURE:

<223> OTHER INFORMATION: Description of Artificial Sequence: Synthetic exemplary core structure "GlXmGn" oligonucleotide

<400> SEQUENCE: 68 gggguuuuggg 10

<210> SEQ ID NO 69
<211> LENGTH: 11
<212> TYPE: RNA
<213> ORGANISM: Artificial Sequence
<220> FEATURE:
<223> OTHER INFORMATION: Description of Artificial Sequence: Synthetic exemplary core structure "GlXmGn" oligonucleotide

<400> SEQUENCE: 69
ggguuuuugg g 11

<210> SEQ ID NO 70
<211> LENGTH: 12
<212> TYPE: RNA
<213> ORGANISM: Artificial Sequence
<220> FEATURE:
<223> OTHER INFORMATION: Description of Artificial Sequence: Synthetic exemplary core structure "GlXmGn" oligonucleotide

<400> SEQUENCE: 70
ggguuuuuug gg 12

<210> SEQ ID NO 71
<211> LENGTH: 13
<212> TYPE: RNA
<213> ORGANISM: Artificial Sequence
<220> FEATURE:
<223> OTHER INFORMATION: Description of Artificial Sequence: Synthetic exemplary core structure "GlXmGn" oligonucleotide

<400> SEQUENCE: 71
ggguuuuuuu ggg 13

<210> SEQ ID NO 72
<211> LENGTH: 14
<212> TYPE: RNA
<213> ORGANISM: Artificial Sequence
<220> FEATURE:
<223> OTHER INFORMATION: Description of Artificial Sequence: Synthetic exemplary core structure "GlXmGn" oligonucleotide

<400> SEQUENCE: 72
ggguuuuuuu uggg 14

<210> SEQ ID NO 73
<211> LENGTH: 15
<212> TYPE: RNA
<213> ORGANISM: Artificial Sequence
<220> FEATURE:
<223> OTHER INFORMATION: Description of Artificial Sequence: Synthetic exemplary core structure "GlXmGn" oligonucleotide

<400> SEQUENCE: 73
ggguuuuuuu uuggg 15

<210> SEQ ID NO 74
<211> LENGTH: 16
<212> TYPE: RNA
<213> ORGANISM: Artificial Sequence
<220> FEATURE:
<223> OTHER INFORMATION: Description of Artificial Sequence: Synthetic exemplary core structure “GlXmGn” oligonucleotide

<400> SEQUENCE: 74
gggguuuuuu uuuggg 16

<210> SEQ ID NO 75
<211> LENGTH: 17
<212> TYPE: RNA
<213> ORGANISM: Artificial Sequence
<220> FEATURE:
<223> OTHER INFORMATION: Description of Artificial Sequence: Synthetic exemplary core structure “GlXmGn” oligonucleotide

<400> SEQUENCE: 75
ggguuuuuuu uuuuggg 17

<210> SEQ ID NO 76
<211> LENGTH: 18
<212> TYPE: RNA
<213> ORGANISM: Artificial Sequence
<220> FEATURE:
<223> OTHER INFORMATION: Description of Artificial Sequence: Synthetic exemplary core structure “GlXmGn” oligonucleotide

<400> SEQUENCE: 76
ggguuuuuuu uuuuuggg 18

<210> SEQ ID NO 77
<211> LENGTH: 19
<212> TYPE: RNA
<213> ORGANISM: Artificial Sequence
<220> FEATURE:
<223> OTHER INFORMATION: Description of Artificial Sequence: Synthetic exemplary core structure “GlXmGn” oligonucleotide

<400> SEQUENCE: 77
ggguuuuuuu uuuuuuggg 19

<210> SEQ ID NO 78
<211> LENGTH: 57
<212> TYPE: RNA
<213> ORGANISM: Artificial Sequence
<220> FEATURE:
<223> OTHER INFORMATION: Description of Artificial Sequence: Synthetic exemplary core structure “GlXmGn” oligonucleotide

<400> SEQUENCE: 78
ggguuuuuuu uuuuuuuugg guuuuuuuuu uuuuuugggu uuuuuuuuuu uuuuggg 57

<210> SEQ ID NO 79
<211> LENGTH: 42
<212> TYPE: RNA
<213> ORGANISM: Artificial Sequence
<220> FEATURE:
<223> OTHER INFORMATION: Description of Artificial Sequence: Synthetic exemplary core structure “GlXmGn” oligonucleotide

<400> SEQUENCE: 79
ggguuuuuuu uuuuuuuugg gggguuuuuu uuuuuuuuug gg 42

<210> SEQ ID NO 80
<211> LENGTH: 51
<212> TYPE: RNA
<213> ORGANISM: Artificial Sequence
<220> FEATURE:
<223> OTHER INFORMATION: Description of Artificial Sequence: Synthetic exemplary core structure “GlXmGn” oligonucleotide

<400> SEQUENCE: 80 gggguuugggu uuggguuugg guuuggguuu ggguuugggu uuggguuugg g 51

<210> SEQ ID NO 81
<211> LENGTH: 57
<212> TYPE: RNA
<213> ORGANISM: Artificial Sequence
<220> FEATURE:
<223> OTHER INFORMATION: Description of Artificial Sequence: Synthetic
exemplary core structure "GlXmGn" oligonucleotide

<400> SEQUENCE: 81
cccuuuuuuu uuuuuuuucc cuuuuuuuuu uuuuuucccu uuuuuuuuuu uuuuccc 57

<210> SEQ ID NO 82
<211> LENGTH: 51
<212> TYPE: RNA
<213> ORGANISM: Artificial Sequence
<220> FEATURE:
<223> OTHER INFORMATION: Description of Artificial Sequence: Synthetic
exemplary core structure "GlXmGn" oligonucleotide

<400> SEQUENCE: 82
cccuuucccu uucccuuucc cuuucccuuu cccuuucccu uucccuuucc c 51

<210> SEQ ID NO 83
<211> LENGTH: 42
<212> TYPE: RNA
<213> ORGANISM: Artificial Sequence
<220> FEATURE:
<223> OTHER INFORMATION: Description of Artificial Sequence: Synthetic
exemplary core structure "GlXmGn" oligonucleotide

<400> SEQUENCE: 83
cccuuuuuuu uuuuuuuucc ccccuuuuuu uuuuuuuuuc cc 42

<210> SEQ ID NO 84
<211> LENGTH: 60
<212> TYPE: RNA
<213> ORGANISM: Artificial Sequence
<220> FEATURE:
<223> OTHER INFORMATION: Description of Artificial Sequence: Synthetic
exemplary oligonucleotide sequence according to formula (I)

<400> SEQUENCE: 84
uagcgaagcu cuuggaccua gguuuuuuuu uuuuuuuggg ugcguuccua gaaguacacg 60

<210> SEQ ID NO 85
<211> LENGTH: 60
<212> TYPE: RNA
<213> ORGANISM: Artificial Sequence
<220> FEATURE:
<223> OTHER INFORMATION: Description of Artificial Sequence: Synthetic
exemplary oligonucleotide sequence according to formula (I)
<220> FEATURE:
<221> NAME/KEY: misc_feature
<222> LOCATION: (1)..(60)
<223> OTHER INFORMATION: Double-stranded RNA

<400> SEQUENCE: 85
uagcgaagcu cuuggaccua gguuuuuuuu uuuuuuuggg ugcguuccua gaaguacacg 60

<210> SEQ ID NO 86
<211> LENGTH: 60
<212> TYPE: RNA
<213> ORGANISM: Artificial Sequence
<220> FEATURE:
<223> OTHER INFORMATION: Description of Artificial Sequence: Synthetic
exemplary oligonucleotide sequence according to formula (Ia)

<400> SEQUENCE: 86
uagcgaagcu cuuggaccua ccuuuuuuuu uuuuuuuccc ugcguuccua gaaguacacg 60

<210> SEQ ID NO 87
<211> LENGTH: 60
<212> TYPE: RNA
<213> ORGANISM: Artificial Sequence
<220> FEATURE:
<223> OTHER INFORMATION: Description of Artificial Sequence: Synthetic
exemplary oligonucleotide sequence according to formula (Ia)
<220> FEATURE:
<221> NAME/KEY: misc_feature
<222> LOCATION: (1)..(60)
<223> OTHER INFORMATION: Double-stranded RNA

<400> SEQUENCE: 87
uagcgaagcu cuuggaccua ccuuuuuuuu uuuuuuuccc ugcguuccua gaaguacacg 60

<210> SEQ ID NO 88
<211> LENGTH: 40
<212> TYPE: RNA
<213> ORGANISM: Artificial Sequence
<220> FEATURE:
<223> OTHER INFORMATION: Description of Artificial Sequence: Synthetic
exemplary oligonucleotide sequence according to formula (II)

<400> SEQUENCE: 88
cccccccccc cccccccccc gguuuuuuuu uuuuuuuggg 40

<210> SEQ ID NO 89
<211> LENGTH: 40
<212> TYPE: RNA
<213> ORGANISM: Artificial Sequence
<220> FEATURE:
<223> OTHER INFORMATION: Description of Artificial Sequence: Synthetic
exemplary oligonucleotide sequence according to formula (II)
<220> FEATURE:
<221> NAME/KEY: misc_feature
<222> LOCATION: (1)..(20)
<223> OTHER INFORMATION: Double-stranded RNA (poly(I:C))

<400> SEQUENCE: 89
cccccccccc cccccccccc gguuuuuuuu uuuuuuuggg 40

<210> SEQ ID NO 90
<211> LENGTH: 40
<212> TYPE: RNA
<213> ORGANISM: Artificial Sequence
<220> FEATURE:
<223> OTHER INFORMATION: Description of Artificial Sequence: Synthetic
exemplary oligonucleotide sequence according to formula (II)
<220> FEATURE:
<221> NAME/KEY: misc_feature
<222> LOCATION: (23)..(37)
<223> OTHER INFORMATION: Double-stranded (A:U)

<400> SEQUENCE: 90
cccccccccc cccccccccc gguuuuuuuu uuuuuuuggg 40

<210> SEQ ID NO 91
<211> LENGTH: 40
<212> TYPE: RNA
<213> ORGANISM: Artificial Sequence
<220> FEATURE:
<223> OTHER INFORMATION: Description of Artificial Sequence: Synthetic -continued exemplary oligonucleotide sequence according to formula (II)
<220> FEATURE:
<221> NAME/KEY: misc_feature
<222> LOCATION: (1)..(40)
<223> OTHER INFORMATION: Double-stranded RNA

<400> SEQUENCE: 91
cccccccccc cccccccccc gguuuuuuuu uuuuuuuggg 40

<210> SEQ ID NO 92
<211> LENGTH: 80
<212> TYPE: RNA
<213> ORGANISM: Artificial Sequence
<220> FEATURE:
<223> OTHER INFORMATION: Description of Artificial Sequence: Synthetic exemplary oligonucleotide sequence according to formula (II)

<400> SEQUENCE: 92
cccccccccc cccccccccc uagcgaagcu cuuggaccua gguuuuuuuu uuuuuuuggg 60
ugcguuccua gaaguacacg 80

<210> SEQ ID NO 93
<211> LENGTH: 80
<212> TYPE: RNA
<213> ORGANISM: Artificial Sequence
<220> FEATURE:
<223> OTHER INFORMATION: Description of Artificial Sequence: Synthetic exemplary oligonucleotide sequence according to formula (II)
<220> FEATURE:
<221> NAME/KEY: misc_feature
<222> LOCATION: (1)..(80)
<223> OTHER INFORMATION: Double-stranded RNA

<400> SEQUENCE: 93
cccccccccc cccccccccc gguuuuuuuu uuuuuuuggg ugcguuccua gaaguacacg 60
uagcgaagcu cuuggaccua 80

<210> SEQ ID NO 94
<211> LENGTH: 80
<212> TYPE: RNA
<213> ORGANISM: Artificial Sequence
<220> FEATURE:
<223> OTHER INFORMATION: Description of Artificial Sequence: Synthetic exemplary oligonucleotide sequence according to formula (II)
<220> FEATURE:
<221> NAME/KEY: misc_feature
<222> LOCATION: (21)..(80)
<223> OTHER INFORMATION: Double-stranded RNA

<400> SEQUENCE: 94
cccccccccc cccccccccc gguuuuuuuu uuuuuuuggg ugcguuccua gaaguacacg 60
uagcgaagcu cuuggaccua 80

<210> SEQ ID NO 95
<211> LENGTH: 20
<212> TYPE: RNA
<213> ORGANISM: Artificial Sequence
<220> FEATURE:
<223> OTHER INFORMATION: Description of Artificial Sequence: Synthetic exemplary oligonucleotide sequence of stem 1 (sequence is palindromic to SEQ ID NO: 96)

<400> SEQUENCE: 95
uagcgaagcu cuuggaccua 20

<210> SEQ ID NO 96

<211> LENGTH: 20
<212> TYPE: RNA
<213> ORGANISM: Artificial Sequence
<220> FEATURE:
<223> OTHER INFORMATION: Description of Artificial Sequence: Synthetic
exemplary oligonucleotide sequence of stem 2
(sequence is palindromic to SEQ ID NO: 95)

<400> SEQUENCE: 96
uagguccaag agcuucgcua 20

<210> SEQ ID NO 97
<211> LENGTH: 11
<212> TYPE: RNA
<213> ORGANISM: Artificial Sequence
<220> FEATURE:
<223> OTHER INFORMATION: Description of Artificial Sequence: Synthetic
exemplary oligonucleotide sequence of stem 1
(sequence is palindromic to SEQ ID NO: 98

<400> SEQUENCE: 97
gccgcgggcc g 11

<210> SEQ ID NO 98
<211> LENGTH: 11
<212> TYPE: RNA
<213> ORGANISM: Artificial Sequence
<220> FEATURE:
<223> OTHER INFORMATION: Description of Artificial Sequence: Synthetic
exemplary oligonucleotide sequence of stem 2
(sequence is palindromic to SEQ ID NO: 97)

<400> SEQUENCE: 98
cggcccgcgg c 11

<210> SEQ ID NO 99
<211> LENGTH: 10
<212> TYPE: RNA
<213> ORGANISM: Artificial Sequence
<220> FEATURE:
<223> OTHER INFORMATION: Description of Artificial Sequence: Synthetic
exemplary oligonucleotide sequence of stem 1
(sequence is palindromic to SEQ ID NO: 100

<400> SEQUENCE: 99
gacacggugc 10

<210> SEQ ID NO 100
<211> LENGTH: 10
<212> TYPE: RNA
<213> ORGANISM: Artificial Sequence
<220> FEATURE:
<223> OTHER INFORMATION: Description of Artificial Sequence: Synthetic
exemplary oligonucleotide sequence of stem 2
(sequence is palindromic to SEQ ID NO: 99)

<400> SEQUENCE: 100
gcaccgugca 10

<210> SEQ ID NO 101
<211> LENGTH: 8
<212> TYPE: RNA
<213> ORGANISM: Artificial Sequence
<220> FEATURE:
<223> OTHER INFORMATION: Description of Artificial Sequence: Synthetic
exemplary oligonucleotide sequence of either
stem 1/stem2 (sequence is intrinsic palindromic)

<400> SEQUENCE: 101

```
accuaggu                                                                 8


<210> SEQ ID NO 102
<211> LENGTH: 8
<212> TYPE: RNA
<213> ORGANISM: Artificial Sequence
<220> FEATURE:
<223> OTHER INFORMATION: Description of Artificial Sequence: Synthetic
      exemplary oligonucleotide sequence of either
      stem 1/stem2 (sequence is intrinsic palindromic)

<400> SEQUENCE: 102

uggaucca                                                                 8


<210> SEQ ID NO 103
<211> LENGTH: 5
<212> TYPE: RNA
<213> ORGANISM: Artificial Sequence
<220> FEATURE:
<223> OTHER INFORMATION: Description of Artificial Sequence: Synthetic
      exemplary oligonucleotide sequence of stem 1
      (sequence is palindromic to SEQ ID NO: 104)

<400> SEQUENCE: 103

ccugc                                                                    5


<210> SEQ ID NO 104
<211> LENGTH: 5
<212> TYPE: RNA
<213> ORGANISM: Artificial Sequence
<220> FEATURE:
<223> OTHER INFORMATION: Description of Artificial Sequence: Synthetic
      exemplary oligonucleotide sequence of stem 2
      (sequence is palindromic to SEQ ID NO: 103)

<400> SEQUENCE: 104

gcagg                                                                    5


<210> SEQ ID NO 105
<211> LENGTH: 5
<212> TYPE: RNA
<213> ORGANISM: Artificial Sequence
<220> FEATURE:
<223> OTHER INFORMATION: Description of Artificial Sequence: Synthetic
      exemplary oligonucleotide sequence of stem 1
      (sequence is palindromic to SEQ ID NO: 106)

<400> SEQUENCE: 105

gcagg                                                                    5


<210> SEQ ID NO 106
<211> LENGTH: 5
<212> TYPE: RNA
<213> ORGANISM: Artificial Sequence
<220> FEATURE:
<223> OTHER INFORMATION: Description of Artificial Sequence: Synthetic
      exemplary oligonucleotide sequence of stem 2
      (sequence is palindromic to SEQ ID NO: 105)

<400> SEQUENCE: 106

ccugc                                                                    5


<210> SEQ ID NO 107
<211> LENGTH: 60
<212> TYPE: RNA
<213> ORGANISM: Artificial Sequence
<220> FEATURE:
```

```
<223> OTHER INFORMATION: Description of Artificial Sequence: Synthetic
      inventive oligonucleotide according to either
      formula (IIIa) or (IIIb)

<400> SEQUENCE: 107

uagcgaagcu cuuggaccua gguuuuuuuu uuuuuuuggg uagguccaag agcuucgcua     60


<210> SEQ ID NO 108
<211> LENGTH: 122
<212> TYPE: RNA
<213> ORGANISM: Artificial Sequence
<220> FEATURE:
<223> OTHER INFORMATION: Description of Artificial Sequence: Synthetic
      inventive oligonucleotide according to either
      formula (IIIa) or (IIIb)

<400> SEQUENCE: 108

uagcgaagcu cuuggaccua gguuuuuuuu uuuuuuuggg ugcguuccua gaaguacacg     60

gccgcgggcc gugcguuccu agaaguacac gcggcccgcg gcugcguucc uagaaguaca    120

cg                                                                   122


<210> SEQ ID NO 109
<211> LENGTH: 18
<212> TYPE: PRT
<213> ORGANISM: Unknown
<220> FEATURE:
<223> OTHER INFORMATION: Description of Unknown: Protamin
      P1 peptide

<400> SEQUENCE: 109

Ser Arg Ser Arg Tyr Tyr Arg Gln Arg Gln Arg Ser Arg Arg Arg Arg
1               5                   10                  15

Arg Arg


<210> SEQ ID NO 110
<211> LENGTH: 21
<212> TYPE: PRT
<213> ORGANISM: Unknown
<220> FEATURE:
<223> OTHER INFORMATION: Description of Unknown: Protamin
      P2 peptide

<400> SEQUENCE: 110

Arg Arg Arg Leu His Arg Ile His Arg Arg Gln His Arg Ser Cys Arg
1               5                   10                  15

Arg Arg Lys Arg Arg
            20


<210> SEQ ID NO 111
<211> LENGTH: 13
<212> TYPE: RNA
<213> ORGANISM: Unknown
<220> FEATURE:
<223> OTHER INFORMATION: Description of Unknown: Kozak
      oligonucleotide

<400> SEQUENCE: 111

gccgccacca ugg                                                        13


<210> SEQ ID NO 112
<211> LENGTH: 15
<212> TYPE: RNA
<213> ORGANISM: Artificial Sequence
<220> FEATURE:
<223> OTHER INFORMATION: Description of Artificial Sequence: Synthetic
```

```
      generic stabilizing oligonucleotide
<220> FEATURE:
<221> NAME/KEY: modified_base
<222> LOCATION: (5)..(5)
<223> OTHER INFORMATION: a, c, u, g, unknown or other
<220> FEATURE:
<221> NAME/KEY: modified_base
<222> LOCATION: (10)..(10)
<223> OTHER INFORMATION: Pyrimidine
<220> FEATURE:
<223> OTHER INFORMATION: see specification as filed for detailed
      description of substitutions and preferred embodiments

<400> SEQUENCE: 112

yccancccwn ucycc                                                    15


<210> SEQ ID NO 113
<211> LENGTH: 20
<212> TYPE: RNA
<213> ORGANISM: Artificial Sequence
<220> FEATURE:
<223> OTHER INFORMATION: Description of Artificial Sequence: Synthetic
      immune-stimulating oligonucleotide RNA40

<400> SEQUENCE: 113

gcccgucugu ugugugacuc                                               20


<210> SEQ ID NO 114
<211> LENGTH: 229
<212> TYPE: RNA
<213> ORGANISM: Artificial Sequence
<220> FEATURE:
<223> OTHER INFORMATION: Description of Artificial Sequence: Synthetic
      exemplary polynucleotide according to formula (I)

<400> SEQUENCE: 114

gggagaaagc ucaagcuugg agcaaugccc gcacauugag gaaaccgagu ugcauaucuc     60

agaguauugg cccccgugua gguuauucuu gacagacagu ggagcuuauu cacucccagg    120

auccgagucg cauacuacgg uacuggugac agaccuaggu cgucaguuga ccaguccgcc    180

acuagacgug aguccgucaa agcaguuaga uguuacacuc uauuagauc                229


<210> SEQ ID NO 115
<211> LENGTH: 547
<212> TYPE: RNA
<213> ORGANISM: Artificial Sequence
<220> FEATURE:
<223> OTHER INFORMATION: Description of Artificial Sequence: Synthetic
      exemplary polynucleotide according to formula (I)

<400> SEQUENCE: 115

gggagaaagc ucaagcuugg agcaaugccc gcacauugag gaaaccgagu ugcauaucuc     60

agaguauugg cccccgugua gguuauucuu gacagacagu ggagcuuauu cacucccagg    120

auccgagucg cauacuacgg uacuggugac agaccuaggu cgucaguuga ccaguccgcc    180

acuagacgug aguccgucaa agcaguuaga uguuacacuc uauuagaucu cggauuacag    240

cuggaaggag caggaguagu guucuugcuc uaaguaccga gugugcccaa uacccgauca    300

gcuuauuaac gaacggcucc uccucuuaga cugcagcgua agugcggaau cuggggauca    360

aauuacugac ugccuggauu acccucggac auauaaccuu guagcacgcu guugcuguau    420

aggugaccaa cgcccacucg aguagaccag cucucuuagu ccggacaaug auaggaggcg    480

cggucaaucu acuucuggcu aguuaagaau aggcugcacc gaccucuaua aguagcgugu    540

ccucuag                                                             547
```

<210> SEQ ID NO 116
<211> LENGTH: 1083
<212> TYPE: RNA
<213> ORGANISM: Artificial Sequence
<220> FEATURE:
<223> OTHER INFORMATION: Description of Artificial Sequence: Synthetic
exemplary polynucleotide according to formula (I)

<400> SEQUENCE: 116
gggagaaagc ucaagcuugg agcaaugccc gcacauugag gaaaccgagu ugcauaucuc 60
agaguauugg cccccgugua gguuauucuu gacagacagu ggagcuuauu cacucccagg 120
auccgagucg cauacuacgg uacuggugac agaccuaggu cgucaguuga ccaguccgcc 180
acuagacgug aguccgucaa agcaguuaga uguuacacuc uauuagaucu cggauuacag 240
cuggaaggag caggaguagu guucuugcuc uaaguaccga gugugcccaa uacccgauca 300
gcuuauuaac gaacggcucc uccucuuaga cugcagcgua agugcggaau cuggggauca 360
aauuacugac ugccuggauu acccucggac auauaaccuu guagcacgcu guugcuguau 420
aggugaccaa cgcccacucg aguagaccag cucucuuagu ccggacaaug auaggaggcg 480
cggucaaucu acuucuggcu aguuaagaau aggcugcacc gaccucuaua aguagcgugu 540
ccucuagagc uacgcagguu cgcaauaaaa gcguugauua gugugcauag aacagaccuc 600
uuauucggug aaacgccaga augcuaaauu ccaauaacuc uucccaaaac gcguacggcc 660
gaagacgcgc gcuuaucuug uguacguucu cgcacaugga agaaucagcg ggcauggugg 720
uagggcaaua ggggagcugg guagcagcga aaaagggccc cugcgcacgu agcuucgcug 780
uucgucugaa acaacccggc auccguugua gcgaucccgu uaucaguguu auucuugugc 840
gcacuaagau ucauggugua gucgacaaua acagcgucuu ggcagauucu ggucacgugc 900
ccuaugcccg ggcuugugcc ucucaggugc acagcgauac uuaaagccuu caagguacuc 960
gacgugggua ccgauucgug acacuucccua agauuauucc acuguguuag ccccgcaccg 1020
ccgaccuaaa cugguccaau guauacgcau ucgcugagcg gaucgauaau aaaagcuuga 1080
auu 1083

<210> SEQ ID NO 117
<211> LENGTH: 229
<212> TYPE: RNA
<213> ORGANISM: Artificial Sequence
<220> FEATURE:
<223> OTHER INFORMATION: Description of Artificial Sequence: Synthetic
exemplary polynucleotide according to formula (I)

<400> SEQUENCE: 117
gggagaaagc ucaagcuuau ccaaguaggc uggucaccug uacaacguag ccgguauuuu 60
uuuuuuuuuu uuuuuuuuga ccgucucaag guccaaguua gucugccuau aaaggugcgg 120
auccacagcu gaugaaagac uugugcggua cgguuaaucu ccccuuuuuu uuuuuuuuuu 180
uuuuuaguaa augcgucuac ugaauccagc gaugaugcug gcccagauc 229

<210> SEQ ID NO 118
<211> LENGTH: 546
<212> TYPE: RNA
<213> ORGANISM: Artificial Sequence
<220> FEATURE:
<223> OTHER INFORMATION: Description of Artificial Sequence: Synthetic
exemplary polynucleotide according to formula (I)

<400> SEQUENCE: 118

```
gggagaaagc ucaagcuuau ccaaguaggc uggucaccug uacaacguag ccgguauuuu     60

uuuuuuuuuu uuuuuuuuga ccgucucaag guccaaguua gucugccuau aaaggugcgg    120

auccacagcu gaugaaagac uugugcggua cgguuaaucu ccccuuuuuu uuuuuuuuuu    180

uuuuuaguaa augcgucuac ugaauccagc gaugaugcug gcccagaucu ucgaccacaa    240

gugcauauag uagucaucga gggucgccuu uuuuuuuuuu uuuuuuuuuu uggcccaguu    300

cugagacuuc gcuagagacu acaguuacag cugcaguagu aaccacugcg gcuauugcag    360

gaaaucccgu ucagguuuuu uuuuuuuuuu uuuuuuccgc ucacuaugau uaagaaccag    420

guggagugu c acugcucucg aggucucacg agagcgcucg auacaguccu uggaagaauc   480

uuuuuuuuuu uuuuuuuuuu uugugcgacg aucacagaga acuucuauuc augcaggucu    540

gcucua                                                               546
```

<210> SEQ ID NO 119
<211> LENGTH: 1083
<212> TYPE: RNA
<213> ORGANISM: Artificial Sequence
<220> FEATURE:
<223> OTHER INFORMATION: Description of Artificial Sequence: Synthetic exemplary polynucleotide according to formula (I)

<400> SEQUENCE: 119

```
gggagaaagc ucaagcuuau ccaaguaggc uggucaccug uacaacguag ccgguauuuu     60

uuuuuuuuuu uuuuuuuuga ccgucucaag guccaaguua gucugccuau aaaggugcgg    120

auccacagcu gaugaaagac uugugcggua cgguuaaucu ccccuuuuuu uuuuuuuuuu    180

uuuuuaguaa augcgucuac ugaauccagc gaugaugcug gcccagaucu ucgaccacaa    240

gugcauauag uagucaucga gggucgccuu uuuuuuuuuu uuuuuuuuuu uggcccaguu    300

cugagacuuc gcuagagacu acaguuacag cugcaguagu aaccacugcg gcuauugcag    360

gaaaucccgu ucagguuuuu uuuuuuuuuu uuuuuuccgc ucacuaugau uaagaaccag    420

guggaguguc acugcucucg aggucucacg agagcgcucg auacaguccu uggaagaauc    480

uuuuuuuuuu uuuuuuuuuu uugugcgacg aucacagaga acuucuauuc augcaggucu    540

gcucuagaac gaacugaccu gacgccugaa cuuaugagcg ugcguauuuu uuuuuuuuuu    600

uuuuuuuuuc cucccaacaa augucgauca auagcugggc uguuggagac gcgucagcaa    660

augccguggc uccauaggac guguagacuu cuauuuuuuu uuuuuuuuuu uuuucccggg    720

accacaaaua auauucuugc uugguugggc gcaagggccc cguaucaggu cauaaacggg    780

uacauguugc acaggcuccu uuuuuuuuuu uuuuuuuuuu uucgcugagu uauuccgguc    840

ucaaaagacg gcagacguca gucgacaaca cggucuaaag cagugcuaca aucugccgug    900

uucguguuuu uuuuuuuuuu uuuuuuguga accuacacgg cgugcacugu aguucgcaau    960

ucauagggua ccggcucaga guuaugccuu gguugaaaac ugcccagcau acuuuuuuuu   1020

uuuuuuuuuu uucauauucc caugcuaagc aagggaugcc gcgagucaug uuaagcuuga   1080

auu                                                                 1083
```

<210> SEQ ID NO 120
<211> LENGTH: 1365
<212> TYPE: RNA
<213> ORGANISM: Artificial Sequence
<220> FEATURE:
<223> OTHER INFORMATION: Description of Artificial Sequence: Synthetic mRNA polynucleotide according to SEQ ID NO: 1, termed “CAP-GgOva(GC)-muag-A70-C30”

<400> SEQUENCE: 120
gggagaaagc uuaccauggg cagcaucggg gccgcgucga uggaguucug cuucgacgug 60
uucaaggagc ugaaggucca ccacgccaac gagaacaucu ucuacugccc gaucgccauc 120
augagcgcgc ucgccauggu guaccugggc gccaaggaca gcacccggac gcagaucaac 180
aagguggucc gcuucgacaa gcugcccggc uucggggacu cgaucgaggc gcagugcggc 240
accagcguga acgugcacag cucgcuccgg gacauccuga accagaucac caagccgaac 300
gacgucuaca gcuucagccu ggccucgcgg cucuacgccg aggagcgcua cccgauccug 360
cccgaguacc ugcagugcgu gaaggagcuc uaccggggcg ggcuggagcc gaucaacuuc 420
cagacggcgg ccgaccaggc ccgggagcug aucaacagcu ggguggagag ccagaccaac 480
ggcaucaucc gcaacgucct ccagccgucg agcguggaca gccagaccgc gauggugcug 540
gucaacgcca ucguguucaa gggccugugg gagaagacgu ucaaggacga ggacacccag 600
gccaugcccu uccgggugac cgagcaggag ucgaagccgg uccagaugau guaccagauc 660
gggcucuucc ggguggcgag cauggccagc gagaagauga agauccugga gcugccguuc 720
gccucgggca cgaugagcau gcucgugcug cugcccgacg aggucagcgg ccucgagcag 780
cuggagucga ucaucaacuu cgagaagcug accgagugga ccagcagcaa cgugauggag 840
gagcgcaaga ucaaggugua ccucccgcgg augaagaugg aggagaagua caaccugacg 900
ucgguccuga uggcgauggg gaucaccgac guguucagca gcucggccaa ccucagcggc 960
aucagcucgg ccgagagccu gaagaucagc caggcggugc acgccgccca cgcggagauc 1020
aacgaggccg gccgggaggu cguggggucg gccgaggcgg gcguggacgc cgccagcguc 1080
agcgaggagu uccgcgcgga ccacccguuc cuguucugca ucaagcacau cgccaccaac 1140
gccgugcucu ucuucggccg gugcgugucg cccugaccac uaguuauaag acugacuagc 1200
ccgaugggcc ucccaacggg cccuccuccc cuccuugcac cgagauuaau aaaaaaaaaa 1260
aaaaaaaaaa aaaaaaaaaa aaaaaaaaaa aaaaaaaaaa aaaaaaaaaa aaaauauucc 1320
cccccccccc cccccccccc cccccccuc uagacaauug gaauu 1365

<210> SEQ ID NO 121
<211> LENGTH: 1816
<212> TYPE: RNA
<213> ORGANISM: Artificial Sequence
<220> FEATURE:
<223> OTHER INFORMATION: Description of Artificial Sequence: Synthetic
mRNA polynucleotide according to SEQ ID NO: 2,
termed “T7TS-Ppluc(wt)-A70”

<400> SEQUENCE: 121
gggagacaag cuuggcauuc cgguacuguu gguaaagcca ccauggaaga cgccaaaaac 60
auaaagaaag gcccggcgcc auucuauccg cuggaagaug gaaccgcugg agagcaacug 120
cauaaggcua ugaagagaua cgcccugguu ccuggaacaa uugcuuuuac agaugcacau 180
aucgaggugg acaucacuua cgcugaguac uucgaaaugu ccguucgguu ggcagaagcu 240
augaaacgau augggcugaa uacaaaucac agaaucgucg uaugcaguga aaacucucuu 300
caauucuuua ugccggugu u gggcgcguua uuuaucggag uugcaguugc gcccgcgaac 360
gacauuuaua augaacguga auugcucaac aguaugggca uuucgcagcc uaccguggug 420
uucguuucca aaaagggguu gcaaaaaauu uugaacgugc aaaaaaagcu cccaaucauc 480
caaaaaauua uuaucaugga uucuaaaacg gauuaccagg gauuucaguc gauguacacg 540

```
uucgucacau cucaucuacc ucccgguuuu aaugaauacg auuuugugcc agaguccuuc    600

gauagggaca agacaauugc acugaucaug aacuccucug gaucuacugg ucugccuaaa    660

ggugucgcuc ugccucauag aacugccugc gugagauucu cgcaugccag agauccuauu    720

uuuggcaauc aaaucauucc ggauacugcg auuuuaagug uuguuccauu ccaucacggu    780

uuuggaaugu uuacuacacu cggauauuug auauguggau uucgagucgu cuuaauguau    840

agauuugaag aagagcuguu ucugaggagc cuucaggauu acaagauuca aagugcgcug    900

cuggugccaa cccuauucuc cuucuucgcc aaaagcacuc ugauugacaa auacgauuua    960

ucuaauuuac acgaaauugc uucuggugggc gcuccccucu cuaaggaagu cggggaagcg   1020

guugccaaga gguuccaucu gccagguauc aggcaaggau augggcucac ugagacuaca   1080

ucagcuauuc ugauuacacc cgagggggau gauaaaccgg gcgcggucgg uaaaguuguu   1140

ccauuuuuug aagcgaaggu uguggaucug gauaccggga aaacgcuggg cguuaaucaa   1200

agaggcgaac ugugugugag agguccuaug auuauguccg guuauguaaa caauccggaa   1260

gcgaccaacg ccuugauuga caaggaugga uggcuacauu cuggagacau agcuuacugg   1320

gacgaagacg aacacuucuu caucguugac cgccugaagu cucugauuaa guacaaaggc   1380

uaucaggugg cucccgcuga auuggaaucc aucuugcucc aacaccccaa caucuucgac   1440

gcaggugucg caggucuucc cgacgaugac gccggugaac uucccgccgc cguuguuguu   1500

uuggagcacg gaaagacgau gacggaaaaa gagaucgugg auuacgucgc cagucaagua   1560

acaaccgcga aaaaguugcg cggaggaguu guguuugugg acgaaguacc gaaaggucuu   1620

accggaaaac ucgacgcaag aaaaaucaga gagauccuca uaaaggccaa gaagggcgga   1680

aagaucgccg uguaauucua guaaaaaaaa aaaaaaaaaa aaaaaaaaaa aaaaaaaaaa   1740

aaaaaaaaaa aaaaaaaaaa aaaaaaaaaa aacugcaggu cgacucuaga ggaucccccgg   1800

guaccgagcu cgaauu                                                   1816
```

<210> SEQ ID NO 122
<211> LENGTH: 13
<212> TYPE: RNA
<213> ORGANISM: Artificial Sequence
<220> FEATURE:
<223> OTHER INFORMATION: Description of Artificial Sequence: Synthetic Kozak oligonucleotide

<400> SEQUENCE: 122

```
gccgccacca ugg                                                        13
```

<210> SEQ ID NO 123
<211> LENGTH: 15
<212> TYPE: RNA
<213> ORGANISM: Artificial Sequence
<220> FEATURE:
<223> OTHER INFORMATION: Description of Artificial Sequence: Synthetic generic stabilizing oligonucleotide
<220> FEATURE:
<221> NAME/KEY: modified_base
<222> LOCATION: (5)..(5)
<223> OTHER INFORMATION: a, c, u, g, unknown or other
<220> FEATURE:
<221> NAME/KEY: modified_base
<222> LOCATION: (10)..(10)
<223> OTHER INFORMATION: Pyrimidine
<220> FEATURE:
<223> OTHER INFORMATION: see specification as filed for detailed description of substitutions and preferred embodiments

<400> SEQUENCE: 123

```
yccancccwn ucycc                                                15

<210> SEQ ID NO 124
<211> LENGTH: 1902
<212> TYPE: RNA
<213> ORGANISM: Influenza virus
<220> FEATURE:
<223> OTHER INFORMATION: mRNA sequence encoding the pathogenic antigen
      hemagglutinin (HA) from influenza virus

<400> SEQUENCE: 124

gggagaaagc uuaccaugaa ggccaaccug cucgugcugc ugugcgcccu cgcggccgcc     60

gacgccgaca ccaucugcau cggcuaccac gccaacaaca gcaccgacac ggucgacacc    120

gugcuggaga agaacgugac cgucacccac uccgugaacc ugcucgagga cagccacaac    180

gggaagcugu gccggcugaa gggcaucgcg ccccuccagc uggggaagug caacaucgcc    240

ggcuggcugc ucgggaaccc ggagugcgac ccccugcugc ccgugcgcuc cuggagcuac    300

aucgucgaga cgcccaacuc cgagaacggc aucugcuacc cgggcgacuu caucgacuac    360

gaggagcucc gggagcagcu gagcuccgug agcuccuucg agcgcuucga gaucuucccc    420

aaggagagcu ccuggcccaa ccacaacacc aacggggu ga ccgccgccug cagccacgag    480

ggcaagucca gcuucuaccg gaaccugcuc uggcugaccg agaaggaggg guccuacccc    540

aagcugaaga acagcuacgu caacaagaag ggcaaggagg ugcucgugcu guggggggauc    600

caccacccgc ccaacuccaa ggagcagcag aaccuguacc agaacgagaa cgcguacguc    660

agcguggu ga cguccaacua caaccgccgg uucacccccg agaucgccga gcgccccaag    720

guccgggacc aggccggccg caugaacuac uacuggaccc uccugaagcc gggcgacacc    780

aucaucuucg aggccaacgg gaaccugauc gccccgaugu acgcguucgc ccucagccgg    840

ggcuucggga gcggcaucau cacguccaac gccagcaugc acgagugcaa caccaagugc    900

cagacccccc ugggcgccau caacuccagc cugcccuacc agaacaucca cccggugacc    960

aucggggagu gccccaagua cgugcgcucc gccaagcucc ggauggucac gggccugcgc   1020

aacaacccca gcauccaguc ccgggggcug uucggcgcga ucgccggguu caucgagggc   1080

ggcuggaccg ggaugaucga cggcugguac ggguaccacc accagaacga gcagggcagc   1140

ggguacgccg ccgaccagaa guccacccag aacgccauca acggcaucac caacaaggug   1200

aacacggu ga ucgagaagau gaacauccag uucaccgcgg ucggcaagga guucaacaag   1260

cucgagaagc gcauggagaa ccugaacaag aagguggacg acggguuccu ggacaucugg   1320

accuacaacg ccgagcuccu ggugcugcuc gagaacgagc ggacccugga cuuccacgac   1380

agcaacguca agaaccugua cgagaaggug aagucccagc ucaagaacaa cgccaaggag   1440

aucggcaacg ggugcuucga guucuaccac aagugcgaca acgagugcau ggagagcguc   1500

cgcaacggca cguacgacua ccccaaguac uccgaggaga gcaagcugaa ccgggagaag   1560

guggacgggg ugaagcugga guccaugggc aucuaccaga uccucgccau cuacagcacc   1620

gucgccucca gccuggugcu gcuggugucc cucggcgcga ucagcuucug gaugugcagc   1680

aacggguccc ugcagugccg caucugcauc ugaccacuag uuauaagacu gacuagcccg   1740

augggccucc caacgggccc uccuccccuc cuugcaccga gauuaauaaa aaaaaaaaaa   1800

aaaaaaaaaa aaaaaaaaaa aaaaaaaaaa aaaaaaaaaa aaaaaaaaaa auauuccccc   1860

cccccccccc cccccccccc cccccucuag acaauuggaa uu                       1902

<210> SEQ ID NO 125
```

-continued

<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 125

Arg Arg Arg Arg Arg Arg Arg
1 5

<210> SEQ ID NO 126
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 126

Arg Arg Arg Arg Arg Arg Arg Arg
1 5

<210> SEQ ID NO 127
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 127

Arg Arg Arg Arg Arg Arg Arg Arg Arg
1 5

<210> SEQ ID NO 128
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 128

His His His Arg Arg Arg Arg Arg Arg Arg Arg Arg
1 5 10

<210> SEQ ID NO 129
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 129

Arg Arg Arg Arg Arg Arg Arg Arg Arg His His His
1 5 10

<210> SEQ ID NO 130
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 130

-continued

His His His Arg Arg Arg Arg Arg Arg Arg Arg Arg His His His
1 5 10 15

<210> SEQ ID NO 131
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 131

Tyr Ser Ser Arg Arg Arg Arg Arg Arg Arg Arg Arg Ser Ser Tyr
1 5 10 15

<210> SEQ ID NO 132
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 132

Arg Lys His Arg Lys His Arg Lys His Arg Lys His
1 5 10

<210> SEQ ID NO 133
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 133

Tyr Arg Lys His Arg Lys His Arg
1 5

<210> SEQ ID NO 134
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 134
uuuaauuuuc 10

<210> SEQ ID NO 135
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 135
uuuuguuuua 10

<210> SEQ ID NO 136
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 136
uuuguuuguu 10

<210> SEQ ID NO 137
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 137
uuguuuuguu 10

<210> SEQ ID NO 138
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 138
uuuuuuuuuu 10

<210> SEQ ID NO 139
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 139

Cys Cys Cys Cys
1

<210> SEQ ID NO 140
<211> LENGTH: 5
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(3)
<223> OTHER INFORMATION: Any non-conserved amino acid

<400> SEQUENCE: 140

Trp Ser Xaa Trp Ser
1 5

<210> SEQ ID NO 141
<211> LENGTH: 70
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 141
aaaaaaaaaa aaaaaaaaaa aaaaaaaaaa aaaaaaaaaa aaaaaaaaaa aaaaaaaaaa 60
aaaaaaaaaa 70

-continued

```
<210> SEQ ID NO 142
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142

cccccccccc cccccccccc cccccccccc                                    30
```